US009862721B2

(12) United States Patent
Ohata et al.

(10) Patent No.: US 9,862,721 B2
(45) Date of Patent: *Jan. 9, 2018

(54) TETRAHYDROCARBOLINE DERIVATIVE

(71) Applicant: ONO PHARMACEUTICAL CO., LTD., Osaka (JP)

(72) Inventors: Akira Ohata, Osaka (JP); Shingo Nakatani, Osaka (JP); Tetsuya Sugiyama, Ibaraki (JP); Takashi Morimoto, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 22 days.

This patent is subject to a terminal disclaimer.

(21) Appl. No.: 14/884,211

(22) Filed: Oct. 15, 2015

(65) Prior Publication Data

US 2016/0031884 A1    Feb. 4, 2016

Related U.S. Application Data

(63) Continuation of application No. 14/005,062, filed as application No. PCT/JP2012/050050 on Jan. 5, 2012, now Pat. No. 9,353,113.

(30) Foreign Application Priority Data

Mar. 18, 2011    (JP) .................. 2011-060765

(51) Int. Cl.
| | |
|---|---|
| C07D 471/14 | (2006.01) |
| C07D 471/12 | (2006.01) |
| A61K 31/437 | (2006.01) |
| A61K 31/435 | (2006.01) |
| A61K 9/00 | (2006.01) |
| A61K 47/26 | (2006.01) |
| A61K 9/19 | (2006.01) |
| A61K 9/20 | (2006.01) |
| C07D 471/04 | (2006.01) |

(52) U.S. Cl.
CPC .......... *C07D 471/14* (2013.01); *A61K 9/0019* (2013.01); *A61K 9/19* (2013.01); *A61K 9/2054* (2013.01); *A61K 31/435* (2013.01); *A61K 31/437* (2013.01); *A61K 47/26* (2013.01); *C07D 471/04* (2013.01); *C07D 471/12* (2013.01)

(58) Field of Classification Search
CPC . C07D 471/14; A61K 31/437; A61K 31/4375
USPC ............................................ 546/80; 514/253
See application file for complete search history.

(56) References Cited

U.S. PATENT DOCUMENTS

| | | | | |
|---|---|---|---|---|
| 9,006,246 B2* | 4/2015 | Ohata | .................. | C07D 471/04 514/253.03 |
| 9,353,113 B2* | 5/2016 | Ohata | .................. | C07D 471/14 |
| 2002/0010189 A1 | 1/2002 | Sui et al. | | |
| 2004/0116458 A1 | 6/2004 | Sawyer et al. | | |
| 2005/0215580 A1 | 9/2005 | Wang et al. | | |
| 2005/0256160 A1 | 11/2005 | Habashita et al. | | |
| 2013/0109699 A1 | 5/2013 | Ohata et al. | | |
| 2015/0231118 A1* | 8/2015 | Ohata | .................. | A61K 31/437 514/253.03 |

FOREIGN PATENT DOCUMENTS

| | | |
|---|---|---|
| EA | 010546 B1 | 10/2008 |
| JP | 2003-533453 A | 11/2003 |
| JP | 2004-518730 A | 6/2004 |
| JP | 2007-518822 A | 7/2007 |
| JP | 2008-297278 A | 12/2008 |
| WO | 03/099765 A1 | 12/2003 |
| WO | 2005/111037 A1 | 11/2005 |
| WO | 2012/005227 A1 | 1/2012 |

(Continued)

OTHER PUBLICATIONS

Communication dated Oct. 13, 2015 by the Russian Intellectual Property Office in Russian Application No. 2013104866/04(007253).
Goldman, et al.; "Cecil Textbook of Medicine", W.B. Saunders Company, 21st Edition, vol. 1, 2000, pp. 1060-1074, 17 pages total.
United States Patent and Trademark Office, Office Action dated Apr. 7, 2016, issued in U.S. Appl. No. 14/630,708.
European Patent Office, European Search Report dated Apr. 9, 2014 issued in European Patent Application No. 11803561.7.

(Continued)

*Primary Examiner* — Rita J Desai
(74) *Attorney, Agent, or Firm* — Sughrue Mion, PLLC

(57) ABSTRACT

An object of the present invention is to provide a drug having the inhibitory activity on ENPP2 which is a different target from that of the existing drug, as a medicament useful in a urinary excretion disorder patient for whom the existing drug has the insufficient effect. The present invention provides a compound represented by the general formula (I):

(wherein definition of each group is as defined in the description) having the ENPP2 inhibitory activity, a salt thereof or a solvate thereof or a prodrug thereof, and an agent for preventing or treating urinary excretion disorder and/or improving symptoms thereof, containing them as an active ingredient.

21 Claims, No Drawings

(56) References Cited

FOREIGN PATENT DOCUMENTS

WO     2012/005227    * 12/2012

OTHER PUBLICATIONS

Jayendra B. Bhonsle et al.; "Novel Method for Mining QSPR-Relevant Conformations"; Chemical Engineering Communications; vol. 195; No. 11; 2008; pp. 1396-1423.

USPTO, Non-Final Office Action dated Mar. 18, 2014, issued in U.S. Appl. No. 13/807,947.

Intellectual Property Office of New Zealand, Office Action dated Aug. 26, 2013, issued in Application No. 603575.

International Searching Authority, International Search Report dated Sep. 13, 2011 issued in International Application No. PCT/JP2011/065312 (PCT/ISA/210).

Seefeld et al., "Inhibitors of bacterial enoyl acyl carrier protein reductase (FabI): 2,9-disubstituted 1,2,3,4-tetrahydropyrido[3,4-b]indoles as potential antibacterial agents", Bioorganic & Medicinal Chemistry Letters, Elsevier Science, Ltd., Sep. 3, 2001, vol. 11, No. 17, pp. 2241-2244.

Stella et al., "Prodrug strategies to overcome poor water solubility", Advanced Drug Delivery Reviews, Elsevier B.V., Jul. 30, 2007, vol. 59, Issue 7, pp. 677-694.

USPTO, Office Action dated Jul. 14, 2014 issued in U.S. Appl. No. 13/807,947.

Xiaoming Zhang, et al., "Oxidative Mehtods for Promoting Iminium Cation Cyclization Reactions", Tetrahedron Letters, vol. 34, No. 33, 1993, pp. 5239-5242.

Nternational Searching Authority,International Search Report dated Mar. 27, 2012, PCT/ISA/210, issued in corresponding PCT/JP2012/050050 of record, filed Sep. 13, 2013.

European Patent Office, Extended European Search Report dated Jun. 4, 2014, issued in European Application No. 12761051.7.

USPTO, U.S. Appl. No. 13/807,947, filed Jan. 2, 2013; inventor = Akira Ohata et al.

Dorwald F.A. Side Reactions in Organic Synthesis, 2005, Wiley: VCH, Weinheim p. IX of Preface.

* cited by examiner

TETRAHYDROCARBOLINE DERIVATIVE

CROSS REFERENCE TO RELATED APPLICATIONS

This application is a continuation application of U.S. application Ser. No. 14/005,062 filed Sep. 13, 2013, which is a National Stage of PCT/JP2012/050050 filed Jan. 5, 2012, which claims benefit of Japanese Application No. 2011-060765 filed Mar. 18, 2011. The entire disclosures of the prior applications are hereby incorporated by reference.

TECHNICAL FIELD

The present invention relates to a tetrahydrocarboline derivative having the ENPP2 inhibitory activity, a salt thereof or a solvate thereof or a prodrug thereof as well as use thereof.

BACKGROUND ART

Urinary excretion disorder is a disorder in which urine becomes difficult to be excreted, and the cause thereof is reduction in bladder contraction due to neurogenic bladder, urethra oppression due to prostatomegaly or the like. In main advanced countries, it is said that even the number of patient with urinary excretion disorder accompanied with prostatomegaly exceeds at least 15 million. Currently, a mainstream drug for urinary excretion disorder is α1 antagonists, but there is reported that in about a half of them, the drug efficacy is insufficient, and the effect is attenuated due to long term use. However, under the current circumstances, development of a therapeutic effective in those patients is not sufficient.

Meanwhile, ENPP2 (Ectonucleotide Pyrophosphatase/Phosphodiesterase 2) is also called Autotaxin or LysoPLD, and is an enzyme producing lysophosphatidic acid (hereinafter, abbreviated as LPA) which is a lysophospholipid, in blood (see Non-Patent Document 1). Since ENPP2 is highly expressed in many cancerous tissues, and promotes mobility of a cancer cell, it was concerned as a molecule involved in metastasis or infiltration of cancer at the beginning (see Non-Patent Document 2), but was later confirmed to be a main enzyme producing LPA, and possibilities of involvement in a variety of physiological functions in which LPA is involved, have been reported (see Non-Patent Document 3, and see Patent Document 1). For example, since LPA is involved in contraction of prostate or urethra, there is a possibility that ENPP2 which is an producing enzyme thereof becomes a new target of treatment of urinary excretion disorder. However, use as a drug for urinary excretion disorder is not shown at all in the prior art documents concerning an ENPP2 inhibitor which have previously been reported, for example, Non-Patent Documents 4 to 6, Patent Document 2 concerning an imidazole derivative, Patent Document 3 concerning piperidine and piperazine derivatives, and Patent Document 4 concerning a thiazole derivative.

On the other hand, as the prior art concerning the present compound, there are the followings. That is, an antibacterial agent having the phosphopantetheineadenyltransferase (PPAT) inhibitory activity consisting of a compound represented by the general formula (A):

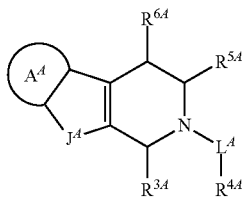

(A)

(wherein ring $A^A$ represents an aryl or hetroaryl group in which an arbitrary substitutable ring atom may be substituted, $J^A$ represents —$NR^{2A'}$— etc. (wherein $R^{2A'}$ represents optionally substituted aralkyl etc.), $R^{3A}$ represents a hydrogen atom etc., $L^A$ represents —(CO)— etc., $R^{4A}$ represents a C1-C8 aliphatic group etc., a group represented by $R^{4A}$ is substituted with —(CO)$OR^A$ etc. (wherein $R^A$ represents a hydrogen atom etc.) and $R^{5A}$ and $R^{6A}$ each represent independently a hydrogen atom etc. (extract of a part of definitions of groups)) (see Patent Document 5), a mitochondrial benzodiazepine (MBR) receptor antagonist consisting of a compound represented by the general formula (B):

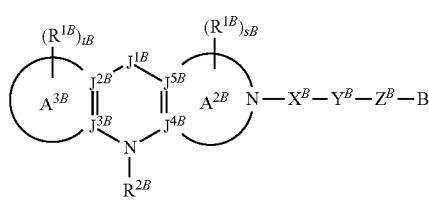

(B)

(wherein ring $A^{2B}$ represents a monocyclic nitrogen-containing hetrocycle, ring $A^{3B}$ represents a monocyclic carbon ring or a monocyclic heterocyclic ring, a plurality of $R^{1B}$s each represent independently a substituent, $R^{2B}$ represents a hydrogen atom or a substituent, tB and sB each represent independently an integer of 0 to 5, a sum of tB and sB is 5 or less, $J^{1B}$ represents a carbon atom optionally having a substituent etc., $J^{2B}$, $J^{3B}$, $J^{4B}$ and $J^{5B}$ each represent independently a carbon atom etc., $X^B$, $Y^B$ and $Z^B$ each represent independently a spacer in which the atom number of a main chain is 1 to 3 etc., and $B^B$ represents a hydrocarbon group optionally having a substituent etc. (extract of a part of definitions of groups)) (see Patent Document 6), an orphan intranuclear receptor agonist consisting of a compound represented by the general formula (D):

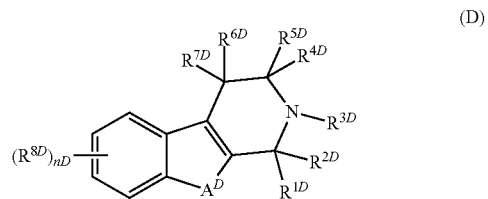

(D)

(wherein $A^D$ represents —$N(R^{9D})$— etc., $R^{1D}$ and $R^{2D}$ each represent independently a hydrogen atom etc., $R^{3D}$ represents —$C(O)R^{10D}$ (wherein $R^{10D}$ represents a hydrogen atom etc.) etc., $R^{4D}$, $R^{5D}$, $R^{6D}$ and $R^{7D}$ each represent independently a hydrogen atom etc. $R^{8D}$s each represent independently a halogen atom, —$C(O)OR^{23D}$ (wherein $R^{23D}$ represents a hydrogen atom etc.) or —$R^{27D}$ (wherein $R^{27D}$ represents optionally substituted alkyl etc.) and $R^{9D}$ represents optionally substituted alkyl etc. (extract of a part of definitions of groups)) (see Patent Document 7), an Xa factor inhibitor consisting of a compound represented by the general formula (E):

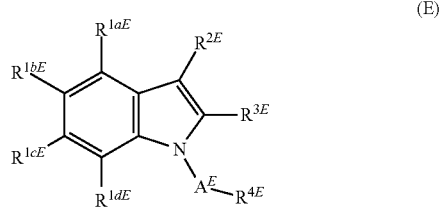

(E)

(wherein $R^{1aE}$, $R^{1bE}$, $R^{1cE}$ and $R^{1dE}$ each represent independently a hydrogen atom, a halogen or a C1-4 alkyl group etc., $R^{2E}$ and $R^{3E}$ are taken together to form —$CH_2$—$CH_2$—N(—CO—$R^{20E}$)—$CH_2$— (wherein $R^{20E}$ is phenyl, phenyl-C1-4 alkyl-, pyridyl or pyridyl-C1-4 alkyl-, phenyl is substituted with $R^{15aE}$, and pyridyl may be substituted with $R^{14E}$ at its nitrogen atom), $A^E$ represents —C1-4 alkyl- etc., and $R^{4E}$ represents phenyl having a substituent or pyridyl optionally having a substituent etc. (extract of a part of definitions of groups)) (see Patent Document 8) and a synthesis intermediate of a cholecystokinin or gastrin receptor binding agent consisting of a compound represented by the general formula (G):

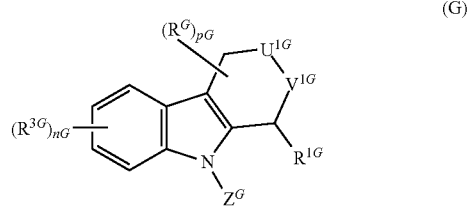

(G)

(wherein $U^{1G}$ represents —$CH_2$— etc., $V^{1G}$ represents —$N(COR^{4G})$— etc. (wherein $R^{4G}$ represents an aryl group optionally having a substituent or an arylalkyl group optionally having a substituent etc.), $Z^G$ represents —C1-3 alkyl-$R^{8G}$ etc. (wherein $R^{8G}$ represents a phenyl group optionally having a substituent), $R^{3G}$ represents a halogen or an alkyl group etc., $R^G$ represents a C1-3 alkyl group, and nG and pG each represent an integer of 0 to 3 (extract of a part of definitions of groups)) (see Patent Document 9).

Further, as the prior art concerning the present compound, there are a PDE inhibitor (see Patent Documents 10 to 15), a histamine receptor antagonist (see Patent Document 16), a 5-HT2 antagonist (see Patent Document 17), a histamine H3 antagonist (see Patent Document 18), a 5-HT6 antagonist (see Patent Document 19), a PPAT inhibitor (see Patent Document 20), a HDAC inhibitor (see Patent Document 21), a sPLA2 inhibitor (see Patent Document 22), a farnesyl-transferase inhibitor (see Patent Document 23), an angiotensin II converting enzyme inhibitor (see Patent Document 24), an EDG-5 antagonist (see Patent Document 25), a PTPase inhibitor (see Patent Document 26), an ADAM-TS inhibitor (see Patent Document 27), an anti-cancer agent (see Patent Document 28), a kinesin-associated protein inhibitor (see Patent Document 29), a FabI inhibitor (see Patent Document 30), a melatonin derivative (see Patent Document 31), a VEGF expression inhibitor (see Patent Document 32) and an insulin receptor antagonist (see Patent Document 33) etc.

However, the present compound is not described in the any prior art, and it is not suggested that a compound described in each prior art has the ENPP2 inhibitory activity or is effective in urinary excretion disorder due to LPA.

PRIOR ART DOCUMENTS

Patent Documents

[Patent Document 1] International Publication No. 02/062389
[Patent Document 2] International Publication No. 09/046804
[Patent Document 3] International Publication No. 09/046841
[Patent Document 4] International Publication No. 09/046842
[Patent Document 5] International Publication No. 04/968802
[Patent Document 6] International Publication No. 04/113300
[Patent Document 7] International Publication No. 03/099821
[Patent Document 8] International Publication No. 99/033800
[Patent Document 9] International Publication No. 97/032860
[Patent Document 10] International Publication No. 02/064590
[Patent Document 11] International Publication No. 02/064591
[Patent Document 12] International Publication No. 00/012076
[Patent Document 13] International Publication No. 02/088123
[Patent Document 14] International Publication No. 01/087038
[Patent Document 15] International Publication No. 02/098875
[Patent Document 16] International Publication No. 09/055828
[Patent Document 17] U.S. Pat. No. 6,350,757
[Patent Document 18] International Publication No. 09/003003
[Patent Document 19] International Publication No. 07/028460
[Patent Document 20] International Publication No. 09/102377
[Patent Document 21] International Publication No. 04/113336
[Patent Document 22] International Publication No. 00/037022
[Patent Document 23] European Patent Application Publication No. 675112
[Patent Document 24] JP-A-60-246385
[Patent Document 25] International Publication No. 04/002531
[Patent Document 26] International Publication No. 03/033496
[Patent Document 27] International Publication No. 01/087883
[Patent Document 28] International Publication No. 08/103470

[Patent Document 29] International Publication No. 05/070930

[Patent Document 30] International Publication No. 00/072846

[Patent Document 31] International Publication No. 95/026723

[Patent Document 32] International Publication No. 06/058088

[Patent Document 33] International Publication No. 00/016798

Non-Patent Documents

[Non-Patent Document 1] Journal of Cell Biology, 2002, vol. 158. pp. 227-233

[Non-Patent Document 2] Journal of Biological Chemistry, 2004, vol. 279, 17th issue, pp. 17634-17639

[Non-Patent Document 3] Biochim Biophys Acta., 2008, 1781st issue, vol. 9, pp. 513-518

[Non-Patent Document 4] Bioorganic & Medicinal Chemistry Letters, 2007, vol. 17, 6th issue, pp. 1634-1640

[Non-Patent Document 5] Journal of Pharmacology And Experimental Therapeutics, 2008, vol. 327, 3rd issue, pp. 809-19

[Non-Patent Document 6] Biochimica et Biophysica Acta, 2008, vol. 1781, 9th issue, pp. 588-94

DISCLOSURE OF THE INVENTION

Problems to be Solved by the Invention

An object of the present invention is to develop a compound having the inhibitory activity on ENPP2 which is a different target from that of the existing drugs in order to provide a drug useful for a patient with urinary excretion disorder for whom the existing drugs have the insufficient effect.

Means to Solve the Problems

The present inventors paid an attention to ENPP2 as a new target for preventing or treating urinary excretion disorder or improving symptoms thereof, and intensively studied in order to find out an inhibitory compound thereof and, as a result, found out compounds represented by any one selected from the general formula (I), the general formula (II), the general formula (III), the general formula (IV), the general formula (V) and the general formula (VI)(hereinafter, can be abbreviated as compounds represented by any one selected from the general formula (I) to the general formula (VI)), salts thereof or solvates thereof or prodrugs thereof (In the present specification, referred to as the present compounds). Further, the present inventors found out that those compounds are effective in preventing or treating urinary excretion disorder or improving symptoms thereof, resulting in completion of the present invention.

That is, the present invention is as follows:
[1] A compound represented by the general formula (I):

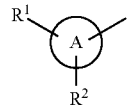

{wherein

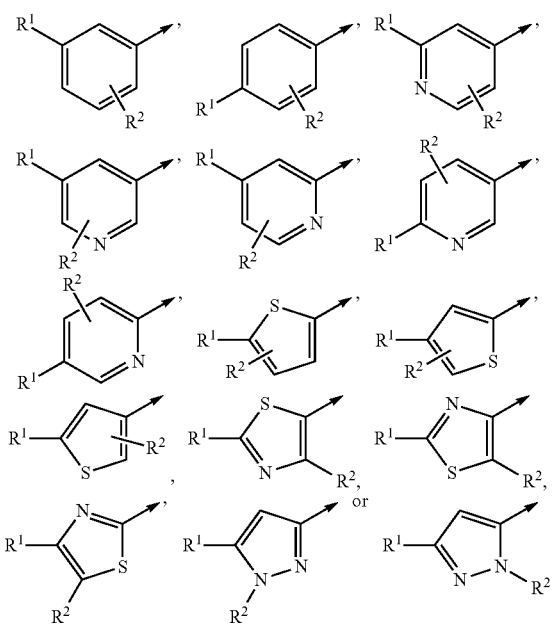

represents:

[wherein $R^1$ represents a C2-4 alkyl group, a dihalomethyl group, a trihalomethyl group, a dihalomethoxy group, a trihalomethoxy group, or

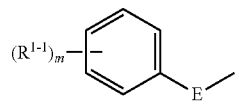

(wherein E represents a bond or an oxygen atom; $R^{1-1}$ represents a dihalomethyl group, a trihalomethyl group, a dihalomethoxy group or a trihalomethoxy group; m represents an integer of zero or one); $R^2$ represents a hydrogen atom, a halogen atom or a methyl group; the bond represented by an arrow binds to the methylene group represented by "a" in the general formula (I), provided that when the ring A is benzene, $R^1$ and $R^2$ each bound to adjacent carbon atoms may be form thiophene, together with the benzene to which they are attached, or when the ring A is thiophene, $R^1$ and $R^2$ each bound to adjacent carbon atoms may be form a benzene, together with the carbon atoms to which they are attached]; $R^3$ represents a hydrogen atom or a C1-4alkyl group, $R^{4a}$ and $R^{4b}$ each independently represent a hydrogen atom or a methyl group, the Ring $U^1$ represents benzene, cyclohexene, pyridine, cyclobutane, cyclopentane, thiophene, bicycle[2, 2, 2]octane, bicycle[2, 2, 1]heptane, adamantine, piperidine, piperazine, diazabicyclo[2, 2, 1]heptane or an ethoxy group, $R^5$ represents a halogen atom, a methyl group, a methoxy group or an ethoxy group, $R^6$ represents a halogen atom or a methyl group, k represents an integer of zero to three, n represents an integer of zero to three, provided that a plurality of groups represented by $R^5$ and $R^6$ may be the same or different, respectively}, a salt thereof or a solvate thereof or a prodrug thereof.

[2] A compound represented by the general formula (II):

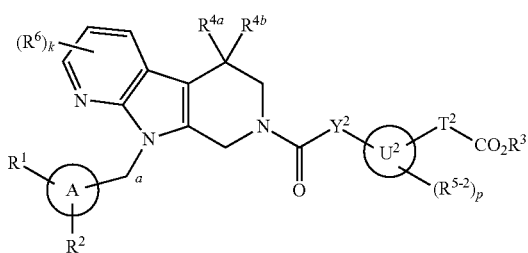

(II)

[wherein the ring $U^2$ represents piperidine, piperazine, thiophene, benzene, diazabicyclo[2, 2, 1]heptane or tetrahydropyridine, $Y^2$ represents a methylene group, an ethylene group or an oxymethylene group, $T^2$ represents a bond, an oxymethylene group or a methylene group optionally substituted by one or two $R^7$(s) (wherein $R^7$ represents a methyl group.), $R^{5\text{-}2}$ represents a methyl group, p represents an integer of zero to two, and other symbols are as defined in the above-mentioned, provided that $T^2$ does not represent an oxymethylene group when $Y^2$ represents an ethylene group or an oxymethylene group.], a salt thereof or a solvate thereof or a prodrug thereof.

[3] The compound according to the above mentioned [2], wherein $Y^2$ represents a methylene group and $T^2$ represents an oxymethylene group.

[4] The compound according to the above mentioned [2], wherein $Y^2$ represents an oxymethylene group and $T^2$ represents a bond or a methylene group optionally substituted by one or two $R^7$(s) (wherein $R^7$ is as defined in the above-mentioned.).

[5] A compound represented by the general formula (III):

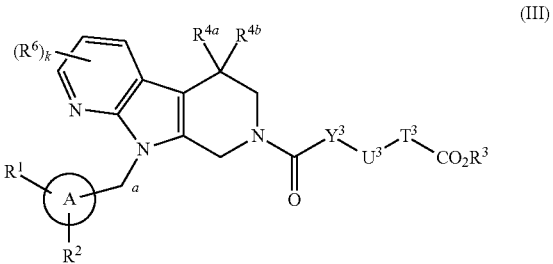

(III)

[wherein $U^3$ represents a methylene group or an oxygen atom, $Y^3$ represents a methylene group or an ethylene group, $T^3$ represents a methylene or ethylene group optionally substituted by one or two $R^7$(s) (wherein $R^7$ represents a methyl group, two of $R^7$s may form cyclopropyl, together with the same carbon atom to which they are each attached.), and other symbols are as defined in the above-mentioned, provided that $T^3$ does not represent an ethylene group optionally substituted by one or two $R^7$(s) when $Y^3$ represents an ethylene group], a salt thereof or a solvate thereof or a prodrug thereof.

[6] The compound according to any of the above mentioned [1] to [5], wherein k represents zero.

[7] The compound according to any of the above mentioned [1] to [6], wherein

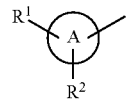

in the general formula (I) to (III) each represents

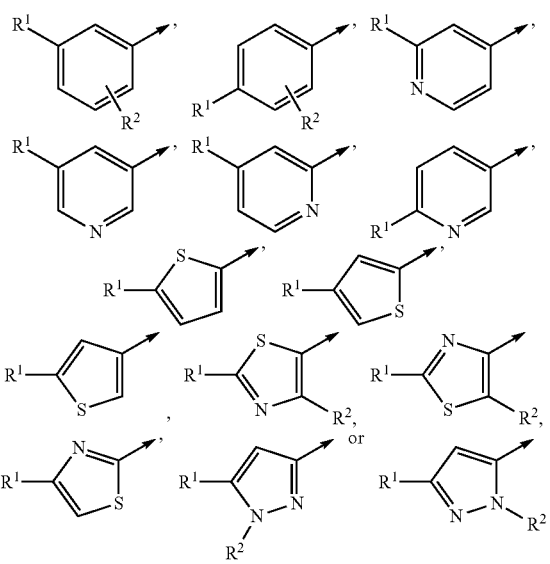

(wherein all symbols are as defined in the above-mentioned)

[8] The compound according to any of the above mentioned [1] to [6], wherein

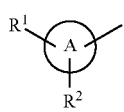

in the general formula (I) to (III) each represents

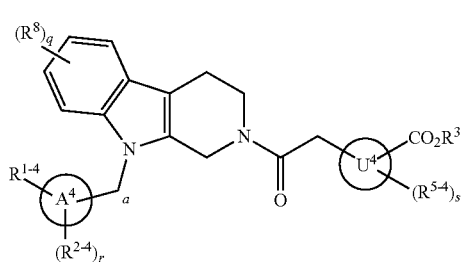

(wherein all symbols are as defined in the above-mentioned.)

[9] A compound represented by the general formula (IV):

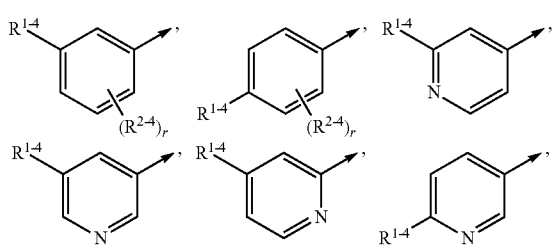 (IV)

[wherein

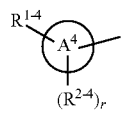

represents

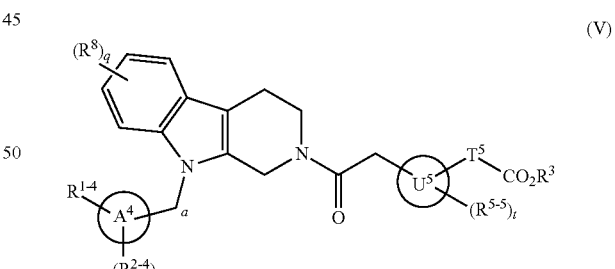

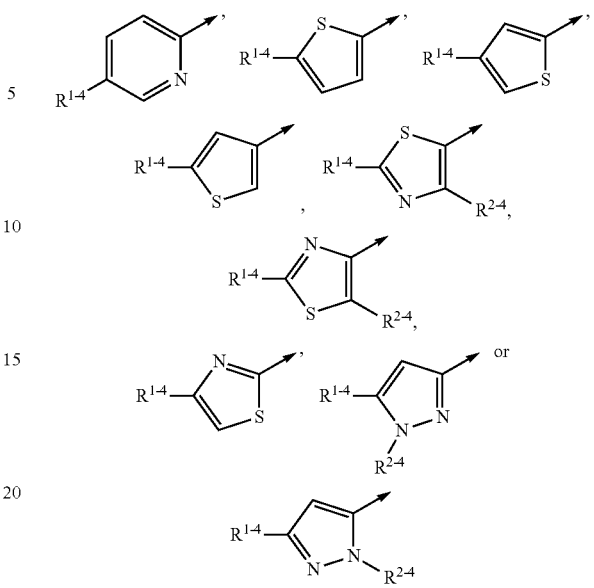

(wherein $R^{1-4}$ represents a halogen atom, a dihalomethyl group, a trihalomethyl group, a dihalomethoxy group, a trihalomethoxy group, phenyl group or phenoxy group, $R^{2-4}$ represents a halogen atom or a methyl group, r represents an integer of zero to two, provided that a plurality of groups represented by $R^{2-4}$ may be the same or different, respectively.), the ring $U^4$ represents benzene, cyclopentane, bicycle[2, 2, 2]octane, bicycle[2, 2, 1]heptane or piperidine, $R^{5-4}$ represents a methyl group or a methoxy group, $R^8$ represents a halogen atom, q represents an integer of zero to two, s represents an integer of zero to three, and other symbols are as defined in the above-mentioned, provided that a plurality of groups represented by $R^{5-4}$ may be the same or different, respectively], a salt thereof or a solvate thereof or a prodrug thereof.

[10] A compound represented by the general formula (V):

(V)

[wherein the ring $U^5$ represents piperidine, pipeadine or benzene, $T^5$ represents an oxymethylene group or a methylene group optionally substituted by one or two $R^7$(s) (wherein $R^7$ is as defined in the above-mentioned.), $R^{5-5}$ represents a methyl group, t represents an integer of zero to three, and other symbols are as defined in the above-mentioned.], a salt thereof or a solvate thereof or a prodrug thereof.

[11] The compound according to any of the above mentioned [9] to [10], wherein

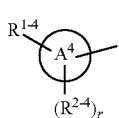

in the general formula (IV) or (V) represents

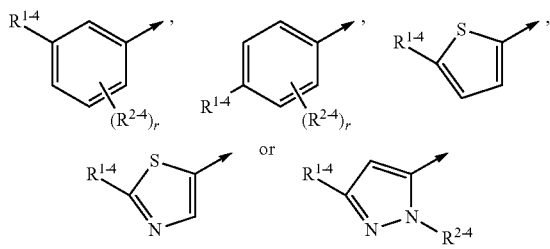

(wherein all symbols are as defined in the above-mentioned.).

[12] A compound represented by the general formula (VI):

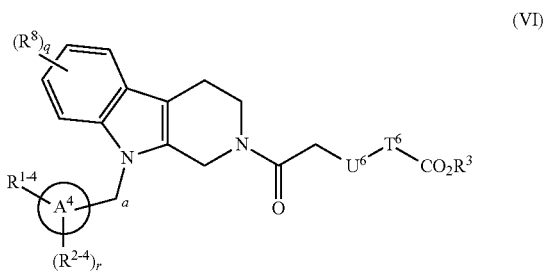

[wherein $U^6$ represents a methylene or an oxygen atom, $T^6$ represents an ethylene optionally substituted by one or two $R^7$(s) (wherein $R^7$ is as defined in the above-mentioned.), and other symbols are as defined in the above-mentioned.], a salt thereof or a solvate thereof or a prodrug thereof.

[13] The compound according to any of the above mentioned [1] to [8], wherein $R^1$ in the general formula (I) to (III) represents an ethyl group, a difluoromethyl group, a trifluoromethyl group, a difluoromethoxy group, a trifluoromethoxyl group, pheny group or phenoxy group.

[14] The compound according to any of the above mentioned [9] to [12], wherein $R^{1-4}$ in the general formula (IV) to (VI) represents a halogen atom, a difluoromethyl group, a trifluoromethyl group, a difluoromethoxy group, a trifluoromethoxyl group, pheny group or phenoxy group.

[15] The compound according to any of the above mentioned [1] to [14], wherein $R^3$ represents a hydrogen atom.

[16] The compound according to the above mentioned [13], wherein the compound represented by the general formula (I) is:

(1) 4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)bicyclo[2.2.2]octane-1-carboxylic acid, (2) 4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]bicyclo[2.2.2]octane-1-carboxylic acid, (3) 4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)bicyclo[2.2.2]octane-1-carboxylic acid, (4) 4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]bicyclo[2.2.1]heptane-1-carboxylic acid, (5) 4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)bicyclo[2.2.1]heptane-1-carboxylic acid, (6) 4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)bicyclo[2.2.1]heptane-1-carboxylic acid, (7) 4-{2-[9-(3-ethylbenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid, (8) 4-{2-[9-(3-isopropoxybenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid, (9) 4-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)bicyclo[2.2.1]heptane-1-carboxylic acid,

(10) 4-(2-{9-[3-(difluoromethoxy)benzyl]-5,6,8,9-tetrahydro-7H-pyrido[4',3':4,5]pyrrolo[2,3-b]pyridin-7-yl}-2-oxoethyl)bicyclo[2.2.1]heptane-1-carboxylic acid,

(11) 5-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)-2-pyridinecarboxylic acid,

(12) 4-(2-{9-[(5-methyl-2-phenyl-1,3-thiazol-4-yl)methyl]-5,6,8,9-tetrahydro-7H-pyrido[4',3':4,5]pyrrolo[2,3-b]pyridin-7-yl}-2-oxoethyl)bicyclo[2.2.1]heptane-1-carboxylic acid,

(13) 5-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)-2-pyridinecarboxylic acid,

(14) 1-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)-4-piperidinecarboxylic acid,

(15) trans-1-methyl-4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]cyclohexanecarboxylic acid, or

(16) 2-methoxy-4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)benzoic acid.

[17] The compound according to the above mentioned [13], wherein the compound represented by the general formula (III) is:

(1) 2,2-dimethyl-6-oxo-6-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)hexanoic acid, or (2) 2,2-dimethyl-3-(2-oxo-2-{9-[4-(trifluoromethyl)benzyl]-5,6,8,9-tetrahydro-7H-pyrido[4',3':4,5]pyrrolo[2,3-b]pyridin-7-yl}ethoxy)propanoic acid.

[18] A pharmaceutical composition containing the compound represented by any one selected from the general formula (I) to (VI), a salt thereof or a solvate thereof or a prodrug thereof as an active ingredient.

[19] An agent for preventing and/or treating urinary excretion disorder, tumor, interstitial pneumonia or pulmonary fibrosis, renal fibrosis, hepatic fibrosis, scleroderma, algia, fibromyalgia syndrome or arthritic rheumatism, containing a compound represented by any one selected from the general formula (I) to (VI), a salt thereof or a solvate thereof or a prodrug thereof as an active ingredient.

[20] An ENPP2 inhibitor, containing a compound represented by any one selected from the general formula (I) to (VI), a salt thereof or a solvate thereof or a prodrug thereof as an active ingredient.

[21] A compound represented by any one selected from the general formula (I) to (VI), a salt thereof or a solvate thereof or a prodrug thereof, for preventing and/or treating urinary excretion disorder, tumor, interstitial pneumonia or pulmonary fibrosis, renal fibrosis, hepatic fibrosis, scleroderma, algia, fibromyalgia syndrome or arthritic rheumatism.

[22] Use of a compound represented by any one selected from the general formula (I) to (VI), a salt thereof or a solvate thereof or a prodrug thereof, for manufacturing a medicament for preventing and/or treating urinary excretion disorder, tumor, interstitial pneumonia or pulmonary fibrosis, renal fibrosis, hepatic fibrosis, scleroderma, algia, fibromyalgia syndrome or arthritic rheumatism.

[23] A method of preventing or treating urinary excretion disorder, tumor, interstitial pneumonia or pulmonary fibrosis, renal fibrosis, hepatic fibrosis, scleroderma, algia, fibromyalgia syndrome or arthritic rheumatism, comprising administering an effective amount of a compound represented by any one selected from the general formula (I) to (VI), a salt thereof or a solvate thereof or a prodrug thereof to a patient in need thereof.

[24] A method for inhibiting ENPP2 activity, comprising administering an effective amount of a compound represented by any one selected from the general formula (I) to (VI), a salt thereof or a solvate thereof or a prodrug thereof to a patient with a disease which can be prevented and/or treated by inhibiting ENPP2 activity.

Effect of the Invention

The present compound is an effective agent for preventing or treating urinary excretion disorder, particularly, a urinary excretion disorder accompanied with prostatomegaly and/or improving symptoms thereof.

DESCRIPTION OF EMBODIMENTS

The present invention will be explained in detail below.

In the present specification, examples of the halogen atom include a fluorine atom, a chlorine atom, a bromine atom and an iodine atom.

In the present specification, examples of the C1-4 alkyl group include a methyl group, an ethyl group, an n-propyl group, an isopropyl group, an n-butyl group, an isobutyl group, a sec-butyl group and a tert-butyl group.

In the present specification, examples of the C2-4 alkyl group include an ethyl group, an n-propyl group, an isopropyl group, an n-butyl group, an isobutyl group, a sec-butyl group and a tert-butyl group.

In the present specification, examples of the dihalomethyl group include a difluoromethyl group and chlorofluoromethyl group.

In the present specification, examples of the trihalomethyl group include a trichloromethyl group, a dichlorofluoromethyl group, a dichlorobromomethyl group, a trifluoromethyl group, a difluorochloromethyl group, a bromodifluoromethyl group, a tribromomethyl group, a dibromochloromethyl group and a dibromofluoromethyl group.

In the present specification, examples of the dihalomethoxy group include a difluoromethoxy group, and a chlorofluoromethoxy group.

In the present specification, examples of the trihalomethoxy group include a trichloromethoxy group, a dichlorofluoromethoxy group, a dichlorobromomethoxy group, a trifluoromethoxy group, a difluorochloromethoxy group, a bromodifluoromethoxy group, a tribromomethoxy group, a dibromochloromethoxy group and a dibromofluoromethoxy group.

In the present specification, examples of the oxymethylene group include —CH$_2$O— and —OCH$_2$—.

In the present invention, unless it is explicitly stated otherwise, as apparent to a person skilled in the art, a symbol:

⌿ represents that a substituent is bound to a far side of a paper plane (i.e. α-configuration),

⌿ represents that a substituent is bound to a near side of a paper plane (i.e. (β-configuration), and

⌿ represents α-configuration, β-configuration or an arbitrary mixture thereof.

Of the present compound, a compound represented by the general formula (I) is preferably:

(1) cis-4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)cyclohexanecarboxylic acid, (2) cis-4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)cyclohexanecarboxylic acid, (3) cis-4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)cyclohexanecarboxylic acid, (4) cis-4-(2-{9-[3-chloro-4-(trifluoromethoxy)benzyl]-5,6,8,9-tetrahydro-7H-pyrido[4',3':4,5]pyrrolo[2,3-b]pyridin-7-yl}-2-oxoethyl)cyclohexanecarboxylic acid, (5) cis-4-(2-{9-[3-fluoro-4-(trifluoromethoxy)benzyl]-5,6,8,9-tetrahydro-7H-pyrido[4',3':4,5]pyrrolo[2,3-b]pyridin-7-yl}-2-oxoethyl)cyclohexanecarboxylic acid, (6) trans-4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)cyclohexanecarboxylic acid, (7) trans-4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)cyclohexanecarboxylic acid, (8) trans-4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)cyclohexanecarboxylic acid, (9) trans-4-(2-{9-[3-chloro-4-(trifluoromethoxy)benzyl]-5,6,8,9-tetrahydro-7H-pyrido[4',3':4,5]pyrrolo[2,3-b]pyridin-7-yl}-2-oxoethyl)cyclohexanecarboxylic acid,

(10) cis-4-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethyl]cyclohexanecarboxylic acid,

(11) trans-4-(2-{9-[3-fluoro-4-(trifluoromethoxy)benzyl]-5,6,8,9-tetrahydro-7H-pyrido[4',3':4,5]pyrrolo[2,3-b]pyridin-7-yl}-2-oxoethyl)cyclohexanecarboxylic acid,

(12) trans-4-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethyl]cyclohexanecarboxylic acid,

(13) cis-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]cyclohexanecarboxylic acid,

(14) trans-4-(2-{9-[2-fluoro-4-(trifluoromethyl)benzyl]-5,6,8,9-tetrahydro-7H-pyrido[4',3':4,5]pyrrolo[2,3-b]pyridin-7-yl}-2-oxoethyl)cyclohexanecarboxylic acid,

(15) trans-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]cyclohexanecarboxylic acid,

(16) trans-4-[2-(9-{[5-(difluoromethyl)-2-thienyl]methyl}-5,6,8,9-tetrahydro-7H-pyrido[4',3':4,5]pyrrolo[2,3-b]pyridin-7-yl)-2-oxoethyl]cyclohexanecarboxylic acid,

(17) cis-4-[2-(9-{[5-(difluoromethyl)-2-thienyl]methyl}-5,6,8,9-tetrahydro-7H-pyrido[4',3':4,5]pyrrolo[2,3-b]pyridin-7-yl)-2-oxoethyl]cyclohexanecarboxylic acid,

(18) trans-4-[2-oxo-2-(9-{[4-(trifluoromethyl)-2-thienyl]methyl}-5,6,8,9-tetrahydro-7H-pyrido[4',3':4,5]pyrrolo[2,3-b]pyridin-7-yl)ethyl]cyclohexanecarboxylic acid,

(19) cis-4-[2-oxo-2-(9-{[4-(trifluoromethyl)-2-thienyl]methyl}-5,6,8,9-tetrahydro-7H-pyrido[4',3':4,5]pyrrolo[2,3-b]pyridin-7-yl)ethyl]cyclohexanecarboxylic acid,

(20) cis-4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)cyclohexanecarboxylic acid,

(21) trans-4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)cyclohexanecarboxylic acid,

(22) cis-4-(2-{9-[4-(difluoromethyl)benzyl]-5,6,8,9-tetrahydro-7H-pyrido[4',3':4,5]pyrrolo[2,3-b]pyridin-7-yl}-2-oxoethyl)cyclohexanecarboxylic acid,

(23) trans-4-(2-{9-[4-(difluoromethyl)benzyl]-5,6,8,9-tetrahydro-7H-pyrido[4',3':4,5]pyrrolo[2,3-b]pyridin-7-yl}-2-oxoethyl)cyclohexanecarboxylic acid,

(24) 4-[2-oxo-2-(9-{[2-(trifluoromethyl)-4-pyridinyl]methyl}-5,6,8,9-tetrahydro-7H-pyrido[4',3':4,5]pyrrolo[2,3-b]pyridin-7-yl)ethyl]benzoic acid,

(25) 4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)benzoic acid,

(26) 2-ethoxy-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]benzoic acid,

(27) 4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]bicyclo[2.2.2]octane-1-carboxylic acid,

(28) cis-3-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]cyclobutanecarboxylic acid,

(29) trans-3-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]cyclobutanecarboxylic acid,

(30) (1R,3R)-1,2,2-trimethyl-3-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]cyclopentanecarboxylic acid,

(31) 4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)bicyclo[2.2.2]octane-1-carboxylic acid,

(32) 4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]bicyclo[2.2.2]octane-1-carboxylic acid,

(33) 4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)bicyclo[2.2.2]octane-1-carboxylic acid,

(34) 4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)bicyclo[2.2.2]octane-1-carboxylic acid,

(35) 4-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethyl]bicyclo[2.2.2]octane-1-carboxylic acid,

(36) (1R,3R)-1,2,2-trimethyl-3-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)cyclopentanecarboxylic acid,

(37) (1R,3R)-1,2,2-trimethyl-3-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)cyclopentanecarboxylic acid,

(38) (1R,3R)-1,2,2-trimethyl-3-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)cyclopentanecarboxylic acid,

(39) (1R,3R)-3-(2-{9-[3-(difluoromethyl)benzyl]-5,6,8,9-tetrahydro-7H-pyrido[4',3':4,5]pyrrolo[2,3-b]pyridin-7-yl}-2-oxoethyl)-1,2,2-trimethylcyclopentanecarboxylic acid,

(40) (1R,3R)-1,2,2-trimethyl-3-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)cyclopentanecarboxylic acid,

(41) 4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)bicyclo[2.2.2]octane-1-carboxylic acid,

(42) 4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)bicyclo[2.2.2]octane-1-carboxylic acid,

(43) (1S,3S)-1,2,2-trimethyl-3-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]cyclopentanecarboxylic acid,

(44) (1R,3R)-1,2,2-trimethyl-3-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethyl]cyclopentanecarboxylic acid,

(45) (1R,3R)-1,2,2-trimethyl-3-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]cyclopentanecarboxylic acid,

(46) (1R,3R)-1,2,2-trimethyl-3-[2-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-2-oxoethyl]cyclopentanecarboxylic acid,

(47) 4-[2-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-2-oxoethyl]bicyclo[2.2.2]octane-1-carboxylic acid,

(48) 4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]bicyclo[2.2.1]heptane-1-carboxylic acid,

(49) 4-[2-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-2-oxoethyl]bicyclo[2.2.1]heptane-1-carboxylic acid,

(50) 4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)bicyclo[2.2.1]heptane-1-carboxylic acid,

(51) 4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)bicyclo[2.2.1]heptane-1-carboxylic acid,

(52) 4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)bicyclo[2.2.1]heptane-1-carboxylic acid,

(53) 4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)bicyclo[2.2.1]heptane-1-carboxylic acid,

(54) 4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)bicyclo[2.2.1]heptane-1-carboxylic acid,

(55) 4-{2-[9-(3-ethylbenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid,

(56) 4-{2-[9-(3-isopropoxybenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid,

(57) 4-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)bicyclo[2.2.1]heptane-1-carboxylic acid,

(58) 4-(2-{9-[3-(difluoromethoxy)benzyl]-5,6,8,9-tetrahydro-7H-pyrido[4',3':4,5]pyrrolo[2,3-b]pyridin-7-yl}-2-oxoethyl)bicyclo[2.2.1]heptane-1-carboxylic acid,

(59) 4-{2-oxo-2-[9-(4-phenoxybenzyl)-5,6,8,9-tetrahydro-7H-pyrido[4',3':4,5]pyrrolo[2,3-b]pyridin-7-yl]ethyl}bicyclo[2.2.1]heptane-1-carboxylic acid,

(60) 4-{2-[9-(4-biphenylylmethyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid,

(61) 4-{2-oxo-2-[9-(3-phenoxybenzyl)-5,6,8,9-tetrahydro-7H-pyrido[4',3':4,5]pyrrolo[2,3-b]pyridin-7-yl]ethyl}bicyclo[2.2.1]heptane-1-carboxylic acid,

(62) 5-{2-oxo-2-[9-(4-phenoxybenzyl)-5,6,8,9-tetrahydro-7H-pyrido[4',3':4,5]pyrrolo[2,3-b]pyridin-7-yl]ethyl}-2-pyridinecarboxylic acid,

(63) 5-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)-2-pyridinecarboxylic acid,

(64) 5-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)-2-pyridinecarboxylic acid,

(65) 4-(2-{9-[(5-methyl-2-phenyl-1,3-thiazol-4-yl)methyl]-5,6,8,9-tetrahydro-7H-pyrido[4',3':4,5]pyrrolo[2,3-b]pyridin-7-yl}-2-oxoethyl)bicyclo[2.2.1]heptane-1-carboxylic acid,

(66) 3-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]-1-adamantanecarboxylic acid,

(67) 5-(2-{9-[3-(difluoromethoxy)benzyl]-5,6,8,9-tetrahydro-7H-pyrido[4',3':4,5]pyrrolo[2,3-b]pyridin-7-yl}-2-oxoethyl)-2-pyridinecarboxylic acid,

(68) 5-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)-2-pyridinecarboxylic acid,

(69) 5-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)-2-pyridinecarboxylic acid,

(70) 5-{2-[9-(3-ethylbenzyl)-5,6,8,9-tetrahydro-7H-pyrido[4',3':4,5]pyrrolo[2,3-b]pyridin-7-yl]-2-oxoethyl}-2-pyridinecarboxylic acid,

(71) 5-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]-2-pyridinecarboxylic acid,

(72) 4-{2-[9-(3-ethylbenzyl)-5,6,8,9-tetrahydro-7H-pyrido[4',3':4,5]pyrrolo[2,3-b]pyridin-7-yl]-2-oxoethyl}-2-methylbenzoic acid,

(73) 2-methyl-4-{2-oxo-2-[9-(4-phenoxybenzyl)-5,6,8,9-tetrahydro-7H-pyrido[4',3':4,5]pyrrolo[2,3-b]pyridin-7-yl]ethyl}benzoic acid,

(74) 4-(2-{9-[3-(difluoromethoxy)benzyl]-5,6,8,9-tetrahydro-7H-pyrido[4',3':4,5]pyrrolo[2,3-b]pyridin-7-yl}-2-oxoethyl)-2-methylbenzoic acid,

(75) 2-methyl-4-(2-oxo-2-{9-[(2-phenyl-1,3-thiazol-5-yl)methyl]-5,6,8,9-tetrahydro-7H-pyrido[4',3':4,5]pyrrolo[2,3-b]pyridin-7-yl}ethyl)benzoic acid,

(76) 1-(2-{5,5-dimethyl-9-[4-(trifluoromethoxy)benzyl]-5,6,8,9-tetrahydro-7H-pyrido[4',3':4,5]pyrrolo[2,3-b]pyridin-7-yl}-2-oxoethyl)-4-piperidinecarboxylic acid,

(77) 1-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)-4-piperidinecarboxylic acid,

(78) 1-(2-{9-[3-chloro-4-(trifluoromethoxy)benzyl]-5,6,8,9-tetrahydro-7H-pyrido[4',3':4,5]pyrrolo[2,3-b]pyridin-7-yl}-2-oxoethyl)-4-piperidinecarboxylic acid,

(79) 1-(2-{9-[3-fluoro-4-(trifluoromethoxy)benzyl]-5,6,8,9-tetrahydro-7H-pyrido[4',3':4,5]pyrrolo[2,3-b]pyridin-7-yl}-2-oxoethyl)-4-piperidinecarboxylic acid,

(80) 1-(2-{9-[3-chloro-4-(trifluoromethoxy)benzyl]-5,5-dimethyl-5,6,8,9-tetrahydro-7H-pyrido[4',3':4,5]pyrrolo[2,3-b]pyridin-7-yl}-2-oxoethyl)-4-piperidinecarboxylic acid,

(81) 1-(2-{9-[3-fluoro-4-(trifluoromethoxy)benzyl]-5,5-dimethyl-5,6,8,9-tetrahydro-7H-pyrido[4',3':4,5]pyrrolo[2,3-b]pyridin-7-yl}-2-oxoethyl)-4-piperidinecarboxylic acid,

(82) 4-methyl-1-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]-4-piperidinecarboxylic acid,

(83) 4-hydroxy-1-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]-4-piperidinecarboxylic acid,

(84) 4-methoxy-1-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]-4-piperidinecarboxylic acid,

(85) rel-{(3R,5S)-3,5-dimethyl-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]-1-piperazinyl}acetic acid,

(86) 1-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]-1,2,3,6-tetrahydro-4-pyridinecarboxylic acid,

(87) 1-{2-oxo-2-[9-(4-phenoxybenzyl)-5,6,8,9-tetrahydro-7H-pyrido[4',3':4,5]pyrrolo[2,3-b]pyridin-7-yl]ethyl}-4-piperidinecarboxylic acid,

(88) 1-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)-4-piperidinecarboxylic acid,

(89) cis-1-methyl-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]cyclohexanecarboxylic acid,

(90) trans-1-methyl-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]cyclohexanecarboxylic acid,

(91) trans-4-(2-{9-[3-(difluoromethoxy)benzyl]-5,6,8,9-tetrahydro-7H-pyrido[4',3':4,5]pyrrolo[2,3-b]pyridin-7-yl}-2-oxoethyl)-1-methylcyclohexanecarboxylic acid,

(92) trans-1-methyl-4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)cyclohexanecarboxylic acid,

(93) trans-1-methyl-4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]cyclohexanecarboxylic acid,

(94) cis-1-methyl-4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)cyclohexanecarboxylic acid,

(95) cis-4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)-1-methylcyclohexanecarboxylic acid,

(96) trans-1-methyl-4-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethyl]cyclohexanecarboxylic acid,

(97) cis-1-methyl-4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]cyclohexanecarboxylic acid,

(98) cis-1-methyl-4-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethyl]cyclohexanecarboxylic acid,

(99) cis-1-methyl-4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)cyclohexanecarboxylic acid, (100) cis-1-methyl-4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)cyclohexanecarboxylic acid, (101) cis-1-methyl-4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)cyclohexanecarboxylic acid, (102) cis-1-methyl-4-[2-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-2-oxoethyl]cyclohexanecarboxylic acid, (103) trans-1-methyl-4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)cyclohexanecarboxylic acid, (104) trans-1-methyl-4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)cyclohexanecarboxylic acid, (105) trans-1-methyl-4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)cyclohexanecarboxylic acid, (106) trans-1-methyl-4-[2-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-2-oxoethyl]cyclohexanecarboxylic acid, (107) cis-1-hydroxy-4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]cyclohexanecarboxylic acid, (108) trans-1-hydroxy-4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]cyclohexanecarboxylic acid, (109) 2-chloro-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]benzoic acid, (110) 2-fluoro-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]benzoic acid, (111) 2-methyl-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]benzoic acid, (112) 2-methoxy-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]benzoic acid, (113) 3-methoxy-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]benzoic acid, (114) 4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)-2-methoxybenzoic acid, (115) 2-methoxy-4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)benzoic acid, (116) 2-methoxy-4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)benzoic acid, (117) 2-methoxy-4-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethyl]benzoic acid, (118) 2-methoxy-4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]benzoic acid, (119) 2-methoxy-4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)benzoic acid, (120) 2-methoxy-4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)benzoic acid, (121) 2-methyl-4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)benzoic acid, (122) 4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)-2-methylbenzoic acid, (123) 2-methyl-4-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethyl]benzoic acid, (124) 2-methyl-4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]benzoic acid, (125) 2-methyl-4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)benzoic acid, (126) 2-methyl-4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)benzoic acid, (127) 2-methyl-4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)benzoic acid, (128) 2-methoxy-4-[2-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-2-oxoethyl]benzoic acid, (129) 2-methyl-4-[2-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-2-oxoethyl]benzoic acid, (130) 2,6-dimethoxy-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]benzoic acid, (131) 2,6-dimethoxy-4-[2-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-2-oxoethyl]benzoic acid, (132) 2,6-dimethoxy-4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)benzoic acid, (133) 2,6-dimethoxy-4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)benzoic acid, (134) 2,6-dimethoxy-4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)benzoic acid, (135) 2,6-dimethoxy-4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)benzoic acid, (136) 4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)-2,6-dimethoxybenzoic acid,
(137) 2,6-dimethoxy-4-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethyl]benzoic acid,
(138) 2,6-dimethoxy-4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]benzoic acid,
(139) 2-methoxy-4-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)benzoic acid,
(140) 2-methoxy-4-{2-oxo-2-[9-(4-phenoxybenzyl)-5,6,8,9-tetrahydro-7H-pyrido[4',3':4,5]pyrrolo[2,3-b]pyridin-7-yl]ethyl}benzoic acid,
(141) 4-{2-[9-(3-ethylbenzyl)-5,6,8,9-tetrahydro-7H-pyrido[4',3':4,5]pyrrolo[2,3-b]pyridin-7-yl]-2-oxoethyl}-2-methoxybenzoic acid, or
(142) 1-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)-4-piperidinecarboxylic acid, a salt thereof or a solvate thereof or a prodrug thereof, more preferably:
(1) 4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)bicyclo[2.2.2]octane-1-carboxylic acid,
(2) 4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]bicyclo[2.2.2]octane-1-carboxylic acid,
(3) 4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)bicyclo[2.2.2]octane-1-carboxylic acid,
(4) 4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]bicyclo[2.2.1]heptane-1-carboxylic acid,
(5) 4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)bicyclo[2.2.1]heptane-1-carboxylic acid,
(6) 4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)bicyclo[2.2.1]heptane-1-carboxylic acid,
(7) 4-{2-[9-(3-ethylbenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid,
(8) 4-{2-[9-(3-isopropoxybenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid,
(9) 4-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)bicyclo[2.2.1]heptane-1-carboxylic acid,
(10) 4-(2-{9-[3-(difluoromethoxy)benzyl]-5,6,8,9-tetrahydro-7H-pyrido[4',3':4,5]pyrrolo[2,3-b]pyridin-7-yl}-2-oxoethyl)bicyclo[2.2.1]heptane-1-carboxylic acid,
(11) 5-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)-2-pyridinecarboxylic acid,
(12) 4-(2-{9-[(5-methyl-2-phenyl-1,3-thiazol-4-yl)methyl]-5,6,8,9-tetrahydro-7H-pyrido[4',3':4,5]pyrrolo[2,3-b]pyridin-7-yl}-2-oxoethyl)bicyclo[2.2.1]heptane-1-carboxylic acid,
(13) 5-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)-2-pyridinecarboxylic acid,
(14) 1-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)-4-piperidinecarboxylic acid,
(15) trans-1-methyl-4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]cyclohexanecarboxylic acid, or
(16) 2-methoxy-4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)benzoic acid, a salt thereof or a solvate thereof or a prodrug thereof.

Of the present compound, a compound represented by the general formula (II) is preferably:
(1) [4-(2-{5,5-dimethyl-9-[4-(trifluoromethoxy)benzyl]-5,6,8,9-tetrahydro-7H-pyrido[4',3':4,5]pyrrolo[2,3-b]pyridin-7-yl}-2-oxoethyl)-1-piperidinyl]acetic acid,
(2) {3-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]phenyl}acetic acid,
(3) 4-[3-oxo-3-(9-{[5-(trifluoromethyl)-2-thienyl]methyl}-5,6,8,9-tetrahydro-7H-pyrido[4',3':4,5]pyrrolo[2,3-b]pyridin-7-yl)propyl]benzoic acid,
(4) 3-[3-oxo-3-(9-{[5-(trifluoromethyl)-2-thienyl]methyl}-5,6,8,9-tetrahydro-7H-pyrido[4',3':4,5]pyrrolo[2,3-b]pyridin-7-yl)propyl]benzoic acid,
(5) 2-[3-oxo-3-(9-{[5-(trifluoromethyl)-2-thienyl]methyl}-5,6,8,9-tetrahydro-7H-pyrido[4',3':4,5]pyrrolo[2,3-b]pyridin-7-yl)propyl]benzoic acid,
(6) 5-[3-oxo-3-(9-{[5-(trifluoromethyl)-2-thienyl]methyl}-5,6,8,9-tetrahydro-7H-pyrido[4',3':4,5]pyrrolo[2,3-b]pyridin-7-yl)propyl]-2-thiophenecarboxylic acid,
(7) {4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]phenyl}acetic acid,
(8) {2-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]phenyl}acetic acid,
(9) (4-{2-oxo-2-[9-(4-phenoxybenzyl)-5,6,8,9-tetrahydro-7H-pyrido[4',3':4,5]pyrrolo[2,3-b]pyridin-7-yl]ethyl}-1-piperidinyl)acetic acid hydrochloride,
(10) [4-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)-1-piperidinyl]acetic acid,
(11) [4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)-1-piperidinyl]acetic acid,
(12) [1-(2-{5,5-dimethyl-9-[4-(trifluoromethoxy)benzyl]-5,6,8,9-tetrahydro-7H-pyrido[4',3':4,5]pyrrolo[2,3-b]pyridin-7-yl}-2-oxoethyl)-4-piperidinyl]acetic acid,
(13) [1-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)-4-piperidinyl]acetic acid,
(14) [1-(2-{9-[3-chloro-4-(trifluoromethoxy)benzyl]-5,6,8,9-tetrahydro-7H-pyrido[4',3':4,5]pyrrolo[2,3-b]pyridin-7-yl}-2-oxoethyl)-4-piperidinyl]acetic acid,
(15) [1-(2-{9-[3-fluoro-4-(trifluoromethoxy)benzyl]-5,6,8,9-tetrahydro-7H-pyrido[4',3':4,5]pyrrolo[2,3-b]pyridin-7-yl}-2-oxoethyl)-4-piperidinyl]acetic acid,
(16) [1-(2-{9-[3-chloro-4-(trifluoromethoxy)benzyl]-5,5-dimethyl-5,6,8,9-tetrahydro-7H-pyrido[4',3':4,5]pyrrolo[2,3-b]pyridin-7-yl}-2-oxoethyl)-4-piperidinyl]acetic acid,
(17) [1-(2-{9-[3-fluoro-4-(trifluoromethoxy)benzyl]-5,5-dimethyl-5,6,8,9-tetrahydro-7H-pyrido[4',3':4,5]pyrrolo[2,3-b]pyridin-7-yl}-2-oxoethyl)-4-piperidinyl]acetic acid,
(18) [4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)-1-piperazinyl]acetic acid,

(19) [4-(2-{9-[3-chloro-4-(trifluoromethoxy)benzyl]-5,6,8,9-tetrahydro-7H-pyrido[4',3':4,5]pyrrolo[2,3-b]pyridin-7-yl}-2-oxoethyl)-1-piperazinyl]acetic acid,

(20) [4-(2-{9-[3-fluoro-4-(trifluoromethoxy)benzyl]-5,6,8,9-tetrahydro-7H-pyrido[4',3':4,5]pyrrolo[2,3-b]pyridin-7-yl}-2-oxoethyl)-1-piperazinyl]acetic acid,

(21) [4-(2-{5,5-dimethyl-9-[4-(trifluoromethoxy)benzyl]-5,6,8,9-tetrahydro-7H-pyrido[4',3':4,5]pyrrolo[2,3-b]pyridin-7-yl}-2-oxoethyl)-1-piperazinyl]acetic acid,

(22) [4-(2-{9-[3-chloro-4-(trifluoromethoxy)benzyl]-5,5-dimethyl-5,6,8,9-tetrahydro-7H-pyrido[4',3':4,5]pyrrolo[2,3-b]pyridin-7-yl}-2-oxoethyl)-1-piperazinyl]acetic acid,

(23) [4-(2-{9-[3-fluoro-4-(trifluoromethoxy)benzyl]-5,5-dimethyl-5,6,8,9-tetrahydro-7H-pyrido[4',3':4,5]pyrrolo[2,3-b]pyridin-7-yl}-2-oxoethyl)-1-piperazinyl]acetic acid,

(24) rel-{(2R,6S)-2,6-dimethyl-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]-1-piperazinyl}acetic acid,

(25) (1-{2-oxo-2-[9-(4-phenoxybenzyl)-5,6,8,9-tetrahydro-7H-pyrido[4',3':4,5]pyrrolo[2,3-b]pyridin-7-yl]ethyl}-4-piperidinyl)acetic acid,

(26) [4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)-1-piperazinyl]acetic acid,

(27) [4-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)-1-piperazinyl]acetic acid,

(28) [1-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)-4-piperidinyl]acetic acid,

(29) [1-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)-4-piperidinyl]acetic acid,

(30) [(1S,4S)-5-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)-2,5-diazabicyclo[2.2.1]hept-2-yl]acetic acid,

(31) 2-methyl-2-{4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]phenyl}propanoic acid,

(32) [4-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)phenoxy]acetic acid,

(33) (4-{2-oxo-2-[9-(4-phenoxybenzyl)-5,6,8,9-tetrahydro-7H-pyrido[4',3':4,5]pyrrolo[2,3-b]pyridin-7-yl]ethoxy}phenyl)acetic acid,

(34) [4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethoxy)phenyl]acetic acid,

(35) [4-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethoxy)phenyl]acetic acid,

(36) [3-(2-oxo-2-{9-[3-(trifluoromethoxy)benzyl]-5,6,8,9-tetrahydro-7H-pyrido[4',3':4,5]pyrrolo[2,3-b]pyridin-7-yl}ethoxy)phenyl]acetic acid,

(37) [3-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethoxy)phenyl]acetic acid,

(38) [3-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)phenoxy]acetic acid,

(39) [3-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)phenoxy]acetic acid,

(40) {4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethoxy]phenyl}acetic acid,

(41) {3-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethoxy]phenyl}acetic acid, or

(42) {4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]phenoxy}acetic acid, a salt thereof or a solvate thereof or a prodrug thereof.

Of the present compound, a compound represented by the general formula (III) is preferably:

(1) 6-oxo-6-{9-[3-(trifluoromethyl)benzyl]-5,6,8,9-tetrahydro-7H-pyrido[4',3':4,5]pyrrolo[2,3-b]pyridin-7-yl}hexanoic acid, (2) 6-(9-{[3-(2-furyl)-1-methyl-1H-pyrazol-5-yl]methyl}-5,6,8,9-tetrahydro-7H-pyrido[4',3':4,5]pyrrolo[2,3-b]pyridin-7-yl)-6-oxohexanoic acid, (3) 2,2-dimethyl-6-oxo-6-{9-[3-(trifluoromethyl)benzyl]-5,6,8,9-tetrahydro-7H-pyrido[4',3':4,5]pyrrolo[2,3-b]pyridin-7-yl}hexanoic acid, (4) 6-[9-(1-benzothiophen-2-ylmethyl)-5,6,8,9-tetrahydro-7H-pyrido[4',3':4,5]pyrrolo[2,3-b]pyridin-7-yl]-2,2-dimethyl-6-oxohexanoic acid, (5) 6-[9-(1-benzothiophen-3-ylmethyl)-5,6,8,9-tetrahydro-7H-pyrido[4',3':4,5]pyrrolo[2,3-b]pyridin-7-yl]-2,2-dimethyl-6-oxohexanoic acid, (6) 6-[9-(1-benzothiophen-5-ylmethyl)-5,6,8,9-tetrahydro-7H-pyrido[4',3':4,5]pyrrolo[2,3-b]pyridin-7-yl]-2,2-dimethyl-6-oxohexanoic acid, (7) 6-(9-{[3-(2-furyl)-1-methyl-1H-pyrazol-5-yl]methyl}-5,6,8,9-tetrahydro-7H-pyrido[4',3':4,5]pyrrolo[2,3-b]pyridin-7-yl)-2,2-dimethyl-6-oxohexanoic acid, (8) 2,2-dimethyl-6-{9-[(1-methyl-3-phenyl-1H-pyrazol-5-yl)methyl]-5,6,8,9-tetrahydro-7H-pyrido[4',3':4,5]pyrrolo[2,3-b]pyridin-7-yl}-6-oxohexanoic acid, (9) 2,2-dimethyl-6-{9-[(5-methyl-2-phenyl-1,3-thiazol-4-yl)methyl]-5,6,8,9-tetrahydro-7H-pyrido[4',3':4,5]pyrrolo[2,3-b]pyridin-7-yl}-6-oxohexanoic acid,

(10) 2,2-dimethyl-6-oxo-6-(9-{[4-(trifluoromethyl)-2-pyridinyl]methyl}-5,6,8,9-tetrahydro-7H-pyrido[4',3':4,5]pyrrolo[2,3-b]pyridin-7-yl)hexanoic acid,

(11) 2,2-dimethyl-6-oxo-6-(9-{[5-(trifluoromethyl)-3-pyridinyl]methyl}-5,6,8,9-tetrahydro-7H-pyrido[4',3':4,5]pyrrolo[2,3-b]pyridin-7-yl)hexanoic acid,

(12) 2,2-dimethyl-6-oxo-6-{9-[3-(trifluoromethoxy)benzyl]-5,6,8,9-tetrahydro-7H-pyrido[4',3':4,5]pyrrolo[2,3-b]pyridin-7-yl}hexanoic acid,

(13) 2,2-dimethyl-6-oxo-6-{9-[4-(trifluoromethoxy)benzyl]-5,6,8,9-tetrahydro-7H-pyrido[4',3':4,5]pyrrolo[2,3-b]pyridin-7-yl}hexanoic acid,

(14) 2,2-dimethyl-6-oxo-6-(9-{[6-(trifluoromethyl)-3-pyridinyl]methyl}-5,6,8,9-tetrahydro-7H-pyrido[4',3':4,5]pyrrolo[2,3-b]pyridin-7-yl)hexanoic acid,

(15) 6-{9-[4-fluoro-3-(trifluoromethyl)benzyl]-5,6,8,9-tetrahydro-7H-pyrido[4',3':4,5]pyrrolo[2,3-b]pyridin-7-yl}-2,2-dimethyl-6-oxohexanoic acid,

(16) 6-{9-[4-(difluoromethoxy)benzyl]-5,6,8,9-tetrahydro-7H-pyrido[4',3':4,5]pyrrolo[2,3-b]pyridin-7-yl}-2,2-dimethyl-6-oxohexanoic acid,

(17) 6-{9-[4-chloro-3-(trifluoromethyl)benzyl]-5,6,8,9-tetrahydro-7H-pyrido[4',3':4,5]pyrrolo[2,3-b]pyridin-7-yl}-2,2-dimethyl-6-oxohexanoic acid,

(18) 2,2-dimethyl-6-oxo-6-(9-{[5-(trifluoromethyl)-2-thienyl]methyl}-5,6,8,9-tetrahydro-7H-pyrrolo[2,3-b]pyridin-7-yl)hexanoic acid,

(19) 6-{9-[3-(difluoromethoxy)benzyl]-5,6,8,9-tetrahydro-7H-pyrido[4',3':4,5]pyrrolo[2,3-b]pyridin-7-yl}-2,2-dimethyl-6-oxohexanoic acid,
(20) 6-{9-[2-fluoro-3-(trifluoromethoxy)benzyl]-5,6,8,9-tetrahydro-7H-pyrido[4',3':4,5]pyrrolo[2,3-b]pyridin-7-yl}-2,2-dimethyl-6-oxohexanoic acid,
(21) 2,2-dimethyl-6-{9-[4-methyl-3-(trifluoromethyl)benzyl]-5,6,8,9-tetrahydro-7H-pyrido[4',3':4,5]pyrrolo[2,3-b]pyridin-7-yl}-6-oxohexanoic acid,
(22) 6-{9-[2-fluoro-4-(trifluoromethyl)benzyl]-5,6,8,9-tetrahydro-7H-pyrido[4',3':4,5]pyrrolo[2,3-b]pyridin-7-yl}-2,2-dimethyl-6-oxohexanoic acid,
(23) 6-{9-[2-fluoro-5-(trifluoromethoxy)benzyl]-5,6,8,9-tetrahydro-7H-pyrido[4',3':4,5]pyrrolo[2,3-b]pyridin-7-yl}-2,2-dimethyl-6-oxohexanoic acid,
(24) 6-{9-[3-fluoro-5-(trifluoromethyl)benzyl]-5,6,8,9-tetrahydro-7H-pyrido[4',3':4,5]pyrrolo[2,3-b]pyridin-7-yl}-2,2-dimethyl-6-oxohexanoic acid,
(25) 6-{9-[3-chloro-5-(trifluoromethoxy)benzyl]-5,6,8,9-tetrahydro-7H-pyrido[4',3':4,5]pyrrolo[2,3-b]pyridin-7-yl}-2,2-dimethyl-6-oxohexanoic acid,
(26) 2,2-dimethyl-6-oxo-6-{9-[4-(trifluoromethyl)benzyl]-5,6,8,9-tetrahydro-7H-pyrido[4',3':4,5]pyrrolo[2,3-b]pyridin-7-yl}hexanoic acid,
(27) 6-{9-[3-chloro-4-(trifluoromethoxy)benzyl]-5,6,8,9-tetrahydro-7H-pyrido[4',3':4,5]pyrrolo[2,3-b]pyridin-7-yl}-2,2-dimethyl-6-oxohexanoic acid,
(28) 6-{9-[3-fluoro-4-(trifluoromethyl)benzyl]-5,6,8,9-tetrahydro-7H-pyrido[4',3':4,5]pyrrolo[2,3-b]pyridin-7-yl}-2,2-dimethyl-6-oxohexanoic acid,
(29) 6-{9-[4-fluoro-3-(trifluoromethoxy)benzyl]-5,6,8,9-tetrahydro-7H-pyrido[4',3':4,5]pyrrolo[2,3-b]pyridin-7-yl}-2,2-dimethyl-6-oxohexanoic acid,
(30) 6-{9-[3-chloro-5-(trifluoromethyl)benzyl]-5,6,8,9-tetrahydro-7H-pyrido[4',3':4,5]pyrrolo[2,3-b]pyridin-7-yl}-2,2-dimethyl-6-oxohexanoic acid,
(31) 6-{9-[4-chloro-3-(trifluoromethoxy)benzyl]-5,6,8,9-tetrahydro-7H-pyrido[4',3':4,5]pyrrolo[2,3-b]pyridin-7-yl}-2,2-dimethyl-6-oxohexanoic acid,
(32) 2,2-dimethyl-6-oxo-6-(9-{[2-(trifluoromethyl)-4-pyridinyl]methyl}-5,6,8,9-tetrahydro-7H-pyrido[4',3':4,5]pyrrolo[2,3-b]pyridin-7-yl)hexanoic acid,
(33) 6-{9-[2-fluoro-5-(trifluoromethyl)benzyl]-5,6,8,9-tetrahydro-7H-pyrido[4',3':4,5]pyrrolo[2,3-b]pyridin-7-yl}-2,2-dimethyl-6-oxohexanoic acid,
(34) 6-{9-[3-fluoro-4-(trifluoromethoxy)benzyl]-5,6,8,9-tetrahydro-7H-pyrido[4',3':4,5]pyrrolo[2,3-b]pyridin-7-yl}-2,2-dimethyl-6-oxohexanoic acid,
(35) 6-{9-[2-fluoro-3-(trifluoromethyl)benzyl]-5,6,8,9-tetrahydro-7H-pyrido[4',3':4,5]pyrrolo[2,3-b]pyridin-7-yl}-2,2-dimethyl-6-oxohexanoic acid,
(36) 2,2-dimethyl-6-oxo-6-(9-{[5-(trifluoromethyl)-3-thienyl]methyl}-5,6,8,9-tetrahydro-7H-pyrido[4',3':4,5]pyrrolo[2,3-b]pyridin-7-yl)hexanoic acid,
(37) 2,2-dimethyl-6-oxo-6-(9-{[4-(trifluoromethyl)-2-thienyl]methyl}-5,6,8,9-tetrahydro-7H-pyrido[4',3':4,5]pyrrolo[2,3-b]pyridin-7-yl)hexanoic acid,
(38) 6-(9-{[5-(difluoromethyl)-2-thienyl]methyl}-5,6,8,9-tetrahydro-7H-pyrido[4',3':4,5]pyrrolo[2,3-b]pyridin-7-yl)-2,2-dimethyl-6-oxohexanoic acid,
(39) 6-{9-[3-(difluoromethyl)benzyl]-5,6,8,9-tetrahydro-7H-pyrido[4',3':4,5]pyrrolo[2,3-b]pyridin-7-yl}-2,2-dimethyl-6-oxohexanoic acid,
(40) 6-{9-[4-(difluoromethyl)benzyl]-5,6,8,9-tetrahydro-7H-pyrido[4',3':4,5]pyrrolo[2,3-b]pyridin-7-yl}-2,2-dimethyl-6-oxohexanoic acid,
(41) 6-[9-(4-isopropylbenzyl)-5,6,8,9-tetrahydro-7H-pyrido[4',3':4,5]pyrrolo[2,3-b]pyridin-7-yl]-2,2-dimethyl-6-oxohexanoic acid,
(42) 6-[9-(4-isopropoxybenzyl)-5,6,8,9-tetrahydro-7H-pyrido[4',3':4,5]pyrrolo[2,3-b]pyridin-7-yl]-2,2-dimethyl-6-oxohexanoic acid,
(43) 2,2-dimethyl-6-oxo-6-[9-(3-phenoxybenzyl)-5,6,8,9-tetrahydro-7H-pyrido[4',3':4,5]pyrrolo[2,3-b]pyridin-7-yl]hexanoic acid,
(44) 2,2-dimethyl-6-oxo-6-[9-(4-phenoxybenzyl)-5,6,8,9-tetrahydro-7H-pyrido[4',3':4,5]pyrrolo[2,3-b]pyridin-7-yl]hexanoic acid,
(45) 2,2-dimethyl-6-oxo-6-(9-{[4-(trifluoromethyl)-1,3-thiazol-2-yl]methyl}-5,6,8,9-tetrahydro-7H-pyrido[4',3':4,5]pyrrolo[2,3-b]pyridin-7-yl)hexanoic acid,
(46) 2,2-dimethyl-6-oxo-6-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)hexanoic acid,
(47) 2,2-dimethyl-6-(9-{[1-methyl-3-(trifluoromethyl)-1H-pyrazol-5-yl]methyl}-5,6,8,9-tetrahydro-7H-pyrido[4',3':4,5]pyrrolo[2,3-b]pyridin-7-yl)-6-oxohexanoic acid,
(48) 2,2-dimethyl-6-(9-{[1-methyl-5-(trifluoromethyl)-1H-pyrazol-3-yl]methyl}-5,6,8,9-tetrahydro-7H-pyrido[4',3':4,5]pyrrolo[2,3-b]pyridin-7-yl)-6-oxohexanoic acid,
(49) 2,2-dimethyl-6-oxo-6-(9-{[2-(trifluoromethyl)-1,3-thiazol-4-yl]methyl}-5,6,8,9-tetrahydro-7H-pyrido[4',3':4,5]pyrrolo[2,3-b]pyridin-7-yl)hexanoic acid,
(50) 6-[9-(3-ethylbenzyl)-5,6,8,9-tetrahydro-7H-pyrido[4',3':4,5]pyrrolo[2,3-b]pyridin-7-yl]-2,2-dimethyl-6-oxohexanoic acid,
(51) 2,2-dimethyl-6-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-6-oxohexanoic acid,
(52) 2,2-dimethyl-6-(9-({4-methyl-2-[4-(trifluoromethyl)phenyl]-1,3-thiazol-5-yl}methyl)-5,6,8,9-tetrahydro-7H-pyrido[4',3':4,5]pyrrolo[2,3-b]pyridin-7-yl)-6-oxohexanoic acid,
(53) 2,2-dimethyl-6-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-6-oxohexanoic acid,
(54) 6-{9-[4-(difluoromethoxy)benzyl]-5,6,8,9-tetrahydro-7H-pyrido[4',3':4,5]pyrrolo[2,3-b]pyridin-7-yl}-3,3-dimethyl-6-oxohexanoic acid,
(55) 3,3-dimethyl-6-oxo-6-{9-[4-(trifluoromethoxy)benzyl]-5,6,8,9-tetrahydro-7H-pyrido[4',3':4,5]pyrrolo[2,3-b]pyridin-7-yl}hexanoic acid,
(56) 3,3-dimethyl-6-oxo-6-{9-[4-(trifluoromethyl)benzyl]-5,6,8,9-tetrahydro-7H-pyrido[4',3':4,5]pyrrolo[2,3-b]pyridin-7-yl}hexanoic acid,
(57) 6-{9-[3-chloro-4-(trifluoromethoxy)benzyl]-5,6,8,9-tetrahydro-7H-pyrido[4',3':4,5]pyrrolo[2,3-b]pyridin-7-yl}-3,3-dimethyl-6-oxohexanoic acid,
(58) 6-{9-[3-fluoro-4-(trifluoromethoxy)benzyl]-5,6,8,9-tetrahydro-7H-pyrido[4',3':4,5]pyrrolo[2,3-b]pyridin-7-yl}-3,3-dimethyl-6-oxohexanoic acid,
(59) 3,3-dimethyl-6-oxo-6-{9-[3-(trifluoromethyl)benzyl]-5,6,8,9-tetrahydro-7H-pyrido[4',3':4,5]pyrrolo[2,3-b]pyridin-7-yl}hexanoic acid,
(60) 3,3-dimethyl-6-oxo-6-(9-{[5-(trifluoromethyl)-3-thienyl]methyl}-5,6,8,9-tetrahydro-7H-pyrido[4',3':4,5]pyrrolo[2,3-b]pyridin-7-yl)hexanoic acid,
(61) 3,3-dimethyl-6-oxo-6-(9-{[5-(trifluoromethyl)-2-thienyl]methyl}-5,6,8,9-tetrahydro-7H-pyrido[4',3':4,5]pyrrolo[2,3-b]pyridin-7-yl)hexanoic acid,
(62) 2,2-dimethyl-3-(2-oxo-2-{9-[4-(trifluoromethyl)benzyl]-5,6,8,9-tetrahydro-7H-pyrido[4',3':4,5]pyrrolo[2,3-b]pyridin-7-yl}ethoxy)propanoic acid,

(63) 2,2-dimethyl-3-(2-oxo-2-{9-[3-(trifluoromethyl)benzyl]-5,6,8,9-tetrahydro-7H-pyrido[4',3':4,5]pyrrolo[2,3-b]pyridin-7-yl}ethoxy)propanoic acid,
(64) 3-(2-{9-[2-fluoro-4-(trifluoromethyl)benzyl]-5,6,8,9-tetrahydro-7H-pyrido[4',3':4,5]pyrrolo[2,3-b]pyridin-7-yl}-2-oxoethoxy)-2,2-dimethylpropanoic acid,
(65) 2,2-dimethyl-3-(2-oxo-2-{9-[4-(trifluoromethoxy)benzyl]-5,6,8,9-tetrahydro-7H-pyrido[4',3':4,5]pyrrolo[2,3-b]pyridin-7-yl}ethoxy)propanoic acid,
(66) 3-(2-{9-[3-chloro-4-(trifluoromethoxy)benzyl]-5,6,8,9-tetrahydro-7H-pyrido[4',3':4,5]pyrrolo[2,3-b]pyridin-7-yl}-2-oxoethoxy)-2,2-dimethylpropanoic acid
(67) 3-(2-{9-[3-fluoro-4-(trifluoromethoxy)benzyl]-5,6,8,9-tetrahydro-7H-pyrido[4',3':4,5]pyrrolo[2,3-b]pyridin-7-yl}-2-oxoethoxy)-2,2-dimethylpropanoic acid,
(68) 2,2-dimethyl-3-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethoxy]propanoic acid,
(69) 2,2-dimethyl-3-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethoxy]propanoic acid,
(70) 2,2-dimethyl-3-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethoxy)propanoic acid,
(71) 2,2-dimethyl-3-{2-oxo-2-[9-(4-phenoxybenzyl)-5,6,8,9-tetrahydro-7H-pyrido[4',3':4,5]pyrrolo[2,3-b]pyridin-7-yl]ethoxy}propanoic acid,
(72) 2,2-dimethyl-3-(2-oxo-2-{9-[3-(trifluoromethoxy)benzyl]-5,6,8,9-tetrahydro-7H-pyrido[4',3':4,5]pyrrolo[2,3-b]pyridin-7-yl}ethoxy)propanoic acid,
(73) 3-{2-[9-(3-ethylbenzyl)-5,6,8,9-tetrahydro-7H-pyrido[4',3':4,5]pyrrolo[2,3-b]pyridin-7-yl]-2-oxoethoxy}-2,2-dimethylpropanoic acid,
(74) 2-methyl-2-(3-oxo-3-{9-[4-(trifluoromethoxy)benzyl]-5,6,8,9-tetrahydro-7H-pyrido[4',3':4,5]pyrrolo[2,3-b]pyridin-7-yl}propoxy)propanoic acid,
(75) 2-(3-{9-[3-chloro-4-(trifluoromethoxy)benzyl]-5,6,8,9-tetrahydro-7H-pyrido[4',3':4,5]pyrrolo[2,3-b]pyridin-7-yl}-3-oxopropoxy)-2-methylpropanoic acid,
(76) 2-(3-{9-[3-fluoro-4-(trifluoromethoxy)benzyl]-5,6,8,9-tetrahydro-7H-pyrido[4',3':4,5]pyrrolo[2,3-b]pyridin-7-yl}-3-oxopropoxy)-2-methylpropanoic acid,
(77) 2-methyl-2-[3-oxo-3-(9-{[5-(trifluoromethyl)-2-thienyl]methyl}-5,6,8,9-tetrahydro-7H-pyrido[4',3':4,5]pyrrolo[2,3-b]pyridin-7-yl)propoxy]propanoic acid,
(78) 2-methyl-2-[3-oxo-3-(9-{[5-(trifluoromethyl)-3-thienyl]methyl}-5,6,8,9-tetrahydro-7H-pyrido[4',3':4,5]pyrrolo[2,3-b]pyridin-7-yl)propoxy]propanoic acid,
(79) 1-[4-oxo-4-(9-{[5-(trifluoromethyl)-2-thienyl]methyl}-5,6,8,9-tetrahydro-7H-pyrido[4',3':4,5]pyrrolo[2,3-b]pyridin-7-yl)butyl]cyclopropanecarboxylic acid,
(80) 1-[4-oxo-4-(9-{[5-(trifluoromethyl)-3-thienyl]methyl}-5,6,8,9-tetrahydro-7H-pyrido[4',3':4,5]pyrrolo[2,3-b]pyridin-7-yl)butyl]cyclopropanecarboxylic acid,
(81) 1-[4-oxo-4-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)butyl]cyclopropanecarboxylic acid, or
(82) 1-[4-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-4-oxobutyl]cyclopropanecarboxylic acid, a salt thereof or a solvate thereof or a prodrug thereof, more preferably:
(1) 2,2-dimethyl-6-oxo-6-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)hexanoic acid, or (2) 2,2-dimethyl-3-(2-oxo-2-{9-[4-(trifluoromethyl)benzyl]-5,6,8,9-tetrahydro-7H-pyrido[4',3':4,5]pyrrolo[2,3-b]pyridin-7-yl}ethoxy)propanoic acid, a salt thereof or a solvate thereof or a prodrug thereof.

Of the present compound, a compound represented by the general formula (IV) is preferably:
(1) cis-4-[2-oxo-2-(9-{[2-(trifluoromethyl)-4-pyridinyl]methyl}-1,3,4,9-tetrahydro-2H-beta-carbolin-2-yl)ethyl]cyclohexanecarboxylic acid,
(2) 4-{2-[9-(2,4-difluorobenzyl)-8-fluoro-1,3,4,9-tetrahydro-2H-beta-carbolin-2-yl]-2-oxoethyl}benzoic acid,
(3) 4-[2-(8-fluoro-9-{[5-(trifluoromethyl)-2-thienyl]methyl}-1,3,4,9-tetrahydro-2H-beta-carbolin-2-yl)-2-oxoethyl]benzoic acid,
(4) 4-{2-[8-fluoro-9-(3-fluorobenzyl)-1,3,4,9-tetrahydro-2H-beta-carbolin-2-yl]-2-oxoethyl}benzoic acid,
(5) 4-{2-[9-(2,4-difluorobenzyl)-8-fluoro-1,3,4,9-tetrahydro-2H-beta-carbolin-2-yl]-2-oxoethyl}bicyclo[2.2.2]octane-1-carboxylic acid,
(6) (1R,3R)-1,2,2-trimethyl-3-[2-oxo-2-(9-{[2-(trifluoromethyl)-1,3-thiazol-5-yl]methyl}-1,3,4,9-tetrahydro-2H-beta-carbolin-2-yl)ethyl]cyclopentanecarboxylic acid,
(7) 4-(2-{9-[3-(difluoromethyl)benzyl]-1,3,4,9-tetrahydro-2H-beta-carbolin-2-yl}-2-oxoethyl)bicyclo[2.2.2]octane-1-carboxylic acid,
(8) 4-[2-oxo-2-(9-{[2-(trifluoromethyl)-1,3-thiazol-5-yl]methyl}-1,3,4,9-tetrahydro-2H-beta-carbolin-2-yl)ethyl]bicyclo[2.2.2]octane-1-carboxylic acid,
(9) (1R,3R)-3-(2-{9-[3-(difluoromethyl)benzyl]-1,3,4,9-tetrahydro-2H-beta-carbolin-2-yl}-2-oxoethyl)-1,2,2-trimethylcyclopentanecarboxylic acid,
(10) 4-[2-(8-fluoro-9-{[2-(trifluoromethyl)-1,3-thiazol-5-yl]methyl}-1,3,4,9-tetrahydro-2H-beta-carbolin-2-yl)-2-oxoethyl]bicyclo[2.2.1]heptane-1-carboxylic acid,
(11) 4-{2-[8-fluoro-9-(4-phenoxybenzyl)-1,3,4,9-tetrahydro-2H-beta-carbolin-2-yl]-2-oxoethyl}bicyclo[2.2.1]heptane-1-carboxylic acid,
(12) 4-[2-(6-fluoro-9-{[2-(trifluoromethyl)-1,3-thiazol-5-yl]methyl}-1,3,4,9-tetrahydro-2H-beta-carbolin-2-yl)-2-oxoethyl]bicyclo[2.2.1]heptane-1-carboxylic acid,
(13) 4-[2-(6,8-difluoro-9-{[2-(trifluoromethyl)-1,3-thiazol-5-yl]methyl}-1,3,4,9-tetrahydro-2H-beta-carbolin-2-yl)-2-oxoethyl]bicyclo[2.2.1]heptane-1-carboxylic acid,
(14) 4-(2-{6-fluoro-9-[3-(trifluoromethoxy)benzyl]-1,3,4,9-tetrahydro-2H-beta-carbolin-2-yl}-2-oxoethyl)bicyclo[2.2.1]heptane-1-carboxylic acid,
(15) 4-{2-[8-fluoro-9-(3-fluorobenzyl)-1,3,4,9-tetrahydro-2H-beta-carbolin-2-yl]-2-oxoethyl}bicyclo[2.2.1]heptane-1-carboxylic acid,
(16) 1-{2-[9-(3-chloro-2,4-difluorobenzyl)-8-fluoro-1,3,4,9-tetrahydro-2H-beta-carbolin-2-yl]-2-oxoethyl}-4-piperidinecarboxylic acid,
(17) 1-(2-{8-fluoro-9-[4-(trifluoromethoxy)benzyl]-1,3,4,9-tetrahydro-2H-beta-carbolin-2-yl}-2-oxoethyl)-4-piperidinecarboxylic acid,
(18) 1-{2-[9-(3,5-dichlorobenzyl)-8-fluoro-1,3,4,9-tetrahydro-2H-beta-carbolin-2-yl]-2-oxoethyl}-4-piperidinecarboxylic acid,
(19) 1-(2-{8-fluoro-9-[3-fluoro-4-(trifluoromethoxy)benzyl]-1,3,4,9-tetrahydro-2H-beta-carbolin-2-yl}-2-oxoethyl)-4-piperidinecarboxylic acid,
(20) 1-(2-{9-[(5-chloro-2-thienyl)methyl]-8-fluoro-1,3,4,9-tetrahydro-2H-beta-carbolin-2-yl}-2-oxoethyl)-4-piperidinecarboxylic acid,
(21) 1-[2-(8-fluoro-9-{[5-(trifluoromethyl)-2-thienyl]methyl}-1,3,4,9-tetrahydro-2H-beta-carbolin-2-yl)-2-oxoethyl]-4-piperidinecarboxylic acid,

(22) 1-[2-oxo-2-(9-{[5-(trifluoromethyl)-2-thienyl]methyl}-1,3,4,9-tetrahydro-2H-beta-carbolin-2-yl)ethyl]-4-piperidinecarboxylic acid,
(23) 1-(2-{9-[(5-chloro-2-thienyl)methyl]-8-fluoro-1,3,4,9-tetrahydro-2H-beta-carbolin-2-yl}-2-oxoethyl)-4-methyl-4-piperidinecarboxylic acid,
(24) 4-methyl-1-[2-oxo-2-(9-{[5-(trifluoromethyl)-2-thienyl]methyl}-1,3,4,9-tetrahydro-2H-beta-carbolin-2-yl)ethyl]-4-piperidinecarboxylic acid,
(25) 1-[2-(8-fluoro-9-{[5-(trifluoromethyl)-2-thienyl]methyl}-1,3,4,9-tetrahydro-2H-beta-carbolin-2-yl)-2-oxoethyl]-4-methyl-4-piperidinecarboxylic acid,
(26) 1-(2-{8-fluoro-9-[3-(trifluoromethoxy)benzyl]-1,3,4,9-tetrahydro-2H-beta-carbolin-2-yl}-2-oxoethyl)-4-piperidinecarboxylic acid,
(27) 1-[2-(6,8-difluoro-9-{[2-(trifluoromethyl)-1,3-thiazol-5-yl]methyl}-1,3,4,9-tetrahydro-2H-beta-carbolin-2-yl)-2-oxoethyl]-4-piperidinecarboxylic acid,
(28) 4-[2-(8-fluoro-9-{[2-(trifluoromethyl)-1,3-thiazol-5-yl]methyl}-1,3,4,9-tetrahydro-2H-beta-carbolin-2-yl)-2-oxoethyl]-2-methoxybenzoic acid,
(29) 4-(2-{8-fluoro-9-[3-(trifluoromethoxy)benzyl]-1,3,4,9-tetrahydro-2H-beta-carbolin-2-yl}-2-oxoethyl)-2-methoxybenzoic acid,
(30) 4-[2-(6,8-difluoro-9-{[2-(trifluoromethyl)-1,3-thiazol-5-yl]methyl}-1,3,4,9-tetrahydro-2H-beta-carbolin-2-yl)-2-oxoethyl]-2-methoxybenzoic acid,
(31) 4-{2-[8-fluoro-9-(4-phenoxybenzyl)-1,3,4,9-tetrahydro-2H-beta-carbolin-2-yl]-2-oxoethyl}-2-methoxybenzoic acid, or
(32) 4-(2-{6-fluoro-9-[3-(trifluoromethoxy)benzyl]-1,3,4,9-tetrahydro-2H-beta-carbolin-2-yl}-2-oxoethyl)-2-methoxybenzoic acid,
a salt thereof or a solvate thereof or a prodrug thereof.

Of the present compound, a compound represented by the general formula (V) is preferably:
(1) {4-[2-(6,8-difluoro-9-{[2-(trifluoromethyl)-1,3-thiazol-5-yl]methyl}-1,3,4,9-tetrahydro-2H-beta-carbolin-2-yl)-2-oxoethyl]-1-piperidinyl}acetic acid,
(2) {4-[2-(8-fluoro-9-{[2-(trifluoromethyl)-1,3-thiazol-5-yl]methyl}-1,3,4,9-tetrahydro-2H-beta-carbolin-2-yl)-2-oxoethyl]-1-piperidinyl}acetic acid,
(3) [1-(2-oxo-2-{9-[4-(trifluoromethoxy)benzyl]-1,3,4,9-tetrahydro-2H-beta-carbolin-2-yl}ethyl)-4-piperidinyl]acetic acid,
(4) [1-(2-{9-[3-fluoro-4-(trifluoromethoxy)benzyl]-1,3,4,9-tetrahydro-2H-beta-carbolin-2-yl}-2-oxoethyl)-4-piperidinyl]acetic acid,
(5) (1-{2-[9-(3-chloro-2,4-difluorobenzyl)-8-fluoro-1,3,4,9-tetrahydro-2H-beta-carbolin-2-yl]-2-oxoethyl}-4-piperidinyl)acetic acid,
(6) [1-(2-{8-fluoro-9-[4-(trifluoromethoxy)benzyl]-1,3,4,9-tetrahydro-2H-beta-carbolin-2-yl}-2-oxoethyl)-4-piperidinyl]acetic acid,
(7) (1-{2-[9-(3,5-dichlorobenzyl)-8-fluoro-1,3,4,9-tetrahydro-2H-beta-carbolin-2-yl]-2-oxoethyl}-4-piperidinyl)acetic acid,
(8) [1-(2-{9-[3-chloro-4-(trifluoromethoxy)benzyl]-8-fluoro-1,3,4,9-tetrahydro-2H-beta-carbolin-2-yl}-2-oxoethyl)-4-piperidinyl]acetic acid,
(9) [1-(2-{8-fluoro-9-[3-fluoro-4-(trifluoromethoxy)benzyl]-1,3,4,9-tetrahydro-2H-beta-carbolin-2-yl}-2-oxoethyl)-4-piperidinyl]acetic acid,
(10) [1-(2-{9-[(5-chloro-2-thienyl)methyl]-8-fluoro-1,3,4,9-tetrahydro-2H-beta-carbolin-2-yl}-2-oxoethyl)-4-piperidinyl]acetic acid,
(11) {1-[2-(8-fluoro-9-{[5-(trifluoromethyl)-2-thienyl]methyl}-1,3,4,9-tetrahydro-2H-beta-carbolin-2-yl)-2-oxoethyl]-4-piperidinyl}acetic acid,
(12) (4-{2-[9-(3-chloro-2,4-difluorobenzyl)-8-fluoro-1,3,4,9-tetrahydro-2H-beta-carbolin-2-yl]-2-oxoethyl}-1-piperazinyl)acetic acid,
(13) [4-(2-{8-fluoro-9-[4-(trifluoromethoxy)benzyl]-1,3,4,9-tetrahydro-2H-beta-carbolin-2-yl}-2-oxoethyl)-1-piperazinyl]acetic acid,
(14) (4-{2-[9-(3,5-dichlorobenzyl)-8-fluoro-1,3,4,9-tetrahydro-2H-beta-carbolin-2-yl]-2-oxoethyl}-1-piperazinyl)acetic acid,
(15) [4-(2-{9-[3-chloro-4-(trifluoromethoxy)benzyl]-8-fluoro-1,3,4,9-tetrahydro-2H-beta-carbolin-2-yl}-2-oxoethyl)-1-piperazinyl]acetic acid,
(16) [4-(2-{8-fluoro-9-[3-fluoro-4-(trifluoromethoxy)benzyl]-1,3,4,9-tetrahydro-2H-beta-carbolin-2-yl}-2-oxoethyl)-1-piperazinyl]acetic acid,
(17) {1-[2-oxo-2-(9-{[5-(trifluoromethyl)-2-thienyl]methyl}-1,3,4,9-tetrahydro-2H-beta-carbolin-2-yl)ethyl]-4-piperidinyl}acetic acid,
(18) {4-[2-oxo-2-(9-{[5-(trifluoromethyl)-2-thienyl]methyl}-1,3,4,9-tetrahydro-2H-beta-carbolin-2-yl)ethyl]-1-piperazinyl}acetic acid,
(19) rel-{(2R,6S)-4-[2-(8-fluoro-9-{[5-(trifluoromethyl)-2-thienyl]methyl}-1,3,4,9-tetrahydro-2H-beta-carbolin-2-yl)-2-oxoethyl]-2,6-dimethyl-1-piperazinyl}acetic acid,
(20) rel-{(2R,6S)-2,6-dimethyl-4-[2-oxo-2-(9-{[5-(trifluoromethyl)-2-thienyl]methyl}-1,3,4,9-tetrahydro-2H-beta-carbolin-2-yl)ethyl]-1-piperazinyl}acetic acid,
(21) rel-[(2R,6S)-4-(2-{9-[(5-chloro-2-thienyl)methyl]-8-fluoro-1,3,4,9-tetrahydro-2H-beta-carbolin-2-yl}-2-oxoethyl)-2,6-dimethyl-1-piperazinyl]acetic acid,
(22) (1-{2-[9-(2,4-difluorobenzyl)-8-fluoro-1,3,4,9-tetrahydro-2H-beta-carbolin-2-yl]-2-oxoethyl}-4-piperidinyl)acetic acid,
(23) [4-(2-{8-fluoro-9-[3-(trifluoromethoxy)benzyl]-1,3,4,9-tetrahydro-2H-beta-carbolin-2-yl}-2-oxoethyl)-1-piperazinyl]acetic acid,
(24) [1-(2-{8-fluoro-9-[3-(trifluoromethoxy)benzyl]-1,3,4,9-tetrahydro-2H-beta-carbolin-2-yl}-2-oxoethyl)-4-piperidinyl]acetic acid,
(25) (1-{2-[8-fluoro-9-(3-fluorobenzyl)-1,3,4,9-tetrahydro-2H-beta-carbolin-2-yl]-2-oxoethyl}-4-piperidinyl)acetic acid,
(26) (1-{2-[8-fluoro-9-(4-fluorobenzyl)-1,3,4,9-tetrahydro-2H-beta-carbolin-2-yl]-2-oxoethyl}-4-piperidinyl)acetic acid,
(27) {4-[2-(6,8-difluoro-9-{[2-(trifluoromethyl)-1,3-thiazol-5-yl]methyl}-1,3,4,9-tetrahydro-2H-beta-carbolin-2-yl)-2-oxoethyl]-1-piperazinyl}acetic acid,
(28) {1-[2-(6,8-difluoro-9-{[2-(trifluoromethyl)-1,3-thiazol-5-yl]methyl}-1,3,4,9-tetrahydro-2H-beta-carbolin-2-yl)-2-oxoethyl]-4-piperidinyl}acetic acid,
(29) {4-[2-(8-fluoro-9-{[2-(trifluoromethyl)-1,3-thiazol-5-yl]methyl}-1,3,4,9-tetrahydro-2H-beta-carbolin-2-yl)-2-oxoethyl]-1-piperazinyl}acetic acid,
(30) (4-{2-[8-fluoro-9-(4-phenoxybenzyl)-1,3,4,9-tetrahydro-2H-beta-carbolin-2-yl]-2-oxoethyl}-1-piperazinyl)acetic acid,
(31) (1-{2-[8-fluoro-9-(4-phenoxybenzyl)-1,3,4,9-tetrahydro-2H-beta-carbolin-2-yl]-2-oxoethyl}-4-piperidinyl)acetic acid,
(32) {1-[2-(6-fluoro-9-{[2-(trifluoromethyl)-1,3-thiazol-5-yl]methyl}-1,3,4,9-tetrahydro-2H-beta-carbolin-2-yl)-2-oxoethyl]-4-piperidinyl}acetic acid,

(33) [4-(2-{6-fluoro-9-[3-(trifluoromethoxy)benzyl]-1,3,4,9-tetrahydro-2H-beta-carbolin-2-yl}-2-oxoethyl)-1-piperazinyl]acetic acid,
(34) [1-(2-{6-fluoro-9-[3-(trifluoromethoxy)benzyl]-1,3,4,9-tetrahydro-2H-beta-carbolin-2-yl}-2-oxoethyl)-4-piperidinyl]acetic acid, or
(35) {4-[2-(6-fluoro-9-{[2-(trifluoromethyl)-1,3-thiazol-5-yl]methyl}-1,3,4,9-tetrahydro-2H-beta-carbolin-2-yl)-2-oxoethyl]phenoxy}acetic acid, a salt thereof or a solvate thereof or a prodrug thereof.

Of the present compound, a compound represented by the general formula (VI) is preferably:
(1) 6-oxo-6-{9-[3-(trifluoromethyl)benzyl]-1,3,4,9-tetrahydro-2H-beta-carbolin-2-yl}hexanoic acid,
(2) 6-[6-fluoro-9-(3-fluorobenzyl)-1,3,4,9-tetrahydro-2H-beta-carbolin-2-yl]-2,2-dimethyl-6-oxohexanoic acid,
(3) 6-[8-fluoro-9-(3-fluorobenzyl)-1,3,4,9-tetrahydro-2H-beta-carbolin-2-yl]-2,2-dimethyl-6-oxohexanoic acid,
(4) 2,2-dimethyl-6-oxo-6-(9-{[2-(trifluoromethyl)-4-pyridinyl]methyl}-1,3,4,9-tetrahydro-2H-beta-carbolin-2-yl)hexanoic acid,
(5) 6-{9-[(1,3-dimethyl-1H-pyrazol-5-yl)methyl]-8-fluoro-1,3,4,9-tetrahydro-2H-beta-carbolin-2-yl}-2,2-dimethyl-6-oxohexanoic acid,
(6) 6-{9-[(5-chloro-2-thienyl)methyl]-8-fluoro-1,3,4,9-tetrahydro-2H-beta-carbolin-2-yl}-2,2-dimethyl-6-oxohexanoic acid,
(7) 3,3-dimethyl-6-oxo-6-(9-{[2-(trifluoromethyl)-4-pyridinyl]methyl}-1,3,4,9-tetrahydro-2H-beta-carbolin-2-yl)hexanoic acid,
(8) 3-{2-[8-fluoro-9-(3-fluorobenzyl)-1,3,4,9-tetrahydro-2H-beta-carbolin-2-yl]-2-oxoethoxy}-2,2-dimethylpropanoic acid,
(9) 3-{2-[9-(2,4-difluorobenzyl)-8-fluoro-1,3,4,9-tetrahydro-2H-beta-carbolin-2-yl]-2-oxoethoxy}-2,2-dimethylpropanoic acid,
(10) 3-[2-(8-fluoro-9-{[5-(trifluoromethyl)-2-thienyl]methyl}-1,3,4,9-tetrahydro-2H-beta-carbolin-2-yl)-2-oxoethoxy]-2,2-dimethylpropanoic acid, or
(11) 2,2-dimethyl-6-oxo-6-(9-{[2-(trifluoromethyl)-1,3-thiazol-5-yl]methyl}-1,3,4,9-tetrahydro-2H-beta-carbolin-2-yl)hexanoic acid, a salt thereof or a solvate thereof or a prodrug thereof.

In the present invention, unless particularly indicated, all isomers are included. For example, an alkyl group includes a straight group and a branched group. Further, an isomer due to the presence of an asymmetric carbon etc. (R, S body, α, β configuration, enantiomer, diastereomer), an optically active body having optical rotation (D, L, d, and l forms), a polar form by chromatographic separation (high polar form, low polar form), an equilibrium compound (e.g. tautomer generated in an amide bond etc.), a rotational isomer, a mixture of them at an arbitrary ratio, and a racemic mixture are all included in the present invention.

The compound represented by any one selected from the general formula (I) to the general formula (VI) is converted into a corresponding salt by the known method. As a salt, a water-soluble salt is preferable. Examples of a suitable salt include acid addition salts (e.g. inorganic acid salts such as hydrochloride, hydrobromide, hydroiodide, sulfate, phosphate and nitrate, organic acid salts such as acetate, lactate, tartrate, benzoate, citrate, methanesulfonate, ethanesulfonate, benzenesulfonate, toluenesulfonate, isethionate, glucuronate, gluconate, etc.), salts of an alkali metal (potassium, sodium etc.), salts of an alkaline earth metal (calcium, magnesium etc.), ammonium salts or salts of a pharmaceutically acceptable organic amine (e.g. tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine etc.) etc.

The compound represented by any one selected from the general formula (I) to the general formula (VI) and a salt thereof can be also converted into a solvate. It is preferable that the solvate is low-toxic and water-soluble. Examples of a suitable solvate include solvates with water, or an alcoholic solvent (e.g. ethanol etc.).

And, the prodrug of the compound represented by any one selected from the general formula (I) to the general formula (VI) refers to a compound which is converted into the compound represented by any one selected from the general formula (I) to the general formula (VI) by a reaction with an enzyme or gastric acid etc. in a living body. Specifically, examples include, when the compound represented by any one selected from the general formula (I) to the general formula (VI) has an amino group, compounds in which the amino group is eicosanoylated, alanylated, pentylaminocarbonized, (5-methyl-2-oxo-1,3-dioxolene-4-yl)methoxycarbonylated, tetrahydrofuranylated, pyrrolidylmethylated, pivaloyloxymethylated, acetoxymethylated, or tert-butylated, when the compound represented by any one selected from the general formula (I) to the general formula (VI) has a hydroxy group, compounds in which the hydroxy group is acetylated, palmitoylated, propanoylated, pivaloylated, succinylated, fumarylated, alanylated, or dimethylaminomethylcarbonylated and, when the compound represented by any one selected from the general formula (I) to the general formula (VI) has a carboxy group, compounds in which the carboxy group is ethylesterified, phenylesterified, carboxymethylesterified, dimethylaminomethylesterified, pivaloyloxymethylesterified, ethoxycarbonyloxyethylesterified, phthalidylesterified, (5-methyl-2-oxo-1,3-dioxolene-4-yl)methylesterified, cyclohexyloxycarbonylethylesterified, or methylamidated, and these compounds can be produced by the known method. And, the prodrug of the compound represented by any one selected from the general formula (I) to the general formula (VI) may be any of a hydrate and a non-hydrate. Alternatively, the prodrug of the compound represented by any one selected from the general formula (I) to the general formula (VI) may be a compound which is changed into the compound represented by the general formula (I) under the physiological condition, as described in "Development of Medicaments", vol. 7 "Molecular Design", p.163-198, published by HirokawaShoten in 1990.

Further, each atom constituting the compound represented by any one selected from the general formula (I) to the general formula (VI) may be substituted with an isotope thereof (e.g. $^2H$, $^3H$, $^{13}C$, $^{14}C$, $^{35}S$, $^{125}I$ etc.) etc.

[Process for Producing the Present Compound]

The compound represented by any one selected from the general formula (I) to the general formula (VI) can be produced, for example, by the following method, the method shown in Examples or a method in accordance with them.

Of the compound represented by the general formula (I), a compound represented by the general formula (I-1):

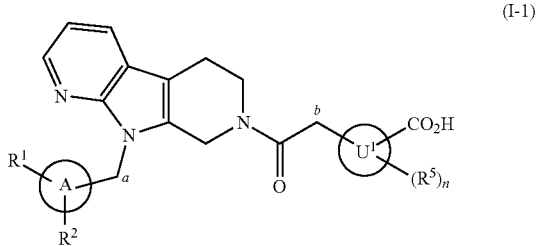

(I-1)

(wherein all symbols are as defined above.)(except for a compound wherein the atom in ring $U^1$ bound to the methylene group represented by "b" in the general formula (I-1) is a nitrogen atom) can be produced by the method shown in the following reaction step formula 1.

iodide etc.) in the presence of a base (e.g. potassium carbonate, sodium carbonate, cesium carbonate, sodium hydride etc.).

In the reaction step formula 1, the reaction 1-2 is known, and can be performed, for example, by a method using a condensing agent, a method using acid halide, a method using a mixed acid anhydride etc.

The method using a condensing agent is performed, for example, by reacting a compound represented by the general formula (I-3) and a compound represented by the general formula (I-7) at 0° C. to a refluxing temperature using a condensing agent (e.g. 1,3-dicyclohexylcarbodiimide (DCC), ethylene dichloride (EDC), 1,1'-carbonyldiimidazole (CDI), 2-chloro-1-methylpyridinium iodine, 1-propylphosphonic acid cyclic anhydride (PPA) etc.) and using or not using 1-hydroxybenzotriazole (HOBt), in an organic solvent (e.g. chloroform, dichloromethane, N,N-dimethyl-

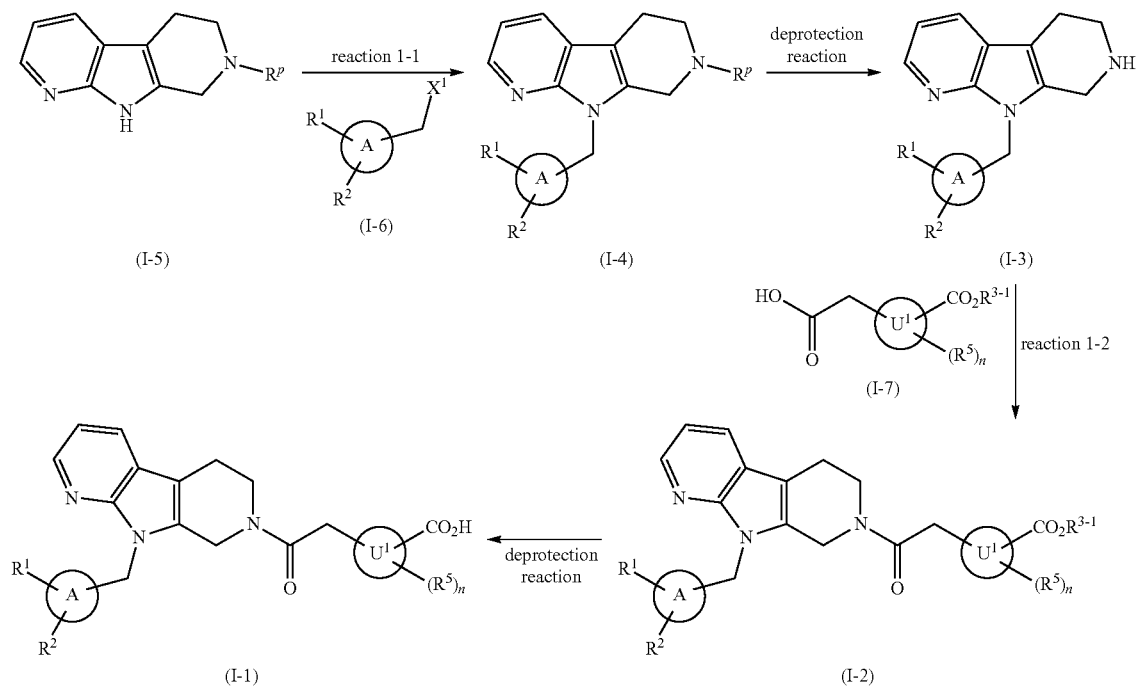

Reaction step formula 1

(wherein $R^p$ represents a protective group for an amino group (e.g. tert-butoxycarbonyl group, benzyloxycarbonyl group, fluorenylcarbonyl group, trityl group, o-nitrobenzenesulfenyl group etc.), $X^1$ represents a halogen atom, $R^{3-1}$ represents C1-4 alkyl group, and other symbols are as defined above.)

In the reaction step formula 1, the reaction 1-1 is known, and can be performed, for example, by reacting a compound represented by the general formula (I-5) and a compound represented by the general formula (I-6) at 0° C. to a refluxing temperature in an organic solvent (e.g. tetrahydrofuran, dichloromethane, chloroform, benzene, toluene, xylene, hexane, heptane, cyclohexane, diethyl ether, dioxane, acetone, ethyl methyl ketone, acetonitrile, dimethyl sulfoxide, N,N-dimethylformamide, dimethylacetamide, ethyl acetate etc.) and in the presence or absence of a catalyst (e.g. potassium iodide, sodium iodide, tetrabutylammonium formamide, diethyl ether, tetrahydrofuran etc.) or without a solvent and in the presence or absence of a base (e.g. pyridine, triethylamine, dimethylaniline, dimethylaminopyridine etc.).

The method using acid halide is performed, for example, by reacting a compound represented by the general formula (I-7) with an acid halidizing agent (e.g. oxalyl chloride, thionyl chloride etc.) at −20° C. to a refluxing temperature in an organic solvent (e.g. chloroform, dichloromethane, diethyl ether, tetrahydrofuran, dimethoxyethane etc.) or without a solvent, and reacting the resulting acid halide with a compound represented by the general formula (I-3) at 0° C. to a refluxing temperature in an organic solvent (e.g. chloroform, dichloromethane, diethyl ether, tetrahydrofuran, acetonitrile, ethyl acetate etc.) in the presence of a base (e.g. pyridine, triethylamine, dimethylaniline, dimethylaminopyridine, diisopropylethylamine etc.). Alternatively, the method using acid halide can be also performed by reacting the resulting acid halide with a compound represented by the general formula (I-3) at 0° C. to a refluxing temperature using an aqueous alkali solution (e.g. aqueous sodium bicarbonate solution or sodium hydroxide solution etc.) in an organic solvent (e.g. dioxane, tetrahydrofuran, dichloromethane etc.) in the presence or absence of a phase transfer catalyst (e.g. quaternary ammonium salt such as tetrabutylammonium chloride, triethylbenzylammonium chloride, trioctylmethylammonium chloride, trimethyldecylammonium chloride, tetramethylammonium bromide etc., and others).

On the other hand, the method using a mixed acid anhydride can be also performed, for example, by reacting a compound represented by the general formula (I-7) with acid halide (e.g. pivaloyl chloride, tosyl chloride, mesyl chloride etc.), or an acid derivative (e.g. ethyl chloroformate, isobutyl chloroformate etc.) at 0° C. to a refluxing temperature in an organic solvent (e.g. chloroform, dichloromethane, diethyl ether, tetrahydrofuran etc.) or without a solvent in the presence of a base (e.g. pyridine, triethylamine, dimethylaniline, dimethylaminopyridine, diisopropylethylamine etc.), and reacting the resulting mixed acid anhydride with a compound represented by the general formula (I-3) at 0° C. to a refluxing temperature in an organic solvent (e.g. chloroform, dichloromethane, diethyl ether, tetrahydrofuran etc.).

It is desirable that these reactions are all performed in the inert gas (argon, nitrogen etc.) atmosphere under the anhydrous condition.

The deprotection reaction, for example, in the case of a deprotection reaction by alkali hydrolysis, can be performed, for example, at 0 to 40° C. in an organic solvent (e.g. methanol, tetrahydrofuran, dioxane etc.) using hydroxide of an alkali metal (e.g. sodium hydroxide, potassium hydroxide, lithium hydroxide etc.), hydroxide of an alkaline earth metal (e.g. barium hydroxide, calcium hydroxide etc.) or carbonate (e.g. sodium carbonate, potassium carbonate etc.) or an aqueous solution thereof or a mixture thereof.

Moreover, the compound represented by the general formula (I-1) (provided that the compound wherein the atom on the ring $U^1$ which is bound to the methylene group represented by b in the general formula (I-1) is a nitrogen atom is excluded) can be also produced by subjecting a compound represented by the general formula (I-8):

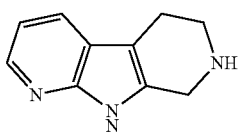
(I-8)

and a compound represented by the general formula (I-7) to a reaction similar to the reaction 1-2 in the reaction step formula 1 and subjecting the resulting product to a reaction similar to the reaction 1-1 in the reaction step formula 1 using the compound represented by the general formula (I-6), followed by subjecting the resulting product to a deprotection reaction.

Among the compounds represented by the general formula (II), a compound represented by the general formula (II-1) (provided that the compound wherein the atom on the ring $U^2$ which is bound to $Y^2$ in the general formula (II-1) is a nitrogen atom is excluded):

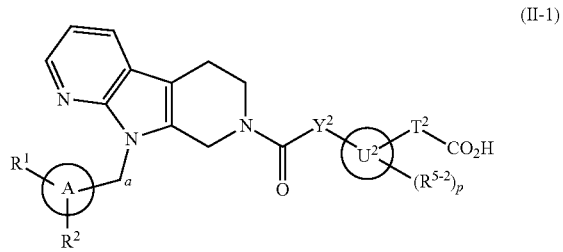
(II-1)

(wherein all symbols represent the same meanings as defined above) can be produced by subjecting a compound represented by the general formula (I-3) and a compound represented by the general formula (II-2):

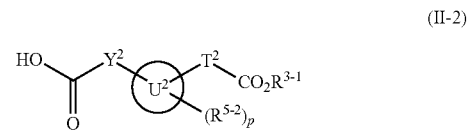
(II-2)

(wherein all symbols represent the same meanings as defined above) to a reaction similar to the reaction 1-2 in the reaction step formula 1 and then subjecting the resulting product to a deprotection reaction.

On the other hand, among the compounds represented by the general formula (I-1), the compound wherein the atom on the ring $U^2$ which is bound to the methylene group represented by b is a nitrogen atom can be produced by subjecting a compound represented by the general formula (I-9):

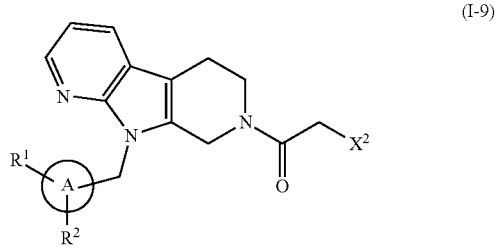
(I-9)

(wherein $X^2$ represents a halogen atom and other symbols represent the same meanings as defined above) and a compound represented by the general formula (I-10):

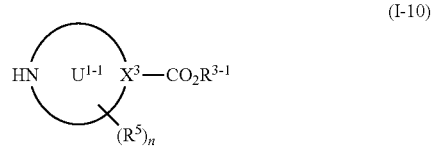
(I-10)

(wherein the ring $U^{1-1}$ represents piperidine, piperazine, diazabicyclo[2.2.1]heptane, or tetrahydropyridine, $X^3$ represents a carbon atom or a nitrogen atom and other symbols represent the same meanings as defined above) to a reaction similar to the reaction 1-1 in the reaction step formula 1 and then subjecting the resulting product to a deprotection reaction.

Similarly, among the compounds represented by the general formula (II-1), the compound wherein the atom on the ring $U^2$ which is bound to $Y^2$ is a nitrogen atom can be produced by subjecting a compound represented by the general formula (II-3):

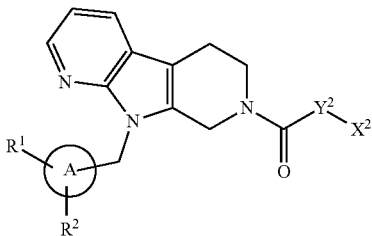

(II-3)

(wherein all symbols represent the same meanings as defined above) and a compound represented by the general formula (II-4):

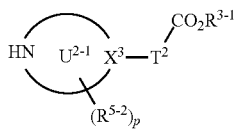

(II-4)

(wherein the ring $U^{2-1}$ represents piperidine, piperazine, diazabicyclo[2.2.1]heptane, or tetrahydropyridine and other symbols represent the same meanings as defined above) to a reaction similar to the reaction 1-1 in the reaction step formula 1 and then subjecting the resulting product to a deprotection reaction.

Among the compounds represented by the general formula (III), a compound represented by the general formula (III-1):

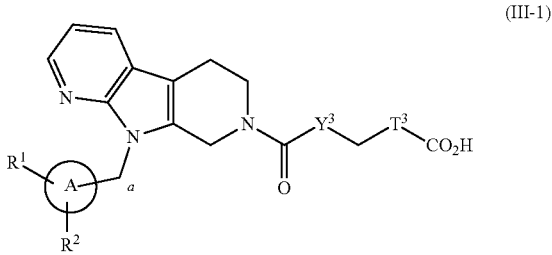

(III-1)

(wherein all symbols represent the same meanings as defined above) can be produced by the method shown in the following reaction step formula 2.

Reaction step formula 2

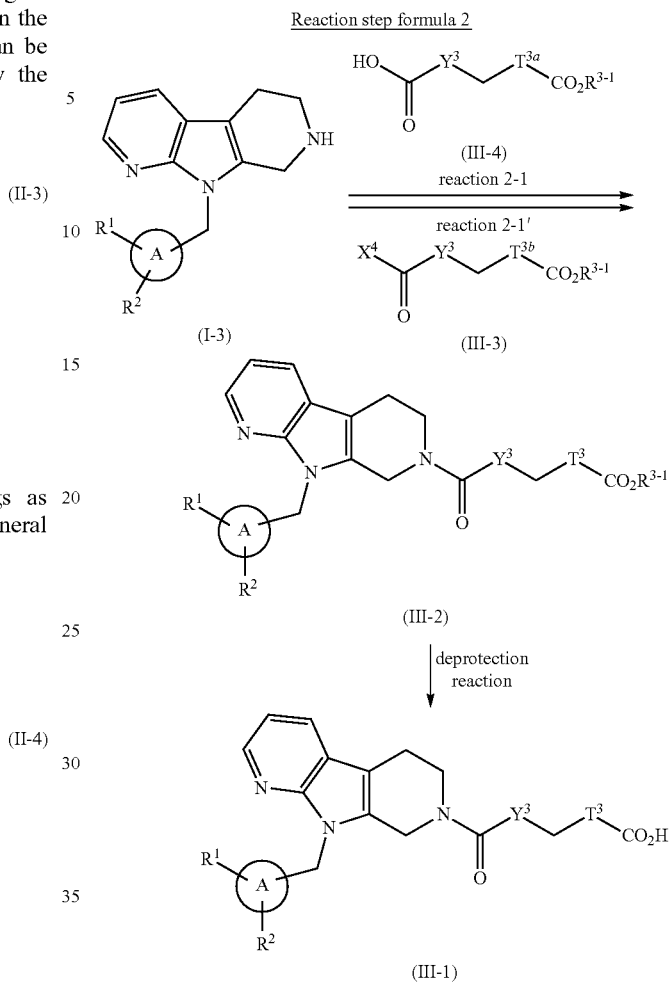

(wherein $X^4$ represents a halogen atom, $T^{3a}$ represents a methylene group or ethylene group substituted with one or two $R^7$ groups, $T^{3b}$ represents an unsubstituted methylene group or ethylene group, and other symbols represent the same meanings as defined above).

In the reaction step formula 2, the reaction 2-1' is known and can be performed, for example, by reacting a compound represented by the general formula (I-3) with a compound represented by the general formula (III-3) at −20° C. to a refluxing temperature in an organic solvent (e.g., chloroform, dichloromethane, diethyl ether, tetrahydrofuran etc.) in the presence of a base (e.g., pyridine, triethylamine, dimethylaniline, dimethylaminopyridine, diisopropylethylamine etc.). Alternatively, the reaction can be also performed by reacting a compound represented by the general formula (I-3) with a compound represented by the general formula (III-3) at 0° C. to a refluxing temperature in an organic solvent (e.g., dioxane, tetrahydrofuran, diethyl ether etc.) using an aqueous alkali solution (e.g., an aqueous sodium bicarbonate solution, an aqueous sodium hydroxide solution etc.). In this connection, the deprotection reaction can be performed in a similar manner to that described above.

On the other hand, in the reaction step formula 2, the reaction 2-1 can be performed in a similar manner to the reaction 1-2 in the reaction step 1 described above.

Among the compounds represented by the general formula (III), a compound represented by the general formula (III-5):

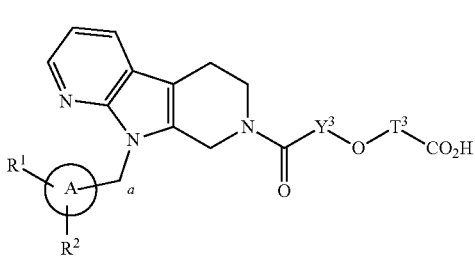

(III-5)

(wherein all symbols represent the same meanings as defined above) can be produced by the method shown in the following reaction step formula 3.

Reaction step formula 3

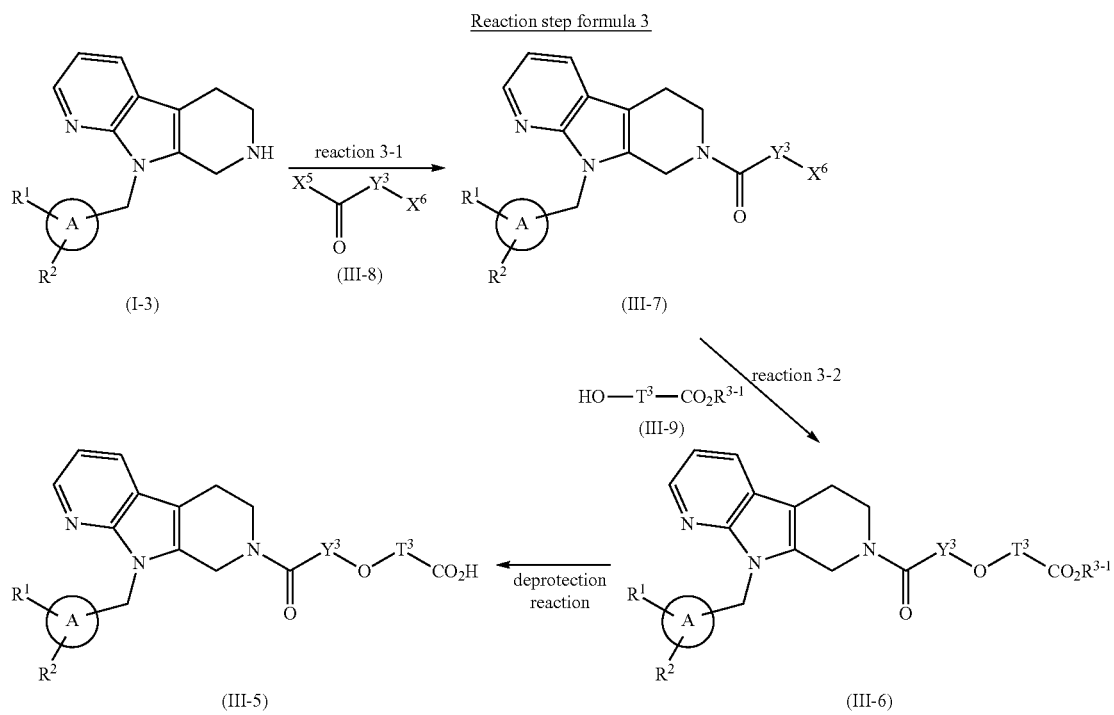

(wherein $X^5$ and $X^6$ represents a halogen atom, respectively and other symbols represent the same meanings as defined above).

In the reaction step formula 3, the reaction 3-1 can be performed in a similar manner to the above reaction 2-1' and the reaction 3-2 can be performed in a similar manner to the above reaction 1-1.

Of the compound represented by the general formula (III-4) in the reaction step formula 2, a compound represented by the general formula (III-4a):

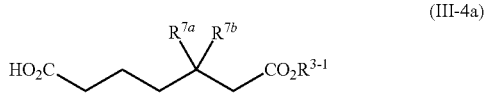

(III-4a)

(wherein, $R^{7a}$ and $R^{7b}$ represents a methylene group, respectively, and other symbols are as defined above.) can be produced by the method shown in the following reaction step formula 4.

Reaction step formula 4

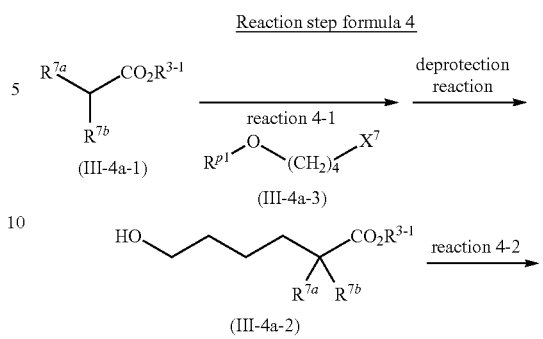

-continued

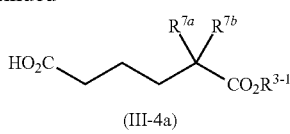

(III-4a)

(wherein, $X^7$ represents a leaving group (e.g. a halogen atom etc.), $R^{p1}$ represents a protective group for a hydroxy group (e.g. methoxymethyl group, benzyl group or tetrahydropyranyl group etc.), and other symbols are as defined above.)

In the reaction step formula 4, the reaction 4-1 is known, and can be performed, for example, by reacting a compound represented by the general formula (III-4a-1) and a compound represented by the general formula (III-4a-3) at −78° C. to a refluxing temperature in an organic solvent (e.g. tetrahydrofuran, benzene, toluene, xylene, hexane, heptane, cyclohexane, diethyl ether, dioxane, dimethyl sulfoxide, N,N-dimethylformamide, dimethylacetamide etc.) in the presence of a base (e.g. lithium hexamethyldisilazide, lithium diisopropylamide and sodium hexamethyldisilazide etc.).

On the other hand, of the compound represented by the general formula (III-4), a compound represented by the general formula (III-4b):

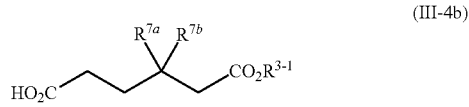

(wherein all symbols are as defined above.) can be produced by the method shown in the following reaction step formula 5.

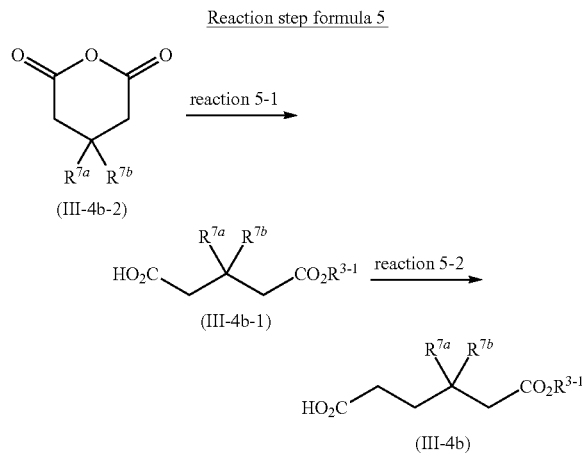

(wherein all symbols are as defined above.)

In the reaction step formula 5, the reaction 5-1 is known, and can be performed, for example, at 0° C. to a refluxing temperature in an organic solvent (e.g. methanol, ethanol etc.) in the presence or absence of a base (e.g. sodium methoxide, sodium ethoxide etc.). And, the reaction 5-2 is known, and can be performed, for example, by reacting a compound represented by the general formula (III-4b-1) with an acid halidizing agent (e.g. oxalyl chloride, thionyl chloride etc.) at −20° C. to a refluxing temperature in an organic solvent (e.g. chloroform, dichloromethane, diethyl ether, tetrahydrofuran, dimethoxyethane etc.) or without a solvent, reacting the resulting acid halide at −20° C. to a refluxing temperature in an organic solvent (e.g. chloroform, dichloromethane, diethyl ether, tetrahydrofuran, acetonitrile, ethyl acetate etc.) in the presence of a diazomethylating agent (e.g. diazomethane, trimethylsilyldiazomethane etc.), and subjecting the resulting diazomethyl ketone to a reaction at −20° C. to a refluxing temperature in an organic solvent (e.g. dioxane, tetrahydrofuran, dichloromethane etc.) or without a solvent in the presence of an alcohol (e.g. methanol, ethanol, propanol, butanol, benzyl alcohol etc.) in the presence of a base (e.g. pyridine, triethylamine, dimethylaniline, dimethylaminopyridine, diisopropylethylamine etc.).

On the other hand, the compound represented by the general formula (IV) can be produced by the same method as the above-mentioned method of producing the compound represented by the general formula (I-1) or the general formula (II-2). The compound represented by the general formula (V) can be produced by the same method as the above-mentioned method of producing the compound represented by the general formula (II-1). The compound represented by the general formula (VI) can be produced by the same method as the above-mentioned method of producing the compound represented by the general formula (III-1) or the general formula (III-2), or the general formula (III-5) or the general formula (III-6).

In the above reaction step formula, a method of introducing a protective group into an amino group can be performed by the method described in T. W. Greene, Protective Groups in Organic Synthesis, Wiley, New York, 1999, for example, in introduction of a protective group such as a tert-butoxycarbonyl group, a benzyloxycarbonyl group, a fluorenylcarbonyl group, a trityl group, an o-nitrobenzenesulfenyl group etc. of $R^P$, can be performed by a reaction at −50 to 100° C. in a solvent such as dichloromethane, chloroform, 1,2-dichloroethane, tetrahydrofuran, dioxane, toluene, ethyl acetate or water using di-tert-butyl dicarbonate, benzyloxycarbonyl chloride, fluorenylcarbonyl chloride, trityl chloride, o-nitrobenzenesulfenyl chloride or the like, respectively. Thereupon, if necessary, the introduction can be performed using a base such as amines such as triethylamine, diisopropylethylamine and the like, organic acid salts such as sodium 2-ethylhexanoate and potassium 2-ethylhexanoate, or inorganic bases such as sodium hydroxide and potassium carbonate.

In the above reaction step formula, a reaction of deprotecting a protective group for a carboxyl group, a hydroxy group or an amino group is well-known, and examples include a deprotection reaction by alkali hydrolysis, a deprotection reaction under the acidic condition, a deprotection reaction by hydrogenolysis, a deprotection reaction of a silyl group, a deprotection reaction using a metal, a deprotection reaction using an organometal and the like.

For example, the deprotection reaction by alkali hydrolysis is performed at a temperature of 0 to 40° C. in an organic solvent (methanol, tetrahydrofuran or 1,4-dioxane alone, or a mixed solvent consisting of a plurality of solvents among them at an arbitrary ratio) using hydroxide of an alkali metal (sodium hydroxide, potassium hydroxide, lithium hydroxide etc.), hydroxide of an alkaline earth metal (barium hydroxide, calcium hydroxide etc.) or carbonate (sodium carbonate, potassium carbonate etc.) or an aqueous solution thereof or a mixture thereof.

On the other hand, the deprotection reaction under the acidic condition is performed, for example, at a temperature of 0 to 100° C. in an organic solvent (dichloromethane, chloroform, 1,4-dioxane, ethyl acetate or anisole alone, or a mixed solvent consisting of a plurality of solvents among them at an arbitrary ratio) in an organic acid (acetic acid, trifluoroacetic acid, methanesulfonic acid, p-toluenesulfonic acid etc.), or an inorganic acid (hydrochloric acid, sulfuric acid etc.) or a mixture thereof (hydrogen bromide/acetic acid etc.).

The deprotection reaction by hydrogenolysis is performed, for example, at a temperature of 0 to 200° C. in a solvent (ether solvent (tetrahydrofuran, 1,4-dioxane, dimethoxyethane, diethyl ether etc.), alcohol solvent (methanol, ethanol etc.), benzene solvent (benzene, toluene etc.), ketone solvent (acetone, methyl etheyl ketone etc.), nitrile solvent (acetonitrile etc.), amide solvent (N,N-dimethylformamide etc.), water, ethyl acetate, acetic acid, or a mixed solvent of two or more of them), in the presence of a catalyst (palladium-carbon, palladium black, palladium hydroxide, platinum oxide, Raney nickel etc.), under the hydrogen atmosphere under ordinary pressure or increased pressure, or in the presence of ammonium formate.

The deprotection reaction of a silyl group is performed, for example, at a temperature of 0 to 40° C. in an organic solvent which is miscible with water (tetrahydrofuran or acetonitrile alone, or a mixed solvent consisting of a plurality of solvents among them at an arbitrary ratio) using tetrabutylammonium fluoride.

The deprotection reaction using a metal is performed, for example, at a temperature of 0 to 40° C. in an acidic solvent (acetic acid, buffer having a pH of 4.2 to 7.2, or a mixed solvent of those solutions and an organic solvent such as tetrahydrofuran) in the presence of a zinc powder by applying ultrasound or applying no ultrasound.

The deprotection reaction using a metal complex is performed, for example, at a temperature of 0 to 40° C. in an organic solvent (dichloromethane, N,N-dimethylformamide, tetrahydrofuran, ethyl acetate, acetonitrile, 1,4-dioxane, ethanol etc.), water or a mixed solvent of them in the presence of a trap reagent (tributyltin hydoride, triethylsilane, dimedone, morpholine, diethylamine, pyrrolidine etc.), an organic acid (acetic acid, formic acid, 2-ethylhexanoic acid etc.) and/or an ortanic acid salt (sodium 2-ethylhexanoate, potassium 2-ethylhexanoate etc.) in the presence or absence of a phosphine reagent (triphenylphosphine etc.), using a metal complex (tetrakistriphenylphosphinepalladium (0), bis(triphenylphosphine)palladium (II) dichloride, palladium (II) acetate, tris(triphenylphosphine)rhodium (I) chloride etc.).

Alternatively, in addition to the foregoing, the deprotection reaction can be performed, for example, by the method described in T. W. Greene, Protective Groups in Organic Synthesis, Wiley, New York, 1999.

Examples of a protective group for a carboxyl group include methyl, ethyl, tert-butyl, trichloroethyl, benzyl (Bn), phenacyl, p-methoxybenzyl, trityl, 2-chlorotrityl etc.

Example of a protective group for an amino group include a benzyloxycarbonyl group, a tert-butoxycarbonyl group, an allyloxycarbonyl (Alloc) group, a 1-methyl-1-(4-biphenyl) ethoxycarbonyl (Bpoc) group, a trifluoroacetyl group, a 9-fluorenylmethoxycarbonyl group, a benzyl (Bn) group, a p-methoxybenzyl group, a benzyloxymethyl (BOM) group, a 2-(trimethylsilyl)ethoxymethyl(SEM) group and the like.

Examples of a protective group for a hydroxy group include methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), tert-butyldimethylsilyl (TBDMS), tert-butyldiphenylsilyl (TBDPS), acetyl (Ac), pivaloyl, benzoyl, benzyl (Bn), p-methoxybenzyl, allyloxycarbonyl (Alloc), 2,2,2-trichloroethoxycarbonyl (Troc) and the like.

Of the present compound, compounds other than those shown above can be produced by the known method, for example, the method described in Comprehensive Organic Transformations: A Guide to Functional Group Preparations, 2nd Edition (Richard C. Larock, John Wiley & Sons Inc, 1999) and the like, or by using a combination of a method in which a part of the known method is modified and the like.

In each reaction in the specification, the compound represented by the general formula (I-9) and the general formula (II-3) can be produced by the same method as the above-mentioned method of producing the compound represented by the general formula (III-7) in the reaction step formula 3.

In each reaction in the present specification, compounds represented by the general formula (I-5), the general formula (I-6), the general formula (I-7), the general formula (I-8), the general formula (I-10), the general formula (II-2), the general formula (II-4), the general formula (III-3), the general formula (III-4), the general formula (III-4a-1), the general formula (III-4a-3), the general formula (III-4b-2), the general formula (III-8) and the general formula (III-9), respectively, which are used as raw materials, are known, or can be easily produced by the known method such as Tetrahedron Letters, 2002, Vol. 43, No. 22, p.4059-4061 and WO 2000/52032 and the like.

In each reaction in the present specification, a reaction accompanying heating can be performed using a water bath, an oil bath, a sand bath or a microwave as apparent to a person skilled in the art.

In each reaction in the present specification, conveniently, a solid phase-supporting reagent supported by a high-molecular polymer (e.g. polystyrene, polyacrylamide, polypropylene, polyethylene glycol etc.) may be used.

In each reaction in the present specification, the reaction product can be purified by the ordinary purification means, for example, a method such as distillation under ordinary pressure or under reduced pressure, high performance liquid chromatography using silica gel or magnesium silicate, thin layer chromatography, ion exchange resin, scavenger resin, column chromatography, washing, or recrystallization. Purification may be performed for every reaction, or may be performed after completion of several reactions.

[Toxicity]

Since toxicity of the present compound is low, it can be used safely as a medicament.

[Application to Medicaments]

The present compound is useful as an agent for preventing or treating urinary excretion disorder, particularly, a urinary excretion disorder accompanied with prostatomegaly and/or improving symptoms thereof accompanied with urinary excretion disorder (slowing of urinary stream, division of urinary stream, interruption of urinary stream, delayed urination, straining at urination, terminal dribbling etc.), or an agent for preventing and/or treating cancer, interstitial pneumonia or pulmonary fibrosis, renal fibrosis, hepatic fibrosis, sclerodermia, pain, fibromyalgia or rheumatoid arthritis.

The present compound may be administered by combining with other drug, (1) complementing and/or enhancing the preventing, treating and/or symptom improving effect thereof, (2) improving dynamics or absorption thereof, reducing a dose thereof, and/or (3) reducing the side effect thereof.

In case that the present compound is used as an agent for preventing and/or treating urinary excretion disorder, and/or improving symptoms thereof accompanied with urinary excretion disorder, it may be administered by combining with an α1 blocker (e.g. tamsulosin, silodosin, prazosin, terazosin, bunazosin, alfuzosin, indoramin, naftopidil, doxazosin mesilate, urapidil, AIO-8507L etc.) and the like, an acetylcholinesterase inhibitor (e.g.distigmine, neostigmine etc.), a 5α-reductase inhibitor (e.g. finasteride, GI-998745 etc.) or an anti-androgen agent (e.g. oxendolone, osaterone acetate, bicalutamide etc.).

A concomitant agent of the present compound and other drug may be administered in a form of a compounding agent in which both ingredients are incorporated in one preparation, or may take a form in which both ingredients are administered by formulating into separate preparations. When administered by formulating into separate preparations, simultaneous administration and administration at different times are included. And, administration at different times may be such that the present compound is administered first, and other drug is administered later, or other drug is administered first, and the present compound is administered later, and respective administration methods may be the same or different.

A dose of the aforementioned other drug can be appropriately selected based on a dose which is clinically used. And, a compounding ratio of the present compound and other drug can be appropriately selected depending on an age and a weight of a subject to be administered, an administration method, an administration time, a target disease, symptom, a combination and the like. For example, other drug may be used at 0.01 to 100 parts by mass based on 1 part by mass of the present compound. Other drug may be administered by combining arbitrary two or more kinds at an appropriate proportion. And, the aforementioned drug includes not only drugs which have been found out up to now, but also drugs which will be found out from now on.

In order to use the present compound or a concomitant agent of the present compound and other drug for the aforementioned purpose, usually, it is systemically or locally administered in an oral or parenteral form.

A dose of the present compound is different depending on an age, a weight, symptom, therapeutic effect, an administration method, a treatment time and the like, but usually, the present compound is orally administered in a range of 1 µg to 1 g per once per adult, once to several times a day, or parenterally administered in a range of 0.1 µg to 300 mg per once per adult, once to several times a day, or intravenously continuously administered in a range of 1 hour to 24 hours a day.

Of course, as described above, since a dose varies depending on a variety of conditions, the dose is sufficient at a dose smaller than the aforementioned dose in some cases, or administration beyond the range is required in some cases.

When the present compound or a concomitant agent of the present compound and other drug is administered, it is used as a solid agent for internal use or a solution for oral administration (internal use), a sustained-release preparation in oral administration, or injectables, external preparations, inhalants or suppositories for parenteral administration.

The solid preparation for oral administration (internal use)includes, for example, tablets, pills, capsules, powders and granulars. The capsules include hard capsules and soft capsules.

In such the solid agent for internal use, one or more active substances are formulated into preparations as they are, or after mixing with excipients (e.g. lactose, mannitol, glucose, microcrystalline cellulose, starch etc.), binders (e.g. hydroxypropylcellulose, polyvinyl pyrrolidone, magnesium aluminate metasilicate etc.), disintegrating agents (e.g. calcium carboxymethylcellulose etc.), lubricants (e.g. magnesium stearate etc.), stabilizers, solubilization aids (e.g. glutamic acid, aspartic acid etc.) or the like, according to the conventional method, and are used. Alternatively, if necessary, active substances may be covered with coating agents (e.g. white sugar, gelatin, hydroxylpropylcellulose, hydroxypropylmethylcellulose phthalate etc.), or may be covered with two or more layers. Further, capsules of substances which can be absorbed, such as gelatin, are also included.

The liquid for oral administration (internal use) includes pharmaceutically acceptable solutions, suspensions, emulsions, syrups and elixirs. In such the liquid formulations, one or more active substances are dissolved, suspended or emulsified in diluents (e.g. purified water, ethanol, or mixed liquids of them etc.) which are generally used. Further, this liquid formulation may contain wetting agents, suspending agents, emulsifiers, sweeteners, flavors, fragrances, preservatives or buffers.

And, sustained-release preparations in oral administration are also effective. A gel forming substance used in these sustained-release preparations is a substance which is swollen while containing a solvent, thereby, mutually linking colloidal particles thereof to have a three dimensional network structure, and can form a jelly-like body which has no flowability. The substance is mainly used as binders, thickeners and sustained-release bases from a view point of preparations. For example, gum arabic, agar, polyvinyl pyrrolidone, sodium alginate, alginic acid propylene glycol ester, carboxyvinyl polymer, carboxymethylcellulose, carboxymethylcellulose sodium, guar gum, gelatin, hydroxypropylmethylcellulose, hydroxypropylcellulose, polyvinyl alcohol, methylcellulose or hydroxyethylmethylcellulose can be used.

Injectables for parenteral administration include solutions, suspensions, emulsions and solid injectables which are used by dissolving or suspending in a solvent upon use. Injectables are used by dissolving, suspending or emulsifying one or more active substances in a solvent. As the solvent, for example, distilled water for injection, physiological saline, vegetable oil, alcohols such as propylene glycol, polyethylene glycol, and ethanol and the like, and a combination of them are used. Further, the injectables may contain stabilizers, solubilization aids (e.g. glutamic acid, aspartic acid, Polysorbate 80 (registered trademark) etc.), suspending agents, emulsifiers, soothing agents, buffers or preservatives. These are produced by sterilization or a sterile operation method at a final step. Alternatively, injectables can be also used as aseptic solid agents (e.g. lyophilized products are produced, and dissolved in distilled water for injection or other solvent which has been sterilized or are aseptic, before use thereof).

A dosage form of the external preparations for parenteral administration includes, for example, sprays, inhalants, spraying agents, aerosols, ointments, gels, creams, fomentations, patches, liniments and nose drops. These contain one or more active substances, and prepared by the known method or formulation which is ordinarily used.

Sprays, inhalants and spraying agents may contain stabilizers such as sodium hydrogen sulfite and buffers imparting isotonicity, for example, isotonics such as sodium chloride, sodium citrate or citric acid, in addition to diluents which are generally used. A method of producing spraying agents is described in detail, for example, in U.S. Pat. Nos. 2,868,691 and 3,095,355.

The inhalants for parenteral administration include aerosols, powders for inhalation or solutions for inhalation, and the solutions for inhalation may be a form which is used by dissolving or suspending in water or other suitable medium upon use.

These inhalants are produced in accordance with the known method.

For example, in the case of solutions for inhalation, they are prepared by appropriately selecting antiseptics (e.g benzalkonium chloride, paraben etc.), colorants, buffering agents (e.g. sodium phosphate, sodium acetate etc.), isotonizing agents (e.g. sodium chloride, concentrated glycerin etc.), thickeners (e.g. carboxyvinyl polymer etc.), absorption enhancers and the like, if necessary.

In the case of powders for inhalation, they are prepared by appropriately selecting lubricants (e.g. stearic acid and a salt thereof etc.), binders (e.g. starch, dextrin etc.), excipients (e.g. lactose, cellulose etc.), colorants, antiseptics (e.g benzalkonium chloride, paraben etc.) or absorption enhancers, if necessary.

When solutions for inhalation are administered, usually, a sprayer (e.g. atomizer, nebulizer etc.) is used and, when powders for inhalation are administered, usually, an inhalation administration equipment for powdery drugs is used.

Ointments are produced by formulation which is known or ordinarily used. For example, ointments are prepared by kneading or melting one or more active substances in a base. An ointment base is selected from ointment bases which are known or orginarily used. For example, ointment bases selected from higher fatty acid or higher fatty acid ester (e.g. adipic acid, myristic acid, palmitic acid, stearic acid, oleic acid, adipic acid ester, myristic acid ester, palmitic acid ester, stearic acid ester, oleic acid ester etc.), waxes (e.g. beeswax, whale wax, ceresin etc.), surfactants (e.g. polyoxyethylene alkyl ether phosphoric acid ester etc.), higher alcohols (e.g. cetanol, stearyl alcohol, cetostearyl alcohol etc.), silicone oils (e.g. dimethylpolysiloxane etc.), hydrocarbons (e.g. hydrophilic vaseline, white vaseline, purified lanolin, liquid paraffin etc.), glycols (e.g. ethylene glycol, diethylene glycol, propylene glycol, polyethylene glycol, macrogol etc.), vegetable oils (e.g. castor oil, olive oil, sesame oil, turpentine oil etc.), animal oils (e.g. mink oil, yolk oil, squalane, squalene etc.), water, absorption enhancers or rash preventing agents are used alone, or by mixing two or more kinds. Further, ointment bases may contain humectants, preservatives, stabilizers, antioxidants or flavoring agents.

Gel agents are produced by formulation which is known or ordinarily used. For example, gel agents are prepared by melting one or more active substances in a base. A gel base is selected from gel bases which are known or ordinarily used. For example, gel bases selected from lower alcohols (e.g. ethanol, isopropyl alcohol etc.), gelling agents (e.g. carboxymethylcellulose, hydroxyethylcellulose, hydroxypropylcellulose, ethylcellulose etc.), neutralizing agents (e.g. triethanolamine, diisopropanolamine etc.), surfactants (e.g. monostearic acid polyethylene glycol etc.), gums, water, absorption enhancers and rash preventing agents are used alone, or by mixing two or more kinds. Further, gel bases may contain preservatives, antioxidants or flavoring agents.

Creams are prepared by formulation which is known or ordinarily used. For example, creams are prepared by melting or emulsifying one or more active substances in a base. A cream base is selected from cream bases which are known or ordinarily used. For example, cream bases selected from higher fatty acid esters, lower alcohols, hydrocarbons, polyhydric alcohols (e.g. propylene glycol, 1,3-butylene glycol etc.), higher alcohols (e.g. 2-hexyldecanol, cetanol etc.), emulsifiers (e.g. polyoxyethylene alkyl ethers, fatty acid esters etc.), water, absorption enhancers and rash preventing agents are used alone, or by mixing two or more kinds. Further, cream bases may contain preservatives, antioxidants or flavoring agents.

Fomentations are produced by formulation which is known or ordinarily used. For example, fomentations are produced by melting one or more active substances in a base, and spreading and coating a melt as a kneaded product on a support. A fomentation is selected from fomentations which are known or ordinarily used. For example, fomentations selected from thickeners (e.g. polyacrylic acid, polyvinyl pyrrolidone, gum arabic, starch, gelatin, methylcellulose etc.), wetting agents (e.g. urea, glycerin, propylene glycol etc.), fillers (e.g. kaolin, zinc oxide, talc, calcium, magnesium etc.), water, solubilization aids, tackiness imparting agents and rash preventing agents are used alone, or by mixing two or more kinds. Further, fomentations may contain preservatives, antioxidants or flavoring agents.

Patches are produced by formulation which is known or ordinarily used. For example, patches are produced by melting one or more active substances in a base, and spreading and coating a melt on a support. A base for patches is selected from bases for patches which are known or ordinarily used. For example, bases for patches selected from polymer bases, fats and oils, higher fatty acids, tackiness imparting agents and rash preventing agents are used alone, or by mixing two or more kinds. Further, bases for patches may contain preservatives, antioxidants or flavoring agents.

Liniments are produced by formulation which is known or ordinarily used. For example, liniments are prepared by dissolving, suspending or emulsifying one or more active substances in a base selected from water, alcohols (e.g. ethanol, polyethylene glycol etc.), higher fatty acid, glycerin, soaps, emulsifiers and suspending agents alone, or two or more kinds of them. Further, liniments may contain preservatives, antioxidants or flavoring agents.

Other composition for parenteral administration includes suppositories for rectal administration or pessaries for intravaginal administration, which contain one or more active substances, and are formulated by the conventional method.

An entire content of all patent documents and non-patent documents or reference documents which are explicitly cited in the present specification is cited herein as a part of the present specification.

EXAMPLES

The present invention will be described in detail below by way of Examples and Biological Example. The present invention is not limited to them, but the present compound does not include compounds shown in Reference manufacturing examples and reference Examples. A name of the compound of the present invention and a name of compounds shown in Examples were named by ACD/Name (version 6.00, manufactured by Advanced Chemistry Development Inc.).

A solvent in parenthesis shown at places of separation by chromatography and in TLC indicates an elution solvent or a development solvent used, and a proportion indicates a volumetric ratio. The numerical value shown at places of NMR is a measurement value of $^1$H-NMR when a described measurement solvent is used.

The reverse phase high performance liquid chromatography analysis conditions for measuring a HPLC retention time are as follows:

Instrument used: Waters LC/MS

Mass spectrometer: ZMD 4000 manufactured by Waters

ELSD detector: 75 ELS detector manufactured by Sedex

Column: UNIZON US-C18, 5 µm, 50×4.6 mm

Column temperature: 50° C.

Flow rate: 3 mL/min

Mobile phase A: 0.1% (trifluoroacetic acid-5% methanol)/aqueous solution

Mobile phase B: 0.1% trifluoroacetic acid-methanol solution
LC-MS/ELS Gradient:

TABLE 1

| Time (min) | % A | % B |
|---|---|---|
| 0 | 95 | 5 |
| 0.5 | 95 | 5 |
| 3 | 0 | 100 |
| 3.5 | 0 | 100 |
| 3.51 | 95 | 5 |
| 5 | 95 | 5 |

Reference Manufacturing Example 9-(3-phenylpropyl)-2,3,4,9-tetrahydro-1H-beta-carboline hydrochloride

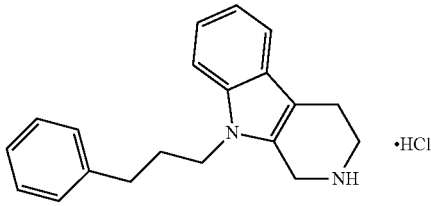 [SMILES: c1ccc(CCCn2c3c(c4ccccc42)CCNC3)cc1 ; Cl]

Tert-butyl 1,3,4,9-tetrahydro-2H-β-carboline-2-carboxylate (CAS No. 168824-94-0) (545 mg) was dissolved in N,N-dimethylformamide (5 mL), (3-bromopropyl)benzene (478 mg), tetrabutylammonium bromide (32 mg) and cesium carbonate (782 mg) were sequentially added and, the mixture was stirred at 60° C. for 4 hours. The reaction mixture was cooled to room temperature, and poured into water, followed by extraction with ethyl acetate. The organic layer was washed sequentially with water and an aqueous satuarated sodium chloride solution, dried with anhydrous magnecium sulfate, and concentrated. The residue was purified by silica gel column chromatography (hexane:ethyl acetate=9:1). Further, to the resulting compound (162 mg) was added a 4N hydrogen chloride dioxane solution (3 mL) at room temperature, and the mixture was stirred for 1 hour. The reaction mixture was concentrated to obtain the title compound (121 mg) having the following physical property values.

TLC:Rf 0.47 (chloroform:methanol=9:1);
$^1$H-NMR (DMSO-$d_6$):δ 1.84-2.04 (m, 2 H), 2.55-2.66 (m, 2 H), 2.94 (t, J=5.5 Hz, 2 H), 3.41 (t, J=5.5 Hz, 2 H), 4.12 (t, J=7.3 Hz, 2 H), 4.40 (s, 2 H), 7.00-7.10 (m, 1 H), 7.10-7.22 (m, 4 H), 7.22-7.34 (m, 2 H), 7.41 (d, J=8.2 Hz, 1 H), 7.47 (d, J=7.7 Hz, 1 H), 9.67 (s, 2 H).

Reference Manufacturing Example 2

6-oxo-6-[9-(3-phenylpropyl)-1,3,4,9-tetrahydro-2H-beta-carbolin-2-yl]hexanoate

To a pyridine (1 ml) solution of the compound (100 mg) produced in Reference manufacturing example 1 was added methyl 6-chloro-6-oxohexanoate (0.052 mL) at room temperature, and the mixture was stirred for 2 hours. To the reaction mixture was added water, followed by extraction with ethyl acetate. The extract was sequentially washed with water and an aqueous saturated sodium chloride solution, dried with anhydrous magnesium sulfate, and concentrated. The residue was purified by silica gel column chromatography (hexane:ethyl acetate=6:4) to obtain the title compound (90 mg) having the following physical property values.

TLC:Rf 0.45 (hexane:ethyl acetate=1:1);
$^1$H-NMR (CDCl$_3$):δ 1.57-1.86 (m, 4 H) 2.00-2.25 (m, 2 H) 2.33-2.42 (m, 2 H) 2.45-2.57 (m, 2 H) 2.59-2.96 (m, 4 H) 3.62-3.71 (m, 3 H) 3.71-3.97 (m, 2 H) 3.97-4.12 (m, 2 H) 4.41-4.87 (m, 2 H) 7.05-7.36 (m, 8 H) 7.43-7.54 (m, 1 H).

Reference Manufacturing Example 3

6-oxo-6-[9-(3-phenylpropyl)-1,3,4,9-tetrahydro-2H-beta-carbolin-2-yl]hexanoic acid

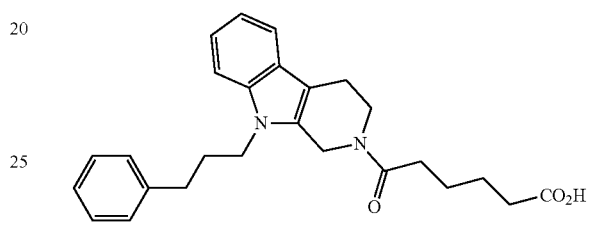

To a mixed solution of the compound (83 mg) produced in Reference manufacturing example 2 in ethylene glycol dimethyl ether (1 mL) and methanol (1 mL) was added a 1 N aqueous sodium hydroxide solution (1 mL) at room temperature, and the mixture was stirred for 2 hours. To the reaction mixture was added 1 N hydrochloric acid (1 mL) and water, followed by extraction with ethyl acetate. The extract was washed with an aqueous saturated sodium chloride solution, dried with anhydrous sodium sulfate, and concentrated. The residue was purified by silica gel column chromatography (chloroform:methanol:water=50:10:1) to obtain the title compound (66 mg) having the following physical property values.

TLC:Rf 0.50 (chloroform:methanol:water=50:10:1);
$^1$H-NMR (CDCl$_3$):δ 1.61-1.89 (m, 4 H) 1.99-2.21 (m, 2 H) 2.30-2.59 (m, 4 H) 2.60-2.76 (m, 2 H) 2.75-2.94 (m, 2 H) 3.69-3.97 (m, 2 H) 3.87-4.11 (m, 2 H) 4.42-4.84 (m, 2 H) 5.52-6.86 (m, 1 H) 7.03-7.38 (m, 8 H) 7.42-7.54 (m, 1 H).

Example 1

6-oxo-6-{9-[3-(trifluoromethyl)benzyl]-1,3,4,9-tetrahydro-2H-beta-carbolin-2-yl}hexanoic acid A β-carboline derivative produced by operation in accordance with Reference manufacturing example 1, and a corresponding carboxylic acid halide in place of methyl 6-chloro-6-oxohexanoate were used, which were subjected to operation in accordance with Reference manufacturing example 2 and further subjected to operation in accordance with Reference manufacturing example 3, to obtain the title compound having the following physical property values.

TLC:Rf 0.46 (chloroform:methanol:water=50:10:1);
$^1$H-NMR (DMSO-$d_6$):δ 1.32-1.66 (m, 4 H) 2.07-2.49 (m, 4 H) 2.59-2.90 (m, 2 H) 3.66-3.88 (m, 2 H) 4.55-4.69 (m, 2 H) 5.46-5.56 (m, 2 H) 6.96-7.67 (m, 8 H) 11.69-12.28 (m, 1 H).

Reference Manufacturing Example 4

N,N-dimethyl-1-(1H-pyrrolo[2,3-b]pyridin-3-yl)methanamine

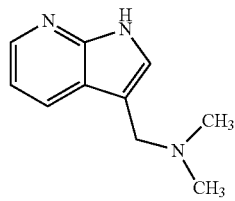

To a mixture of 7-azaindole (150 g), dimethylamine hydrochloride (114 g) and 1-butanol (1.275 L) was added a 37% aqueous formaldehyde solution (103 g), and the mixture was stirred on a 120° C. oil bath for 2.5 hours. The reaction solution was cooled to around 40° C., and placed into water (1.35 L), concentrated hydrochloric acid (54 mL) and methyl tert-butyl ether (MTBE) (630 mL) were added, the mixture was stirred, the layers were separated, and the aqueous layer was taken. This aqueous layer was further washed with MTBE, and a 48% aqueous sodium hydroxide solution was added. This was extracted with chloroform, and a small amount of methanol was added to the extraction solution, followed by drying with anhydrous sodium sulfate. A desiccant was distilled off, followed by concentration under reduced pressure, to obtain the title compound (179 g) having the following physical property values.

TLC:Rf 0.29 (chloroform:methanol:water=50:10:1);
$^1$H-NMR (CDCl$_3$):δ 2.27 (s, 6 H) 3.60 (s, 2 H) 7.08 (dd, J=8.00, 5.00 Hz, 1 H) 8.06 (dd, J=8.00, 1.50 Hz, 1 H) 8.31 (dd, J=5.00, 1.50 Hz, 1 H) 9.80 (s, 1 H).

Reference Manufacturing Example 5

3-(2-nitroethyl)-1H-pyrrolo[2,3-b]pyridine

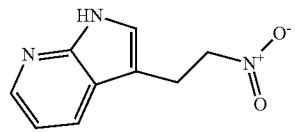 [SMILES: O=[N+]([O-])CCc1c[nH]c2ncccc12]

The compound (70.8 g) produced in Reference manufacturing example 4 was dissolved in a mixed solution of methanol (600 mL) and nitromethane (600 mL), the solution was cooled to 6° C., dimethyl sulfate (42 mL) was added for about 30 seconds and, thereafter, the mixture was stirred on an ice bath for about 4 minutes. After stirred at room temperature for 15 minutes, the mixture was cooled again with an ice, and a 28% sodium methoxide/methanol solution (90.6 mL) was added dropwise for 14 minutes. The ice bath was removed, the mixture was stirred for 1.5 hours, and the precipitated pale yellowish white powder was filtered off. To the filtrate was added toluene (600 mL), this was concentrated on a 30° C. water bath under reduced pressure to obtain a yellowish white paste. To this were added ethyl acetate (600 mL) and an aqueous saturated sodium bicarbonate solution (1200 mL), this was shaken well to mix, insolubles (pale yellowish white powder) were filtered off using Celite, and layers were separated. The aqueous layer was extracted with ethyl acetate (600 mL), and the organic layers were combined, washed with an aqueous saturated sodium chloride solution (300 mL), and dried with anhydrous sodium sulfate. The solvent was distilled off under reduced pressure to obtain the title compound (51.25 g) having the following physical property values.

TLC:Rf 0.68 (chloroform:methanol:water=50:10:1);
$^1$H-NMR (CDCl$_3$):δ 3.49 (t, J=7.0 Hz, 2 H) 4.67 (t, J=7.0 Hz, 2 H) 7.12 (dd, J=8.00, 5.00 Hz, 1 H) 7.91 (dd, J=8.00, 1.50 Hz, 1 H) 8.34 (dd, J=5.00, 1.50 Hz, 1 H) 9.60 (s, 1 H).

Reference Manufacturing Example 6

2-(1H-pyrrolo[2,3-b]pyridine-3-yl)ethanamine

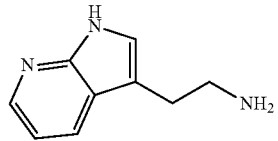 [SMILES: NCCc1c[nH]c2ncccc12]

The compound (114.9 g) produced in Reference manufacturing example 5 was suspended in ethanol (1.15 L), and 20% palladium hydroxide/carbon (50% hydrous product, 57.7 g) was added. The mixture was stirred on a water bath at 70° C. for about 8 hours under the hydrogen atmosphere. After a temperature was returned to room temperature, the reaction was allowed to stand overnight under the nitrogen atmosphere, hydrogen replacement operation was performed again, and the reaction was stirred on a water bath at 70° C. for about 8 hours under the hydrogen atmosphere. After a temperature was returned to room temperature, a catalyst was filtered off using Celite. The filtrate was concentrated under reduced pressure to obtain the title compound (99.6 g) having the following physical property values.

TLC:Rf 0.14 (chloroform:methanol:water=90:10:1);
$^1$H-NMR (CDCl$_3$):δ 2.89 (t, J=6.5 Hz, 2 H) 3.01 (t, J=7.0 Hz, 2 H) 7.07 (dd, J=8.00, 5.00 Hz, 1 H) 7.15 (s, 1 H) 7.92 (dd, J=8.00, 1.50 Hz, 1 H) 8.29 (dd, J=5.00, 1.50 Hz, 1 H) 10.12 (s, 1 H).

Reference Manufacturing Example 7

6,7,8,9-tetrahydro-5H-pyrido[4',3':4,5]pyrrolo[2,3-b]pyridine hydrochloride

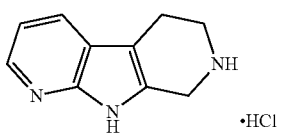 [SMILES: c1cnc2[nH]c3c(c2c1)CCNC3 ; Cl]

The compound (99.6 g) produced in Reference manufacturing example 6 was dissolved in ethanol (2.89 L), a 4M hydrogen chloride/1,4-dioxane solution (150.5 mL) and a 37% aqueous formaldehyde solution (53.65 g) were added, and the mixture was heated to reflux for 3 hours. After allowed to cool to below 40° C., the reaction was diluted with diisopropyl ether (IPE) (3.4 L) and MTBE (2.38 L), and a crystal was filtered off. This crystal was washed with about 500 mL of MTBE, and dried under reduced pressure to obtain the title compound (85.72 g) having the following physical property values.

TLC:Rf 0.27 (chloroform:methanol:28% aqueous ammonia=90:10:1);

¹H-NMR (CDCl₃):δ 2.94 (t, J=6.0 Hz, 2 H) 3.40-3.44 (m, 2 H) 4.33 (s, 2 H), 7.14 (dd, J=8.00, 5.00 Hz, 1 H) 8.01 (dd, J=8.00, 1.50 Hz, 1 H) 8.23 (dd, J=5.00, 1.50 Hz, 1 H) 9.75 (s, 2 H), 11.87 (s, 1 H).

Reference Manufacturing Example 8 tert-butyl 5,6,8,9-tetrahydro-7H-pyrido[4',3':4,5]pyrrolo[2,3-b]pyridine-7-carboxylate

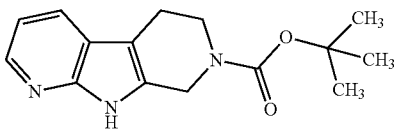 [SMILES: CC(C)(C)OC(=O)N1CCc2c([nH]c3ncccc23)C1]

The compound (95.9 g) produced in Reference manufacturing example 7 was suspended in 1,4-dioxane (1.94 L), and a 1M aqueous sodium hydroxide solution (480 mL, 0.48 mol) was added. This solution was cooled with ice, di-tert-butyl dicarbonate (104.8 g) was added, and the mixture was stirred at room temperature for 12.5 hours. The reaction solution was placed into an aqueous saturated sodium dicarbonate solution (6 L), followed by extraction with ethyl acetate (2 L) three times. The extract solution was washed with an aqueous saturated sodium chloride solution (2 L), dried using anhydrous sodium sulfate, and concentrated under reduced pressure. The resulting pale brown solid was treated with a silica gel column (ethyl acetate) to collect target fractions. The solvent was distilled off under reduced pressure, hexane (880 mL) was added, and this was mixed, and allowed to stand overnight at room temperature. A crystal was filtered off, washed using a mixed solution (150 mL) of hexane:ethyl acetate (10:1) and dried at room temperature under reduced pressure to obtained the title compound (72.1 g) having the following physical property values.

TLC:Rf 0.60 (chloroform:methanol:28% aqueous ammonia=90:10:1);

¹H-NMR (CDCl₃):δ 1.51 (s, 9 H) 2.79 (t, J=6.0 Hz, 2 H) 3.79 (t, J=6.0 Hz, 2 H) 4.71 (s, 2 H), 7.05 (dd, J=8.00, 5.00 Hz, 1 H) 7.79 (m, 1 H) 8.23 (m, 1 H) 10.10-10.75 (m, 1 H).

Reference Manufacturing Example 9

6-[9-(3-fluorobenzyl)-5,6,8,9-tetrahydro-7H-pyrido[4',3':4,5]pyrrolo[2,3-b]pyridin-7-yl]-6-oxohexanoic acid

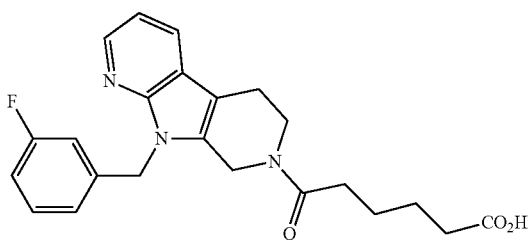 [SMILES: O=C(O)CCCCC(=O)N1CCc2c(n(Cc3cccc(F)c3)c3ncccc23)C1]

The compound produced in Reference manufacturing example 8 in place of tert-butyl 1,3,4,9-tetrahydro-2H-β-carboline-2-carboxylate, and 1-(bromomethyl)-3-fluorobenzene in place of (3-bromopropyl)benzene were used, which were subjected to operation in accordance with Reference manufacturing example 1→Reference manufacturing example 2→Reference manufacturing example 3 to obtain the title compound (81.5 mg) having the following physical property values.

TLC:Rf 0.43 (chloroform:methanol:water=50:10:1);

¹H-NMR (DMSO-d₆):δ 1.31-1.66 (m, 4 H) 2.09-2.48 (m, 4 H) 2.57-2.89 (m, 2 H) 3.63-3.89 (m, 2 H) 4.55-4.69 (m, 2 H) 5.42-5.54 (m, 2 H) 6.85-7.15 (m, 4 H) 7.26-7.40 (m, 1 H) 7.84-7.94 (m, 1 H) 8.16-8.25 (m, 1 H) 11.93 (s, 1 H).

Example 2(1)-Example 2(2)

A corresponding alkyl halide in place of 1-(bromomethyl)-3-fluorobenzene, and the compound produced in Reference manufacturing example 8 in place of tert-butyl 1,3,4,9-tetrahydro-2H-β-carboline-2-carboxylate were used, which were subjected to operation in accordance with Reference manufacturing example 1 and, further, a corresponding ester in place of methyl 6-chloro-6-oxohexanoate was used, which was subjected to operation in accordance with Reference manufacturing example 2→Reference manufacturing example 3 to obtain the following compounds.

Example 2(1)

6-oxo-6-{9-[3-(trifluoromethyl)benzyl]-5,6,8,9-tetrahydro-7H-pyrido[4',3':4,5]pyrrolo[2,3-b]pyridin-7-yl}hexanoic acid TLC:Rf 0.47 (ethyl acetate);

¹H-NMR (CDCl₃):δ 1.46-1.86 (m, 4 H), 2.10-2.56 (m, 4 H), 2.73-2.97 (m, 2 H), 3.67-4.00 (m, 2 H), 4.35-4.78 (m, 2 H), 5.41-5.61 (m, 2 H), 7.02-7.16 (m, 1 H), 7.17-7.32 (m, 1 H), 7.32-7.62 (m, 3 H), 7.74-7.92 (m, 1 H), 8.22-8.40 (m, 1 H).

Example 2(2)

6-(9-{[3-(2-furyl)-1-methyl-1H-pyrazol-5-yl]methyl}-5,6,8,9-tetrahydro-7H-pyrido[4',3':4,5]pyrrolo[2,3-b]pyridin-7-yl)-6-oxohexanoic acid HPLC retention time (min): 4.04;
MS (ESI, Pos. 20 V): m/z=462 (M+H)⁺.

Reference Manufacturing Example 10

6-methoxy-5,5-dimethyl-6-xohexanoic acid

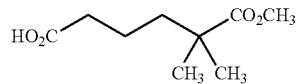

To tetrahydrofuran (THF) (180 mL) was added a 2.0M lithium diisopropylamide/THF-ethylbenzene-heptane solution (272 mL), the mixture was cooled to −68° C. in a dry ice-methanol bath, and a solution of methyl isobutyrate (55.38 g) in THF (180 mL) was added dropwise at −64° C. or lower for 50 minutes. The mixture was stirred at around −65° C. for 1 hour, and then a solution of [(4-bromobutoxy)methyl]benzene (40.0 g) and hexamethylphosphoric acid triamide (29.48 g) in THF (90 mL) was added dropwise at −62° C. or lower for about 30 minutes. After the mixture was stirred at the same temperature for 30 minutes, the dry ice bath was removed, followed by stirring for about 1.5 hours. The reaction solution was placed into an aqueous saturated ammonium chloride solution (1.4 L), followed by extraction with a mixed solution (1.6 L) of hexane:ethyl acetate (3:1). The extract solution was washed with water and an aqueous saturated sodium chloride solution, dried with anhydrous sodium sulfate, and concentrated under reduced pressure. The resulting orange liquid was treated with a silica gel column (hexane:ethyl acetate=15:1). The resulting compound (82.0 g) was dissolved in methanol (820 mL), a 4N hydrogen chloride/1,4-dioxane solution (82 mL) and 10% palladium carbon (50% hydrous product, 8.2 g) were added, and hydrogen was blown into the solution for 3.5 hours while stirring on a hot bath at 50° C. After cooled to room temperature, the system was replaced with nitrogen, and the catalyst was filtered off using Celite, followed by concentration under reduced pressure. Operation of adding toluene to the residue, and concentrating this again under reduced pressure was performed two times, followed by purification with a silica gel column (hexane:ethyl acetate=4:1→2:1). The resulting compound (23.88 g), carbon tetrachloride (170 mL) and sodium periodate (65.9 g) were added to a mixed solution of water (255 mL) and acetonitrile (170 mL), and then ruthenium trichloride (n-hydrate) (716 mg) was added for about 3 minutes in portions. After stirred at room temperature for 4 hours, the reaction mixture was dispersed in water (0.8 L), followed by extraction with ethyl acetate. After the extract solution was washed with water, an aqueous saturated sodium chloride solution was added, the mixture was stirred and filtered with Celite, and layers were separated. The organic layer was dried with anhydrous sodium sulfate, and concentrated under reduced pressure. The resulting residue was dissolved in toluene, and concentration operation was performed two times to obtain the title compound (27.2 g) having the following physical property values.

TLC:Rf 0.36 (hexane:ethyl acetate=1:1);
$^1$H-NMR (CDCl$_3$):δ 1.18 (s, 6 H) 1.51-1.64 (m, 4 H) 2.30-2.39 (m, 2 H) 3.66 (s, 3 H).

Reference Manufacturing Example 11 methyl 6-[9-(3-fluorobenzyl)-5,6,8,9-tetrahydro-7H-pyrido[4',3':4,5]pyrrolo[2,3-b]pyridin-7-yl]-2,2-dimethyl-6-oxohexanoate To a solution of the compound produced in Reference manufacturing example 10 (77 mg), and 9-(3-fluorobenzyl)-6,7,8,9-tetrahydro-5H-pyrido[4',3':4,5]pyrrolo[2,3-b]pyridine (120 mg) in N,N-dimethylformamide (2.5 mL) were added triethylamine (0.075 mL), EDC (115 mg) and HOBt (67 mg) at room temperature, and the mixture was stirred for 3 hours. To the reaction mixture were added an aqueous saturated sodium hydroxide solution and water, followed by extraction with ethyl acetate. The extract was sequentially washed with water and an aqueous saturated sodium chloride solution, dried with anhydrous magnesium sulfate, and concentrated. The residue was purified by silica gel column chromatography (hexane:ethyl acetate=6:4) to obtain the title compound (133 mg) having the following physical property values.

TLC:Rf 0.55 (hexane:ethyl acetate=1:1);
$^1$H-NMR (CDCl$_3$):δ 1.11-1.23 (m, 6 H) 1.42-1.72 (m, 4 H) 2.09-2.49 (m, 2 H) 2.71-2.93 (m, 2 H) 3.57-3.68 (m, 3 H) 3.68-3.96 (m, 2 H) 4.39-4.71 (m, 2 H) 5.39-5.52 (m, 2 H) 6.71-6.82 (m, 1 H) 6.83-7.01 (m, 2 H) 7.02-7.14 (m, 1 H) 7.17-7.31 (m, 1 H) 7.73-7.86 (m, 1 H) 8.25-8.34 (m, 1 H).

Reference Manufacturing Example 12

6-[9-(3-fluorobenzyl)-5,6,8,9-tetrahydro-7H-pyrido[4',3':4,5]pyrrolo[2,3-b]pyridin-7-yl]-2,2-dimethyl-6-oxohexanoic acid

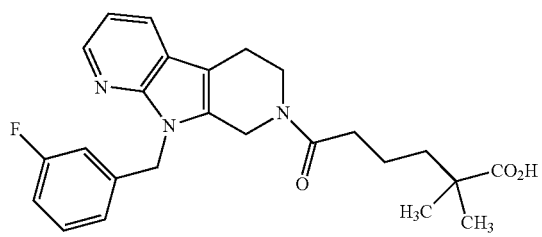 [SMILES: CC(C)(CCCC(=O)N1CCc2c(n(Cc3cccc(F)c3)c3ncccc23)C1)C(=O)O]

The compound produced in Reference manufacturing example 11 was subjected to operation in accordance with Reference manufacturing example 3 to obtain the title compound having the following physical property values.

TLC:Rf 0.49 (chloroform:methanol:water=50:10:1);
$^1$H-NMR (DMSO-d$_6$):δ 0.96-1.13 (m, 6 H) 1.32-1.53 (m, 4 H) 2.22-2.46 (m, 2 H) 2.62-2.84 (m, 2 H) 3.67-3.83 (m, 2 H) 4.62 (s, 2 H) 5.39-5.56 (m, 2 H) 6.85-7.14 (m, 4 H) 7.27-7.39 (m, 1 H) 7.84-7.94 (m, 1 H) 8.18-8.23 (m, 1 H) 12.00 (s, 1 H).

Example 3(1)-Example 3(58) and Reference example 1

A corresponding alkyl halide in place of (3-bromopropyl)benzene, and a tetrahydropyridopyrrolopyridine derivative (tert-butyl 5,6,8,9-tetrahydro-7H-pyrido[4',3':4,5]pyrrolo[2,3-b]pyridin-7-carboxylate) produced by operation in accordance with Reference manufacturing example 4→Reference manufacturing example 5→Reference manufacturing example 6→Reference manufacturing example 7→Reference manufacturing example 8 or the corresponding β-carboline derivative were used, which were subjected to operation in accordance with Reference manufacturing example 1, and the resulting compound and the compound produced in Reference manufacturing example 10 or the corresponding ester were used, which were subjected to operation in accordance with Reference manufacturing example 11, and further subjected to operation in accordance with Reference manufacturing example 3 to obtain the following compounds.

Example 3(1)

2,2-dimethyl-6-oxo-6-{9-[3-(trifluoromethyl)benzyl]-5,6,8,9-tetrahydro-7H-pyrido[4',3':4,5]pyrrolo[2,3-b]pyridin-7-yl}hexanoic acid TLC:Rf 0.70 (ethyl acetate);
$^1$H-NMR (CDCl$_3$):δ 1.07-1.28 (m, 6 H), 1.42-1.76 (m, 4 H), 2.08-2.53 (m, 2 H), 2.72-2.95 (m, 2 H), 3.67-4.00 (m, 2

H), 4.36-4.74 (m, 2 H), 5.42-5.59 (m, 2 H), 7.02-7.15 (m, 1 H), 7.15-7.31 (m, 1 H), 7.32-7.59 (m, 3 H), 7.73-7.89 (m, 1 H), 8.21-8.41 (m, 1 H).
MS (ESI, Pos. 20 V): m/z=466 (M+H)$^+$.

Example 3(2)

6-[9-(1-benzothiophen-2-ylmethyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 4.48;
MS (ESI, Pos. 20 V): m/z=476 (M+H)$^+$.

Example 3(3)

6-[9-(1-benzothiophen-3-ylmethyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 4.46;
MS (ESI, Pos. 20 V): m/z=476 (M+H)$^+$.

Example 3(4)

6-[9-(1-benzothiophen-5-ylmethyl)-5,6,8,9-tetrahydro-7H-pyrido[4',3':4,5]pyrrolo[2,3-b]pyridin-7-yl]-2,2-dimethyl-6-oxohexanoic acid HPLC retention time (min): 4.40;
MS (ESI, Pos. 20 V): m/z=476 (M+H)$^+$.

Example 3(5)

6-(9-{[3-(2-furyl)-1-methyl-1H-pyrazol-5-yl]methyl}-5,6,8,9-tetrahydro-7H-pyrido[4',3':4,5]pyrrolo[2,3-b]pyridin-7-yl)-2,2-dimethyl-6-oxohexanoic acid HPLC retention time (min): 4.26;
MS (ESI, Pos. 20 V): m/z=490 (M+H)$^+$.

Example 3(6)

2,2-dimethyl-6-{9-[(1-methyl-3-phenyl-1H-pyrazol-5-yl)methyl]-5,6,8,9-tetrahydro-7H-pyrido[4',3':4,5]pyrrolo[2,3-b]pyridin-7-yl}-6-oxohexanoic acid TLC:Rf 0.34 (chloroform:methanol:water=50:10:1);
$^1$H-NMR (DMSO-d$_6$):δ 0.93-1.14 (m, 6 H) 1.29-1.54 (m, 4 H) 2.29-2.47 (m, 2 H) 2.62-2.87 (m, 2 H) 3.70-3.85 (m, 2 H) 3.85-3.96 (m, 3 H) 4.65-4.85 (m, 2 H) 5.54-5.66 (m, 2 H) 6.30-6.54 (m, 1 H) 7.12 (dd, J=8.00, 5.00 Hz, 1 H) 7.19-7.39 (m, 3 H) 7.62-7.75 (m, 2 H) 7.87-7.96 (m, 1 H) 8.20-8.28 (m, 1 H) 12.04 (s, 1 H).

Example 3(7)

2,2-dimethyl-6-{9-[(5-methyl-2-phenyl-1,3-thiazol-4-yl)methyl]-5,6,8,9-tetrahydro-7H-pyrido[4',3':4,5]pyrrolo[2,3-b]pyridin-7-yl}-6-oxohexanoic acid TLC:Rf 0.53 (chloroform:methanol:water=50:10:1);
$^1$H-NMR (DMSO-d$_6$):δ 0.99-1.12 (m, 6 H) 1.38-1.53 (m, 4 H) 2.34-2.47 (m, 2 H) 2.58 (s, 3 H) 2.62-2.86 (m, 2 H) 3.65-3.88 (m, 2 H) 4.77 (br. s., 2 H) 5.54-5.79 (m, 2 H) 7.13 (dd, J=8.00, 5.00 Hz, 1 H) 7.35-7.48 (m, 3 H) 7.74-7.84 (m, 2 H) 7.86-7.94 (m, 1 H) 8.28 (d, 1 H) 12.05 (s, 1 H).

Example 3(8)

2,2-dimethyl-6-oxo-6-(9-{[4-(trifluoromethyl)-2-pyridinyl]methyl}-5,6,8,9-tetrahydro-7H-pyrido[4',3':4,5]pyrrolo[2,3-b]pyridin-7-yl)hexanoic acid TLC:Rf 0.30 (methylene chloride:ethyl acetate:methanol=8:4:1);
$^1$H-NMR (DMSO-d$_6$):δ 0.99-1.12 (m, 6 H), 1.36-1.53 (m, 4 H), 2.28-2.46 (m, 2 H), 2.65-2.84 (m, 2 H), 3.69-3.85 (m, 2 H), 4.66-4.82 (m, 2 H), 5.62-5.70 (m, 2 H), 7.03-7.11 (m, 1 H), 7.60-7.71 (m, 2 H), 7.83-7.92 (m, 1 H), 8.15 (dd, J=4.6, 1.5 Hz, 1 H), 8.73 (d, J=4.8 Hz, 1 H), 12.05 (s, 1 H).

Example 3(9)

2,2-dimethyl-6-oxo-6-(9-{[5-(trifluoromethyl)-3-pyridinyl]methyl}-5,6,8,9-tetrahydro-7H-pyrido[4',3':4,5]pyrrolo[2,3-b]pyridin-7-yl)hexanoic acid MS (LC-MS, ESI, Pos.): m/z=489 (M+H)$^+$.
$^1$H-NMR (DMSO-d$_6$):δ 1.00-1.10 (m, 6 H), 1.36-1.52 (m, 4 H), 2.28-2.47 (m, 2 H), 2.66-2.83 (m, 2 H), 3.70-3.83 (m, 2 H), 4.68-4.76 (m, 2 H), 5.61 (s, 2 H), 7.12 (dd, J=7.8, 4.7 Hz, 1 H), 7.87-7.94 (m, 1 H), 8.01-8.12 (m, 1 H), 8.19-8.24 (m, 1 H), 8.57-8.69 (m, 1 H), 8.87 (s, 1 H), 12.05 (s, 1 H).

Example 3(10)

2,2-dimethyl-6-oxo-6-{9-[3-(trifluoromethoxy)benzyl]-5,6,8,9-tetrahydro-7H-pyrido[4',3':4,5]pyrrolo[2,3-b]pyridin-7-yl}hexanoic acid TLC:Rf 0.56 (chloroform:methanol:water=10:2:0.2);
$^1$H-NMR (DMSO-d$_6$):δ 0.97-1.12 (m, 6 H), 1.32-1.53 (m, 4 H), 2.24-2.51 (m, 2 H), 2.61-2.85 (m, 2 H), 3.65-3.85 (m, 2 H), 4.63 (s, 2 H), 5.45-5.58 (m, 2 H), 7.00-7.30 (m, 4 H), 7.42 (t, J=7.9 Hz, 1 H), 7.86-7.96 (m, 1 H), 8.16-8.26 (m, 1 H), 12.04 (s, 1 H).

Example 3(11)

2,2-dimethyl-6-oxo-6-{9-[4-(trifluoromethoxy)benzyl]-5,6,8,9-tetrahydro-7H-pyrido[4',3':4,5]pyrrolo[2,3-b]pyridin-7-yl}hexanoic acid TLC:Rf 0.33 (hexane:ethyl acetate=1:2);
$^1$H-NMR (DMSO-d$_6$):δ 0.98-1.11 (m, 6 H), 1.33-1.51 (m, 4 H), 2.34-2.47 (m, 2 H), 2.62-2.83 (m, 2 H), 3.68-3.83 (m, 2 H), 4.63 (s, 2 H), 5.46-5.54 (m, 2 H), 7.10 (dd, J=7.8, 4.7 Hz, 1 H), 7.17-7.34 (m, 4 H), 7.90 (dd, J=7.8, 1.5 Hz, 1 H), 8.18-8.23 (m, 1 H), 12.04 (s, 1 H).

Example 3(12)

2,2-dimethyl-6-oxo-6-(9-{[6-(trifluoromethyl)-3-pyridinyl]methyl}-5,6,8,9-tetrahydro-7H-pyrido[4',3':4,5]pyrrolo[2,3-b]pyridin-7-yl)hexanoic acid TLC:Rf 0.32 (methylene chloride:ethyl acetate:methanol=8:4:1);
$^1$H-NMR (DMSO-d$_6$):δ 0.99-1.11 (m, 6 H), 1.36-1.52 (m, 4 H), 2.28-2.47 (m, 2 H), 2.65-2.83 (m, 2 H), 3.70-3.84 (m, 2 H), 4.69 (s, 2 H), 5.58-5.66 (m, 2 H), 7.11 (dd, J=7.8, 4.8

Hz, 1 H), 7.64-7.74 (m, 1 H), 7.79-7.86 (m, 1 H), 7.92 (dd, J=7.8, 1.5 Hz, 1 H), 8.20 (dd, J=4.8, 1.5 Hz, 1 H), 8.59-8.71 (m, 1 H), 12.04 (s, 1 H).

Example 3(13)

6-{9-[4-fluoro-3-(trifluoromethyl)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.49 (chloroform:methanol:water=50:10:1);
$^1$H-NMR (DMSO-$d_6$):δ 0.96-1.12 (m, 6 H), 1.32-1.55 (m, 4 H), 2.23-2.46 (m, 2 H), 2.62-2.84 (m, 2 H), 3.66-3.83 (m, 2 H), 4.64 (s, 2 H), 5.47-5.59 (m, 2 H), 7.10 (dd, J=7.5, 4.5 Hz, 1 H), 7.30-7.47 (m, 2 H), 7.65-7.79 (m, 1 H), 7.86-7.93 (m, 1 H), 8.18-8.25 (m, 1 H), 12.03 (s, 1 H).

Example 3(14)

6-{9-[4-(difluoromethoxy)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.20 (hexane:ethyl acetate=1:2);
$^1$H-NMR (DMSO-$d_6$):δ 0.94-1.15 (m, 6 H), 1.31-1.54 (m, 4 H), 2.33-2.84 (m, 4 H), 3.65-3.85 (m, 2 H), 4.63 (s, 2 H), 5.37-5.53 (m, 2 H), 6.86-7.45 (m, 2 H), 7.83-7.94 (m, 1 H), 8.15-8.26 (m, 1 H), 12.04 (s, 1 H).

Example 3(15)

6-{9-[4-chloro-3-(trifluoromethyl)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.52 (chloroform:methanol:water=50:10:1);
$^1$H-NMR (DMSO-$d_6$):δ 0.95-1.13 (m, 6 H), 1.31-1.54 (m, 4 H), 2.21-2.45 (m, 2 H), 2.62-2.83 (m, 2 H), 3.66-3.83 (m, 2 H), 4.63 (s, 2 H), 5.49-5.61 (m, 2 H), 7.10 (dd, J=7.5, 4.5 Hz, 1 H), 7.20-7.32 (m, 1 H), 7.59-7.66 (m, 1 H), 7.72-7.84 (m, 1 H), 7.86-7.94 (m, 1 H), 8.16-8.24 (m, 1 H), 11.95 (s, 1 H).

Example 3(16)

2,2-dimethyl-6-oxo-6-(9-{[5-(trifluoromethyl)-2-thienyl]methyl}-5,6,8,9-tetrahydro-7H-pyrido[4',3':4,5]pyrrolo[2,3-b]pyridin-7-yl)hexanoic acid TLC:Rf 0.46 (methylene chloride:ethyl acetate:methanol=8:4:1);
$^1$H-NMR (DMSO-$d_6$):δ 0.97-1.14 (m, 6 H), 1.34-1.54 (m, 4 H), 2.30-2.45 (m, 2 H), 2.61-2.82 (m, 2 H), 3.67-3.85 (m, 2 H), 4.76 (s, 2 H), 5.63-5.76 (m, 2 H), 7.07-7.24 (m, 2 H), 7.55 (dd, J=3.7, 1.1 Hz, 1 H), 7.89 (d, J=7.9 Hz, 1 H), 8.25 (d, J=4.8 Hz, 1 H), 12.05 (s, 1 H).

Example 3(17)

6-{9-[3-(difluoromethoxy)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.22 (hexane:ethyl acetate=1:2);
$^1$H-NMR (DMSO-$d_6$):δ 0.97-1.11 (m, 6 H), 1.34-1.54 (m, 4 H), 2.33-2.84 (m, 4 H), 3.65-3.84 (m, 2 H), 4.63 (s, 2 H), 5.42-5.54 (m, 2 H), 6.84-7.45 (m, 6 H), 7.84-7.94 (m, 1 H), 8.16-8.25 (m, 1 H), 12.04 (s, 1 H).

Example 3(18)

6-{9-[2-fluoro-3-(trifluoromethoxy)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.54 (chloroform:methanol:water=50:10:1);
$^1$H-NMR (DMSO-$d_6$):δ 0.96-1.14 (m, 6 H), 1.33-1.54 (m, 4 H), 2.26-2.46 (m, 2 H), 2.64-2.86 (m, 2 H), 3.67-3.86 (m, 2 H), 4.65 (s, 2 H), 5.48-5.66 (m, 2 H), 6.77-6.86 (m, 1 H), 7.10 (dd, J=7.5, 4.5 Hz, 1 H), 7.13-7.22 (m, 1 H), 7.42-7.52 (m, 1 H), 7.90 (d, J=7.5 Hz, 1 H), 8.18 (dd, J=4.5, 1.5 Hz, 1 H), 12.04 (s, 1 H).

Example 3(19)

2,2-dimethyl-6-{9-[4-methyl-3-(trifluoromethyl)benzyl]-5,6,8,9-tetrahydro-7H-pyrido[4',3':4,5]pyrrolo[2,3-b]pyridin-7-yl}-6-oxohexanoic acid TLC:Rf 0.54 (chloroform:methanol:water=50:10:1);
$^1$H-NMR (DMSO-$d_6$):δ 0.97-1.11 (m, 6 H), 1.29-1.55 (m, 4 H), 2.16-2.47 (m, 5 H), 2.62-2.83 (m, 2 H), 3.65-3.82 (m, 2 H), 4.62 (s, 2 H), 5.44-5.57 (m, 2 H), 7.10 (dd, J=7.5, 4.5 Hz, 1 H), 7.14-7.24 (m, 1 H), 7.30-7.38 (m, 1 H), 7.51-7.64 (m, 1 H), 7.86-7.93 (m, 1 H), 8.18-8.24 (m, 1 H), 12.04 (s, 1 H).

Example 3(20)

6-{9-[2-fluoro-4-(trifluoromethyl)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.28 (hexane:ethyl acetate=1:2);
$^1$H-NMR (DMSO-$d_6$):δ 0.96-1.13 (m, 6 H), 1.32-1.53 (m, 4 H), 2.22-2.86 (m, 4 H), 3.68-3.86 (m, 2 H), 4.66 (s, 2 H), 5.53-5.66 (m, 2 H), 6.88-7.00 (m, 1 H), 7.06-7.15 (m, 1 H), 7.42-7.52 (m, 1 H), 7.68-7.78 (m, 1 H), 7.87-7.96 (m, 1 H), 8.13-8.22 (m, 1 H), 12.05 (s, 1 H).

Example 3(21)

6-{9-[2-fluoro-5-(trifluoromethoxy)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.31 (hexane:ethyl acetate=1:2);
$^1$H-NMR (DMSO-$d_6$):δ 0.96-1.13 (m, 6 H), 1.34-1.55 (m, 4 H), 2.23-2.86 (m, 4 H), 3.67-3.87 (m, 2 H), 4.67 (s, 2 H), 5.45-5.62 (m, 2 H), 6.82-6.95 (m, 1 H), 7.06-7.17 (m, 1 H), 7.29-7.47 (m, 2 H), 7.84-7.96 (m, 1 H), 8.15-8.25 (m, 1 H), 12.05 (s, 1 H).

Example 3(23)

6-{9-[3-fluoro-5-(trifluoromethyl)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.49 (chloroform:methanol:water=50:10:1);
$^1$H-NMR (DMSO-$d_6$):δ 0.95-1.13 (m, 6 H), 1.31-1.53 (m, 4 H), 2.26-2.46 (m, 2 H), 2.62-2.85 (m, 2 H), 3.67-3.84 (m, 2 H), 4.59-4.72 (m, 2 H), 5.57 (s, 2 H), 7.07-7.26 (m, 2 H), 7.39-7.52 (m, 1 H), 7.54-7.62 (m, 1 H), 7.87-7.95 (m, 1 H), 8.18-8.24 (m, 1 H), 12.03 (s, 1 H).

Example 3(24)

6-{9-[3-chloro-5-(trifluoromethoxy)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.49 (chloroform:methanol:water=50:10:1);
$^1$H-NMR (DMSO-$d_6$):δ 0.95-1.13 (m, 6 H), 1.35-1.52 (m, 4 H), 2.26-2.47 (m, 2 H), 2.62-2.85 (m, 2 H), 3.68-3.83 (m, 2 H), 4.58-4.70 (m, 2 H), 5.52 (s, 2 H), 7.07-7.28 (m, 3 H), 7.44 (s, 1 H), 7.87-7.95 (m, 1 H), 8.17-8.25 (m, 1 H), 12.03 (s, 1 H).

Example 3(25)

2,2-dimethyl-6-oxo-6-{9-[4-(trifluoromethyl)benzyl]-5,6,8,9-tetrahydro-7H-pyrido[4',3':4,5]pyrrolo[2,3-b]pyridin-7-yl}hexanoic acid TLC:Rf 0.52 (chloroform:methanol:water=50:10:1);
$^1$H-NMR (DMSO-$d_6$):δ 0.95-1.13 (m, 6 H), 1.31-1.55 (m, 4 H), 2.19-2.45 (m, 2 H), 2.63-2.85 (m, 2 H), 3.66-3.83 (m, 2 H), 4.61 (s, 2 H), 5.50-5.64 (m, 2 H), 7.10 (dd, J=7.5, 4.5 Hz, 1 H), 7.23-7.35 (m, 2 H), 7.66 (d, J=8.0 Hz, 2 H), 7.86-7.94 (m, 1 H), 8.17-8.23 (m, 1 H), 12.04 (s, 1 H).

Example 3(26)

6-{9-[3-chloro-4-(trifluoromethoxy)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.52 (chloroform:methanol:water=50:10:1);
$^1$H-NMR (DMSO-$d_6$):δ 0.95-1.13 (m, 6 H), 1.32-1.53 (m, 4 H), 2.24-2.45 (m, 2 H), 2.63-2.84 (m, 2 H), 3.67-3.85 (m, 2 H), 4.64 (s, 2 H), 5.45-5.55 (m, 2 H), 7.05-7.16 (m, 2 H), 7.45-7.57 (m, 2 H), 7.86-7.94 (m, 1 H), 8.16-8.24 (m, 1 H), 12.04 (s, 1 H).

Example 3(27)

6-{9-[3-fluoro-4-(trifluoromethyl)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.43 (methylene chloride:ethyl acetate:methanol=8:4:1);
$^1$H-NMR (DMSO-$d_6$):δ 0.99-1.09 (m, 6 H) 1.33-1.55 (m, 4 H) 2.23-2.85 (m, 4 H) 3.66-3.84 (m, 2 H) 4.64 (s, 2 H) 5.52-5.64 (m, 2 H) 6.97-7.07 (m, 1 H) 7.11 (dd, J=7.9, 4.8 Hz, 1 H) 7.19-7.33 (m, 1 H) 7.66-7.76 (m, 1 H) 7.87-7.96 (m, 1 H) 8.15-8.24 (m, 1 H) 12.03 (br. s., 1 H).

Example 3(28)

6-{9-[4-fluoro-3-(trifluoromethoxy)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.26 (hexane:ethyl acetate=1:2);
$^1$H-NMR (DMSO-$d_6$):δ 0.99-1.15 (m, 6 H), 1.32-1.54 (m, 4 H), 2.31-2.89 (m, 4 H), 3.64-3.87 (m, 2 H), 4.64 (s, 2 H), 5.42-5.58 (m, 2 H), 7.00-7.22 (m, 2 H), 7.33-7.57 (m, 2 H), 7.83-7.98 (m, 1 H), 8.15-8.28 (m, 1 H), 12.04 (s, 1 H).

Example 3(29)

6-{9-[3-chloro-5-(trifluoromethyl)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.37 (hexane:ethyl acetate=1:2);
$^1$H-NMR (DMSO-$d_6$):δ 0.98-1.12 (m, 6 H), 1.34-1.54 (m, 4 H), 2.22-2.86 (m, 4 H), 3.66-3.85 (m, 2 H), 4.61-4.72 (m, 2 H), 5.57 (s, 2 H), 7.12 (dd, J=7.8, 4.7 Hz, 1 H), 7.38-7.51 (m, 1 H), 7.50-7.64 (m, 1 H), 7.73-7.81 (m, 1 H), 7.87-7.97 (m, 1 H), 8.18-8.27 (m, 1 H), 12.05 (s, 1 H).

Example 3(30)

6-{9-[4-chloro-3-(trifluoromethoxy)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.28 (hexane:ethyl acetate=1:2);
$^1$H-NMR (DMSO-$d_6$):δ 0.99-1.11 (m, 6 H), 1.34-1.52 (m, 4 H), 2.33-2.84 (m, 4 H), 3.66-3.83 (m, 2 H), 4.63 (s, 2 H), 5.46-5.59 (m, 2 H), 6.99-7.15 (m, 2 H), 7.36-7.51 (m, 1 H), 7.60 (d, J=8.2 Hz, 1 H), 7.86-7.94 (m, 1 H), 8.17-8.24 (m, 1 H), 12.04 (s, 1 H).

Example 3(31)

2,2-dimethyl-6-oxo-6-(9-{[2-(trifluoromethyl)-4-pyridinyl]methyl}-5,6,8,9-tetrahydro-7H-pyrido[4',3':4,5]pyrrolo[2,3-b]pyridin-7-yl)hexanoic acid TLC:Rf 0.47 (methylene chloride:ethyl acetate:methanol=8:4:1);
$^1$H-NMR (DMSO-$d_6$):δ 0.98-1.11 (m, 6 H) 1.36-1.52 (m, 4 H) 2.24-2.85 (m, 4 H) 3.71-3.85 (m, 2 H) 4.59-4.70 (m, 2 H) 5.63 (s, 2 H) 7.08-7.21 (m, 2 H) 7.69-7.79 (m, 1 H) 7.89-7.98 (m, 1 H) 8.19 (dd, J=4.9, 1.4 Hz, 1 H) 8.64 (d, J=4.9 Hz, 1 H) 12.05 (br. s., 1 H).

Example 3(32)

6-{9-[2-fluoro-5-(trifluoromethyl)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.45 (chloroform:methanol=10:1);
$^1$H-NMR (DMSO-$d_6$):δ 0.97-1.13 (m, 6 H), 1.36-1.53 (m, 4 H), 2.20-2.52 (m, 2 H), 2.62-2.85 (m, 2 H), 3.65-3.83 (m, 2 H), 4.68 (s, 2 H), 5.49-5.65 (m, 2 H), 7.04-7.15 (m, 1 H), 7.31-7.56 (m, 2 H), 7.67-7.79 (m, 1 H), 7.85-7.95 (m, 1 H), 8.14-8.25 (m, 1 H), 12.04 (s, 1 H).

Example 3(33)

6-{9-[3-fluoro-4-(trifluoromethoxy)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.47 (methylene chloride:ethyl acetate:methanol=8:4:1);
$^1$H-NMR (DMSO-$d_6$):δ 0.96-1.13 (m, 6 H) 1.34-1.55 (m, 4 H) 2.30-2.86 (m, 4 H) 3.69-3.83 (m, 2 H) 4.65 (s, 2 H) 5.46-5.54 (m, 2 H) 6.89-7.03 (m, 1 H) 7.10 (dd, J=7.5, 4.8

Hz, 1 H) 7.22-7.36 (m, 1 H) 7.44-7.53 (m, 1 H) 7.85-7.94 (m, 1 H) 8.17-8.23 (m, 1 H) 12.04 (br. s., 1 H).

Example 3(34)

6-{9-[2-fluoro-3-(trifluoromethyl)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.49 (methylene chloride:ethyl acetate:methanol=8:4:1);
$^1$H-NMR (DMSO-$d_6$):δ 1.01-1.11 (m, 6 H) 1.35-1.52 (m, 4 H) 2.23-2.86 (m, 4 H) 3.70-3.85 (m, 2 H) 4.63-4.70 (m, 2 H) 5.54-5.64 (m, 2 H) 7.02-7.16 (m, 2 H) 7.23-7.32 (m, 1 H) 7.63-7.73 (m, 1 H) 7.87-7.94 (m, 1 H) 8.14-8.20 (m, 1 H) 12.04 (br. s., 1 H).

Example 3(35)

2,2-dimethyl-6-oxo-6-(9-{[5-(trifluoromethyl)-3-thienyl]methyl}-5,6,8,9-tetrahydro-7H-pyrido[4',3':4,5]pyrrolo[2,3-b]pyridin-7-yl)hexanoic acid TLC:Rf 0.39 (methylene chloride:ethyl acetate:methanol=8:4:1);
MS (ESI, Pos. 20 V): m/z=494 (M+H)$^+$.

Example 3(36)

6-[6-fluoro-9-(3-fluorobenzyl)-1,3,4,9-tetrahydro-2H-beta-carbolin-2-yl]-2,2-dimethyl-6-oxohexanoic acid TLC:Rf 0.33 (ethyl acetate);
$^1$H-NMR (DMSO-$d_6$):δ 1.00-1.14 (m, 6 H) 1.34-1.57 (m, 4 H) 2.26-2.83 (m, 4 H) 3.66-3.86 (m, 2 H) 4.56-4.73 (m, 2 H) 5.33-5.49 (m, 2 H) 6.75-6.97 (m, 3 H) 7.00-7.13 (m, 1 H) 7.18-7.48 (m, 3 H) 12.04 (s, 1 H).

Example 3(37)

6-[8-fluoro-9-(3-fluorobenzyl)-1,3,4,9-tetrahydro-2H-beta-carbolin-2-yl]-2,2-dimethyl-6-oxohexanoic acid TLC:Rf 0.40 (ethyl acetate);
$^1$H-NMR (DMSO-$d_6$):δ 1.00-1.14 (m, 6 H) 1.33-1.56 (m, 4 H) 2.25-2.87 (m, 4 H) 3.67-3.87 (m, 2 H) 4.60-4.71 (m, 2 H) 5.41-5.54 (m, 2 H) 6.70-7.14 (m, 5 H) 7.24-7.41 (m, 2 H) 12.04 (s, 1 H).

Example 3(38)

2,2-dimethyl-6-oxo-6-(9-{[2-(trifluoromethyl)-4-pyridinyl]methyl}-1,3,4,9-tetrahydro-2H-beta-carbolin-2-yl)hexanoic acid TLC:Rf 0.56 (chloroform:methanol:water=50:10:1);
MS (ESI, Pos. 20 V): m/z=488 (M+H)$^+$.

Example 3(39)

2,2-dimethyl-6-oxo-6-(9-{[4-(trifluoromethyl)-2-thienyl]methyl}-5,6,8,9-tetrahydro-7H-pyrido[4',3':4,5]pyrrolo[2,3-b]pyridin-7-yl)hexanoic acid TLC:Rf 0.46 (methylene chloride:ethyl acetate:methanol=8:4:1);
$^1$H-NMR (DMSO-$d_6$):δ 0.97-1.14 (m, 6 H), 1.35-1.54 (m, 4 H), 2.30-2.50 (m, 2 H), 2.62-2.83 (m, 2 H), 3.68-3.84 (m, 2 H), 4.76 (s, 2 H), 5.60-5.70 (m, 2 H), 7.11 (dd, J=7.8, 4.8 Hz, 1 H), 7.34-7.48 (m, 1 H), 7.89 (d, J=7.8 Hz, 1 H), 8.05-8.10 (m, 1 H), 8.22-8.29 (m, 1 H), 12.05 (s, 1 H).

Example 3(40)

6-{9-[(1,3-dimethyl-1H-pyrazol-5-yl)methyl]-8-fluoro-1,3,4,9-tetrahydro-2H-beta-carbolin-2-yl}-2,2-dimethyl-6-oxohexanoic acid TLC:Rf 0.25 (methylene chloride:ethyl acetate:methanol=8:4:1);
MS (ESI, Pos.): m/z=455 (M+H)$^+$.

Example 3(41)

6-{9-[(5-chloro-2-thienyl)methyl]-8-fluoro-1,3,4,9-tetrahydro-2H-beta-carbolin-2-yl}-2,2-dimethyl-6-oxohexanoic acid TLC:Rf 0.43 (methylene chloride:ethyl acetate:methanol=8:4:1);
MS (ESI, Pos.): m/z=477 (M+H)$^+$.

Example 3(42)

6-(9-{[5-(difluoromethyl)-2-thienyl]methyl}-5,6,8,9-tetrahydro-7H-pyrido[4',3':4,5]pyrrolo[2,3-b]pyridin-7-yl)-2,2-dimethyl-6-oxohexanoic acid TLC:Rf 0.50 (ethyl acetate);
MS (FAB, Pos.): m/z=476 (M+H)$^+$.

Example 3(43)

6-{9-[3-(difluoromethyl)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.24 (hexane:ethyl acetate=1:2);
MS (ESI, Pos.): m/z=470 (M+H)$^+$.

Example 3(44)

6-{9-[4-(difluoromethyl)benzyl]-5,6,8,9-tetrahydro-7H-pyrido[4',3':4,5]pyrrolo[2,3-b]pyridin-7-yl}-2,2-dimethyl-6-oxohexanoic acid TLC:Rf 0.55 (ethyl acetate);
MS (ESI, Pos. 20 V): m/z=470 (M+H)$^+$.

Example 3(45)

6-[9-(4-isopropylbenzyl)-5,6,8,9-tetrahydro-7H-pyrido[4',3':4,5]pyrrolo[2,3-b]pyridin-7-yl]-2,2-dimethyl-6-oxohexanoic acid TLC:Rf 0.70 (ethyl acetate);
MS (FAB, Pos.): m/z=462 (M+H)$^+$.

Example 3(46)

6-[9-(4-isopropoxybenzyl)-5,6,8,9-tetrahydro-7H-pyrido[4',3':4,5]pyrrolo[2,3-b]pyridin-7-yl]-2,2-dimethyl-6-oxohexanoic acid TLC:Rf 0.39 (hexane:ethyl acetate=1:2);
MS (ESI, Pos. 20 V): m/z=478 (M+H)+.

Example 3(47)

2,2-dimethyl-6-oxo-6-[9-(3-phenoxybenzyl)-5,6,8,9-tetrahydro-7H-pyrido[4',3':4,5]pyrrolo[2,3-b]pyridin-7-yl]hexanoic acid TLC:Rf 0.47 (hexane:ethyl acetate=1:2);
MS (ESI, Pos. 20 V): m/z=512 (M+H)+.

Example 3(48)

2,2-dimethyl-6-oxo-6-[9-(4-phenoxybenzyl)-5,6,8,9-tetrahydro-7H-pyrido[4',3':4,5]pyrrolo[2,3-b]pyridin-7-yl]hexanoic acid TLC:Rf 0.44 (methylene chloride:methanol=9:1);
MS (ESI, Pos. 20 V): m/z=512 (M+H)+.

Example 3(49)

2,2-dimethyl-6-oxo-6-(9-{[4-(trifluoromethyl)-1,3-thiazol-2-yl]methyl}-5,6,8,9-tetrahydro-7H-pyrido[4',3':4,5]pyrrolo[2,3-b]pyridin-7-yl)hexanoic acid TLC:Rf 0.26 (chloroform:methanol:water=50:10:1);
MS (ESI, Pos. 20 V): m/z=989 (2M+H)+, 495 (M+H)+.

Example 3(50)

2,2-dimethyl-6-oxo-6-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)hexanoic acid

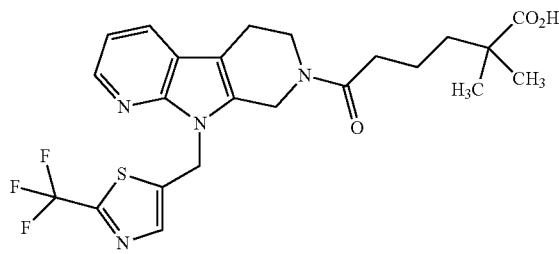 [SMILES: CC(C)(CCCC(=O)N1CCc2c(n(Cc3cnc(C(F)(F)F)s3)c3ncccc23)C1)C(=O)O]

TLC:Rf 0.55 (chloroform:methanol:water=50:10:1);
MS (ESI, Pos. 20 V): m/z=989 (2M+H)+, 495 (M+H)+.

Example 3(51)

2,2-dimethyl-6-(9-{[1-methyl-3-(trifluoromethyl)-1H-pyrazol-5-yl]methyl}-5,6,8,9-tetrahydro-7H-pyrido[4',3':4,5]pyrrolo[2,3-b]pyridin-7-yl)-6-oxohexanoic acid TLC:Rf 0.39 (chloroform:methanol:water=50:10:1);
MS (ESI, Pos. 20 V): m/z=492 (M+H)+.

Example 3(52)

2,2-dimethyl-6-(9-{[1-methyl-5-(trifluoromethyl)-1H-pyrazol-3-yl]methyl}-5,6,8,9-tetrahydro-7H-pyrido[4',3':4,5]pyrrolo[2,3-b]pyridin-7-yl)-6-oxohexanoic acid TLC:Rf 0.39 (chloroform:methanol:water=50:10:1);
MS (ESI, Pos. 20 V): m/z=492 (M+H)+.

Example 3(53)

2,2-dimethyl-6-oxo-6-(9-{[2-(trifluoromethyl)-1,3-thiazol-4-yl]methyl}-5,6,8,9-tetrahydro-7H-pyrido[4',3':4,5]pyrrolo[2,3-b]pyridin-7-yl)hexanoic acid TLC:Rf 0.39 (methylene chloride:ethyl acetate:methanol=8:4:1);
MS (FAB, Pos.): m/z=495 (M+H)+.

Example 3(54)

6-[9-(3-ethylbenzyl)-5,6,8,9-tetrahydro-7H-pyrido[4',3':4,5]pyrrolo[2,3-b]pyridin-7-yl]-2,2-dimethyl-6-oxohexanoic acid TLC:Rf 0.18 (hexane:ethyl acetate=1:1);
MS (ESI, Pos. 20 V): m/z=448 (M+H)+.

Example 3(55)

2,2-dimethyl-6-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-6-oxohexanoic acid TLC:Rf 0.39 (methylene chloride:methanol:water=90:10:1);
MS (FAB, Pos.): m/z=517 (M+H)+.

Example 3(56)

2,2-dimethyl-6-[9-({4-methyl-2-[4-(trifluoromethyl)phenyl]-1,3-thiazol-5-yl}methyl)-5,6,8,9-tetrahydro-7H-pyrido[4',3':4,5]pyrrolo[2,3-b]pyridin-7-yl]-6-oxohexanoic acid TLC:Rf 0.50 (methylene chloride:methanol:water=90:10:1);
MS (FAB, Pos.): m/z=585 (M+H)+.

Example 3(57)

2,2-dimethyl-6-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-6-oxohexanoic acid TLC:Rf 0.33 (chloroform:methanol:water=10:1:0.1);
MS (ESI, Pos.20V.): m/z=509 (M+H)+.

Example 3(58)

2,2-dimethyl-6-oxo-6-(9-{[2-(trifluoromethyl)-1,3-thiazol-5-yl]methyl}-1,3,4,9-tetrahydro-2H-beta-carbolin-2-yl)hexanoic acid TLC:Rf 0.53 (methylene chloride:methanol=9:1);
MS (APCI, Pos.): m/z=494 (M+H)+.

Reference Example 1

2,2-dimethyl-6-oxo-6-(9-{[3-(trifluoromethyl)-2-thienyl]methyl}-5,6,8,9-tetrahydro-7H-pyrido[4',3':4,5]pyrrolo[2,3-b]pyridin-7-yl)hexanoic acid TLC:Rf 0.58 (methylene chloride:ethyl acetate:methanol=8:4:1);
$^1$H-NMR (DMSO-$d_6$):δ 0.99-1.13 (m, 6 H), 1.34-1.54 (m, 4 H), 2.28-2.45 (m, 2 H), 2.64-2.86 (m, 2 H), 3.67-3.85 (m, 2 H), 4.60-4.74 (m, 2 H), 5.71-5.84 (m, 2 H), 7.13 (dd, J=7.6, 4.7 Hz, 1 H), 7.29 (d, J=5.3 Hz, 1 H), 7.50 (d, J=5.3 Hz, 1 H), 7.92 (d, J=7.6 Hz, 1 H), 8.20 (d, J=4.7 Hz, 1 H), 12.05 (s, 1 H).

Reference Manufacturing Example 13 ethyl 6-diazo-3,3-dimethyl-5-oxohexanoate

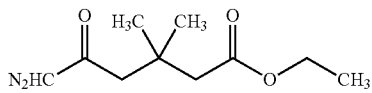

4,4-Dimethyldihydro-2H-pyran-2,6-(3 H)-dione (7.11 g) was dissolved in ethanol (50 ml), and the solution was stirred at 100° C. for 16 hours. After cooled to room temperature, the reaction solution was concentrated under reduced pressure. The reaction mixture was diluted with ethyl acetate, and extracted with an aqueous saturated sodium bicarbonate solution. To the aqueous layer was added 5N hydrochloric acid to make the solution acidic, followed by extraction with ethyl acetate. The organic layer was dried with anhydrous magnesium sulfate, and concentrated. The residue was purified by silica gel column chromatography (hexane:ethyl acetate=7:3). The resulting compound (1.50 g) was dissolved in ethyl acetate (13.3 mL), thionyl chloride (1.16 mL) was added, and the mixture was stirred at 60° C. for 8 hours. After cooled to room temperature, the reaction solution was concentrated under reduced pressure. To a mixed solution (15 mL) of THF:acetonitrile (1:1) was added a 2.0M trimethylsilyldiazomethane/hexane solution (8.8 mL), this was cooled to 0° C., a THF:acetonitrile (1:1) mixed solution (6 mL) of the acid chloride was added, a temperature was raised to room temperature, and the mixture was stirred for 1 hour. The reaction solution was concentrated under reduced pressure, and the resulting yellow oil was treated with a silica gel column (hexane:ethyl acetate=90:10→70:30) to obtain the title compound (1.21 g) having the following physical property values.

TLC:Rf 0.28 (hexane:ethyl acetate=4:1);
$^1$H-NMR (CDCl$_3$):δ 1.12 (s, 6 H), 1.26 (t, J=7.1 Hz, 3 H), 2.34-2.47 (m, 4 H), 4.13 (q, J=7.1 Hz, 2 H), 5.38 (s, 1 H).

Reference Manufacturing Example 14

6-ethoxy-4,4-dimethyl-6-oxohexanoic acid

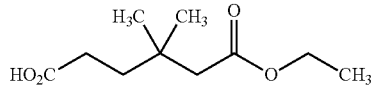

The compound (1.06 g) produced in Reference manufacturing example 13 was dissolved in benzyl alcohol (5.0 mL), triethylamine (1.39 mL) and silver acetate (17 mg) were sequentially added, and the mixture was stirred at room temperature for 15 minutes. Further, a temperature was raised to 60° C., the mixture was stirred for 1 hour, and cooled to room temperature, and the reaction solution was placed into 1N hydrochloric acid (10 mL), followed by extraction with hexane (30 mL). The extract solution was washed with 1N hydrochloric acid (5 mL) and an aqueous saturated sodium chloride solution (10 mL), dried with anhydrous magnesium sulfate, and concentrated under reduced pressure. The resulting pale yellow liquid was treated with a silica gel column (hexane:ethyl acetate=100:0→90:10→85:15). The resulting compound (728 mL) was dissolved in ethanol (5.0 mL), 10% palladium carbon (50% hydrous product, 73 mg) was added under the nitrogen atmosphere, and hydrogen was blown into the solution for 1.5 hours while stirred at room temperature. After the system was replaced with nitrogen, the catalyst was filtered off using Celite, followed by concentration under reduced pressure, to obtain the title compound (459 mg) having the following physical property values.

TLC:Rf 0.39 (hexane:ethyl acetate=2:1);
$^1$H-NMR (CDCl$_3$):δ 1.02 (s, 6 H), 1.26 (t, J=7.1 Hz, 3 H), 1.63-1.76 (m, 2 H), 2.20 (s, 2 H), 2.31-2.44 (m, 2 H), 4.12 (q, J=7.1 Hz, 2 H).

Reference Manufacturing Example 15

6-(9-benzyl-1,3,4,9-tetrahydro-2H-beta-carbolin-2-yl)-3,3-dimethyl-6-oxohexanoic acid

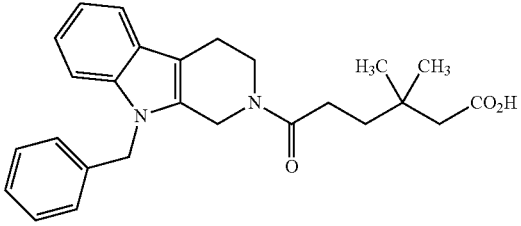 [SMILES: CC(C)(CCC(=O)N1CCc2c(n(Cc3ccccc3)c3ccccc23)C1)CC(=O)O]

A corresponding alkyl halide in place of (3-bromopropyl)benzene was used, which was subjected to operation in accordance with Reference manufacturing example 1, and the resulting compound and the compound produced in Reference manufacturing example 14 were used, which were subjected to operation in accordance with Reference manufacturing example 11, and further subjected to operation in accordance with Reference manufacturing example 3 to obtain the compound having the following physical property values.

TLC:Rf 0.38 (hexane:ethyl acetate=2:3);

$^1$H-NMR (DMSO-$d_6$):δ 0.86-1.01 (m, 6 H) 1.43-1.62 (m, 2 H) 2.03-2.52 (m, 4 H) 2.64-2.85 (m, 2 H) 3.72-3.84 (m, 2 H) 4.60-4.69 (m, 2 H) 5.31-5.44 (m, 2 H) 6.96-7.12 (m, 4 H) 7.17-7.33 (m, 3 H) 7.37-7.48 (m, 2 H) 11.94 (s, 1 H).

Example 4(1)-Example 4(9)

A corresponding alkyl halide in place of (3-bromopropyl) benzene, and a tetrahydropyridopyrrolopyridine derivative produced by operation in accordance with Reference manufacturing example 4→Reference manufacturing example 5→Reference manufacturing example 6→Reference manufacturing example 7→Reference manufacturing example 8 or the corresponding β-carboline derivative were used, which were subjected to operation in accordance with Reference manufacturing example 1, and the resulting compound and the compound produced in Reference manufacturing example 14 were used, which were subjected to operation in accordance with Reference manufacturing example 11, and further subjected to operation in accordance with Reference manufacturing example 3 to obtain the following compounds.

Example 4(1)

6-{9-[4-(difluoromethoxy)benzyl]-5,6,8,9-tetrahydro-7H-pyrido[4',3':4,5]pyrrolo[2,3-b]pyridin-7-yl}-3,3-dimethyl-6-oxohexanoic acid TLC:Rf 0.31 (ethyl acetate);

$^1$H-NMR (DMSO-$d_6$):δ 0.84-1.04 (m, 6 H) 1.40-1.63 (m, 2 H) 2.05-2.18 (m, 2 H) 2.20-2.89 (m, 4 H) 3.68-3.86 (m, 2 H) 4.58-4.74 (m, 2 H) 5.38-5.56 (m, 2 H) 6.85-7.44 (m, 6 H) 7.85-7.98 (m, 1 H) 8.16-8.29 (m, 1 H) 11.97 (s, 1 H).

Example 4(2)

3,3-dimethyl-6-oxo-6-{9-[4-(trifluoromethoxy)benzyl]-5,6,8,9-tetrahydro-7H-pyrido[4',3':4,5]pyrrolo[2,3-b]pyridin-7-yl}hexanoic acid TLC:Rf 0.53 (ethyl acetate);

$^1$H-NMR (DMSO-$d_6$):δ 0.82-1.04 (m, 6 H) 1.40-1.65 (m, 2 H) 2.02-2.19 (m, 2 H) 2.23-2.88 (m, 4 H) 3.70-3.87 (m, 2 H) 4.59-4.74 (m, 2 H) 5.45-5.59 (m, 2 H) 7.06-7.16 (m, 1 H) 7.17-7.40 (m, 4 H) 7.85-7.97 (m, 1 H) 8.17-8.28 (m, 1 H) 11.97 (s, 1 H).

Example 4(3)

3,3-dimethyl-6-oxo-6-{9-[4-(trifluoromethyl)benzyl]-5,6,8,9-tetrahydro-7H-pyrido[4',3':4,5]pyrrolo[2,3-b]pyridin-7-yl}hexanoic acid TLC:Rf 0.43 (ethyl acetate:methanol=19:1);

$^1$H-NMR (DMSO-$d_6$):δ 0.82-1.02 (m, 6 H) 1.41-1.62 (m, 2 H) 2.02-2.16 (m, 2 H) 2.19-2.47 (m, 2 H) 2.65-2.88 (m, 2 H) 3.71-3.86 (m, 2 H) 4.58-4.72 (m, 2 H) 5.51-5.65 (m, 2 H) 7.12 (dd, J=7.68, 4.76 Hz, 1 H) 7.25-7.36 (m, 2 H) 7.68 (d, J=8.23 Hz, 2 H) 7.88-7.97 (m, 1 H) 8.15-8.25 (m, 1 H) 11.97 (s, 1 H).

Example 4(4)

6-{9-[3-chloro-4-(trifluoromethoxy)benzyl]-5,6,8,9-tetrahydro-7H-pyrido[4',3':4,5]pyrrolo[2,3-b]pyridin-7-yl}-3,3-dimethyl-6-oxohexanoic acid TLC:Rf 0.52 (chloroform:methanol:water=50:10:1);

MS (ESI, Pos. 20 V): m/z=538 (M+H)$^+$.

Example 4(5)

6-{9-[3-fluoro-4-(trifluoromethoxy)benzyl]-5,6,8,9-tetrahydro-7H-pyrido[4',3':4,5]pyrrolo[2,3-b]pyridin-7-yl}-3,3-dimethyl-6-oxohexanoic acid TLC:Rf 0.52 (chloroform:methanol:water=50:10:1);

MS (ESI, Pos. 20 V): m/z=522 (M+H)$^+$.

Example 4(6)

3,3-dimethyl-6-oxo-6-{9-[3-(trifluoromethyl)benzyl]-5,6,8,9-tetrahydro-7H-pyrido[4',3':4,5]pyrrolo[2,3-b]pyridin-7-yl}hexanoic acid TLC:Rf 0.36 (methylene chloride:ethyl acetate:methanol=8:4:1);

MS (ESI, Pos. 20 V): m/z=488 (M+H)$^+$.

Example 4(7)

3,3-dimethyl-6-oxo-6-(9-{[2-(trifluoromethyl)-4-pyridinyl]methyl}-1,3,4,9-tetrahydro-2H-beta-carbolin-2-yl)hexanoic acid TLC:Rf 0.41 (chloroform:methanol=10:1);

MS (FAB, Pos.): m/z=488 (M+H)$^+$.

Example 4(8)

3,3-dimethyl-6-oxo-6-(9-{[5-(trifluoromethyl)-3-thienyl]methyl}-5,6,8,9-tetrahydro-7H-pyrido[4',3':4,5]pyrrolo[2,3-b]pyridin-7-yl)hexanoic acid TLC:Rf 0.42 (methylene chloride:ethyl acetate:methanol=8:4:1);

MS (ESI, Pos. 20 V): m/z=494 (M+H)$^+$.

Example 4(9)

3,3-dimethyl-6-oxo-6-(9-{[5-(trifluoromethyl)-2-thienyl]methyl}-5,6,8,9-tetrahydro-7H-pyrido[4',3':4,5]pyrrolo[2,3-b]pyridin-7-yl)hexanoic acid TLC:Rf 0.38 (methylene chloride:ethyl acetate:methanol=8:4:1);

$^1$H-NMR (DMSO-$d_6$):δ 0.90-1.03 (m, 6 H) 1.44-1.65 (m, 2 H) 2.09-2.18 (m, 2 H) 2.31-2.52 (m, 2 H) 2.61-2.85 (m, 2 H) 3.73-3.85 (m, 2 H) 4.72-4.85 (m, 2 H) 5.66-5.78 (m, 2 H)

7.08-7.23 (m, 2 H) 7.51-7.59 (m, 1 H) 7.86-7.95 (m, 1 H) 8.23-8.29 (m, 1 H) 11.98 (s, 1 H).

Reference Manufacturing Example 16

7-(chloroacetyl)-9-(3-fluorobenzyl)-6,7,8,9-tetrahydro-5H-pyrido[4',3':4,5]pyrrolo[2,3-b]pyridine

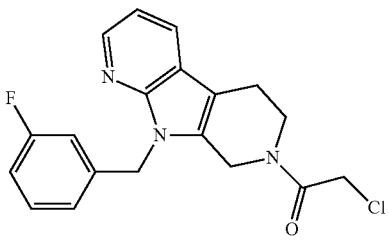 [SMILES: O=C(CCl)N1CCc2c(n(Cc3cccc(F)c3)c3ncccc23)C1]

To a suspension of 9-(3-fluorobenzyl)-6,7,8,9-tetrahydro-5H-pyrido[4',3':4,5]pyrrolo[2,3-b]pyridine (500 mg) produced by operation in accordance with Reference manufacturing example 1 in THF (10 mL) were sequentially added triethylamine (0.59 mL) and chloroacetyl chloride (0.135 mL), and the mixture was stirred for 30 minutes. The reaction mixture was poured into an aqueous saturated sodium bicarbonate solution, followed by extraction with ethyl acetate. The organic layer was washed with an aqueous saturated sodium chloride solution, dried with anhydrous magnesium sulfate, and concentrated. The residue was purified by silica gel column chromatography (hexane:ethyl acetate=1:1) to obtain the title compound (459 mg) having the following physical property values.

TLC:Rf 0.29 (hexane:ethyl acetate=3:2);
$^1$H-NMR (CDCl$_3$):δ 2.80-3.02 (m, 2 H) 3.76-4.23 (m, 4 H) 4.50-4.75 (m, 2 H) 5.42-5.52 (m, 2 H) 6.71-6.85 (m, 1 H) 6.86-7.03 (m, 2 H) 7.06-7.15 (m, 1 H) 7.19-7.34 (m, 1 H) 7.77-7.88 (m, 1 H) 8.26-8.37 (m, 1 H).

Reference Manufacturing Example 17 methyl 3-{2-[9-(3-fluorobenzyl)-5,6,8,9-tetrahydro-7H-pyrido[4',3':4,5]pyrrolo[2,3-b]pyridin-7-yl]-2-oxoethoxy}-2,2-dimethylpropanoate To a solution of methyl 3-hydroxy-2,2-dimethylpropanoate (0.04 mL) in N,N-dimethylformamide (2 mL) was added sodium hydride (60% in oil, 12 mg) at 0° C., and the mixture was stirred for 20 minutes. To the reaction mixture was added dropwise a solution of the compound (54 mg) produced in Reference manufacturing example 16 in N,N-dimethylformamide (1 mL), and the mixture was stirred for 1 hour. The reaction mixture was poured into ice water, followed by extraction with ethyl acetate. The organic layer was sequentially washed with water, and an aqueous saturated sodium chloride solution, dried with anhydrous magnesium sulfate, and concentrated. The residue was purified by silica gel column chromatography (hexame:ethyl acetate=1:2) to obtain the title compound (28 mg) having the following physical property values.

TLC:Rf 0.48 (hexane:ethyl acetate=1:2);
$^1$H-NMR (CDCl$_3$):δ 1.04-1.33 (m, 6 H) 2.77-2.92 (m, 2 H) 3.38-3.57 (m, 2 H) 3.57-3.70 (m, 3 H) 3.74-3.96 (m, 2 H) 4.01-4.27 (m, 2 H) 4.53-4.67 (m, 2 H) 5.43-5.51 (m, 2 H) 6.71-7.00 (m, 3 H) 7.05-7.14 (m, 1 H) 7.18-7.31 (m, 1 H) 7.76-7.86 (m, 1 H) 8.26-8.34 (m, 1 H).

Reference Manufacturing Example 18

3-{2-[9-(3-fluorobenzyl)-5,6,8,9-tetrahydro-7H-pyrido[4',3':4,5]pyrrolo[2,3-b]pyridin-7-yl]-2-oxoethoxy}-2,2-dimethylpropanoic acid To the compound (28 mg) produced in Reference manufacturing example 17 in a mixture solution of ethylene glycol dimethyl ether (1 mL) and methanol (1 mL) was added a 1N aqueous sodium hydroxide solution (1 mL) at room temperature, and the mixture was stirred overnight. To the reaction mixture were added 1N hydrochloric acid (1 mL) and water, followed by extraction with ethyl acetate. The extract was washed with an aqueous saturated sodium chloride solution, dried with anhydrous sodium sulfate, and concentrated. The residue was purified by silica gel column chromatography (chloroform:methanol:water=50:10:1) to obtain the title compound (11 mg) having the following physical property values.

TLC:Rf 0.51 (chloroform:methanol:water=50:10:1);
$^1$H-NMR (DMSO-d$_6$):δ 0.97-1.14 (m, 6 H) 2.66-2.88 (m, 2 H) 3.35-3.50 (m, 2 H) 3.62-3.85 (m, 2 H) 4.07-4.29 (m, 2 H) 4.61 (s, 2 H) 5.48 (s, 2 H) 6.84-7.01 (m, 2 H) 7.02-7.11 (m, 1 H) 7.11 (dd, J=8.00, 4.50 Hz, 1 H) 7.33 (ddd, J=8.00, 8.00, 6.00 Hz, 1 H) 7.90 (dd, J=8.00, 1.50 Hz, 1 H) 8.21 (dd, J=4.50, 1.50 Hz, 1 H) 12.19 (s, 1 H).

Example 5(1)-5(15)

A corresponding alkyl halide in place of (3-bromopropyl)benzene, and a tetrahydropyridopyrrolopyridine derivative produced by operation in accordance with Reference manufacturing example 4→Reference manufacturing example 5→Reference manufacturing example 6→Reference manufacturing example 7→Reference manufacturing example 8 or the corresponding β-carboline derivative were used, which were subjected to operation in accordance with Reference manufacturing example 1 and further subjected to operation in accordance with Reference manufacturing example 16→Reference manufacturing example 17→Reference manufacturing example 18 to obtain the following compounds.

Example 5(1)

2,2-dimethyl-3-(2-oxo-2-{9-[4-(trifluoromethyl)benzyl]-5,6,8,9-tetrahydro-7H-pyrido[4',3':4,5]pyrrolo[2,3-b]pyridin-7-yl}ethoxy)propanoic acid TLC:Rf 0.16 (chloroform:methanol:water=10:1:0.1);
MS (ESI, Pos.): m/z=490 (M+H)$^+$.

Example 5(2)

2,2-dimethyl-3-(2-oxo-2-{9-[3-(trifluoromethyl)benzyl]-5,6,8,9-tetrahydro-7H-pyrido[4',3':4,5]pyrrolo[2,3-b]pyridin-7-yl}ethoxy)propanoic acid TLC:Rf 0.31 (chloroform:methanol:water=10:1:0.1);
MS (ESI, Pos.): m/z=490 (M+H)$^+$.

Example 5(3)

3-(2-{9-[2-fluoro-4-(trifluoromethyl)benzyl]-5,6,8,9-tetrahydro-7H-pyrido[4',3':4,5]pyrrolo[2,3-b]pyridin-7-yl}-2-oxoethoxy)-2,2-dimethylpropanoic acid TLC:Rf 0.27 (chloroform:methanol:water=10:1:0.1);
MS (ESI, Pos.): m/z=508 (M+H)$^+$.

Example 5(4)

2,2-dimethyl-3-(2-oxo-2-{9-[4-(trifluoromethoxy)benzyl]-5,6,8,9-tetrahydro-7H-pyrido[4',3':4,5]pyrrolo[2,3-b]pyridin-7-yl}ethoxy)propanoic acid TLC:Rf 0.29 (chloroform:methanol:water=10:1:0.1);
MS (ESI, Pos.): m/z=506 (M+H)$^+$.

Example 5(5)

3-(2-{9-[3-chloro-4-(trifluoromethoxy)benzyl]-5,6,8,9-tetrahydro-7H-pyrido[4',3':4,5]pyrrolo[2,3-b]pyridin-7-yl}-2-oxoethoxy)-2,2-dimethylpropanoic acid TLC:Rf 0.24 (chloroform:methanol:water=10:1:0.1);
MS (FAB, Pos.): m/z=540 (M+H)$^+$.

Example 5(6)

3-(2-{9-[3-fluoro-4-(trifluoromethoxy)benzyl]-5,6,8,9-tetrahydro-7H-pyrido[4',3':4,5]pyrrolo[2,3-b]pyridin-7-yl}-2-oxoethoxy)-2,2-dimethylpropanoic acid TLC:Rf 0.22 (chloroform:methanol:water=10:1:0.1);
MS (FAB, Pos.): m/z=524 (M+H)$^+$.

Example 5(7)

2,2-dimethyl-3-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethoxy]propanoic acid TLC:Rf 0.28 (chloroform:methanol:water=10:1:0.1);
$^1$H-NMR (DMSO-d$_6$):δ 1.00-1.18 (m, 6 H) 2.65-2.84 (m, 2 H) 3.32-3.51 (m, 2 H) 3.65-3.86 (m, 2 H) 4.18-4.28 (m, 2 H) 4.68-4.80 (m, 2 H) 5.63-5.75 (m, 2 H) 7.08-7.19 (m, 2 H) 7.52-7.60 (m, 1 H) 7.85-7.94 (m, 1 H) 8.22-8.29 (m, 1 H) 12.20 (br s, 1 H).

Example 5(8)

2,2-dimethyl-3-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethoxy]propanoic acid TLC:Rf 0.29 (chloroform:methanol:water=10:1:0.1);
$^1$H-NMR (DMSO-d$_6$):δ 0.97-1.17 (m, 6 H) 2.63-2.85 (m, 2 H) 3.33-3.52 (m, 2 H) 3.66-3.86 (m, 2 H) 4.16-4.30 (m, 2 H) 4.64-4.76 (m, 2 H) 5.40-5.53 (m, 2 H) 7.06-7.18 (m, 1 H) 7.52-7.65 (m, 2 H) 7.86-7.95 (m, 1 H) 8.20-8.27 (m, 1 H) 12.20 (br s, 1 H).

Example 5(9)

3-{2-[8-fluoro-9-(3-fluorobenzyl)-1,3,4,9-tetrahydro-2H-beta-carbolin-2-yl]-2-oxoethoxy}-2,2-dimethylpropanoic acid TLC:Rf 0.36 (methylene chloride:ethyl acetate:methanol=8:4:1);
MS (FAB, Pos.): m/z=457 (M+H)$^+$.

Example 5(10)

3-{2-[9-(2,4-difluorobenzyl)-8-fluoro-1,3,4,9-tetrahydro-2H-beta-carbolin-2-yl]-2-oxoethoxy}-2,2-dimethylpropanoic acid TLC:Rf 0.36 (methylene chloride:ethyl acetate:methanol=8:4:1);
MS (FAB, Pos.): m/z=475 (M+H)$^+$.

Example 5(11)

3-[2-(8-fluoro-9-{[5-(trifluoromethyl)-2-thienyl]methyl}-1,3,4,9-tetrahydro-2H-beta-carbolin-2-yl)-2-oxoethoxy]-2,2-dimethylpropanoic acid TLC:Rf 0.36 (methylene chloride:ethyl acetate:methanol=8:4:1);
MS (FAB, Pos.): m/z=513 (M+H)$^+$.

Example 5(12)

2,2-dimethyl-3-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethoxy)propanoic acid TLC:Rf 0.42 (methylene chloride:ethyl acetate:methanol=8:4:1);
MS (ESI, Pos.): m/z=519 (M+H)$^+$.

Example 5(13)

2,2-dimethyl-3-{2-oxo-2-[9-(4-phenoxybenzyl)-5,6,8,9-tetrahydro-7H-pyrido[4',3':4,5]pyrrolo[2,3-b]pyridin-7-yl]ethoxy}propanoic acid TLC:Rf 0.51 (methylene chloride:ethyl acetate:methanol=8:4:1);
MS (ESI, Pos.): m/z=514 (M+H)$^+$.

Example 5(14)

2,2-dimethyl-3-(2-oxo-2-{9-[3-(trifluoromethoxy)benzyl]-5,6,8,9-tetrahydro-7H-pyrido[4',3':4,5]pyrrolo[2,3-b]pyridin-7-yl}ethoxy)propanoic acid TLC:Rf 0.61 (methylene chloride:ethyl acetate:methanol=8:4:1);
MS (ESI, Pos.): m/z=506 (M+H)$^+$.

Example 5(15)

3-{2-[9-(3-ethylbenzyl)-5,6,8,9-tetrahydro-7H-pyrido[4',3':4,5]pyrrolo[2,3-b]pyridin-7-yl]-2-oxoethoxy}-2,2-dimethylpropanoic acid TLC:Rf 0.46 (methylene chloride:ethyl acetate:methanol=8:4:1);
MS (ESI, Pos.): m/z=450 (M+H)$^+$.

Reference Manufacturing Example 19 methyl cis-4-(diazoacetyl)cyclohexanecarboxylate

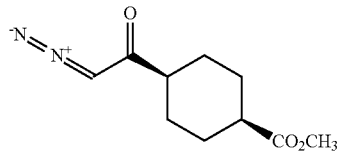

To an ethyl acetate solution (5.0 mL) of cis-4-(methoxycarbonyl)cyclohexanecarboxylic acid (5.89 g) was added thionyl chloride (4.6 mL), and the mixture was stirred at 60° C. for 6 hours. After cooled to room temperature, the reaction was concentrated, and azeotroped with toluene. A THF:acetonitrile (1:1) solution (26 mL) of the resulting oil was added to a 2.0 M solution (100 mL) of trimethylsilyl-diazomethane (32 mL) in a mixture of THF:acetonitrile (1:1), and the mixture was stirred at room temperature overnight. After acetic acid (5 mL) and water (20 mL) were added, THF and acetonitrile were distilled off, and an aqueous saturated sodium bicarbonate solution was added. This was extracted with ethyl acetate, and the organic layer was washed with an aqueous saturated sodium chloride solution, dried with anhydrous sodium sulfate, and concentrated. The resulting residue was isolation-purified by column chromatography (hexane:ethyl acetate=80:20→65:35→50:50) to obtain the title compound (5.16 g) having the following physical property values.

TLC: 0.33 (ethyl acetate);
$^1$H-NMR (CDCl$_3$):δ 1.52-1.79 (m, 6 H) 2.00-2.16 (m, 2 H) 2.26-2.42 (m, 1 H) 2.56 (quin, J=4.94 Hz, 1 H) 3.69 (s, 3 H) 5.30 (s, 1 H).

Reference Manufacturing Example 20

[cis-4-(methoxycarbonyl)cyclohexyl]acetic acid

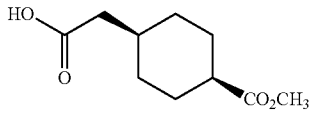 [SMILES: COC(=O)[C@H]1CC[C@@H](CC(=O)O)CC1]

A solution (41 mL) of the compound (6.06 g) produced in Reference manufacturing example 19 in a mixture of THF:water (10:1) was added dropwise to a solution (80 mL) of silver trifluoroacetate (318 mg) and triethylamine (12.1 mL) in a mixture of THF:water (10:1) at room temperature over 1 hour, and the mixture was stirred at room temperature overnight. After THF was distilled off, t-butyl methyl ether (120 mL) was added, and this was filtered with Celite, and extracted with an aqueous saturated sodium bicarbonate solution (350 mL). The aqueous phase was separated, and 5N hydrochloric acid (65 mL) was added, followed by extraction with ethyl acetate. The organic layer was washed with an aqueous saturated sodium chloride solution, dried with anhydrous sodium sulfate, and concentrated to obtain the title compound (3.75 g) having the following physical property values.

TLC:Rf 0.70 (ethyl acetate);
$^1$H-NMR (CDCl$_3$):δ 1.25-1.40 (m, 2 H) 1.50-1.74 (m, 4 H) 1.87-2.07 (m, 3 H) 2.30 (d, J=7.32 Hz, 2 H) 2.57 (quin, J=5.03 Hz, 1 H) 3.69 (s, 3 H).

Reference Manufacturing Example 21 cis-4-{2-[9-(4-fluorobenzyl)-5,6,8,9-tetrahydro-7H-pyrido[4',3':4,5]pyrrolo[2,3-b]pyridin-7-yl]-2-oxoethyl}cyclohexanecarboxylic acid

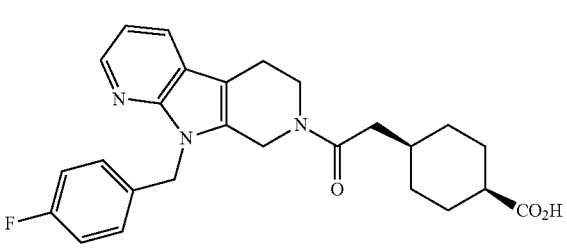 [SMILES: O=C(C[C@H]1CC[C@@H](C(=O)O)CC1)N1CCc2c(n(Cc3ccc(F)cc3)c3ncccc23)C1]

A corresponding alkyl halide in place of (3-bromopropyl)benzene, and a tetrahydropyridopyrrolopyridine derivative produced by operation in accordance with Reference manufacturing Example 4→Reference manufacturing Example 5→Reference manufacturing Example 6→Reference manufacturing Example 7→Reference manufacturing Example 8 were used, which were subjected to operation in accordance with Reference manufacturing example 1, and the resulting compound and the compound produced in Reference manufacturing Example 20 were used, which were subjected to operation in accordance with Reference manufacturing example 1 and further subjected to operation in accordance with Reference manufacturing example 3 to obtain the title compound (53 mg) having the following physical property values.

TLC:Rf 0.34 (ethyl acetate:methanol=19:1);
$^1$H-NMR (DMSO-d$_6$):δ 1.04-1.29 (m, 2 H) 1.32-1.63 (m, 4 H) 1.65-1.96 (m, 3 H) 2.13-2.47 (m, 3 H) 2.62-2.85 (m, 2 H) 3.70-3.84 (m, 2 H) 4.64 (s, 2 H) 5.39-5.54 (m, 2 H) 7.02-7.30 (m, 5 H) 7.81-7.94 (m, 1 H) 8.16-8.28 (m, 1 H) 12.04 (s, 1 H).

Example 6(1)-Example 6(103) and Reference example 2

A corresponding alkyl halide in place of (3-bromopropyl)benzene, and a tetrahydropyridopyrrolopyridine derivative produced by operation in accordance with Reference manufacturing Example 4→Reference manufacturing Example 5→Reference manufacturing Example 6→Reference manufacturing Example 7→Reference manufacturing Example 8 or the corresponding beta-carboline derivative were used, which were subjected to operation in accordance with Reference manufacturing example 1, and the resulting compound and the compound produced in Reference manufacturing Example 20 or the corresponding ester were used, which were subjected to operation in accordance with Reference manufacturing example 11 and further subjected to operation in accordance with Reference manufacturing example 3 to obtain the following compounds.

Example 6(1)

cis-4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)cyclohexanecarboxylic acid TLC:Rf 0.45 (ethyl acetate:methanol=19:1);
$^1$H-NMR (DMSO-$d_6$):δ 1.02-1.30 (m, 2 H) 1.31-1.61 (m, 4 H) 1.63-1.95 (m, 3 H) 2.13-2.47 (m, 3 H) 2.63-2.85 (m, 2 H) 3.70-3.86 (m, 2 H) 4.57-4.70 (m, 2 H) 5.49-5.67 (m, 2 H) 7.06-7.17 (m, 1 H) 7.25-7.37 (m, 2 H) 7.63-7.73 (m, 2 H) 7.87-7.96 (m, 1 H) 8.15-8.25 (m, 1 H) 12.03 (br s, 1 H).

Example 6(2)

cis-4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)cyclohexanecarboxylic acid TLC:Rf 0.43 (methylene chloride:ethyl acetate:methanol=8:4:1);
MS (ESI, Pos. 20 V): m/z=500 (M+H)$^+$.

Example 6(3)

cis-4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)cyclohexanecarboxylic acid TLC:Rf 0.43 (methylene chloride:ethyl acetate:methanol=8:4:1);
MS (ESI, Pos. 20 V): m/z=516 (M+H)$^+$.

Example 6(4)

cis-4-[2-oxo-2-(9-{[2-(trifluoromethyl)-4-pyridinyl]methyl}-1,3,4,9-tetrahydro-2H-beta-carbolin-2-yl)ethyl]cyclohexanecarboxylic acid TLC:Rf 0.45 (methylene chloride:ethyl acetate:methanol=8:4:1);
$^1$H-NMR (DMSO-$d_6$):δ 1.06-1.31 (m, 2 H) 1.34-1.63 (m, 4 H) 1.68-1.95 (m, 3 H) 2.18-2.47 (m, 3 H) 2.65-2.87 (m, 2 H) 3.74-3.87 (m, 2 H) 4.59-4.70 (m, 2 H) 5.55-5.65 (m, 2 H) 6.97-7.14 (m, 3 H) 7.30-7.43 (m, 1 H) 7.45-7.53 (m, 1 H) 7.58-7.68 (m, 1 H) 8.59-8.67 (m, 1 H) 12.03 (s,1 H).

Example 6(5)

cis-4-(2-{9-[3-chloro-4-(trifluoromethoxy)benzyl]-5,6,8,9-tetrahydro-7H-pyrido[4',3':4,5]pyrrolo[2,3-b]pyridin-7-yl}-2-oxoethyl)cyclohexanecarboxylic acid TLC:Rf 0.41 (chloroform:methanol=10:1);
MS (FAB, Pos.): m/z=550 (M+H)$^+$.

Example 6(6)

cis-4-(2-{9-[3-fluoro-4-(trifluoromethoxy)benzyl]-5,6,8,9-tetrahydro-7H-pyrido[4',3':4,5]pyrrolo[2,3-b]pyridin-7-yl}-2-oxoethyl)cyclohexanecarboxylic acid TLC:Rf 0.37 (chloroform:methanol=10:1);
MS (FAB, Pos.): m/z=534 (M+H)$^+$.

Example 6(7)

trans-4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)cyclohexanecarboxylic acid TLC:Rf 0.33 (methylene chloride:ethyl acetate:methanol=8:4:1);
$^1$H-NMR (DMSO-$d_6$):δ 0.68-1.09 (m, 2 H) 1.10-1.37 (m, 2 H) 1.44-1.93 (m, 5 H) 1.93-2.38 (m, 3 H) 2.62-2.87 (m, 2 H) 3.68-3.88 (m, 2 H) 4.59-4.70 (m, 2 H) 5.49-5.64 (m, 2 H) 7.12 (dd, J=7.78, 4.67 Hz, 1 H) 7.24-7.37 (m, 2 H) 7.63-7.75 (m, 2 H) 7.88-7.97 (m, 1 H) 8.16-8.26 (m, 1 H) 12.02 (br s, 1 H).

Example 6(8)

trans-4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)cyclohexanecarboxylic acid TLC:Rf 0.57 (chloroform:methanol:water=50:10:1);
MS (ESI, Pos. 20 V): m/z=500 (M+H)$^+$.

Example 6(9)

trans-4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)cyclohexanecarboxylic acid TLC:Rf 0.57 (chloroform:methanol:water=50:10:1);
MS (ESI, Pos. 20 V): m/z=516 (M+H)$^+$.

Example 6(10)

trans-4-(2-{9-[3-chloro-4-(trifluoromethoxy)benzyl]-5,6,8,9-tetrahydro-7H-pyrido[4',3':4,5]pyrrolo[2,3-b]pyridin-7-yl}-2-oxoethyl)cyclohexanecarboxylic acid TLC:Rf 0.44 (methylene chloride:ethyl acetate:methanol=8:4:1);
$^1$H-NMR (DMSO-$d_6$):δ 0.74-1.11 (m, 2 H) 1.12-1.40 (m, 2 H) 1.50-1.93 (m, 5 H) 1.97-2.40 (m, 3 H) 2.61-2.87 (m, 2 H) 3.67-3.90 (m, 2 H) 4.60-4.74 (m, 2 H) 5.45-5.59 (m, 2 H) 7.03-7.19 (m, 2 H) 7.44-7.60 (m, 2 H) 7.81-7.97 (m, 1 H) 8.15-8.28 (m, 1 H) 11.97 (br s, 1 H).

Example 6(11)

cis-4-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethyl]cyclohexanecarboxylic acid TLC:Rf 0.36 (methylene chloride:ethyl acetate:methanol=8:4:1);
$^1$H-NMR (DMSO-$d_6$):δ 1.08-1.31 (m, 2 H) 1.36-1.63 (m, 4 H) 1.72-1.96 (m, 3 H) 2.21-2.47 (m, 3 H) 2.61-2.84 (m, 2 H) 3.72-3.87 (m, 2 H) 4.67-4.78 (m, 2 H) 5.39-5.52 (m, 2 H)

7.11 (dd, J=7.68, 4.76 Hz, 1 H) 7.50-7.68 (m, 2 H) 7.84-7.93 (m, 1 H) 8.19-8.27 (m, 1 H) 12.04 (br s, 1 H).

Example 6(12)

trans-4-(2-{9-[3-fluoro-4-(trifluoromethoxy)benzyl]-5,6,8,9-tetrahydro-7H-pyrido[4',3':4,5]pyrrolo[2,3-b]pyridin-7-yl}-2-oxoethyl)cyclohexanecarboxylic acid TLC:Rf 0.39 (methylene chloride:ethyl acetate:methanol=8:4:1);
MS (ESI, Pos. 20 V): m/z=534 (M+H)⁺.

Example 6(13)

trans-4-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethyl]cyclohexanecarboxylic acid

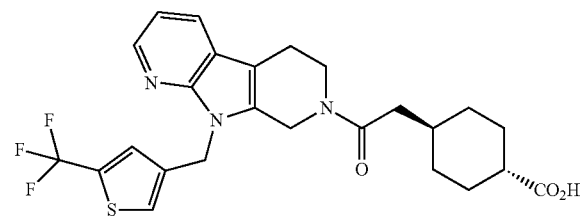 [SMILES: O=C(C[C@H]1CC[C@H](C(=O)O)CC1)N1CCc2c(n(Cc3csc(C(F)(F)F)c3)c3ncccc23)C1]

TLC:Rf 0.39 (methylene chloride:ethyl acetate:methanol=8:4:1);
¹H-NMR (DMSO-d₆):δ 0.76-1.37 (m, 4 H), 1.50-1.92 (m, 5 H), 1.94-2.40 (m, 3 H), 2.62-2.84 (m, 2 H), 3.68-3.90 (m, 2 H), 4.72 (s, 2 H), 5.34-5.58 (m, 2 H), 7.10 (dd, J=7.8, 1.5 Hz, 1 H), 7.48-7.67 (m, 2 H), 7.88 (d, J=7.8 Hz, 1 H), 8.17-8.26 (m, 1 H), 11.95 (s, 1 H).

Example 6(14)

cis-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]cyclohexanecarboxylic acid TLC:Rf 0.37 (methylene chloride:ethyl acetate:methanol=8:4:1);
¹H-NMR (DMSO-d₆):δ 1.07-1.32 (m, 2 H) 1.34-1.64 (m, 4 H) 1.70-1.99 (m, 3 H) 2.18-2.51 (m, 3 H) 2.59-2.89 (m, 2 H) 3.65-3.91 (m, 2 H) 4.66-4.88 (m, 2 H) 5.58-5.84 (m, 2 H) 7.02-7.31 (m, 2 H) 7.46-7.65 (m, 1 H) 7.82-8.04 (m, 1 H) 8.16-8.34 (m, 1 H) 12.04 (br s, 1 H).

Example 6(15)

trans-4-(2-{9-[2-fluoro-4-(trifluoromethyl)benzyl]-5,6,8,9-tetrahydro-7H-pyrido[4',3':4,5]pyrrolo[2,3-b]pyridin-7-yl}-2-oxoethyl)cyclohexanecarboxylic acid TLC:Rf 0.47 (chloroform:methanol:water=50:10:1);
MS (ESI, Pos. 20 V): m/z=518 (M+H)⁺.

Example 6(16)

trans-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]cyclohexanecarboxylic acid

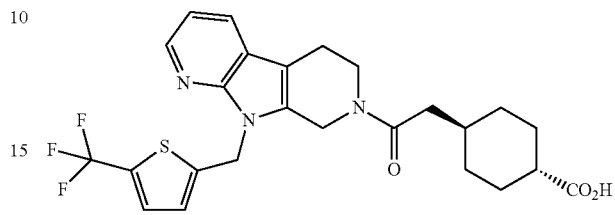

TLC:Rf 0.36 (methylene chloride:ethyl acetate:methanol=8:4:1);
¹H-NMR (DMSO-d₆):δ 0.78-1.09 (m, 2 H) 1.12-1.38 (m, 2 H) 1.50-1.94 (m, 5 H) 1.97-2.18 (m, 1 H) 2.21-2.40 (m, 2 H) 2.60-2.83 (m, 2 H) 3.68-3.87 (m, 2 H) 4.72-4.85 (m, 2 H) 5.64-5.78 (m, 2 H) 7.06-7.26 (m, 2 H) 7.52-7.63 (m, 1 H) 7.85-7.95 (m, 1 H) 8.22-8.30 (m, 1 H) 11.98 (br s, 1 H).

Example 6(17)

trans-4-[2-(9-{[5-(difluoromethyl)-2-thienyl]methyl}-5,6,8,9-tetrahydro-7H-pyrido[4',3':4,5]pyrrolo[2,3-b]pyridin-7-yl)-2-oxoethyl]cyclohexanecarboxylic acid TLC:Rf 0.39 (ethyl acetate);
MS (FAB, Pos.): m/z=488 (M+H)⁺.

Example 6(18)

cis-4-[2-(9-{[5-(difluoromethyl)-2-thienyl]methyl}-5,6,8,9-tetrahydro-7H-pyrido[4',3':4,5]pyrrolo[2,3-b]pyridin-7-yl)-2-oxoethyl]cyclohexanecarboxylic acid TLC:Rf 0.50 (ethyl acetate);
MS (FAB, Pos.): m/z=488 (M+H)⁺.

Example 6(19)

trans-4-[2-oxo-2-(9-{[4-(trifluoromethyl)-2-thienyl]methyl}-5,6,8,9-tetrahydro-7H-pyrido[4',3':4,5]pyrrolo[2,3-b]pyridin-7-yl)ethyl]cyclohexanecarboxylic acid TLC:Rf 0.56 (ethyl acetate);
MS (FAB, Pos.): m/z=506 (M+H)⁺.

Example 6(20)

cis-4-[2-oxo-2-(9-{[4-(trifluoromethyl)-2-thienyl]methyl}-5,6,8,9-tetrahydro-7H-pyrido[4',3':4,5]pyrrolo[2,3-b]pyridin-7-yl)ethyl]cyclohexanecarboxylic acid TLC:Rf 0.61 (ethyl acetate);
MS (FAB, Pos.): m/z=506 (M+H)⁺.

Example 6(21)

cis-4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)cyclohexanecarboxylic acid TLC:Rf 0.17 (hexane:ethyl acetate=1:2);
MS (ESI, Pos.): m/z=482 (M+H)$^+$.

Example 6(22)

trans-4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)cyclohexanecarboxylic acid TLC:Rf 0.15 (hexane:ethyl acetate=1:2);
MS (ESI, Pos.): m/z=482 (M+H)$^+$.

Example 6(23)

cis-4-(2-{9-[4-(difluoromethyl)benzyl]-5,6,8,9-tetrahydro-7H-pyrido[4',3':4,5]pyrrolo[2,3-b]pyridin-7-yl}-2-oxoethyl)cyclohexanecarboxylic acid TLC:Rf 0.46 (ethyl acetate);
MS (ESI, Pos. 20 V): m/z=482 (M+H)$^+$.

Example 6(24)

trans-4-(2-{9-[4-(difluoromethyl)benzyl]-5,6,8,9-tetrahydro-7H-pyrido[4',3':4,5]pyrrolo[2,3-b]pyridin-7-yl}-2-oxoethyl)cyclohexanecarboxylic acid TLC:Rf 0.42 (ethyl acetate);
MS (ESI, Pos. 20 V): m/z=482 (M+H)$^+$.

Example 6(25)

4-[2-oxo-2-(9-{[2-(trifluoromethyl)-4-pyridinyl]methyl}-5,6,8,9-tetrahydro-7H-pyrido[4',3':4,5]pyrrolo[2,3-b]pyridin-7-yl)ethyl]benzoic acid TLC:Rf 0.19 (methylene chloride:ethyl acetate:methanol=8:4:1);
MS (ESI, Pos.): m/z=495 (M+H)$^+$.

Example 6(26)

4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)benzoic acid TLC:Rf 0.36 (chloroform:methanol:water=50:10:1);
MS (ESI, Pos. 20 V): m/z=987 (2M+H)$^+$, 494 (M+H)$^+$.

Example 6(27)

[4-(2-{5,5-dimethyl-9-[4-(trifluoromethoxy)benzyl]-5,6,8,9-tetrahydro-7H-pyrido[4',3':4,5]pyrrolo[2,3-b]pyridin-7-yl}-2-oxoethyl)-1-piperidinyl]acetic acid hydrochloride TLC:Rf 0.41 (methylene chloride:methanol:28% aqueous ammonia=15:5:1);
MS (ESI, Pos.): m/z=559 (M+H)$^+$.

Example 6(28)

2-ethoxy-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]benzoic acid TLC:Rf 0.60 (chloroform:methanol:water=50:10:1);
MS (ESI, Pos. 20 V): m/z=544 (M+H)$^+$.

Example 6(29)

4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]bicyclo[2.2.2]octane-1-carboxylic acid TLC:Rf 0.11 (n-hexane:ethyl acetate=1:1);
MS (FAB, Pos.): m/z=532 (M+H)$^+$.

Example 6(30)

{3-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]phenyl}acetic acid TLC:Rf 0.65 (chloroform:methanol:water=50:10:1);
MS (ESI, Pos. 20 V): m/z=514 (M+H)$^+$.

Example 6(31)

4-[3-oxo-3-(9-{[5-(trifluoromethyl)-2-thienyl]methyl}-5,6,8,9-tetrahydro-7H-pyrido[4',3':4,5]pyrrolo[2,3-b]pyridin-7-yl)propyl]benzoic acid TLC:Rf 0.40 (methylene chloride:ethyl acetate:methanol=8:4:1);
$^1$H-NMR (DMSO-d$_6$):δ 2.60-2.98 (m, 6 H), 3.66-3.86 (m, 2 H), 4.70-4.82 (m, 2 H), 5.69 (s, 2 H), 7.06-7.18 (m, 2 H), 7.30-7.42 (m, 2 H), 7.46-7.58 (m, 1 H), 7.75-7.85 (m, 2 H), 7.88 (d, J=8.1 Hz, 1 H), 8.24 (d, J=4.5 Hz, 1 H), 12.7 (brs, 1 H).

Example 6(32)

3-[3-oxo-3-(9-{[5-(trifluoromethyl)-2-thienyl]methyl}-5,6,8,9-tetrahydro-7H-pyrido[4',3':4,5]pyrrolo[2,3-b]pyridin-7-yl)propyl]benzoic acid TLC:Rf 0.38 (methylene chloride:ethyl acetate:methanol=8:4:1);
$^1$H-NMR (DMSO-d$_6$):δ 2.58-2.98 (m, 6 H), 3.68-3.84 (m, 2 H), 4.68-4.82 (m, 2 H), 5.60-5.70 (m, 2 H), 7.05-7.18 (m, 2 H), 7.28-7.40 (m, 1 H), 7.43-7.56 (m, 2 H), 7.62-7.90 (m, 3 H), 8.23 (dd, J=4.8, 1.5 Hz, 1 H), 12.8 (brs, 1 H).

Example 6(33)

cis-3-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]cyclobutanecarboxylic acid TLC:Rf 0.41 (ethyl acetate);
MS (ESI, Pos. 20 V): m/z=478 (M+H)$^+$.

Example 6(34)

trans-3-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]cyclobutanecarboxylic acid TLC:Rf 0.21 (ethyl acetate);
MS (ESI, Pos. 20 V): m/z=478 (M+H)$^+$.

Example 6(35)

2-[3-oxo-3-(9-{[5-(trifluoromethyl)-2-thienyl]methyl}-5,6,8,9-tetrahydro-7H-pyrido[4',3':4,5]pyrrolo[2,3-b]pyridin-7-yl)propyl]benzoic acid TLC:Rf 0.36 (methylene chloride:ethyl acetate:methanol=8:4:1);
MS (ESI, Pos. 20V): m/z=514 (M+H)$^+$.

Example 6(36)

4-{2-[9-(2,4-difluorobenzyl)-8-fluoro-1,3,4,9-tetrahydro-2H-beta-carbolin-2-yl]-2-oxoethyl}benzoic acid TLC:Rf 0.33 (methylene chloride:ethyl acetate:methanol=8:4:1);
MS (FAB, Pos.): m/z=479 (M+H)$^+$.

Example 6(37)

4-[2-(8-fluoro-9-{[5-(trifluoromethyl)-2-thienyl]methyl}-1,3,4,9-tetrahydro-2H-beta-carbolin-2-yl)-2-oxoethyl]benzoic acid TLC:Rf 0.33 (methylene chloride:ethyl acetate:methanol=8:4:1);
MS (FAB, Pos.): m/z=517 (M+H)$^+$.

Example 6(38)

4-{2-[8-fluoro-9-(3-fluorobenzyl)-1,3,4,9-tetrahydro-2H-beta-carbolin-2-yl]-2-oxoethyl}benzoic acid TLC:Rf 0.27 (methylene chloride:ethyl acetate:methanol=8:4:1);
MS (FAB, Pos.): m/z=461 (M+H)$^+$.

Example 6(39)

5-[3-oxo-3-(9-{[5-(trifluoromethyl)-2-thienyl]methyl}-5,6,8,9-tetrahydro-7H-pyrido[4',3':4,5]pyrrolo[2,3-b]pyridin-7-yl)propyl]-2-thiophenecarboxylic acid TLC:Rf 0.12 (ethyl acetate);
MS (ESI, Pos. 20 V): m/z=520 (M+H)$^+$.

Example 6(40)

{4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]phenyl}acetic acid TLC:Rf 0.36 (methylene chloride:methanol=9:1);
MS (FAB, Pos.): m/z=514 (M+H)$^+$.

Example 6(41)

{2-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]phenyl}acetic acid TLC:Rf 0.30 (methylene chloride:methanol=9:1);
MS (FAB, Pos.): m/z=514 (M+H)$^+$.

Example 6(42)

4-{2-[9-(2,4-difluorobenzyl)-8-fluoro-1,3,4,9-tetrahydro-2H-beta-carbolin-2-yl]-2-oxoethyl}bicyclo[2.2.2]octane-1-carboxylic acid TLC:Rf 0.57 (n-hexane:ethyl acetate=1:1);
MS (FAB, Pos.): m/z=511 (M+H)+.

Example 6(43)

(1R,3R)-1,2,2-trimethyl-3-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]cyclopentanecarboxylic acid TLC:Rf 0.34 (chloroform:methanol:water=10:1:0.1);
MS (FAB, Pos.): m/z=534 (M+H)$^+$.

Example 6(44)

4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)bicyclo[2.2.2]octane-1-carboxylic acid TLC:Rf 0.50 (ethyl acetate);
MS (FAB, Pos.): m/z=508 (M+H)$^+$.

Example 6(45)

4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]bicyclo[2.2.2]octane-1-carboxylic acid TLC:Rf 0.64 (ethyl acetate);
MS (ESI, Pos. 20 V): m/z=533 (M+H)$^+$.

Example 6(46)

4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)bicyclo[2.2.2]octane-1-carboxylic acid TLC:Rf 0.70 (ethyl acetate);
MS (ESI, Pos. 20 V): m/z=526 (M+H)$^+$.

Example 6(47)

4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)bicyclo[2.2.2]octane-1-carboxylic acid TLC:Rf 0.72 (ethyl acetate);
MS (ESI, Pos. 20 V): m/z=526 (M+H)$^+$.

Example 6(48)

4-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethyl]bicyclo[2.2.2]octane-1-carboxylic acid TLC:Rf 0.73 (ethyl acetate);
MS (ESI, Pos. 20 V): m/z=532 (M+H)$^+$.

Example 6(49)

(1R,3R)-1,2,2-trimethyl-3-[2-oxo-2-(9-{[2-(trifluoromethyl)-1,3-thiazol-5-yl]methyl}-1,3,4,9-tetrahydro-2H-beta-carbolin-2-yl)ethyl]cyclopentanecarboxylic acid

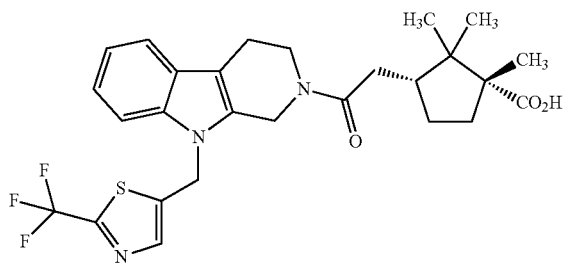 [SMILES: CC1(C)[C@@H](CC(=O)N2CCc3c(n(Cc4cnc(C(F)(F)F)s4)c4ccccc34)C2)CC[C@@]1(C)C(=O)O]

TLC:Rf 0.48 (methylene chloride:methanol:water=90:10:1);
MS (FAB, Pos.): m/z=534 (M+H)$^+$.

Example 6(50)

4-(2-{9-[3-(difluoromethyl)benzyl]-1,3,4,9-tetrahydro-2H-beta-carbolin-2-yl}-2-oxoethyl)bicyclo[2.2.2]octane-1-carboxylic acid TLC:Rf 0.19 (hexane:ethyl acetate=1:1);
MS (ESI, Pos. 20 V): m/z=507 (M+H)$^+$.

Example 6(51)

4-[2-oxo-2-(9-{[2-(trifluoromethyl)-1,3-thiazol-5-yl]methyl}-1,3,4,9-tetrahydro-2H-beta-carbolin-2-yl)ethyl]bicyclo[2.2.2]octane-1-carboxylic acid TLC:Rf 0.39 (methylene chloride:methanol:water=90:10:1);
MS (FAB, Pos.): m/z=532 (M+H)$^+$.

Example 6(52)

(1R,3R)-3-(2-{9-[3-(difluoromethyl)benzyl]-1,3,4,9-tetrahydro-2H-beta-carbolin-2-yl}-2-oxoethyl)-1,2,2-trimethylcyclopentanecarboxylic acid TLC:Rf 0.32 (hexane:ethyl acetate=1:1);
MS (ESI, Pos. 20 V): m/z=509 (M+H)$^+$.

Example 6(53)

(1R,3R)-1,2,2-trimethyl-3-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)cyclopentanecarboxylic acid

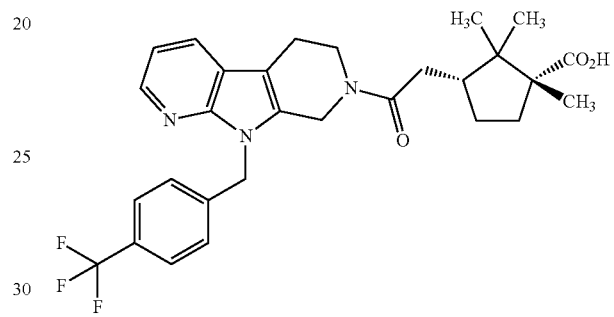

TLC:Rf 0.43 (chloroform:methanol:water=100:10:1);
MS (ESI, Pos. 20 V): m/z=528 (M+H)$^+$.

Example 6(54)

(1R,3R)-1,2,2-trimethyl-3-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)cyclopentanecarboxylic acid TLC:Rf 0.40 (chloroform:methanol:water=100:10:1);
MS (ESI, Pos. 20 V): m/z=544 (M+H)$^+$.

Example 6(55)

(1R,3R)-1,2,2-trimethyl-3-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)cyclopentanecarboxylic acid TLC:Rf 0.38 (chloroform:methanol:water=100:10:1);
MS (ESI, Pos. 20 V): m/z=544 (M+H)$^+$.

Example 6(56)

(1R,3R)-3-(2-{9-[3-(difluoromethyl)benzyl]-5,6,8,9-tetrahydro-7H-pyrido[4',3':4,5]pyrrolo[2,3-b]pyridin-7-yl}-2-oxoethyl)-1,2,2-trimethylcyclopentanecarboxylic acid TLC:Rf 0.45 (chloroform:methanol:water=100:10:1);
MS (ESI, Pos. 20 V): m/z=510 (M+H)$^+$.

Example 6(57)

(1R,3R)-1,2,2-trimethyl-3-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)cyclopentanecarboxylic acid TLC:Rf 0.50 (chloroform:methanol:water=100:10:1);
MS (ESI, Pos. 20 V): m/z=528 (M+H)$^+$.

Example 6(58)

4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)bicyclo[2.2.2]octane-1-carboxylic acid TLC:Rf 0.33 (hexane:ethyl acetate=1:2);
MS (ESI, Pos. 20 V): m/z=542 (M+H)$^+$.

Example 6(59)

4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)bicyclo[2.2.2]octane-1-carboxylic acid TLC:Rf 0.31 (hexane:ethyl acetate=1:2);
MS (ESI, Pos. 20 V): m/z=542 (M+H)$^+$.

Example 6(60)

(1S,3S)-1,2,2-trimethyl-3-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]cyclopentanecarboxylic acid TLC:Rf 0.15 (n-hexane:ethyl acetate=1:1);
MS (FAB, Pos): m/z=535 (M+H)$^+$.

Example 6(61)

(1R,3R)-1,2,2-trimethyl-3-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethyl]cyclopentanecarboxylic acid TLC:Rf 0.70 (ethyl acetate);
MS (ESI, Pos. 20V): m/z=534 (M+H)$^+$.

Example 6(62)

(1R,3R)-1,2,2-trimethyl-3-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]cyclopentanecarboxylic acid TLC:Rf 0.65 (ethyl acetate);
MS (ESI, Pos. 20V): m/z=535 (M+H)$^+$.

Example 6(63)

(1R,3R)-1,2,2-trimethyl-3-[2-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-2-oxoethyl]cyclopentanecarboxylic acid

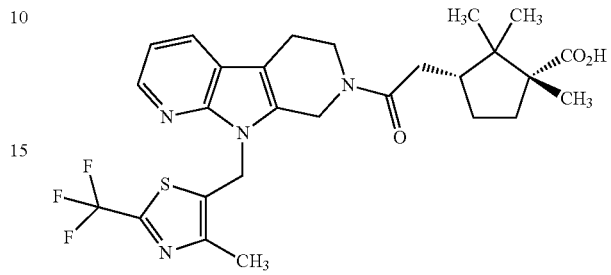

TLC:Rf 0.25 (chloroform:methanol:water=100:10:1);
MS (ESI, Pos. 20 V): m/z=549 (M+H)$^+$, 255.

Example 6(64)

4-[2-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-2-oxoethyl]bicyclo[2.2.2]octane-1-carboxylic acid TLC:Rf 0.34 (ethyl acetate);
MS (ESI, Pos. 20V): m/z=547 (M+H)$^+$.

Example 6(65)

4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]bicyclo[2.2.1]heptane-1-carboxylic acid

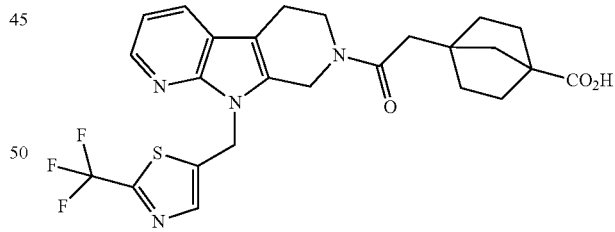

TLC:Rf 0.65 (chloroform:methanol:water=50:10:1);
MS (ESI, Pos. 20 V): m/z=519 (M+H)$^+$.

Example 6(66)

4-[2-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-2-oxoethyl]bicyclo[2.2.1]heptane-1-carboxylic acid TLC:Rf 0.31 (chloroform:methanol:water=100:10:1);
MS (ESI, Pos. 20V): m/z=533 (M+H)$^+$.

Example 6(67)

4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)bicyclo[2.2.1]heptane-1-carboxylic acid TLC:Rf 0.34 (chloroform:methanol:water=100:10:1);
MS (ESI, Pos. 20 V): m/z=494 (M+H)$^+$.

Example 6(68)

4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)bicyclo[2.2.1]heptane-1-carboxylic acid

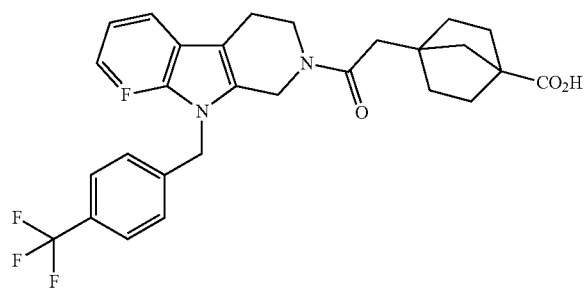

TLC:Rf 0.61 (chloroform:methanol:water=50:10:1);
MS (ESI, Pos. 20 V): m/z=512 (M+H)$^+$.

Example 6(69)

4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)bicyclo[2.2.1]heptane-1-carboxylic acid TLC:Rf 0.55 (methylene chloride:methanol=9:1);
MS (APCI, Pos. 40 V): m/z=512 (M+H)$^+$.

Example 6(70)

4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)bicyclo[2.2.1]heptane-1-carboxylic acid TLC:Rf 0.61 (methylene chloride:methanol=9:1);
MS (ES, Pos.): m/z=528 (M+H)$^+$.

Example 6(71)

4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)bicyclo[2.2.1]heptane-1-carboxylic acid TLC:Rf 0.61 (chloroform:methanol:water=50:10:1);
MS (ESI, Pos. 20 V): m/z=528 (M+H)$^+$.

Example 6(72)

4-{2-[9-(3-ethylbenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid

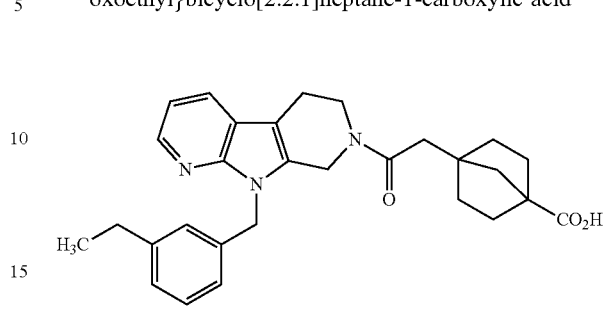

TLC:Rf 0.42 (n-hexane:ethyl acetate=1:2);
MS (ESI, Pos.): m/z=472 (M+H)$^+$.

Example 6(73)

4-{2-[9-(3-isopropoxybenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid TLC:Rf 0.38 (n-hexane:ethyl acetate=1:2);
MS (ESI, Pos.): m/z=502 (M+H)$^+$.

Example 6(74)

4-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)bicyclo[2.2.1]heptane-1-carboxylic acid TLC:Rf 0.30 (methylene chloride:ethyl acetate:methanol=8:4:1);
MS (ESI, Pos.): m/z=541 (M+H)$^+$.

Example 6(75)

4-[2-(8-fluoro-9-{[2-(trifluoromethyl)-1,3-thiazol-5-yl]methyl}-1,3,4,9-tetrahydro-2H-beta-carbolin-2-yl)-2-oxoethyl]bicyclo[2.2.1]heptane-1-carboxylic acid TLC:Rf 0.36 (methylene chloride:ethyl acetate:methanol=8:4:1);
MS (ESI, Pos.): m/z=536 (M+H)$^+$.

Example 6(76)

4-(2-{9-[3-(difluoromethoxy)benzyl]-5,6,8,9-tetrahydro-7H-pyrido[4',3':4,5]pyrrolo[2,3-b]pyridin-7-yl}-2-oxoethyl)bicyclo[2.2.1]heptane-1-carboxylic acid TLC:Rf 0.60 (ethyl acetate);
MS (ESI, Pos.): m/z=510 (M+H)$^+$.

Example 6(77)

4-{2-oxo-2-[9-(4-phenoxybenzyl)-5,6,8,9-tetrahydro-7H-pyrido[4',3':4,5]pyrrolo[2,3-b]pyridin-7-yl]ethyl}bicyclo[2.2.1]heptane-1-carboxylic acid TLC:Rf 0.38 (methylene chloride:ethyl acetate:methanol=8:4:1);
MS (ESI, Pos.): m/z=536 (M+H)$^+$.

Example 6(78)

4-{2-[9-(4-biphenylylmethyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid TLC:Rf 0.38 (methylene chloride:ethyl acetate:methanol=8:4:1);
MS (ESI, Pos.): m/z=520 (M+H)$^+$.

Example 6(79)

4-{2-oxo-2-[9-(3-phenoxybenzyl)-5,6,8,9-tetrahydro-7H-pyrido[4',3':4,5]pyrrolo[2,3-b]pyridin-7-yl]ethyl}bicyclo[2.2.1]heptane-1-carboxylic acid TLC:Rf 0.38 (methylene chloride:ethyl acetate:methanol=8:4:1);
MS (ESI, Pos.): m/z=536 (M+H)$^+$.

Example 6(80)

5-{2-oxo-2-[9-(4-phenoxybenzyl)-5,6,8,9-tetrahydro-7H-pyrido[4',3':4,5]pyrrolo[2,3-b]pyridin-7-yl]ethyl}-2-pyridinecarboxylic acid TLC:Rf 0.45 (chloroform:methanol:water=50:10:1);
MS (ESI, Pos.): m/z=519 (M+H)$^+$.

Example 6(81)

5-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)-2-pyridinecarboxylic acid TLC:Rf 0.41 (chloroform:methanol:water=50:10:1);
MS (ESI, Pos.): m/z=511 (M+H)$^+$.

Example 6(82)

{4-[2-(6,8-difluoro-9-{[2-(trifluoromethyl)-1,3-thiazol-5-yl]methyl}-1,3,4,9-tetrahydro-2H-beta-carbolin-2-yl)-2-oxoethyl]-1-piperidinyl}acetic acid hydrochloride TLC:Rf 0.21 (chloroform:methanol:water=50:10:1);
MS (ESI, Pos.): m/z=557 (M+H)$^+$.

Example 6(83)

5-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl]-2-oxoethyl)-2-pyridinecarboxylic acid TLC:Rf 0.49 (chloroform:methanol:water=50:10:1);
MS (ESI, Pos.): m/z=524 (M+H)$^+$.

Example 6(84)

(4-{2-oxo-2-[9-(4-phenoxybenzyl)-5,6,8,9-tetrahydro-7H-pyrido[4',3':4,5]pyrrolo[2,3-b]pyridin-7-yl]ethyl}-1-piperidinyl)acetic acid hydrochloride TLC:Rf 0.50 (chloroform:methanol:water=50:10:1);
MS (ESI, Pos.): m/z=539 (M+H)$^+$.

Example 6(85)

[4-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)-1-piperidinyl]acetic acid hydrochloride TLC:Rf 0.47 (chloroform:methanol:water=50:10:1);
MS (ESI, Pos.): m/z=544 (M+H)$^+$.

Example 6(86)

{4-[2-(8-fluoro-9-{[2-(trifluoromethyl)-1,3-thiazol-5-yl]methyl}-1,3,4,9-tetrahydro-2H-beta-carbolin-2-yl)-2-oxoethyl]-1-piperidinyl}acetic acid hydrochloride TLC:Rf 0.28 (chloroform:methanol:water=50:10:1);
MS (ESI, Pos.): m/z=539 (M+H)$^+$.

Example 6(87)

[4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)-1-piperidinyl]acetic acid hydrochloride TLC:Rf 0.48 (chloroform:methanol:water=50:10:1);
MS (ESI, Pos.): m/z=531 (M+H)$^+$.

Example 6(88)

4-(2-{9-[(5-methyl-2-phenyl-1,3-thiazol-4-yl)methyl]-5,6,8,9-tetrahydro-7H-pyrido[4',3':4,5]pyrrolo[2,3-b]pyridin-7-yl}-2-oxoethyl)bicyclo[2.2.1]heptane-1-carboxylic acid TLC:Rf 0.44 (chloroform:methanol=9:1);
MS (ESI, Pos.): m/z=541 (M+H)$^+$.

Example 6(89)

4-{2-[8-fluoro-9-(4-phenoxybenzyl)-1,3,4,9-tetrahydro-2H-beta-carbolin-2-yl]-2-oxoethyl}bicyclo[2.2.1]heptane-1-carboxylic acid TLC:Rf 0.47 (methylene chloride:methanol=9:1);
MS (ESI, Pos.): m/z=553 (M+H)$^+$.

Example 6(90)

4-[2-(6-fluoro-9-{[2-(trifluoromethyl)-1,3-thiazol-5-yl]methyl}-1,3,4,9-tetrahydro-2H-beta-carbolin-2-yl)-2-oxoethyl]bicyclo[2.2.1]heptane-1-carboxylic acid TLC:Rf 0.51 (methylene chloride:methanol=9:1);
MS (ESI, Pos.): m/z=536 (M+H)$^+$.

Example 6(91)

4-[2-(6,8-difluoro-9-{[2-(trifluoromethyl)-1,3-thiazol-5-yl]methyl}-1,3,4,9-tetrahydro-2H-beta-carbolin-2-yl)-2-oxoethyl]bicyclo[2.2.1]heptane-1-carboxylic acid TLC:Rf 0.63 (chloroform:methanol:water=50:10:1);
MS (ESI, Pos.): m/z=554 (M+H)$^+$.

Example 6(92)

4-(2-{6-fluoro-9-[3-(trifluoromethoxy)benzyl]-1,3,4,9-tetrahydro-2H-beta-carbolin-2-yl}-2-oxoethyl)bicyclo[2.2.1]heptane-1-carboxylic acid TLC:Rf 0.48 (methylene chloride:ethyl acetate:methanol=8:4:1);
MS (ESI, Pos.): m/z=545 (M+H)$^+$.

Example 6(93)

4-{2-[8-fluoro-9-(3-fluorobenzyl)-1,3,4,9-tetrahydro-2H-beta-carbolin-2-yl]-2-oxoethyl}bicyclo[2.2.1]heptane-1-carboxylic acid TLC:Rf 0.50 (chloroform:methanol:water=50:10:1);
MS (ESI, Pos.): m/z=479 (M+H)$^+$.

Example 6(94)

3-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]-1-adamantanecarboxylic acid TLC:Rf 0.56 (ethyl acetate);
MS (ESI, Pos.): m/z=559 (M+H)$^+$.

Example 6(95)

5-(2-{9-[3-(difluoromethoxy)benzyl]-5,6,8,9-tetrahydro-7H-pyrido[4',3':4,5]pyrrolo[2,3-b]pyridin-7-yl}-2-oxoethyl)-2-pyridinecarboxylic acid TLC:Rf 0.24 (chloroform:methanol:water=50:10:1);
MS (ESI, Pos.): m/z=493 (M+H)$^+$.

Example 6(96)

5-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)-2-pyridinecarboxylic acid TLC:Rf 0.36 (chloroform:methanol:water=50:10:1);
MS (ESI, Pos.): m/z=495 (M+H)$^+$.

Example 6(97)

5-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)-2-pyridinecarboxylic acid TLC:Rf 0.32 (chloroform:methanol:water=50:10:1);
MS (ESI, Pos.): m/z=511 (M+H)$^+$.

Example 6(98)

5-{2-[9-(3-ethylbenzyl)-5,6,8,9-tetrahydro-7H-pyrido[4',3':4,5]pyrrolo[2,3-b]pyridin-7-yl]-2-oxoethyl}-2-pyridinecarboxylic acid TLC:Rf 0.31 (chloroform:methanol:water=50:10:1);
MS (ESI, Pos.): m/z=455 (M+H)$^+$.

Example 6(99)

5-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]-2-pyridinecarboxylic acid TLC:Rf 0.19 (chloroform:methanol:water=50:10:1);
MS (ESI, Pos.): m/z=502 (M+H)$^+$.

Example 6(100)

4-{2-[9-(3-ethylbenzyl)-5,6,8,9-tetrahydro-7H-pyrido[4',3':4,5]pyrrolo[2,3-b]pyridin-7-yl]-2-oxoethyl}-2-methylbenzoic acid TLC:Rf 0.21 (hexane:ethyl acetate=1:1);
MS (ESI, Pos.): m/z=468 (M+H)$^+$.

Example 6(101)

2-methyl-4-{2-oxo-2-[9-(4-phenoxybenzyl)-5,6,8,9-tetrahydro-7H-pyrido[4',3':4,5]pyrrolo[2,3-b]pyridin-7-yl]ethyl}benzoic acid TLC:Rf 0.18 (hexane:ethyl acetate=1:1);
MS (ESI, Pos.): m/z=532 (M+H)$^+$.

Example 6(102)

4-(2-{9-[3-(difluoromethoxy)benzyl]-5,6,8,9-tetrahydro-7H-pyrido[4',3':4,5]pyrrolo[2,3-b]pyridin-7-yl}-2-oxoethyl)-2-methylbenzoic acid TLC:Rf 0.51 (chloroform:methanol:water=50:10:1);
MS (ESI, Pos.): m/z=506 (M+H)$^+$.

Example 6(103)

2-methyl-4-(2-oxo-2-{9-[(2-phenyl-1,3-thiazol-5-yl)methyl]-5,6,8,9-tetrahydro-7H-pyrido[4',3':4,5]pyrrolo[2,3-b]pyridin-7-yl}ethyl)benzoic acid TLC:Rf 0.49 (chloroform:methanol:water=50:10:1);
MS (ESI, Pos.): m/z=537 (M+H)+.

Reference Example 2 trans-4-{2-[9-(2,4-difluorobenzyl)-5,6,8,9-tetrahydro-7H-pyrido[4',3':4,5]pyrrolo[2,3-b]pyridin-7-yl]-2-oxoethyl}cyclohexanecarboxylic acid

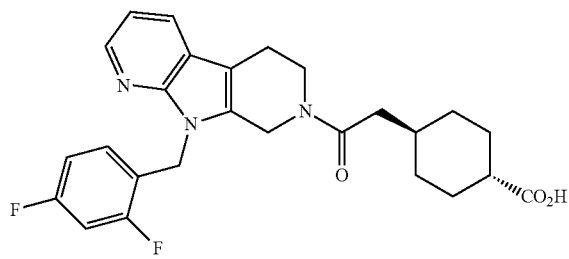 [SMILES: O=C(C[C@H]1CC[C@H](C(=O)O)CC1)N1CCc2c(n(Cc3ccc(F)cc3F)c3ncccc23)C1]

TLC:Rf 0.37 (methylene chloride:ethyl acetate:methanol=8:4:1);

$^1$H-NMR (DMSO-d$_6$):δ 0.75-1.37 (m, 4 H), 1.45-1.92 (m, 5 H), 1.92-2.38 (m, 3 H), 2.62-2.84 (m, 2 H), 3.68-3.84 (m, 2 H), 4.65 (s, 2 H), 5.38-5.56 (m, 2 H), 6.86-7.03 (m, 2 H), 7.10 (dd, J=7.8, 4.8 Hz), 7.21-7.36 (m, 1 H), 7.84-7.94 (m, 1 H), 8.20 (dd, J=4.8, 1.2 Hz, 1 H), 11.97 (s, 1 H).

Reference Manufacturing Example 22 tert-butyl 1-[2-(benzyloxy)-2-oxoethyl]piperidine-4-carboxylate

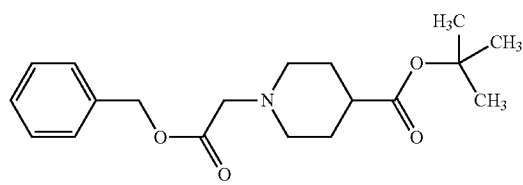 [SMILES: CC(C)(C)OC(=O)C1CCN(CC(=O)OCc2ccccc2)CC1]

To a suspension (39 mL) of tert-butyl piperidine-4-carboxylate (2.6 g) in acetonitrile was added diisopropylethylamine (4.4 mL), subsequently, benzyl bromoacetate (2.0 mL) was added at room temperature in portions, and the mixture was stirred for 4 hours. To the reaction mixture was added water, followed by extraction with ethyl acetate. This was washed with an aqueous saturated sodium chloride solution, dried with anhydrous sodium sulfate, and concentrated. The residue was purified by silica gel column chromatography (hexane:ethyl acetate=1:3→0:1) to obtain the title compound (3.4 g) having the following physical property values.

TLC:Rf 0.66 (hexane:ethyl acetate=2:1);

$^1$H-NMR (CDCl$_3$):δ 1.44 (s, 9 H) 1.68-1.92 (m, 4 H) 2.10-2.35 (m, 3 H) 2.83-2.96 (m, 2 H) 3.26 (s, 2 H) 5.16 (s, 2 H) 7.25-7.41 (m, 5 H).

Reference Manufacturing Example 23

[4-(tert-butoxycarbonyl)piperidin-1-yl]acetic acid

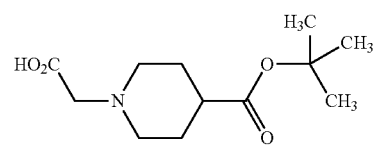 [SMILES: CC(C)(C)OC(=O)C1CCN(CC(=O)O)CC1]

The compound (3.4 g) produced in Reference manufacturing example 22 was dissolved in ethanol (41 mL), 5% Pd/C (50% hydrous product, 340 mg) was added under the argon atmosphere, and hydrogen was blown into the solution for 2.5 hours while stirred at room temperature. After the system was replaced with argon, the catalyst was filtered off using Celite, and this was concentrated under reduced pressure to obtain the title compound (2.5 g) having the following physical property values.

TLC:Rf 0.30 (chloroform:methanol:28% aqueous ammonia=85:13:2);

$^1$H-NMR (CDCl$_3$):δ 1.44 (s, 9 H) 1.97-2.25 (m, 4 H) 2.40-2.54 (m, 1 H) 2.95-3.45 (m, 4 H) 3.46 (s, 2 H) 7.43-7.96 (br.s, 1 H).

Reference Manufacturing Example 24 tert-butyl 1-{2-[9-(3-chloro-2,4-difluorobenzyl)-5,6,8,9-tetrahydro-7H-pyrido[4',3':4,5]pyrrolo[2,3-b]pyridin-7-yl]-2-oxoethyl}piperidine-4-carboxylate A corresponding alkyl halide in place of (3-bromopropyl)benzene, and a tetrahydropyridopyrrolopyridine derivative produced by operation in accordance with Reference manufacturing example 4→Reference manufacturing example 5→Reference manufacturing example 6→Reference manufacturing example 7→Reference manufacturing example 8 were used, which were subjected to operation in accordance with Reference manufacturing example 1, and the resulting compound and the compound produced in Reference manufacturing example 23 were used, which were subjected to operation in accordance with Reference manufacturing example 11 to obtain the title compound (50 mg) having the following physical property values.

TLC:Rf 0.58 (dichloromethane:ethyl acetate:methanol=8:4:1);

$^1$H-NMR (CDCl$_3$):δ 1.42-1.44 (m, 9 H) 1.48-1.95 (m, 4 H) 2.00-2.28 (m, 3 H) 2.68-2.96 (m, 4 H) 3.13-3.30 (m, 2 H) 3.84-3.98 (m, 2 H) 4.65-4.88 (m, 2 H) 5.47 (s, 2 H) 6.70-7.16 (m, 3 H) 7.81 (dd, J=7.8, 1.5 Hz, 1 H) 8.23-8.34 (m, 1 H).

Reference Manufacturing Example 25

1-{2-[9-(3-chloro-2,4-difluorobenzyl)-5,6,8,9-tetrahydro-7H-pyrido[4',3':4,5]pyrrolo[2,3-b]pyridin-7-yl]-2-oxoethyl}-4-piperidinecarboxylic acid hydrochloride

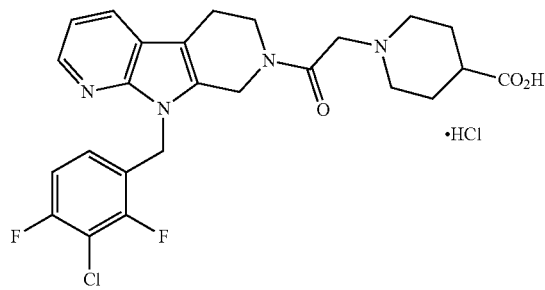 [SMILES: O=C(O)C1CCN(CC(=O)N2CCc3c(n(Cc4ccc(F)c(Cl)c4F)c4ncccc34)C2)CC1 ; Cl]

To the compound (30 mg) produced in Reference manufacturing example 24 were sequentially added a 4N solution (4 mL) of hydrogen chloride in dioxane, and water (0.1 mL) at room temperature, and the mixture was stirred overnight. The reaction mixture was concentrated, and the resulting solid was washed with ethyl acetate, filtered off and dried to obtain the title compound (25 mg) having the following physical property values.

TLC:Rf 0.23 (chloroform:methanol:water=50:10:1);
$^1$H-NMR (DMSO-$d_6$):δ 1.71-2.31 (m, 4 H) 2.64-4.53 (m, 12 H) 4.63-4.80 (m, 2 H) 5.51-5.63 (m, 2 H) 6.91-7.04 (m, 1 H) 7.14 (dd, J=7.7, 4.8 Hz, 1 H) 7.18-7.28 (m, 1 H) 7.87-8.02 (m, 1 H) 8.23 (dd, J=4.7, 1.4 Hz, 1 H) 9.47-9.77 (m, 1 H).

Example 7(1)-Example 7(78)

A corresponding alkyl halide in place of (3-bromopropyl) benzene, and a tetrahydropyridopyrrolopyridine derivative produced by operation in accordance with Reference manufacturing example 4→Reference manufacturing example 5→Reference manufacturing example 6→Reference manufacturing example 7→Reference manufacturing example 8 or the corresponding beta-carboline derivative were used, which were subjected to operation in accordance with Reference manufacturing example 1, and the resulting compound and the compound produced in Reference manufacturing example 23 or the corresponding ester were used, which were subjected to operation in accordance with Reference manufacturing example 11 and further subjected to operation in accordance with Reference manufacturing example 25 to obtain the following compounds.

Example 7(1)

1-(2-{5,5-dimethyl-9-[4-(trifluoromethoxy)benzyl]-5,6,8,9-tetrahydro-7H-pyrido[4',3':4,5]pyrrolo[2,3-b]pyridin-7-yl}-2-oxoethyl)-4-piperidinecarboxylic acid TLC:Rf 0.53 (methylene chloride:methanol:28% aqueous ammonia=15:5:1);
$^1$H-NMR (DMSO-$d_6$):δ 1.20-1.74 (m, 11 H), 1.80-2.05 (m, 2 H), 2.50-2.80 (m, 2 H), 3.00-3.20 (m, 2 H), 3.45-3.68 (m, 2 H), 4.50-4.90 (m, 2 H), 5.35-5.55 (m, 2 H), 7.07 (dd, J=7.5, 4.8 Hz, 1 H), 7.16-7.38 (m, 4 H), 8.02-8.12 (m, 1 H), 8.21 (dd, J=4.8, 1.2 Hz, 1 H).

Example 7(2)

[1-(2-{5,5-dimethyl-9-[4-(trifluoromethoxy)benzyl]-5,6,8,9-tetrahydro-7H-pyrido[4',3':4,5]pyrrolo[2,3-b]pyridin-7-yl}-2-oxoethyl)-4-piperidinyl]acetic acid TLC:Rf 0.55 (methylene chloride:methanol:28% aqueous ammonia=15:5:1);
MS (ESI, Pos. 20 V): m/z=559 (M+H)$^+$.

Example 7(3)

1-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)-4-piperidinecarboxylic acid hydrochloride

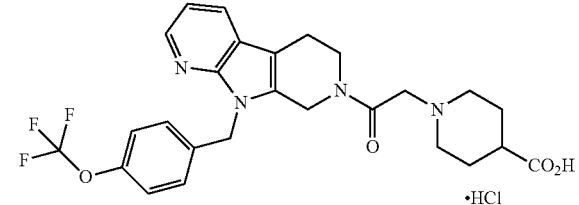 [SMILES: O=C(O)C1CCN(CC(=O)N2CCc3c(n(Cc4ccc(OC(F)(F)F)cc4)c4ncccc34)C2)CC1 ; Cl]

TLC:Rf 0.22 (chloroform:methanol:water=50:10:1);
MS (ESI, Pos. 20 V): m/z=517 (M+H)$^+$.

Example 7(4)

1-(2-{9-[3-chloro-4-(trifluoromethoxy)benzyl]-5,6,8,9-tetrahydro-7H-pyrido[4',3':4,5]pyrrolo[2,3-b]pyridin-7-yl}-2-oxoethyl)-4-piperidinecarboxylic acid hydrochloride TLC:Rf 0.21 (chloroform:methanol:water=50:10:1);
MS (ESI, Pos. 20 V): m/z=551 (M+H)$^+$.

Example 7(5)

1-(2-{9-[3-fluoro-4-(trifluoromethoxy)benzyl]-5,6,8,9-tetrahydro-7H-pyrido[4',3':4,5]pyrrolo[2,3-b]pyridin-7-yl}-2-oxoethyl)-4-piperidinecarboxylic acid hydrochloride TLC:Rf 0.20 (chloroform:methanol:water=50:10:1);
MS (ESI, Pos. 20 V): m/z=535 (M+H)$^+$.

Example 7(6)

1-(2-{9-[3-chloro-4-(trifluoromethoxy)benzyl]-5,5-dimethyl-5,6,8,9-tetrahydro-7H-pyrido[4',3':4,5]pyrrolo[2,3-b]pyridin-7-yl}-2-oxoethyl)-4-piperidinecarboxylic acid hydrochloride TLC:Rf 0.25 (chloroform:methanol:water=50:10:1);
MS (ESI, Pos. 20 V): m/z=579 (M+H)$^+$.

Example 7(7)

[1-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)-4-piperidinyl]acetic acid hydrochloride TLC:Rf 0.34 (chloroform:methanol:water=50:10:1);
MS (ESI, Pos. 20 V): m/z=531 (M+H)$^+$.

Example 7(8)

[1-(2-{9-[3-chloro-4-(trifluoromethoxy)benzyl]-5,6,8,9-tetrahydro-7H-pyrido[4',3':4,5]pyrrolo[2,3-b]pyridin-7-yl}-2-oxoethyl)-4-piperidinyl]acetic acid hydrochloride TLC:Rf 0.38 (chloroform:methanol:water=50:10:1);
MS (ESI, Pos. 20 V): m/z=565 (M+H)$^+$.

Example 7(9)

[1-(2-oxo-2-{9-[4-(trifluoromethoxy)benzyl]-1,3,4,9-tetrahydro-2H-beta-carbolin-2-yl}ethyl)-4-piperidinyl]acetic acid hydrochloride TLC:Rf 0.41 (chloroform:methanol:water=50:10:1);
MS (ESI, Pos. 20 V): m/z=530 (M+H)$^+$.

Example 7(10)

1-(2-{9-[3-fluoro-4-(trifluoromethoxy)benzyl]-5,5-dimethyl-5,6,8,9-tetrahydro-7H-pyrido[4',3':4,5]pyrrolo[2,3-b]pyridin-7-yl}-2-oxoethyl)-4-piperidinecarboxylic acid hydrochloride TLC:Rf 0.30 (chloroform:methanol:water=50:10:1);
MS (ESI, Pos. 20 V): m/z=563 (M+H)$^+$.

Example 7(11)

[1-(2-{9-[3-fluoro-4-(trifluoromethoxy)benzyl]-5,6,8,9-tetrahydro-7H-pyrido[4',3':4,5]pyrrolo[2,3-b]pyridin-7-yl}-2-oxoethyl)-4-piperidinyl]acetic acid hydrochloride TLC:Rf 0.25 (chloroform:methanol:water=50:10:1);
MS (ESI, Pos. 20 V): m/z=549 (M+H)$^+$.

Example 7(12)

[1-(2-{9-[3-fluoro-4-(trifluoromethoxy)benzyl]-1,3,4,9-tetrahydro-2H-beta-carbolin-2-yl}-2-oxoethyl)-4-piperidinyl]acetic acid hydrochloride TLC:Rf 0.32 (chloroform:methanol:water=50:10:1);
MS (FAB, Pos.): m/z=548 (M+H)$^+$.

Example 7(13)

[1-(2-{9-[3-chloro-4-(trifluoromethoxy)benzyl]-5,5-dimethyl-5,6,8,9-tetrahydro-7H-pyrido[4',3':4,5]pyrrolo[2,3-b]pyridin-7-yl}-2-oxoethyl)-4-piperidinyl]acetic acid hydrochloride TLC:Rf 0.27 (chloroform:methanol:water=50:10:1);
MS (ESI, Pos. 20 V): m/z=593 (M+H)$^+$.

Example 7(14)

[1-(2-{9-[3-fluoro-4-(trifluoromethoxy)benzyl]-5,5-dimethyl-5,6,8,9-tetrahydro-7H-pyrido[4',3':4,5]pyrrolo[2,3-b]pyridin-7-yl}-2-oxoethyl)-4-piperidinyl]acetic acid hydrochloride TLC:Rf 0.26 (chloroform:methanol:water=50:10:1);
MS (ESI, Pos. 20 V): m/z=577 (M+H)$^+$.

Example 7(15)

(1-{2-[9-(3-chloro-2,4-difluorobenzyl)-8-fluoro-1,3,4,9-tetrahydro-2H-beta-carbolin-2-yl]-2-oxoethyl}-4-piperidinyl)acetic acid hydrochloride TLC:Rf 0.24 (chloroform:methanol:water=50:10:1);
MS (ESI, Pos. 20 V): m/z=534 (M+H)$^+$.

Example 7(16)

[1-(2-{8-fluoro-9-[4-(trifluoromethoxy)benzyl]-1,3,4,9-tetrahydro-2H-beta-carbolin-2-yl}-2-oxoethyl)-4-piperidinyl]acetic acid hydrochloride TLC:Rf 0.24 (chloroform:methanol:water=50:10:1);
MS (ESI, Pos. 20 V): m/z=548 (M+H)$^+$.

Example 7(17)

(1-{2-[9-(3,5-dichlorobenzyl)-8-fluoro-1,3,4,9-tetrahydro-2H-beta-carbolin-2-yl]-2-oxoethyl}-4-piperidinyl)acetic acid hydrochloride TLC:Rf 0.26 (chloroform:methanol:water=50:10:1);
MS (ESI, Pos. 20 V): m/z=532 (M+H)$^+$.

Example 7(18)

[1-(2-{9-[3-chloro-4-(trifluoromethoxy)benzyl]-8-fluoro-1,3,4,9-tetrahydro-2H-beta-carbolin-2-yl}-2-oxoethyl)-4-piperidinyl]acetic acid hydrochloride TLC:Rf 0.24 (chloroform:methanol:water=50:10:1);
MS (ESI, Pos. 20 V): m/z=582 (M+H)$^+$.

Example 7(19)

[1-(2-{8-fluoro-9-[3-fluoro-4-(trifluoromethoxy)benzyl]-1,3,4,9-tetrahydro-2H-beta-carbolin-2-yl}-2-oxoethyl)-4-piperidinyl]acetic acid hydrochloride TLC:Rf 0.23 (chloroform:methanol:water=50:10:1);
MS (ESI, Pos. 20 V): m/z=566 (M+H)$^+$.

Example 7(20)

1-{2-[9-(3-chloro-2,4-difluorobenzyl)-8-fluoro-1,3,4,9-tetrahydro-2H-beta-carbolin-2-yl]-2-oxoethyl}-4-piperidinecarboxylic acid hydrochloride TLC:Rf 0.45 (chloroform:methanol:water=50:10:1);
MS (ESI, Pos. 20 V): m/z=520 (M+H)$^+$.

Example 7(21)

1-(2-{8-fluoro-9-[4-(trifluoromethoxy)benzyl]-1,3,4,9-tetrahydro-2H-beta-carbolin-2-yl}-2-oxoethyl)-4-piperidinecarboxylic acid hydrochloride TLC:Rf 0.46 (chloroform:methanol:water=50:10:1);
MS (ESI, Pos. 20 V): m/z=534 (M+H)$^+$.

Example 7(22)

1-{2-[9-(3,5-dichlorobenzyl)-8-fluoro-1,3,4,9-tetrahydro-2H-beta-carbolin-2-yl]-2-oxoethyl}-4-piperidinecarboxylic acid hydrochloride TLC:Rf 0.51 (chloroform:methanol:water=50:10:1);
MS (ESI, Pos. 20 V): m/z=518 (M+H)$^+$.

Example 7(23)

1-(2-{8-fluoro-9-[3-fluoro-4-(trifluoromethoxy)benzyl]-1,3,4,9-tetrahydro-2H-beta-carbolin-2-yl}-2-oxoethyl)-4-piperidinecarboxylic acid hydrochloride TLC:Rf 0.43 (chloroform:methanol:water=50:10:1);
MS (ESI, Pos. 20 V): m/z=552 (M+H)$^+$.

Example 7(24)

1-(2-{9-[(5-chloro-2-thienyl)methyl]-8-fluoro-1,3,4,9-tetrahydro-2H-beta-carbolin-2-yl}-2-oxoethyl)-4-piperidinecarboxylic acid hydrochloride TLC:Rf 0.50 (chloroform:methanol:water=50:10:1);
MS (ESI, Pos. 20 V): m/z=490 (M+H)$^+$.

Example 7(25)

1-[2-(8-fluoro-9-{[5-(trifluoromethyl)-2-thienyl]methyl}-1,3,4,9-tetrahydro-2H-beta-carbolin-2-yl)-2-oxoethyl]-4-piperidinecarboxylic acid hydrochloride TLC:Rf 0.50 (chloroform:methanol:water=50:10:1);
MS (ESI, Pos. 20 V): m/z=524 (M+H)$^+$.

Example 7(26)

[1-(2-{9-[(5-chloro-2-thienyl)methyl]-8-fluoro-1,3,4,9-tetrahydro-2H-beta-carbolin-2-yl}-2-oxoethyl)-4-piperidinyl]acetic acid hydrochloride TLC:Rf 0.48 (chloroform:methanol:water=50:10:1);
MS (ESI, Pos. 20 V): m/z=504 (M+H)$^+$.

Example 7(27)

{1-[2-(8-fluoro-9-{[5-(trifluoromethyl)-2-thienyl]methyl}-1,3,4,9-tetrahydro-2H-beta-carbolin-2-yl)-2-oxoethyl]-4-piperidinyl}acetic acid hydrochloride TLC:Rf 0.47 (chloroform:methanol:water=50:10:1);
MS (ESI, Pos. 20 V): m/z=538 (M+H)$^+$.

Example 7(28)

[4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)-1-piperazinyl]acetic acid dihydrochloride TLC:Rf 0.05 (chloroform:methanol:28% aqueous ammonia=85:13:2);
$^1$H-NMR (DMSO-d$_6$):δ 2.65-2.96 (m, 2 H) 3.34-5.69 (m, 21 H) 7.10-7.39 (m, 5 H) 7.93-8.04 (m, 1 H) 8.25 (dd, J=4.8, 1.3 Hz, 1 H).

Example 7(29)

[4-(2-{9-[3-chloro-4-(trifluoromethoxy)benzyl]-5,6,8,9-tetrahydro-7H-pyrido[4',3':4,5]pyrrolo[2,3-b]pyridin-7-yl}-2-oxoethyl)-1-piperazinyl]acetic acid dihydrochloride TLC:Rf 0.06 (chloroform:methanol:28% aqueous ammonia=85:13:2);
$^1$H-NMR (DMSO-d$_6$):δ 2.65-3.01 (m, 2 H) 3.25-5.92 (m, 21 H) 7.05-7.36 (m, 2 H) 7.45-7.68 (m, 2 H) 7.91-8.03 (m, 1 H) 8.20-8.40 (m, 1 H).

Example 7(30)

[4-(2-{9-[3-fluoro-4-(trifluoromethoxy)benzyl]-5,6,8,9-tetrahydro-7H-pyrido[4',3':4,5]pyrrolo[2,3-b]pyridin-7-yl}-2-oxoethyl)-1-piperazinyl]acetic acid dihydrochloride TLC:Rf 0.05 (chloroform:methanol:28% aqueous ammonia=85:13:2);
$^1$H-NMR (DMSO-d$_6$):δ 2.66-2.96 (m, 2 H) 3.34-5.80 (m, 21 H) 6.93-7.60 (m, 4 H) 7.93-8.03 (m, 1 H) 8.21-8.27 (m, 1 H).

Example 7(31)

[4-(2-{5,5-dimethyl-9-[4-(trifluoromethoxy)benzyl]-5,6,8,9-tetrahydro-7H-pyrido[4',3':4,5]pyrrolo[2,3-b]pyridin-7-yl}-2-oxoethyl)-1-piperazinyl]acetic acid dihydrochloride TLC:Rf 0.17 (chloroform:methanol:water=50:10:1);
MS (ESI, Pos. 20 V): m/z=560 (M+H)$^+$.

Example 7(32)

[4-(2-{9-[3-chloro-4-(trifluoromethoxy)benzyl]-5,5-dimethyl-5,6,8,9-tetrahydro-7H-pyrido[4',3':4,5]pyrrolo[2,3-b]pyridin-7-yl}-2-oxoethyl)-1-piperazinyl]acetic acid dihydrochloride TLC:Rf 0.17 (chloroform:methanol:water=50:10:1);
MS (ESI, Pos. 20 V): m/z=594 (M+H)$^+$.

Example 7(33)

[4-(2-{9-[3-fluoro-4-(trifluoromethoxy)benzyl]-5,5-dimethyl-5,6,8,9-tetrahydro-7H-pyrido[4',3':4,5]pyrrolo[2,3-b]pyridin-7-yl}-2-oxoethyl)-1-piperazinyl]acetic acid dihydrochloride TLC:Rf 0.15 (chloroform:methanol:water=50:10:1);
MS (ESI, Pos. 20 V): m/z=578 (M+H)$^+$.

Example 7(34)

(4-{2-[9-(3-chloro-2,4-difluorobenzyl)-8-fluoro-1,3,4,9-tetrahydro-2H-beta-carbolin-2-yl]-2-oxoethyl}-1-piperazinyl)acetic acid dihydrochloride TLC:Rf 0.29 (chloroform:methanol:water=50:10:1);
MS (ESI, Pos. 20 V): m/z=535 (M+H)+.

Example 7(35)

[4-(2-{8-fluoro-9-[4-(trifluoromethoxy)benzyl]-1,3,4,9-tetrahydro-2H-beta-carbolin-2-yl}-2-oxoethyl)-1-piperazinyl]acetic acid dihydrochloride TLC:Rf 0.29 (chloroform:methanol:water=50:10:1);
MS (ESI, Pos. 20 V): m/z=549 (M+H)+.

Example 7(36)

(4-{2-[9-(3,5-dichlorobenzyl)-8-fluoro-1,3,4,9-tetrahydro-2H-beta-carbolin-2-yl]-2-oxoethyl}-1-piperazinyl)acetic acid dihydrochloride TLC:Rf 0.32 (chloroform:methanol:water=50:10:1);
MS (ESI, Pos. 20 V): m/z=533 (M+H)+.

Example 7(37)

[4-(2-{9-[3-chloro-4-(trifluoromethoxy)benzyl]-8-fluoro-1,3,4,9-tetrahydro-2H-beta-carbolin-2-yl}-2-oxoethyl)-1-piperazinyl]acetic acid dihydrochloride TLC:Rf 0.31 (chloroform:methanol:water=50:10:1);
MS (ESI, Pos. 20 V): m/z=583 (M+H)+.

Example 7(38)

[4-(2-{8-fluoro-9-[3-fluoro-4-(trifluoromethoxy)benzyl]-1,3,4,9-tetrahydro-2H-beta-carbolin-2-yl}-2-oxoethyl)-1-piperazinyl]acetic acid dihydrochloride TLC:Rf 0.29 (chloroform:methanol:water=50:10:1);
MS (ESI, Pos. 20 V): m/z=567 (M+H)+.

Example 7(39)

4-methyl-1-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]-4-piperidinecarboxylic acid

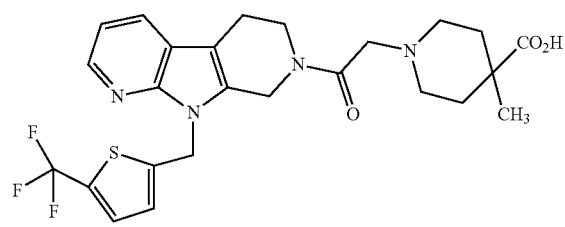 [SMILES: CC1(C(=O)O)CCN(CC(=O)N2CCc3c(n(Cc4ccc(C(F)(F)F)s4)c4ncccc34)C2)CC1]

TLC:Rf 0.45 (chloroform:methanol=4:1);
MS (FAB, Pos.): m/z=521 (M+H)+.

Example 7(40)

4-hydroxy-1-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]-4-piperidinecarboxylic acid TLC:Rf 0.25 (chloroform:methanol:water=50:10:1);
MS (FAB, Pos.): m/z=523 (M+H)+.

Example 7(41)

rel-{(2R,6S)-2,6-dimethyl-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]-1-piperazinyl}acetic acid dihydrochloride

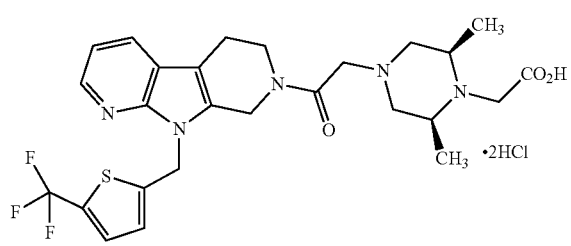 [SMILES: C[C@@H]1CN(CC(=O)N2CCc3c(n(Cc4ccc(C(F)(F)F)s4)c4ncccc34)C2)C[C@H](C)N1CC(=O)O]

TLC:Rf 0.17 (chloroform:methanol:28% aqueous ammonia=85:13:2);
MS (ESI, Pos. 20 V): m/z=550 (M+H)+.

Example 7(42)

4-methoxy-1-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]-4-piperidinecarboxylic acid TLC:Rf 0.14 (chloroform:methanol:water=80:20:1);
MS (FAB, Pos.): m/z=537 (M+H)+.

Example 7(43)

rel-{(3R,5S)-3,5-dimethyl-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]-1-piperazinyl}acetic acid TLC:Rf 0.06 (chloroform:methanol:28% aqueous ammonia=85:13:2);
MS (ESI, Pos. 20 V): m/z=550 (M+H)+.

Example 7(44)

{1-[2-oxo-2-(9-{[5-(trifluoromethyl)-2-thienyl]methyl}-1,3,4,9-tetrahydro-2H-beta-carbolin-2-yl)ethyl]-4-piperidinyl}acetic acid hydrochloride TLC:Rf 0.27 (chloroform:methanol:water=50:10:1);
MS (ESI, Pos. 20 V): m/z=520 (M+H)+.

Example 7(45)

1-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]-1,2,3,6-tetrahydro-4-pyridinecarboxylic acid

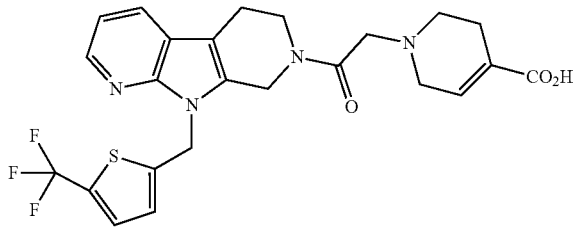 [SMILES: O=C(O)C1=CCN(CC(=O)N2CCc3c(n(Cc4ccc(C(F)(F)F)s4)c4ncccc34)C2)CC1]

TLC:Rf 0.25 (chloroform:methanol:water=90:10:1);
MS (FAB, Pos.): m/z=505 (M+H)$^+$.

Example 7(46)

1-[2-oxo-2-(9-{[5-(trifluoromethyl)-2-thienyl]methyl}-1,3,4,9-tetrahydro-2H-beta-carbolin-2-yl)ethyl]-4-piperidinecarboxylic acid hydrochloride TLC:Rf 0.16 (chloroform:methanol:water=50:10:1);
MS (ESI, Pos. 20 V): m/z=506 (M+H)$^+$.

Example 7(47)

{4-[2-oxo-2-(9-{[5-(trifluoromethyl)-2-thienyl]methyl}-1,3,4,9-tetrahydro-2H-beta-carbolin-2-yl)ethyl]-1-piperazinyl}acetic acid dihydrochloride TLC:Rf 0.07 (chloroform:methanol:water=50:10:1);
MS (ESI, Pos. 20 V): m/z=521 (M+H)$^+$.

Example 7(48)

2-amino-6-oxo-6-(9-{[5-(trifluoromethyl)-2-thienyl]methyl}-5,6,8,9-tetrahydro-7H-pyrido[4',3':4,5]pyrrolo[2,3-b]pyridin-7-yl)hexanoic acid hydrochloride TLC:Rf 0.11 (chloroform:methanol:water=80:20:1);
MS (FAB, Pos.): m/z=481 (M+H)$^+$.

Example 7(49)

rel-{(2R,6S)-4-[2-(8-fluoro-9-{[5-(trifluoromethyl)-2-thienyl]methyl}-1,3,4,9-tetrahydro-2H-beta-carbolin-2-yl)-2-oxoethyl]-2,6-dimethyl-1-piperazinyl}acetic acid dihydrochloride TLC:Rf 0.50 (chloroform:methanol:water=50:10:1);
MS (ESI, Pos. 20 V): m/z=567 (M+H)$^+$.

Example 7(50)

rel-{(2R,6S)-2,6-dimethyl-4-[2-oxo-2-(9-{[5-(trifluoromethyl)-2-thienyl]methyl}-1,3,4,9-tetrahydro-2H-beta-carbolin-2-yl)ethyl]-1-piperazinyl}acetic acid dihydrochloride TLC:Rf 0.49 (chloroform:methanol:water=50:10:1);
MS (ESI, Pos. 20 V): m/z=549 (M+H)$^+$.

Example 7(51)

rel-[(2R,6S)-4-(2-{9-[(5-chloro-2-thienyl)methyl]-8-fluoro-1,3,4,9-tetrahydro-2H-beta-carbolin-2-yl}-2-oxoethyl)-2,6-dimethyl-1-piperazinyl]acetic acid dihydrochloride TLC:Rf 0.56 (chloroform:methanol:water=50:10:1);
MS (ESI, Pos. 20 V): m/z=533 (M+H)$^+$.

Example 7(52)

1-(2-{9-[(5-chloro-2-thienyl)methyl]-8-fluoro-1,3,4,9-tetrahydro-2H-beta-carbolin-2-yl}-2-oxoethyl)-4-methyl-4-piperidinecarboxylic acid TLC:Rf 0.31 (methylene chloride:methanol:water=90:10:1);
MS (FAB, Pos.): m/z=504 (M+H)$^+$.

Example 7(53)

4-methyl-1-[2-oxo-2-(9-{[5-(trifluoromethyl)-2-thienyl]methyl}-1,3,4,9-tetrahydro-2H-beta-carbolin-2-yl)ethyl]-4-piperidinecarboxylic acid TLC:Rf 0.37 (methylene chloride:methanol:water=90:10:1);
MS (FAB, Pos.): m/z=520 (M+H)$^+$.

Example 7(54)

1-[2-(8-fluoro-9-{[5-(trifluoromethyl)-2-thienyl]methyl}-1,3,4,9-tetrahydro-2H-beta-carbolin-2-yl)-2-oxoethyl]-4-methyl-4-piperidinecarboxylic acid TLC:Rf 0.37 (methylene chloride:methanol:water=90:10:1);
MS (FAB, Pos.): m/z=538 (M+H)$^+$.

Example 7(55)

(1-{2-[9-(2,4-difluorobenzyl)-8-fluoro-1,3,4,9-tetrahydro-2H-beta-carbolin-2-yl]-2-oxoethyl}-4-piperidinyl)acetic acid hydrochloride TLC:Rf 0.47 (chloroform:methanol:water=50:10:1);
MS (ESI, Pos. 20 V): m/z=500 (M+H)$^+$.

Example 7(56)

1-{2-oxo-2-[9-(4-phenoxybenzyl)-5,6,8,9-tetrahydro-7H-pyrido[4',3':4,5]pyrrolo[2,3-b]pyridin-7-yl]ethyl}-4-piperidinecarboxylic acid hydrochloride TLC:Rf 0.51 (chloroform:methanol:water=50:10:1);
MS (ESI, Pos.): m/z=525 (M+H)$^+$.

Example 7(57)

1-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)-4-piperidinecarboxylic acid hydrochloride TLC:Rf 0.48 (chloroform:methanol:water=50:10:1);
MS (ESI, Pos.): m/z=517 (M+H)$^+$.

Example 7(58)

(1-{2-oxo-2-[9-(4-phenoxybenzyl)-5,6,8,9-tetrahydro-7H-pyrido[4',3':4,5]pyrrolo[2,3-b]pyridin-7-yl]ethyl}-4-piperidinyl)acetic acid hydrochloride TLC:Rf 0.36 (chloroform:methanol:water=50:10:1);
MS (ESI, Pos.): m/z=539 (M+H)$^+$.

Example 7(59)

[4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)-1-piperazinyl]acetic acid dihydrochloride TLC:Rf 0.31 (chloroform:methanol:water=50:10:1);
MS (ESI, Pos.): m/z=532 (M+H)$^+$.

Example 7(60)

[4-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)-1-piperazinyl]acetic acid dihydrochloride TLC:Rf 0.32 (chloroform:methanol:water=50:10:1);
MS (ESI, Pos.): m/z=545 (M+H)$^+$.

Example 7(61)

[1-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)-4-piperidinyl]acetic acid hydrochloride TLC:Rf 0.40 (chloroform:methanol:water=50:10:1);
MS (ESI, Pos.): m/z=531 (M+H)$^+$.

Example 7(62)

[1-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)-4-piperidinyl]acetic acid hydrochloride TLC:Rf 0.44 (chloroform:methanol:water=50:10:1);
MS (ESI, Pos.): m/z=544 (M+H)$^+$.

Example 7(63)

[4-(2-{8-fluoro-9-[3-(trifluoromethoxy)benzyl]-1,3,4,9-tetrahydro-2H-beta-carbolin-2-yl}-2-oxoethyl)-1-piperazinyl]acetic acid dihydrochloride TLC:Rf 0.32 (chloroform:methanol:water=50:10:1);
MS (ESI, Pos.): m/z=549 (M+H)$^+$.

Example 7(64)

1-(2-{8-fluoro-9-[3-(trifluoromethoxy)benzyl]-1,3,4,9-tetrahydro-2H-beta-carbolin-2-yl}-2-oxoethyl)-4-piperidinecarboxylic acid hydrochloride TLC:Rf 0.39 (chloroform:methanol:water=50:10:1);
MS (ESI, Pos.): m/z=534 (M+H)$^+$.

Example 7(65)

[1-(2-{8-fluoro-9-[3-(trifluoromethoxy)benzyl]-1,3,4,9-tetrahydro-2H-beta-carbolin-2-yl}-2-oxoethyl)-4-piperidinyl]acetic acid hydrochloride TLC:Rf 0.41 (chloroform:methanol:water=50:10:1);
MS (ESI, Pos.): m/z=548 (M+H)$^+$.

Example 7(66)

(1-{2-[8-fluoro-9-(3-fluorobenzyl)-1,3,4,9-tetrahydro-2H-beta-carbolin-2-yl]-2-oxoethyl}-4-piperidinyl)acetic acid hydrochloride TLC:Rf 0.44 (chloroform:methanol:water=50:10:1);
MS (ESI, Pos.): m/z=482 (M+H)$^+$.

Example 7(67)

(1-{2-[8-fluoro-9-(4-fluorobenzyl)-1,3,4,9-tetrahydro-2H-beta-carbolin-2-yl]-2-oxoethyl}-4-piperidinyl)acetic acid hydrochloride TLC:Rf 0.44 (chloroform:methanol:water=50:10:1);
MS (ESI, Pos.): m/z=482 (M+H)$^+$.

Example 7(68)

{4-[2-(6,8-difluoro-9-{[2-(trifluoromethyl)-1,3-thiazol-5-yl]methyl}-1,3,4,9-tetrahydro-2H-beta-carbolin-2-yl)-2-oxoethyl]-1-piperazinyl}acetic acid dihydrochloride TLC:Rf 0.12 (chloroform:methanol:water=50:10:1);
MS (ESI, Pos.): m/z=558 (M+H)$^+$.

Example 7(69)

1-[2-(6,8-difluoro-9-{[2-(trifluoromethyl)-1,3-thiazol-5-yl]methyl}-1,3,4,9-tetrahydro-2H-beta-carbolin-2-yl)-2-oxoethyl]-4-piperidinecarboxylic acid hydrochloride TLC:Rf 0.29 (chloroform:methanol:water=50:10:1);
MS (ESI, Pos.): m/z=543 (M+H)$^+$.

Example 7(70)

{1-[2-(6,8-difluoro-9-{[2-(trifluoromethyl)-1,3-thiazol-5-yl]methyl}-1,3,4,9-tetrahydro-2H-beta-carbolin-2-yl)-2-oxoethyl]-4-piperidinyl}acetic acid hydrochloride TLC:Rf 0.21 (chloroform:methanol:water=50:10:1);
MS (ESI, Pos.): m/z=557 (M+H)$^+$.

Example 7(71)

{4-[2-(8-fluoro-9-{[2-(trifluoromethyl)-1,3-thiazol-5-yl]methyl}-1,3,4,9-tetrahydro-2H-beta-carbolin-2-yl)-2-oxoethyl]-1-piperazinyl}acetic acid dihydrochloride TLC:Rf 0.21 (chloroform:methanol:water=50:10:1);
MS (ESI, Pos.): m/z=540 (M+H)$^+$.

Example 7(72)

(4-{2-[8-fluoro-9-(4-phenoxybenzyl)-1,3,4,9-tetra-hydro-2H-beta-carbolin-2-yl]-2-oxoethyl}-1-piperazinyl)acetic acid dihydrochloride TLC:Rf 0.38 (chloroform:methanol:water=50:10:1);
MS (ESI, Pos.): m/z=557 (M+H)$^+$.

Example 7(73)

(1-{2-[8-fluoro-9-(4-phenoxybenzyl)-1,3,4,9-tetra-hydro-2H-beta-carbolin-2-yl]-2-oxoethyl}-4-piperidinyl)acetic acid hydrochloride TLC:Rf 0.47 (chloroform:methanol:water=50:10:1);
MS (ESI, Pos.): m/z=556 (M+H)$^+$.

Example 7(74)

{1-[2-(6-fluoro-9-{[2-(trifluoromethyl)-1,3-thiazol-5-yl]methyl}-1,3,4,9-tetrahydro-2H-beta-carbolin-2-yl)-2-oxoethyl]-4-piperidinyl}acetic acid hydrochloride TLC:Rf 0.21 (methylene chloride:methanol=9:1);
MS (ESI, Pos.): m/z=539 (M+H)$^+$.

Example 7(75)

[4-(2-{6-fluoro-9-[3-(trifluoromethoxy)benzyl]-1,3,4,9-tetrahydro-2H-beta-carbolin-2-yl}-2-oxoethyl)-1-piperazinyl]acetic acid TLC:Rf 0.10 (methylene chloride:methanol=9:1);
MS (ESI, Pos.): m/z=549 (M+H)$^+$.

Example 7(76)

[1-(2-{6-fluoro-9-[3-(trifluoromethoxy)benzyl]-1,3,4,9-tetrahydro-2H-beta-carbolin-2-yl}-2-oxoethyl)-4-piperidinyl]acetic acid TLC:Rf 0.24 (methylene chloride:methanol=9:1);
MS (ESI, Pos.): m/z=548 (M+H)$^+$.

Example 7(77)

[(1S,4S)-5-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)-2,5-diazabicyclo[2.2.1]hept-2-yl]acetic acid TLC:Rf 0.47 (methylene chloride:ethyl acetate:methanol=8:4:1);
MS (FAB, Pos.): m/z=544 (M+H)$^+$.

Example 7(78)

1-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)-4-piperidinecarboxylic acid hydrochloride TLC:Rf 0.45 (chloroform:methanol:water=50:10:1);
MS (ESI, Pos.): m/z=530 (M+H)$^+$.

Reference Manufacturing Example 26 tert-butyl 2-methyl-2-[3-(tetrahydro-2H-pyran-2-yloxy)propoxy]propanoate

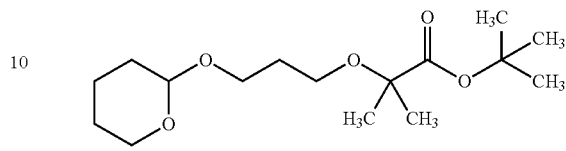

To a solution (22 mL) of tert-butyl 2-hydroxy-2-methylpropanoate (1.0 g) in N,N-dimethylformamide was added sodium hydride (250 mg) under an ice bath, and the mixture was stirred at room temperature for 1 hour. Thereafter, under an ice bath, 2-(3-bromopropoxy)tetrahydro-2H-pyran (0.88 mL) was added dropwise, and the mixture was stirred at room temperature overnight. To the reaction mixture were added water and 1N hydrochloric acid under an ice bath, followed by extraction with t-butyl methyl ether. The organic layer was sequentially washed with an aqueous saturated sodium bicarbonate solution and an aqueous saturated sodium chloride solution, dried with anhydrous sodium sulfate, and concentrated. The residue was purified by silica gel column chromatography (hexane:ethyl acetate=8:1) to obtain the title compound having the following physical property values, as a mixture (400 mg) with tert-butyl 2-hydroxy-2-methylpropanoate.

TLC:Rf 0.23 (hexane:ethyl acetate=8:1);
$^1$H-NMR (CDCl$_3$):δ 1.37 (s, 6 H) 1.47 (s, 9 H) 1.31-1.93 (m, 8 H) 3.42-3.56 (m, 4 H) 3.77-3.91 (m, 2 H) 4.55-4.60 (m, 1 H).

Reference Manufacturing Example 27 tert-butyl 2-(3-hydroxypropoxy)-2-methylpropanoate

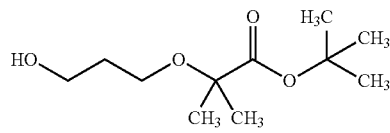

To a solution (4.3 mL) of the compound produced in Reference manufacturing example 26 (400 mg: mixture with tert-butyl 2-hydroxy-2-methylpropanoate) in methanol was added p-toluenesulfonic acid monohydrate (26 mg) at room temperature, and the mixture was stirred at room temperature for 2 hours. To the reaction mixture was added triethylamine (18 L), this was concentrated, and the resulting residue was purified by silica gel column chromatography (hexane:ethyl acetate=8:1→4:1→2:1) to obtain the title compound (130 mg) having the following physical property values.

TLC:Rf 0.22 (hexane:ethyl acetate=4:1);
$^1$H-NMR (CDCl$_3$):δ 1.37 (s, 6 H) 1.46 (s, 9 H) 1.64-1.84 (m, 2 H) 3.31 (br.s, 1 H) 3.51-3.60 (m, 2 H) 3.73-3.84 (m, 2 H).

Reference Manufacturing Example 28

3-(2-tert-butoxy-1,1-dimethyl-2-oxoethoxy)propionic acid

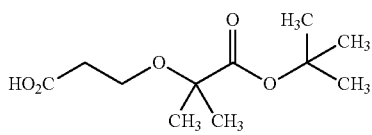

To a solution of the compound (116 mg) produced in Reference manufacturing example 27 in acetonitrile were sequentially added a buffer solution of sodium dihydrogen phosphate (2.7 mL, pH: 6.58), 2,2,6,6-tetramethylpiperidine 1-oxyl (9 mg) and an aqueous solution (1.2 mL) of sodium chlorite (97 mg) and a sodium hypochlorite solution (50 μL) at room temperature, a temperature was raised to 50° C., and the mixture was stirred for 2.5 hours. To the reaction mixture was added an aqueous saturated sodium sulfite solution under an ice bath, and it was confirmed that the solution became colorless and transparent, followed by concentration. To the resulting residue was added 5N hydrochloric acid, this was extracted with ethyl acetate two times, and the extract was dried with anhydrous sodium sulfate, and concentrated to obtain the title compound (118 mg) having the following physical property values.

TLC:Rf 0.23 (hexane:ethyl acetate=2:1);
$^1$H-NMR (CDCl$_3$):δ 1.41 (s, 6 H) 1.48 (s, 9 H) 2.69 (t, J=6.0 Hz, 2 H) 3.69 (t, J=6.0 Hz, 2 H).

Reference Manufacturing Example 29

2-{3-[9-(3-fluorobenzyl)-5,6,8,9-tetrahydro-7H-pyrido[4',3':4,5]pyrrolo[2,3-b]pyridin-7-yl]-3-oxopropoxy}-2-methylpropanoic acid hydrochloride

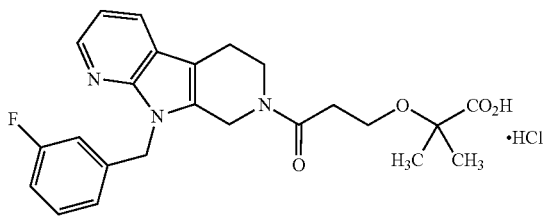 [SMILES: CC(C)(OCCC(=O)N1CCc2c(n(Cc3cccc(F)c3)c3ncccc23)C1)C(=O)O ; Cl]

A corresponding alkyl halide in place of (3-bromopropyl)benzene and a tetrahydropyridopyrrolopyridine derivative produced by operation in accordance with Reference manufacturing example 4→Reference manufacturing example 5→Reference manufacturing example 6→Reference manufacturing example 7→Reference manufacturing example 8 were used, which were subjected to operation in accordance with Reference manufacturing example 1, and the resulting compound and the compound produced in Reference manufacturing example 28 were used, which were subjected to operation in accordance with Reference manufacturing example 11 and further subjected to operation in accordance with Reference manufacturing example 25 to obtain the title compound (59 mg) having the following physical property values.

TLC:Rf 0.09 (chloroform:methanol:28% aqueous ammonia=85:13:2);
$^1$H-NMR (DMSO-d$_6$):δ 1.20-1.34 (m, 6 H) 2.23-2.87 (m, 4 H) 3.50-3.84 (m, 4 H) 4.21-5.05 (m, 4 H) 5.47-5.57 (m, 2 H) 6.87-7.17 (m, 4 H) 7.28-7.39 (m, 1 H) 7.90-7.98 (m, 1 H) 8.20-8.25 (m, 1 H).

Example 8(1)-Example 8(5)

A corresponding alkyl halide in place of (3-bromopropyl)benzene and a tetrahydropyridopyrrolopyridine derivative produced by operation in accordance with Reference manufacturing Example 4→Reference manufacturing example 5→Reference manufacturing example 6→Reference manufacturing example 7→Reference manufacturing example 8 were used, which were subjected to operation in accordance with Reference manufacturing example 1, and the resulting compound and the compound produced in Reference manufacturing example 28 were used, which were subjected to operation in accordance with Reference manufacturing example 11 and further subjected to operation in accordance with Reference manufacturing example 25 to obtain the following compounds.

Example 8(1)

2-methyl-2-(3-oxo-3-{9-[4-(trifluoromethoxy)benzyl]-5,6,8,9-tetrahydro-7H-pyrido[4',3':4,5]pyrrolo[2,3-b]pyridin-7-yl}propoxy)propanoic acid TLC:Rf 0.18 (chloroform:methanol:28% aqueous ammonia=85:13:2);
MS (ESI, Pos.): m/z=506 (M+H)$^+$.

Example 8(2)

2-(3-{9-[3-chloro-4-(trifluoromethoxy)benzyl]-5,6,8,9-tetrahydro-7H-pyrido[4',3':4,5]pyrrolo[2,3-b]pyridin-7-yl}-3-oxopropoxy)-2-methylpropanoic acid TLC:Rf 0.17 (chloroform:methanol:28% aqueous ammonia=85:13:2);
MS (ESI, Pos.): m/z=540 (M+H)$^+$.

Example 8(3)

2-(3-{9-[3-fluoro-4-(trifluoromethoxy)benzyl]-5,6,8,9-tetrahydro-7H-pyrido[4',3':4,5]pyrrolo[2,3-b]pyridin-7-yl}-3-oxopropoxy)-2-methylpropanoic acid TLC:Rf 0.15 (chloroform:methanol:28% aqueous ammonia=85:13:2);
MS (ESI, Pos.): m/z=524 (M+H)$^+$.

Example 8(4)

2-methyl-2-[3-oxo-3-(9-{[5-(trifluoromethyl)-2-thienyl]methyl}-5,6,8,9-tetrahydro-7H-pyrido[4',3':4,5]pyrrolo[2,3-b]pyridin-7-yl)propoxy]propanoic acid TLC:Rf 0.16 (chloroform:methanol:28% aqueous ammonia=85:13:2);
MS (ESI, Pos.): m/z=496 (M+H)$^+$.

Example 8(5)

2-methyl-2-[3-oxo-3-(9-{[5-(trifluoromethyl)-3-thienyl]methyl}-5,6,8,9-tetrahydro-7H-pyrido[4',3':4,5]pyrrolo[2,3-b]pyridin-7-yl)propoxy]propanoic acid TLC:Rf 0.16 (chloroform:methanol:28% aqueous ammonia=85:13:2);
MS (ESI, Pos.): m/z=496 (M+H)$^+$.

Reference Manufacturing Example 30 tert-butyl 1-[4-(tetrahydro-2H-pyran-2-yloxy)butyl]cyclopropanecarboxylate

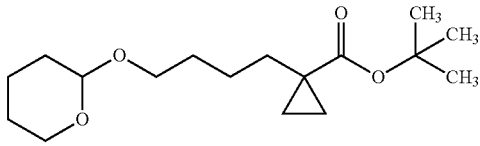 [SMILES: CC(C)(C)OC(=O)C1(CCCCOC2CCCCO2)CC1]

Under the argon atmosphere, tert-butyl cyclopropylcarboxylate (3.76 g) and 2-(4-bromobutoxy)tetrahydro-2H-pyran (7.52 g) were dissolved in anhydrous/THF (106 mL), followed by cooling to an inner temperature of −65° C. A lithium diisopropylamide solution (2.0M, THF:heptane:ethylbenzene solution) (19.8 mL) was added dropwies over 15 minutes. After completion of addition, the mixture was stirred at room temperature for 8 hours. An aqueous saturated ammonium chloride solution was added to stop the reaction, and water, and hexane:ethyl acetate (1:1) were added, followed by extraction. The organic layer was washed with dilute hydrochloric acid, water and an aqueous saturated sodium chloride solution, and dried with anhydrous sodium sulfate. The residue obtained by concentration was purified by silica gel column chromatography (hexane:ethyl acetate, 98:2→90:10) to obtain the title compound (3.86 g) having the following physical property values.

TLC:Rf 0.40 (hexane:ethyl acetate=9:1);
$^1$H-NMR (CDCl$_3$): δ 0.60 (2 H), 1.10 (2 H), 1.42 (9 H), 1.45-1.90 (12 H), 3.34-3.43 (1 H), 3.45-3.54 (1 H), 3.68-3.78 (1 H), 3.82-3.91 (1 H), 4.54-4.60 (1 H).

Reference Manufacturing Example 31

4-[1-(tert-butoxycarbonyl)cyclopropyl]butanoic acid

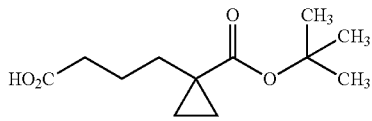

To a solution of the compound (4.32 g) produced in Reference manufacturing example 30 in methanol (29 mL) was added p-toluenesulfonic acid monohydrate (28 mg), and the mixture was stirred at room temperature for 24 hours. Water and an aqueous saturated sodium bicarbonate solution were added, thereafter, methanol was distilled off, followed by extraction with ethyl acetate. The organic layer was washed with an aqueous saturated sodium chloride solution, dried with anhydrous sodium sulfate, and concentrated to obtain tert-butyl 1-(4-hydroxybutyl)cyclopropanecarboxylate (3.20 g). This was dissolved in acetonitrile (118 mL), a phosphate buffer (pH 6.6, 79 mL) was added, and the mixture was stirred at 40° C. A 2,2,6,6-tetramethylpiperidine 1-oxyl free radical (TEMPO, 227 mg), an aqueous sodium chlorite solution (sodium chlorite 2.62 g, water 16 mL) and an aqueous sodium hypochlorite solution (0.5%, 16 mL) were added, and the mixture was stirred for 15 hours. After allowing to cool, an aqueous sodium sulfite solution and 2N hydrochloric acid were added, followed by extraction with ethyl acetate. This was reverse-extracted with an aqueous saturated sodium bicarbonate solution, 2N hydrochloric acid was added to make the solution acidic, followed by extraction with ethyl acetate. This was washed with water and an aqueous saturated sodium chloride solution, dried with anhydrous sodium sulfate, and concentrated to obtain the title compound (3.08 g) having the following physical property values.

TLC:Rf 0.38 (hexane:ethyl acetate=2:1);
$^1$H-NMR (DMSO-d$_6$): δ 0.64 (2 H), 0.97 (2 H), 1.36 (s, 9 H), 1.36-1.46 (2 H), 1.54-1.70 (2 H), 2.16 (2 H), 12.0 (1 H).

Reference Manufacturing Example 32

1-{4-[9-(3-fluorobenzyl)-5,6,8,9-tetrahydro-7H-pyrido[4',3':4,5]pyrrolo[2,3-b]pyridin-7-yl]-4-oxobutyl}cyclopropanecarboxylic acid

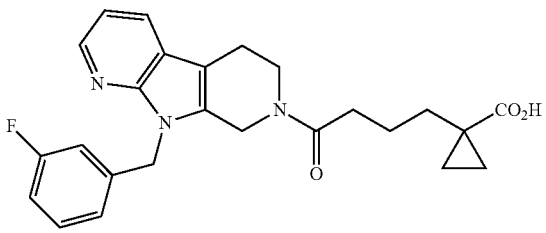 [SMILES: O=C(CCCC1(C(=O)O)CC1)N1CCc2c(n(Cc3cccc(F)c3)c3ncccc23)C1]

A corresponding alkyl halide in place of (3-bromopropyl)benzene and a tetrahydropyridopyrrolopyridine derivative produced by operation in accordance with Reference manufacturing Example 4→Reference manufacturing example 5→Reference manufacturing example 6→Reference manufacturing example 7→Reference manufacturing example 8 were used, which were subjected to operation in accordance with Reference manufacturing example 1, and the resulting compound and the compound produced in Reference manufacturing example 31 were used, which were subjected to operation in accordance with Reference manufacturing example 11 and further subjected to operation in accordance with Reference manufacturing example 25 to obtain the title compound having the following physical property values.

TLC:Rf 0.46 (methylene chloride:ethyl acetate:methanol=8:4:1);
$^1$H-NMR (DMSO-d$_6$): δ 0.56-0.72 (m, 2 H), 0.95-1.06 (m, 2 H), 1.32-1.72 (m, 4 H), 2.22-2.45 (m, 2 H), 2.63-2.84 (m, 2 H), 3.68-3.82 (m, 2 H), 4.62 (s, 2 H), 5.42-5.54 (m, 2 H), 6.85-7.05 (m, 4 H), 7.28-7.38 (m, 1H), 7.85-7.94 (m, 1 H), 8.20 (dd, J=4.8, 1.5 Hz, 1 H), 11.97 (brs, 1 H).

Example 9(1)-Example 9(4)

A corresponding alkyl halide in place of (3-bromopropyl)benzene and a tetrahydropyridopyrrolopyridine derivative produced by operation in accordance with Reference manufacturing Example 4→Reference manufacturing example 5→Reference manufacturing example 6→Reference manufacturing example 7→Reference manufacturing example 8 were used, which were subjected to operation in accordance with Reference manufacturing example 1, and the resulting compound and the compound produced in Reference manufacturing example 31 were used, which were subjected to operation in accordance with Reference manufacturing example 11 and further subjected to operation in accordance with Reference manufacturing example 25 to obtain the following compounds.

Example 9(1)

1-[4-oxo-4-(9-{[5-(trifluoromethyl)-2-thienyl]methyl}-5,6,8,9-tetrahydro-7H-pyrido[4',3':4,5]pyrrolo[2,3-b]pyridin-7-yl)butyl]cyclopropanecarboxylic acid

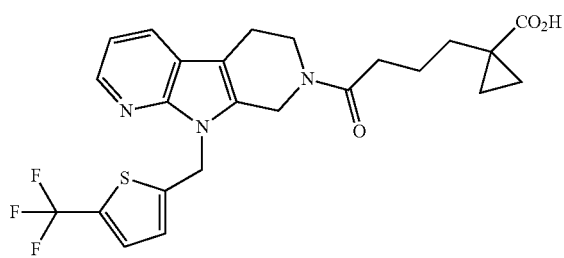 [SMILES: O=C(CCCC1(C(=O)O)CC1)N1CCc2c(n(Cc3ccc(C(F)(F)F)s3)c3ncccc23)C1]

TLC:Rf 0.47 (methylene chloride:ethyl acetate:methanol=8:4:1);
$^1$H-NMR (DMSO-d$_6$): δ 0.55-0.78 (m, 2 H), 0.90-1.10 (m, 2 H), 1.36-1.76 (m, 4 H), 2.30-2.58 (m, 2 H), 2.62-2.90 (m, 2 H), 3.63-3.88 (m, 2 H), 4.76 (s, 2 H), 5.58-5.78 (m, 2 H), 7.02-7.24 (m, 2 H), 7.48-7.58 (m, 1H), 7.89 (d, J=8.1 Hz, 1H), 8.24 (d, J=4.5 Hz, 1 H), 12.02 (brs, 1 H).

Example 9(2)

1-[4-oxo-4-(9-{[5-(trifluoromethyl)-3-thienyl]methyl}-5,6,8,9-tetrahydro-7H-pyrido[4',3':4,5]pyrrolo[2,3-b]pyridin-7-yl)butyl]cyclopropanecarboxylic acid TLC:Rf 0.36 (methylene chloride:ethyl acetate:methanol=8:4:1);
MS (ESI, Pos. 20V): m/z=492 (M+H)$^+$.

Example 9(3)

1-[4-oxo-4-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)butyl]cyclopropanecarboxylic acid TLC:Rf 0.33 (methylene chloride:ethyl acetate:methanol=8:4:1);
MS (ESI, Pos. 20V): m/z=493 (M+H)$^+$.

Example 9(4)

1-[4-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-4-oxobutyl]cyclopropanecarboxylic acid TLC:Rf 0.38 (methylene chloride:ethyl acetate:methanol=8:4:1);
MS (ESI, Pos. 20V): m/z=507 (M+H)$^+$.

Reference Manufacturing Example 33 ethyl 8-methyl-1,4-dioxaspiro[4.5]decane-8-carboxylate

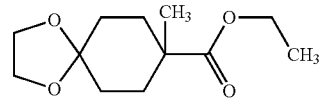

Ethyl-4-oxocyclohexanecarboxylate (25.1 g) and ethylene glycol (32.3 g) were dissolved in 80 mL of toluene, p-toluenesulfonic acid monohydrate (563 mg) was added while stirring at room temperature, and the mixture was stirred at that temperature overnight. After completion of the reaction, a hexane:ethyl acetate=3:1 solution (150 mL) was added to dilute the reaction, thereafter, 100 mL of water was added, and extraction operation was performed. The resulting organic layer was sequentaily washed with an aqueous saturated sodium bicarbonate solution and an aqueous saturated sodium chloride solution, dried with magnesium sulfate, and the solvent was distilled off under reduced pressure to obtain the crude product. This was azeotroped with toluene to obtain a ketal intermediate (32.1 g).

Lithium diisopropylamide (37.5 mL) was dissolved in 50 mL of THF, and a solution of the ketal intermediate (10.7 g) in 12 mL of THF was added dropwise over 5 minutes while stirring at an inner temperature of −30° C. After this solution was stirred at an inner temperature of −30° C. for 20 minutes, and a solution of methyl iodide (14.2 g) in 12 mL of THF was added dropwise at that temperature over 5 minutes. An inner temperature at that time was raised to −5° C. This solution was stirred for 1 hour until an inner temperature became 23° C., water was added to stop the reaction, extraction operation (THF, once) was performed, the aqueous layer was neutralized with 2N hydrochloric acid, and re-extraction operation (ethyl acetate, two times) was performed. The resulting organic layer was sequentially washed with water and an aqueous saturated sodium chloride solution, and dried with magnesium sulfate, and the solvent was distilled off under reduced pressure to obtain the title compound (12.8 g) having the following physical property values.

TLC:Rf 0.51 (hexane:ethyl acetate=4:1);
$^1$H-NMR (CDCl$_3$): δ 1.19 (s, 3 H), 1.25 (t, J=7.2 Hz, 3 H), 1.43-1.71 (m, 6 H), 2.09-2.17 (m, 2 H), 3.93 (s, 4 H), 4.15 (q, J=7.2 Hz, 2 H).

Reference Manufacturing Example 34 ethyl 1-methyl-4-oxocyclohexanecarboxylate

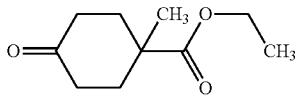

The compound (12.8 g) produced in Reference manufacturing example 33 was dissolved in 100 mL of acetone, 50 mL of 2N hydrochloric acid was added while stirring at room temperature, and the mixture was stirred at that temperature overnight. After completion of the reaction, the solvent was distilled off under reduced pressure, 100 mL of tetrabutyl methyl ether was added, and extraction operation was performed. The resulting organic layer was sequentially washed with an aqueous saturated sodium bicarbonate solution and an aqueous saturated sodium chloride solution, and dried with magnesium sulfate, and the solvent was distilled off under reduced pressure to obtain 9.7 g of the crude product. The crude product was purified by silica gel column chromatography (ethyl acetate/hexane=3%→25%) to obtain the title compound (8.34 g) having the following physical property values.

TLC:Rf 0.41 (hexane:ethyl acetate=4:1);

$^1$H-NMR (CDCl$_3$): δ 1.25-1.32 (m, 6 H), 1.58-1.73 (m, 2 H), 2.27-2.51 (m, 6 H), 4.22 (q, J=7.2 Hz, 2 H).

Reference Manufacturing Example 35 ethyl trans-4-(2,2-dimethyl-4,6-dioxo-1,3-dioxan-5-yl)-1-methylcyclohexanecarboxylate The compound (3.68 g) produced in Reference manufacturing example 34 and Meldrum's acid (3.17 g) were dissolved in 40 mL of dimethylformamide, sodium triacetoxyborohydride (5.09 g) was added while stirring at room temperature, and the mixture was stirred at that temperature for 4 hours. After completion of the reaction, 300 mL of water was added, and extraction operation (hexane:ethyl acetate=3:1) was performed. The resulting organic layer was sequentially washed with an aqueous saturated sodium bicarbonate solution and an aqueous saturated sodium chloride solution, and dried with magnesium sulfate, and the solvent was distilled off under reduced pressure to obtain 6.8 g of the crude product. The crude product was purified by silica gel column chromatography (ethyl acetate/hexane=18%→29%) to obtain an isomer mixture (3.36 g) of trans: cis=10:11. The isomer mixture was dissolved in 4 mL of ethyl acetate, and the solution was allowed to stand at room temperature overnight. The precipitated crystal was filtered, and dried under reduced pressure to obtain the title compound (437 mg) having the following physical property values.

TLC:Rf 0.48 (hexane:ethyl acetate=2:1);

$^1$H-NMR (CDCl$_3$): δ 1.12-1.29 (m, 8 H), 1.48-1.60 (m, 2 H), 1.67-1.87 (m, 8 H), 2.24-2.46 (m, 3 H), 3.33 (d, J=3.3 Hz, 1 H), 4.17 (q, J=7.2 Hz, 2 H).

Reference Manufacturing Example 36

[trans-4-(ethoxycarbonyl)-4-methylcyclohexyl]acetic acid

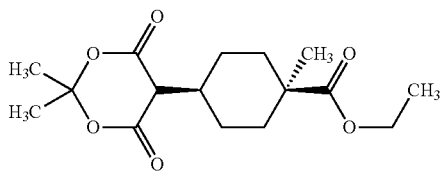 [SMILES: CCOC(=O)[C@]1(C)CC[C@H](C2C(=O)OC(C)(C)OC2=O)CC1]

The compound (370 mg) produced in Reference manufacturing example 35 was dissolved in 2.5 mL of dimethylformamide and 0.25 mL of water, and the solution was stirred at 115° C. for 2 hours. After completion of the reaction, 30 mL of water was added, and extraction operation (hexane:ethyl acetate=1:1) was performed. The resulting organic layer was washed using an aqueous saturated sodium chloride solution, and dried with magnesium sulfate, and the solvent was distilled off under reduced pressure to obtain the title compound (274 mg) having the following physical property values.

TLC:Rf 0.41 (hexane:ethyl acetate=2:1);

$^1$H-NMR (CDCl$_3$): δ 0.98-1.29 (m, 10 H), 1.63-1.80 (m, 3 H), 2.15-2.27 (m, 4 H), 4.13 (q, J=7.2 Hz, 2 H).

Reference Manufacturing Example 37 cis-4-{2-[9-(3-fluorobenzyl)-5,6,8,9-tetrahydro-7H-pyrido[4',3':4,5]pyrrolo[2,3-b]pyridin-7-yl]-2-oxoethyl}-1-methylcyclohexanecarboxylic acid

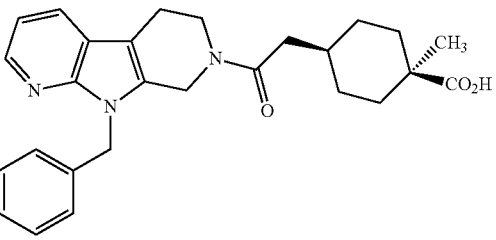

A corresponding alkyl halide in place of (3-bromopropyl)benzene and a tetrahydropyridopyrrolopyridine derivative produced by operation in accordance with Reference manufacturing Example 4→Reference manufacturing example 5→Reference manufacturing example 6→Reference manufacturing example 7→Reference manufacturing example 8 were used, which were subjected to operation in accordance with Reference manufacturing example 1, and the resulting compound and the compound produced in Reference manufacturing example 36 were used, which were subjected to operation in accordance with Reference manufacturing example 11 and further subjected to operation in accordance with Reference manufacturing example 3 to obtain the title compound having the following physical property values.

TLC:Rf 0.26 (n-hexane:ethyl acetate=1:1);

MS (FAB, Pos.): m/z=464 (M+H)$^+$.

Example 10(1)-Example 10(20)

A corresponding alkyl halide in place of (3-bromopropyl)benzene and a tetrahydropyridopyrrolopyridine derivative produced by operation in accordance with Reference manufacturing Example 4→Reference manufacturing example 5→Reference manufacturing example 6→Reference manufacturing example 7→Reference manufacturing example 8 were used, which were subjected to operation in accordance with Reference manufacturing example 1, and the resulting compound and the compound produced in Reference manufacturing example 36 were used, which were subjected to operation in accordance with Reference manufacturing example 11 and further subjected to operation in accordance with Reference manufacturing example 3 to obtain the following compounds.

Example 10(1)

cis-1-methyl-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]cyclohexanecarboxylic acid TLC:Rf 0.25 (n-hexane:ethyl acetate=1:1);
MS (FAB, Pos.): m/z=520 (M+H)$^+$.

Example 10(2)

trans-1-methyl-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]cyclohexanecarboxylic acid

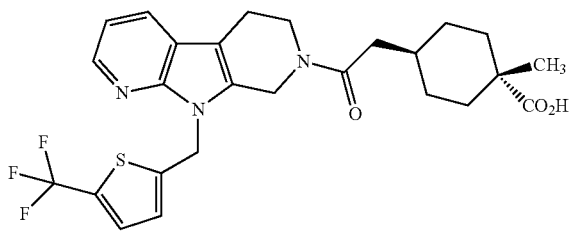 [SMILES: C[C@]1(C(=O)O)CC[C@H](CC(=O)N2CCc3c(n(Cc4ccc(C(F)(F)F)s4)c4ncccc34)C2)CC1]

TLC:Rf 0.62 (chloroform:methanol:water=50:10:1);
MS (ESI, Pos. 20 V): m/z=520 (M+H)$^+$.

Example 10(3)

trans-4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)-1-methylcyclohexanecarboxylic acid TLC:Rf 0.45 (ethyl acetate);
MS (ESI, Pos. 20 V): m/z=496 (M+H)$^+$.

Example 10(4)

trans-1-methyl-4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)cyclohexanecarboxylic acid TLC:Rf 0.36 (hexane:ethyl acetate=1:2);
MS (ESI, Pos. 20 V): m/z=514 (M+H)$^+$.

Example 10(5)

trans-1-methyl-4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]cyclohexanecarboxylic acid

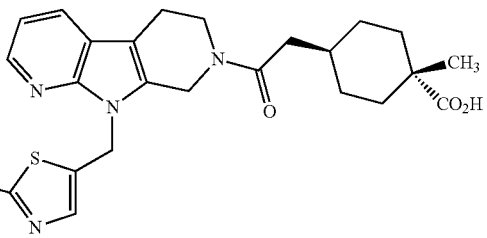

TLC:Rf 0.25 (hexane:ethyl acetate=1:2);
MS (FAB, Pos.): m/z=521 (M+H)$^+$.

Example 10(6)

cis-1-methyl-4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)cyclohexanecarboxylic acid TLC:Rf 0.35 (ethyl acetate:n-hexane=2:1);
MS (ESI, Pos. 20V): m/z=514 (M+H)$^+$.

Example 10(7)

cis-4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)-1-methylcyclohexanecarboxylic acid TLC:Rf 0.27 (ethyl acetate:n-hexane=2:1);
MS (ESI, Pos. 20V): m/z=496 (M+H)$^+$.

Example 10(8)

trans-1-methyl-4-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethyl]cyclohexanecarboxylic acid TLC:Rf 0.35 (hexane:ethyl acetate=1:2);
MS (ESI, Pos. 20 V): m/z=520 (M+H)$^+$.

Example 10(9)

cis-1-methyl-4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]cyclohexanecarboxylic acid TLC:Rf 0.50 (ethyl acetate);
MS (ESI, Pos. 20V): m/z=521 (M+H)$^+$.

Example 10(10)

cis-1-methyl-4-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethyl)cyclohexanecarboxylic acid TLC:Rf 0.59 (ethyl acetate);
MS (ESI, Pos. 20V): m/z=520 (M+H)$^+$.

Example 10(11)

cis-1-methyl-4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)cyclohexanecarboxylic acid TLC:Rf 0.61 (ethyl acetate);
MS (ESI, Pos. 20V): m/z=514 (M+H)$^+$.

Example 10(12)

cis-1-methyl-4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)cyclohexanecarboxylic acid TLC:Rf 0.63 (ethyl acetate);
MS (ESI, Pos. 20V): m/z=530 (M+H)$^+$.

Example 10(13)

cis-1-methyl-4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)cyclohexanecarboxylic acid TLC:Rf 0.62 (ethyl acetate);
MS (ESI, Pos. 20V): m/z=530 (M+H)$^+$.

Example 10(14)

cis-1-methyl-4-[2-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-2-oxoethyl]cyclohexanecarboxylic acid TLC:Rf 0.51 (ethyl acetate);
MS (ESI, Pos. 20V): m/z=535 (M+H)$^+$.

Example 10(15)

trans-1-methyl-4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)cyclohexanecarboxylic acid TLC:Rf 0.29 (hexane:ethyl acetate=1:2);
MS (ESI, Pos. 20 V): m/z=530 (M+H)$^+$.

Example 10(16)

trans-1-methyl-4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)cyclohexanecarboxylic acid TLC:Rf 0.33 (hexane:ethyl acetate=1:2);
MS (ESI, Pos. 20 V): m/z=530 (M+H)$^+$.

Example 10(17)

trans-1-methyl-4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)cyclohexanecarboxylic acid TLC:Rf 0.28 (hexane:ethyl acetate=1:2);
MS (ESI, Pos. 20 V): m/z=514 (M+H)$^+$.

Example 10(18)

trans-1-methyl-4-[2-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-2-oxoethyl]cyclohexanecarboxylic acid TLC:Rf 0.30 (hexane:ethyl acetate=1:2);
MS (ESI, Pos. 20 V): m/z=535 (M+H)$^+$.

Example 10(19)

cis-1-hydroxy-4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]cyclohexanecarboxylic acid TLC:Rf 0.23 (chloroform:methanol:water=50:10:1);
MS (ESI, Pos. 20 V): m/z=523 (M+H)$^+$.

Example 10(20)

trans-1-hydroxy-4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]cyclohexanecarboxylic acid TLC:Rf 0.26 (chloroform:methanol:water=50:10:1);
MS (ESI, Pos.): m/z=523 (M+H)$^+$.

Reference Manufacturing Example 38 methyl 4-(2-tert-butoxy-2-oxoethyl)-2-chlorobenzoate

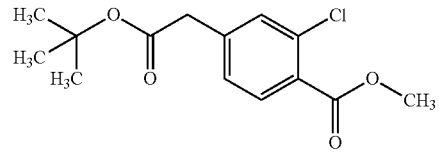 [SMILES: COC(=O)c1ccc(CC(=O)OC(C)(C)C)cc1Cl]

To anhydrous THF (4.5 mL) suspension containing active zinc (530 mg) were added tert-butyl bromoacetate (800 μL) and 1,2-dibromoethane (15 μL), and a reaction was performed at 90° C. for 3 minutes using a microwave synthesis apparatus initiator manufactured by Biotage. Centrifugation was performed to obtain the supernatant, to prepare a solution of 2-tert-butoxy-2-oxoethylzinc bromide in THF.

To methyl 2-chloro-4-iodobenzoate (296 mg) was added a solution (4.5 mL) of 2-tert-butoxy-2-oxoethylzinc bromide in THF, then, bis(tri-tert-butylphosphine)palladium (51 mg) was added, and a reaction was performed at 50 W and 80° C. for 10 minutes using a microwave synthesis apparatus manufactured by CEM Co. The reaction solution was poured into an aqueous saturated ammonium chloride solution, and ethyl acetate was added. Insolubles were filtered off with Celite, and layers were separated. The organic layer was washed with an aqueous saturated sodium chloride solution, dried with anhydrous sodium sulfate, and concentrated under reduced pressure. The resulting residue was purified by medium pressure preparative liquid chromatography W-prep 2XY (column:main column M, inject column S; automatic condition setting:n-hexane:ethyl acetate=4:1, Rf=0.60) to obtain the title compound (94 mg) having following physical property values.

TLC:Rf 0.58 (n-hexane:ethyl acetate=4:1);
$^1$H-NMR (CDCl$_3$):δ 7.80 (d, 1H), 7.38 (d, 1H), 7.22 (dd, 1H), 3.92 (s, 3H), 3.53 (s, 2H), 1.44 (s, 9H).

Reference Manufacturing Example 39 methyl 4-(carboxymethyl)-2-chlorobenzoate

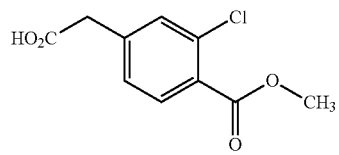

To a solution of the compound (87 mg) produced in Reference manufacturing example 38 in methylene chloride (1.0 mL) was added trifluoroacetic acid (0.5 mL), and the mixture was stirred at room temperature for 1 hour. The reaction solution was concentrated to dryness under reduced pressure to obtain the title compound having the following physical property values.

TLC:Rf 0.28 (methylene chloride:methanol=9:1);
$^1$H-NMR (CDCl$_3$): δ 7.82 (d, 1H), 7.40 (d, 1H), 7.24 (dd, 1H), 3.93 (s, 3H), 3.68 (s, 2H).

Reference Manufacturing Example 40

2-chloro-4-{2-[9-(3-fluorobenzyl)-5,6,8,9-tetrahydro-7H-pyrido[4',3':4,5]pyrrolo[2,3-b]pyridin-7-yl]-2-oxoethyl}benzoic acid

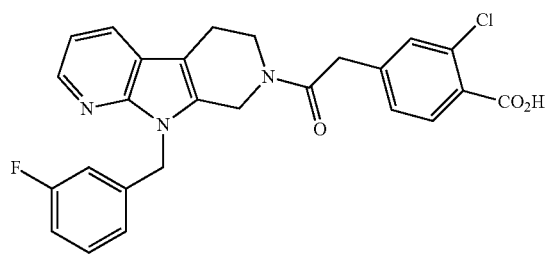 [SMILES: O=C(O)c1ccc(CC(=O)N2CCc3c(n(Cc4cccc(F)c4)c4ncccc34)C2)cc1Cl]

A corresponding alkyl halide in place of (3-bromopropyl) benzene and a tetrahydropyridopyrrolopyridine derivative produced by operation in accordance with Reference manufacturing Example 4→Reference manufacturing example 5→Reference manufacturing example 6→Reference manufacturing example 7→Reference manufacturing example 8 were used, which were subjected to operation in accordance with Reference manufacturing example 1, and the resulting compound and the compound produced in Reference manufacturing example 39 were used, which were subjected to operation in accordance with Reference manufacturing example 11 and further subjected to operation in accordance with Reference manufacturing example 3 to obtain the title compound having the following physical property values.

TLC:Rf 0.26 (chloroform:methanol=9:1);
MS (ESI, Pos. 20 V): m/z=478 (M+H)$^+$.

Example 11(1)-Example 11(39)

A corresponding alkyl halide in place of (3-bromopropyl) benzene, and a tetrahydropyridopyrrolopyridine derivative produced by operation in accordance with Reference manufacturing example 4→Reference manufacturing example 5→Reference manufacturing example 6→Reference manufacturing example 7→Reference manufacturing example 8 or the corresponding beta-carboline derivative were used, which were subjected to operation in accordance with Reference manufacturing example 1, and the resulting compound and the compound produced in Reference manufacturing example 39 or the corresponding ester were used, which were subjected to operation in accordance with Reference manufacturing example 11 and further subjected to operation in accordance with Reference manufacturing example 3 to obtain the following compounds.

Example 11(1)

2-chloro-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]benzoic acid TLC:Rf 0.24 (methylene chloride:methanol=9:1);
MS (ESI, Pos. 20 V): m/z=534 (M+H)$^+$.

Example 11(2)

2-fluoro-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]benzoic acid TLC:Rf 0.23 (methylene chloride:methanol=9:1);
MS (APCI, Pos. 20 V): m/z=518 (M+H)$^+$.

Example 11(3)

2-methyl-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]benzoic acid TLC:Rf 0.47 (methylene chloride:methanol=9:1);
MS (APCI, Pos. 20 V): m/z=514 (M+H)$^+$.

Example 11(4)

2-methoxy-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]benzoic acid TLC:Rf 0.51 (methylene chloride:methanol=9:1);
MS (APCI, Pos. 20 V): m/z=530 (M+H)$^+$.

Example 11(5)

3-methoxy-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]benzoic acid TLC:Rf 0.43 (methylene chloride:methanol=9:1);
MS (APCI, Pos. 20 V): m/z=530 (M+H)$^+$.

Example 11(6)

2-methyl-2-{4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]phenyl}propanoic acid TLC:Rf 0.48 (methylene chloride:methanol=9:1);
MS (APCI, Pos. 20 V): m/z=542 (M+H)$^+$.

Example 11(7)

4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)-2-methoxybenzoic acid TLC:Rf 0.50 (methylene chloride:methanol=9:1);
MS (APCI, Pos. 20 V): m/z=506 (M+H)$^+$.

Example 11(8)

2-methoxy-4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)benzoic acid

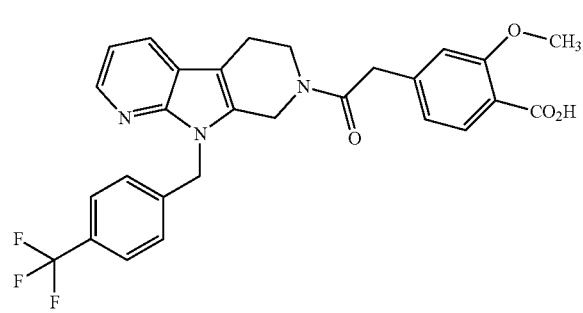 [SMILES: COc1cc(CC(=O)N2CCc3c(n(Cc4ccc(C(F)(F)F)cc4)c4ncccc34)C2)ccc1C(=O)O]

TLC:Rf 0.45 (methylene chloride:methanol=9:1);
MS (FAB, Pos.): m/z=524 (M+H)$^+$.

Example 11(9)

2-methoxy-4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)benzoic acid TLC:Rf 0.43 (methylene chloride:methanol=9:1);
MS (FAB, Pos.): m/z=524 (M+H)$^+$.

Example 11(10)

2-methoxy-4-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethyl]benzoic acid TLC:Rf 0.46 (methylene chloride:methanol=9:1);
MS (FAB, Pos.): m/z=530 (M+H)$^+$.

Example 11(11)

2-methoxy-4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]benzoic acid TLC:Rf 0.44 (methylene chloride:methanol=9:1);
MS (FAB, Pos.): m/z=531 (M+H)$^+$.

Example 11(12)

2-methoxy-4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)benzoic acid

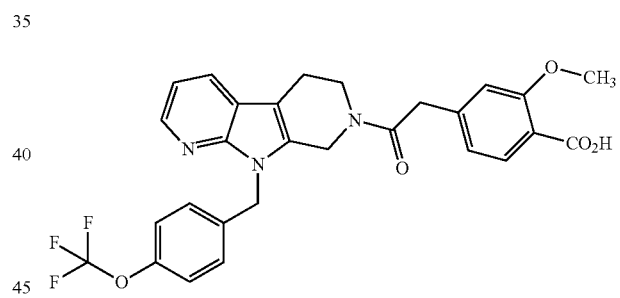

TLC:Rf 0.50 (methylene chloride:methanol=9:1);
MS (FAB, Pos.): m/z=540 (M+H)$^+$.

Example 11(13)

2-methoxy-4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)benzoic acid TLC:Rf 0.50 (methylene chloride:methanol=9:1);
MS (AB, Pos.): m/z=540 (M+H)$^+$.

Example 11(14)

2-methyl-4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)benzoic acid TLC:Rf 0.39 (methylene chloride:methanol:water=90:10:1);
MS (FAB, Pos.): m/z=508 (M+H)$^+$.

Example 11(15)

4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)-2-methylbenzoic acid TLC:Rf 0.39 (methylene chloride:methanol:water=90:10:1);
MS (FAB, Pos.): m/z=490 (M+H)$^+$.

Example 11(16)

2-methyl-4-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethyl]benzoic acid TLC:Rf 0.45 (methylene chloride:methanol:water=90:10:1);
MS (FAB, Pos.): m/z=514 (M+H)$^+$.

Example 11(17)

2-methyl-4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]benzoic acid TLC:Rf 0.44 (methylene chloride:methanol:water);
MS (FAB, Pos.): m/z=515 (M+H)$^+$.

Example 11(18)

2-methyl-4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)benzoic acid TLC:Rf 0.35 (methylene chloride:methanol:water=90:10:1);
MS (FAB, Pos.): m/z=524 (M+H)$^+$.

Example 11(19)

2-methyl-4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)benzoic acid TLC:Rf 0.35 (methylene chloride:methanol:water=90:10:1);
MS (FAB, Pos.): m/z=524 (M+H)$^+$.

Example 11(20)

2-methyl-4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)benzoic acid TLC:Rf 0.47 (chloroform:methanol=9:1);
MS (FAB, Pos.): m/z=508 (M+H)$^+$.

Example 11(21)

2-methoxy-4-[2-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-2-oxoethyl]benzoic acid TLC:Rf 0.55 (methylene chloride:methanol=9:1);
MS (ESI, Pos. 20 V): m/z=545 (M+H)$^+$.

Example 11(22)

2-methyl-4-[2-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-2-oxoethyl]benzoic acid TLC:Rf 0.57 (methylene chloride:methanol=9:1);
MS (ESI, Pos. 20 V): m/z=529 (M+H)$^+$.

Example 11(23)

2,6-dimethoxy-4-[2-oxo-2-(9-{[5-(trifluoromethyl)-2-thienyl]methyl}-5,6,8,9-tetrahydro-7H-pyrido[4',3':4,5]pyrrolo[2,3-b]pyridin-7-yl)ethyl]benzoic acid TLC:Rf 0.50 (chloroform:methanol:water=50:10:1);
MS (ESI, Pos. 20 V): m/z=560 (M+H)$^+$.

Example 11(24)

2,6-dimethoxy-4-[2-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-2-oxoethyl]benzoic acid

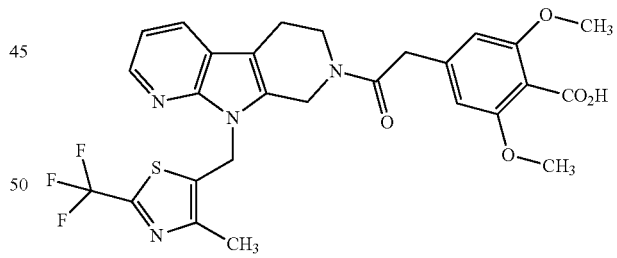

TLC:Rf 0.10 (ethyl acetate:methanol=9:1);
MS (ESI, Pos. 20V): m/z=575 (M+H)$^+$.

Example 11(25)

2,6-dimethoxy-4-(2-oxo-2-{9-[4-(trifluoromethyl)benzyl]-5,6,8,9-tetrahydro-7H-pyrido[4',3':4,5]pyrrolo[2,3-b]pyridin-7-yl}ethyl)benzoic acid TLC:Rf 0.12 (chloroform:methanol:water=10:1:0.1);
MS (ESI, Pos. 20V): m/z=554 (M+H)$^+$.

Example 11(26)

2,6-dimethoxy-4-(2-oxo-2-{9-[3-(trifluoromethyl)benzyl]-5,6,8,9-tetrahydro-7H-pyrido[4',3':4,5]pyrrolo[2,3-b]pyridin-7-yl}ethyl)benzoic acid TLC:Rf 0.12 (chloroform:methanol:water=10:1:0.1);
MS (ESI, Pos. 20V): m/z=554 (M+H)$^+$.

Example 11(27)

2,6-dimethoxy-4-(2-oxo-2-{9-[4-(trifluoromethoxy)benzyl]-5,6,8,9-tetrahydro-7H-pyrido[4',3':4,5]pyrrolo[2,3-b]pyridin-7-yl}ethyl)benzoic acid TLC:Rf 0.12 (chloroform:methanol:water=10:1:0.1);
MS (ESI, Pos. 20V): m/z=570 (M+H)$^+$.

Example 11(28)

2,6-dimethoxy-4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)benzoic acid TLC:Rf 0.12 (chloroform:methanol:water=10:1:0.1);
MS (ESI, Pos. 20V): m/z=570 (M+H)$^+$.

Example 11(29)

4-(2-{9-[3-(difluoromethyl)benzyl]-5,6,8,9-tetrahydro-7H-pyrido[4',3':4,5]pyrrolo[2,3-b]pyridin-7-yl}-2-oxoethyl)-2,6-dimethoxybenzoic acid TLC:Rf 0.42 (methylene chloride:methanol:water=90:10:1);
MS (FAB, Pos.): m/z=536 (M+H)$^+$.

Example 11(30)

2,6-dimethoxy-4-[2-oxo-2-(9-{[5-(trifluoromethyl)-3-thienyl]methyl}-5,6,8,9-tetrahydro-7H-pyrido[4',3':4,5]pyrrolo[2,3-b]pyridin-7-yl)ethyl]benzoic acid TLC:Rf 0.91 (ethyl acetate:acetic acid:water=3:1:1);
MS (ESI, Pos. 20 V): m/z=560 (M+H)$^+$.

Example 11(31)

2,6-dimethoxy-4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]benzoic acid TLC:Rf 0.85 (ethyl acetate:acetic acid:water=3:1:1);
MS (ESI, Pos. 20 V): m/z=561 (M+H)$^+$, 255.

Example 11(32)

4-[2-(8-fluoro-9-{[2-(trifluoromethyl)-1,3-thiazol-5-yl]methyl}-1,3,4,9-tetrahydro-2H-beta-carbolin-2-yl)-2-oxoethyl]-2-methoxybenzoic acid TLC:Rf 0.30 (methylene chloride:ethyl acetate:methanol=8:4:1);
MS (ESI, Pos.): m/z=548 (M+H)$^+$, 530.

Example 11(33)

2-methoxy-4-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)benzoic acid TLC:Rf 0.52 (methylene chloride:methanol=9:1);
MS (APCI, Pos.): m/z=553 (M+H)$^+$.

Example 11(34)

2-methoxy-4-{2-oxo-2-[9-(4-phenoxybenzyl)-5,6,8,9-tetrahydro-7H-pyrido[4',3':4,5]pyrrolo[2,3-b]pyridin-7-yl]ethyl}benzoic acid TLC:Rf 0.56 (methylene chloride:methanol=9:1);
MS (APCI, Pos.): m/z=548 (M+H)$^+$.

Example 11(35)

4-(2-{8-fluoro-9-[3-(trifluoromethoxy)benzyl]-1,3,4,9-tetrahydro-2H-beta-carbolin-2-yl}-2-oxoethyl)-2-methoxybenzoic acid TLC:Rf 0.80 (chloroform:methanol:water=50:10:1);
MS (ESI, Pos.): m/z=557 (M+H)$^+$.

Example 11(36)

4-[2-(6,8-difluoro-9-{[2-(trifluoromethyl)-1,3-thiazol-5-yl]methyl}-1,3,4,9-tetrahydro-2H-beta-carbolin-2-yl)-2-oxoethyl]-2-methoxybenzoic acid TLC:Rf 0.45 (methylene chloride:methanol=20:1);
MS (ESI, Pos.): m/z=548 (M+H)$^+$.

Example 11(37)

4-{2-[8-fluoro-9-(4-phenoxybenzyl)-1,3,4,9-tetrahydro-2H-beta-carbolin-2-yl]-2-oxoethyl}-2-methoxybenzoic acid TLC:Rf 0.40 (methylene chloride:methanol=9:1):
MS (ESI, Pos.): m/z=565 (M+H)$^+$.

Example 11(38)

4-(2-{6-fluoro-9-[3-(trifluoromethoxy)benzyl]-1,3,4,9-tetrahydro-2H-beta-carbolin-2-yl}-2-oxoethyl)-2-methoxybenzoic acid TLC:Rf 0.42 (methylene chloride:ethyl acetate:methanol=8:4:1);
MS (ESI, Pos.): m/z=557 (M+H)$^+$.

Example 11(39)

4-{2-[9-(3-ethylbenzyl)-5,6,8,9-tetrahydro-7H-pyrido[4',3':4,5]pyrrolo[2,3-b]pyridin-7-yl]-2-oxoethyl}-2-methoxybenzoic acid TLC:Rf 0.76 (chloroform:methanol:water=50:10:1);
MS (ESI, Pos.): m/z=484 (M+H)$^+$.

Reference Manufacturing Example 40

(4E)-6-methoxy-6-oxo-4-hexenoic acid

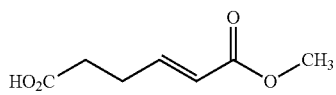

4-oxobutanoic acid (5.0 mL, about 15% aqueous solution) and trimethyl phosphoacetate (7.8 g) were dissolved in 10 mL of water, potassium carbonate (4.06 g) was added while stirring at 0° C., and the mixture was stirred at 60° C. overnight. To this solution was added 100 mL of an aqueous saturated sodium bicarbonate solution, reverse extraction operation (ethyl acetate, three times) was performed, the aqueous layer was made acidic (pH4) with 1N hydrochloric acid, and extraction operation (ethyl acetate, three times) was performed. The resulting organic layer was dried with magnesium sulfate, and the solvent was distilled off under reduced pressure to obtain the title compound (1.01 g) having the following physical property values.

TLC:Rf 0.45 (hexane:ethyl acetate=1:3);
$^1$H-NMR (CDCl$_3$): δ 2.52-2.57 (m, 4 H), 3.74 (s, 3 H), 5.83-5.91 (m, 1 H), 6.89-7.02 (m, 1 H).

Reference Manufacturing Example 41

(2E)-6-[9-(3-fluorobenzyl)-5,6,8,9-tetrahydro-7H-pyrido[4',3':4,5]pyrrolo[2,3-b]pyridin-7-yl]-6-oxo-2-hexenoic acid

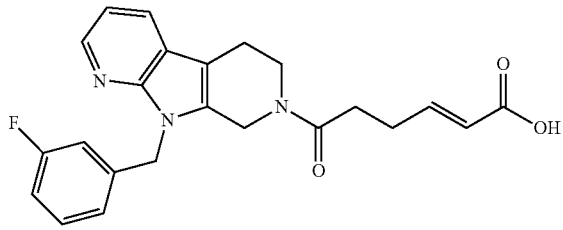 [SMILES: O=C(O)/C=C/CCC(=O)N1CCc2c(n(Cc3cccc(F)c3)c3ncccc23)C1]

A corresponding alkyl halide in place of (3-bromopropyl) benzene and a tetrahydropyridopyrrolopyridine derivative produced by operation in accordance with Reference manufacturing Example 4→Reference manufacturing example 5→Reference manufacturing example 6→Reference manufacturing example 7→Reference manufacturing example 8 were used, which were subjected to operation in accordance with Reference manufacturing example 1, and the resulting compound and the compound produced in Reference manufacturing example 40 were used, which were subjected to operation in accordance with Reference manufacturing example 11 and further subjected to operation in accordance with Reference manufacturing example 3 to obtain the title compound having the following physical property values.

TLC:Rf 0.29 (n-hexane:ethyl acetate=1:3);
MS (FAB, Pos.): m/z=408 (M+H)$^+$.

Example 12(1)

A corresponding alkyl halide in place of (3-bromopropyl) benzene and a tetrahydropyridopyrrolopyridine derivative produced by operation in accordance with Reference manufacturing Example 4→Reference manufacturing example 5→Reference manufacturing example 6→Reference manufacturing example 7→Reference manufacturing example 8 were used, which were subjected to operation in accordance with Reference manufacturing example 1, and the resulting compound and the compound produced in Reference manufacturing example 40 were used, which were subjected to operation in accordance with Reference manufacturing example 11 and further subjected to operation in accordance with Reference manufacturing example 3 to obtain the following compounds.

Example 12(1)

(2E)-6-oxo-6-(9-{[5-(trifluoromethyl)-2-thienyl]methyl}-5,6,8,9-tetrahydro-7H-pyrido[4',3':4,5]pyrrolo[2,3-b]pyridin-7-yl)-2-hexenoic acid TLC:Rf 0.26 (n-hexane:ethyl acetate=1:3);
MS (FAB, Pos.): m/z=464 (M+H)$^+$.

Reference Manufacturing Example 42 tert-butyl {4-[2-(benzyloxy)-2-oxoethyl]phenoxy}acetate

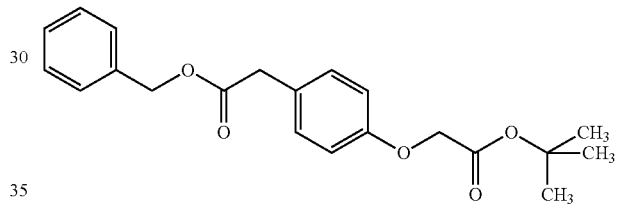

Potassium carbonate (1.38 g) and tert-butyl bromoacetate (1.07 g) were added to a dehydrated N,N-dimethylformamide (17 mL) solution of benzyl (4-hydroxyphenyl)acetate (1.21 g) at room temperature, followed by stirring for 1 hour. Thereafter, water was added to the reaction mixture on an ice bath, and extraction was performed with hexane:ethyl acetate=2:1. The resulting organic phase was washed with an aqueous saturated sodium chloride solution and dried with anhydrous sodium sulfate, followed by concentration under reduced pressure. The residue was purified by silica gel column chromatography (hexane:ethyl acetate=9:1→8:2) to obtain the title compound (1.75 g) having the following physical property values.

TLC:Rf 0.64 (hexane:ethyl acetate=2:1);
$^1$H NMR (CDCl$_3$): δ 1.49 (s, 9 H) 3.61 (s, 2 H) 4.50 (s, 2 H) 5.12 (s, 2 H) 6.80-6.89 (m, 2 H) 7.16-7.40 (m, 7 H).

Reference Manufacturing Example 43

[4-(2-tert-butoxy-2-oxoethoxy)phenyl]acetic acid

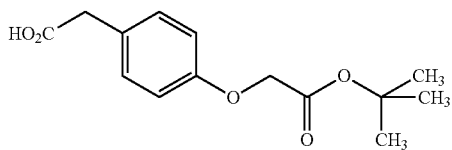 [SMILES: CC(C)(C)OC(=O)COc1ccc(CC(=O)O)cc1]

The compound (0.89 g) produced in Reference manufacturing example 42 was dissolved in ethanol (8.3 mL); 5% palladium carbon (50% hydrous product, 89 mg) was added under an argon atmosphere; and hydrogen was blown into the solution for 40 minutes with stirring at room temperature. After replacing the system with argon, the catalyst was filtered off with using Celite, followed by concentration under reduced pressure, to obtain the title compound (0.64 g) having the following physical property values.

TLC:Rf 0.12 (hexane:ethyl acetate=2:1);
$^1$H NMR (CDCl$_3$): δ 1.49 (s, 9 H) 3.59 (s, 2 H) 4.49 (s, 2 H) 6.86 (d, J=8.4 Hz, 2 H) 7.20 (d, J=8.4 Hz, 2 H).

Example 13

[4-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)phenoxy]acetic acid

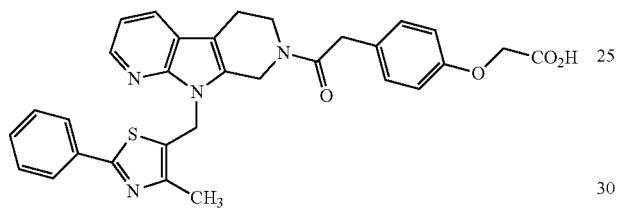

A corresponding alkyl halide in place of (3-bromopropyl)benzene and a tetrahydropyridopyrrolopyridine derivative produced by operation in accordance with Reference manufacturing example 4→Reference manufacturing example 5→Reference manufacturing example 6→Reference manufacturing example 7→Reference manufacturing example 8 were used, which were subjected to operation in accordance with Reference manufacturing example 1, and the resulting compound and the compound produced in Reference manufacturing example 43 were used, which were subjected to operation in accordance with Reference manufacturing example 11 and further subjected to operation in accordance with Reference manufacturing example 3 to obtain the title compound having the following physical property values.

TLC:Rf 0.11 (chloroform:methanol=9:1);
MS (ESI, Pos.): m/z=553 (M+H)$^+$.

Example 13(1)-Example 13(4)

A corresponding alkyl halide in place of (3-bromopropyl)benzene, and a tetrahydropyridopyrrolopyridine derivative produced by operation in accordance with Reference manufacturing example 4→Reference manufacturing example 5→Reference manufacturing example 6→Reference manufacturing example 7→Reference manufacturing example 8 or the corresponding beta-carboline derivative were used, which were subjected to operation in accordance with Reference manufacturing example 1, and the resulting compound and the compound produced in Reference manufacturing example 43 or the corresponding ester were used, which were subjected to operation in accordance with Reference manufacturing example 11 and further subjected to operation in accordance with Reference manufacturing example 3 to obtain the following compounds.

Example 13(1)

[3-(2-oxo-2-{9-[3-(trifluoromethoxy)benzyl]-5,6,8,9-tetrahydro-7H-pyrido[4',3':4,5]pyrrolo[2,3-b]pyridin-7-yl}ethyl)phenoxy]acetic acid TLC:Rf 0.15 (chloroform:methanol=9:1);
MS (ESI, Pos.): m/z=540 (M+H)$^+$.

Example 13(2)

[3-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethyl)phenoxy]acetic acid TLC:Rf 0.13 (chloroform:methanol=9:1);
MS (ESI, Pos.): m/z=553 (M+H)$^+$.

Example 13(3)

{4-[2-(6-fluoro-9-{[2-(trifluoromethyl)-1,3-thiazol-5-yl]methyl}-1,3,4,9-tetrahydro-2H-beta-carbolin-2-yl)-2-oxoethyl]phenoxy}acetic acid TLC:Rf 0.48 (methylene chloride:methanol=9:1);
MS (ESI, Pos.): m/z=548 (M+H)$^+$.

Example 13(4)

{4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethyl]phenoxy}acetic acid TLC:Rf 0.18 (chloroform:methanol:water=50:10:1);
MS (ESI, Pos.): m/z=531 (M+H)$^+$.

Reference Manufacturing Example 44

{4-[2-(benzyloxy)-2-oxoethyl]phenoxy}acetic acid

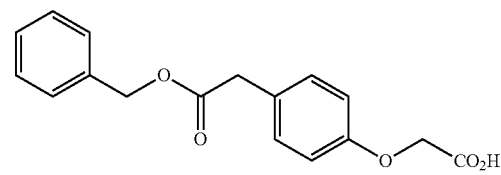 [SMILES: O=C(O)COc1ccc(CC(=O)OCc2ccccc2)cc1]

To the compound (0.76 g) produced in Reference manufacturing example 42, 4N dioxane solution of hydrogen chloride (4 mL) was added at room temperature, followed by stirring for 2.5 hours. After concentration of the reaction mixture, methylene chloride (4 mL) and trifluoroacetic acid (1 mL) were added, followed by stirring at room temperature for another 5 hours. The reaction mixture was concentrated, and the resulting crude product was washed with hexane:ethyl acetate=2:1 and then filtered off to obtain the title compound (0.50 g) having the following physical property values.

TLC:Rf 0.11 (hexane:ethyl acetate=2:1);
$^1$H NMR (CDCl$_3$): δ 3.62 (s, 2 H) 4.67 (s, 2 H) 5.13 (s, 2 H) 6.83-6.95 (m, 2 H) 7.20-7.42 (m, 7 H).

Example 14

(4-{2-oxo-2-[9-(4-phenoxybenzyl)-5,6,8,9-tetrahydro-7H-pyrido[4',3':4,5]pyrrolo[2,3-b]pyridin-7-yl]ethoxy}phenyl)acetic acid

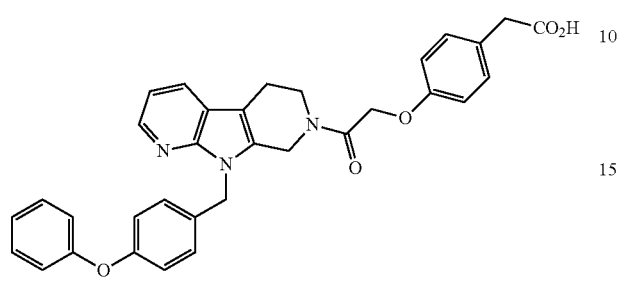

A corresponding alkyl halide in place of (3-bromopropyl) benzene and a tetrahydropyridopyrrolopyridine derivative produced by operation in accordance with Reference manufacturing example 4→Reference manufacturing example 5→Reference manufacturing example 6→Reference manufacturing example 7→Reference manufacturing example 8 were used, which were subjected to operation in accordance with Reference manufacturing example 1, and the resulting compound and the compound produced in Reference manufacturing example 44 were used, which were subjected to operation in accordance with Reference manufacturing example 11 and further subjected to operation in accordance with Reference manufacturing example 3 to obtain the title compound having the following physical property values.

TLC:Rf 0.54 (chloroform:methanol=9:1);
MS (ESI, Pos.): m/z=548 (M+H)+.

Example 14(1)-Example 14(5)

A corresponding alkyl halide in place of (3-bromopropyl) benzene and a tetrahydropyridopyrrolopyridine derivative produced by operation in accordance with Reference manufacturing example 4→Reference manufacturing example 5→Reference manufacturing example 6→Reference manufacturing example 7→Reference manufacturing example 8 were used, which were subjected to operation in accordance with Reference manufacturing example 1, and the resulting compound and the compound produced in Reference manufacturing example 44 or the corresponding ester were used, which were subjected to operation in accordance with Reference manufacturing example 11 and further subjected to operation in accordance with Reference manufacturing example 3 to obtain the following compounds.

Example 14(1)

[4-(2-oxo-2-{9-[3-(trifluoromethoxy)benzyl]-5,6,8,9-tetrahydro-7H-pyrido[4',3':4,5]pyrrolo[2,3-b]pyridin-7-yl}ethoxy)phenyl]acetic acid TLC:Rf 0.46 (chloroform:methanol=9:1);
MS (ESI, Pos.): m/z=540 (M+H)+.

Example 14(2)

[4-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethoxy)phenyl]acetic acid TLC:Rf 0.48 (chloroform:methanol=9:1);
MS (ESI, Pos.): m/z=553 (M+H)+.

Example 14(3)

[3-(2-oxo-2-{9-[3-(trifluoromethoxy)benzyl]-5,6,8,9-tetrahydro-7H-pyrido[4',3':4,5]pyrrolo[2,3-b]pyridin-7-yl}ethoxy)phenyl]acetic acid TLC:Rf 0.28 (chloroform:methanol=9:1);
MS (ESI, Pos.): m/z=540 (M+H)+.

Example 14(4)

[3-(2-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-2-oxoethoxy)phenyl]acetic acid TLC:Rf 0.30 (chloroform:methanol=9:1);
MS (ESI, Pos.): m/z=553 (M+H)+.

Example 14(5)

{4-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethoxy]phenyl}acetic acid TLC:Rf 0.50 (chloroform:methanol:water=50:10:1);
MS (ESI, Pos.): m/z=531 (M+H)+.

Example 14(5)

{3-[2-oxo-2-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)ethoxy]phenyl}acetic acid TLC:Rf 0.48 (chloroform:methanol:water=50:10:1);
MS (ESI, Pos.): m/z=531 (M+H)+.

Example 15

9-(3-fluorobenzyl)-5,6,8,9-tetrahydro-7H-pyrido[4',3':4,5]pyrrolo[2,3-b]pyridine-7-carboxamide In 3 mL of methylene chloride, 9-(3-Fluorobenzyl)-6,7,8,9-tetrahydro-5H-pyrido[4',3':4,5]pyrrolo[2,3-b]pyridine (100 mg) produced by operation in accordance with Reference manufacturing example 1, and triethylamine (263 μL) were dissolved. Trimethylsilyl isocyanate (311 mg) was added with stirring at room temperature, followed by stirring at room temperature for 10 minutes. An aqueous saturated sodium bicarbonate solution was added to the solution and extraction operation (methylene chloride, once) was performed. After drying the resulting organic layer with magnesium sulfate, the solvent was distilled off under reduced pressure to obtain a crude product. This was washed with ethyl acetate, and then dried under reduced pressure to obtain the title compound (72 mg) having the following physical property values.

TLC:Rf 0.28 (chloroform:methanol=10:1);

$^1$H-NMR (DMSO-d$_6$): δ 2.67-2.73 (m, 2 H), 3.58-3.67 (m, 2 H), 4.50 (s, 2 H), 5.43 (s, 2 H), 6.17 (s, 2 H), 6.90-7.37 (m, 5 H), 7.84-7.91 (m, 1 H), 8.17-8.21 (m, 1 H).

Example 15(1)-Example 15(2)

A corresponding tetrahydropyridopyrrolopyridine derivative in place of 9-(3-fluorobenzyl)-6,7,8,9-tetrahydro-5H-pyrido[4',3':4,5]pyrrolo[2,3-b]pyridine was used, which was subjected to operation in accordance with Reference Example 15 to obtain the following compounds.

Example 15(1)

9-{[2-(trifluoromethyl)-1,3-thiazol-5-yl]methyl}-5,6,8,9-tetrahydro-7H-pyrido[4',3':4,5]pyrrolo[2,3-b]pyridine-7-carboxamide TLC:Rf 0.36 (chloroform:methanol:water=100:10:1);
MS (ESI, Pos. 20 V): m/z=382 (M+H)$^+$.

Example 15(2)

9-{[4-methyl-2-(trifluoromethyl)-1,3-thiazol-5-yl]methyl}-5,6,8,9-tetrahydro-7H-pyrido[4',3':4,5]pyrrolo[2,3-b]pyridine-7-carboxamide TLC:Rf 0.37 (chloroform:methanol:water=100:10:1);
MS (ESI, Pos. 20 V): m/z=396 (M+H)$^+$.

Example 16

Measurement of Human ENPP2 Inhibitory Activity

10 μL of a test compound solution (10% dimethyl sulfoxide) at each concentration and 40 μL of a 5 μg/mL human ENPP2 solution (buffer A: 100 mmol/L Tris-HCl (pH 9.0), 500 mmol/L NaCl, 5 mmol/L MgCl$_2$, 0.05% Triton X-100) were mixed, 50 μL of a 2 mmol/L 16:0-lysophosphatidylcholine (LPC) solution (buffer A) was further added to react at 37° C. for 24 hours. Subsequently, to 10 μL of the reaction solution was added 90 μL of a measurement buffer (0.5 mmol/L aminoantipyrine, 0.3 mmol/L N-ethyl-N-(2-hydroxy-3-sulfopropyl)-3-methylaniline, 1 U/mL peroxidase, 3 U/mL choline oxidase, 100 mmol/L Tris-HCl (pH 8.5), 5 mmol/L CaCl$_2$) to react at 37° C. for 20 minutes, and spectrophotometric determination was performed at 555 nm.

Using a standard curve, a choline production amount (enzyme activity) in each test compound was calculated, and the inhibitory activity rate of each test compound was calculated, wherein the enzyme activity in a positive control to which a test compound is not added, was a 0% inhibition rate, and the enzyme activity in a negative control to which a test compound and human ENPP2 are not added, were 100% inhibition. Further, concerning the present compounds shown in Table 3, an IC$_{50}$ value was calculated from inhibitory activity rate at each concentration.
[Results]

As shown in Table 2 and Table 3, the present compounds have significant ENPP2 inhibitory activities even at 1 μM.

TABLE 2

| Ex. No | ENPP2 inhibitory activity rate (%) |
|---|---|
| 6 (13) | 99.21 |
| 6 (16) | 99.05 |
| 6 (49) | 99.09 |
| 7 (39) | 99.49 |
| 10 (5) | 97.36 |
| 6 (68) | 99.20 |
| 6 (72) | 99.31 |

TABLE 3

| Ex. No | ENPP2 inhibitory activity IC$_{50}$ (μM) |
|---|---|
| 3 (50) | 0.0045 |
| 6 (53) | 0.01 |
| 6 (63) | 0.008 |
| 6 (65) | 0.0051 |
| 7 (3) | 0.028 |
| 7 (41) | 0.0049 |
| 7 (45) | 0.016 |
| 9 (1) | 0.012 |
| 10 (2) | 0.017 |
| 10 (5) | 0.0038 |
| 11 (12) | 0.0054 |
| 11 (24) | 0.0084 |
| Ref. Ex. 2 | 0.014 |

Example 17

Measurement of Urethra Internal Pressure in Rat Under Anesthesia

A SD male rat (Crl: CD(SD), Charles River Laboratories Japan, Inc., 7-10 weeks old) which has fasted since the evening of the day before this experiment was anesthetized by subcutaneous administration of 1.5 g/kg urethane at a back of a neck. After an abdominal part was median incised, a catheter for duodenum was inserted within lumen of duodenum and then tied down by string. A lower abdominal part was median incised, and a urethra was ligated at around pubis. A urethral catheter for measuring a urethra internal pressure, equipped with a collar at a tip and filled with a physiological saline was inserted into a urethra through an incised bladder top, and ligation-fixed at a bladder neck part. The urethral catheter was connected to a pressure transducer (manufactured by Nihon Kohden Corporation), and a urethra internal pressure was measured. Concerning a urethra internal pressure, first, a physiological saline was injected into a urethra to adjust at about 20 mmHg, thereafter, it was confirmed that a urethra internal pressure was reduced and stabilized (reduction in a pressure for 10 minutes is within 0.75 mmHg), and individuals having an internal pressure at stabilization of 10 mmHg or higher were used in an experiment. The compound described in Example 6(72) (dose: 1.0 mg/kg) was administered intravenously and, after about 30 minutes, 1 mL of somnopentyl was administered intravenously. A urethra internal pressure reduction rate (%) was calculated based on a urethra internal pressure after compound administration, wherein a value obtained by subtracting a postmorten basline value (minimum value of urethra internal pressure for 10 minutes after administration of somnopentyl) from a urethra internal pressure value before compound administration (0 minute) was 100%.

[Results]

The compound described in Example 6(72) reduced a urethra internal pressure by 25% at a dose of 1.0 mg/kg.

Example 18

Measurement of Blood Pressure.Heart Rate in Rat Under Wakefulness

A Crl:CD (Sparague-Dawley) male rat (Charles River Laboratories Japan, Inc., 8 weeks old) was anesthetized by inhalation of isoflurane. A catheter (INTRAMEDIC POLYETHYLENE Tubing PE50, CLAY ADAMS) was inserted and indwelled in a femoral artery and another end was exposed from dorsal skin. The rat was placed in a rearing cage for blood pressure measurement. After elapse of 2 hours or more from the insertion of the catheter, each of the compound of Reference Example 2 and the compound of Example 6(72) (dose: 100, 300 mg/kg) was forcedly orally administered, and blood pressure was measured under no anesthesia and no restraint. The blood pressure was measured by connecting the catheter inserted in the femoral artery and a blood pressure transducer (DX-360, Nihon Kohden Corporation) and passing through an amplifier for blood pressure measurement (Coupler.Amplifier PP-101H.AP-101H, Nihon Kohden Corporation). Blood pressure signals were captured into a data acquisition analysis system (HEM 3.5, NOTOCORD SYSTEM S.A.) through a polygraph system (PEG-1000, Nihon Kohden Corporation) to measure blood pressure (systolic pressure, diastolic pressure, mean blood pressure) and heart rate (measured from blood pressure pulse wave). Time points for measurement were before administration, and 15, 30, 45, 60, 75, 90, 105, 120, 135, 150, 165, and 180 minutes after administration. The numerical data were all indiated as average values±standard deviation (integer values). The data were accumulated as measured values at respective time points and % variation values in which each value before administration was taken as 100.

[Results]

An influence of the compound of Reference Example 2 on a circulatory organ was observed at the test dose while no influence of the compound of Example 6(72) that is a compound of the present invention was observed on a circulatory organ.

Preparation Example 1

The following respective ingredients were mixed and compressed by the conventional method to obtain 10000 tablets, one tablet containing 5 mg of an active ingredient.

| | |
|---|---|
| 4-{2-[9-(3-ethylbenzyl)-5,6,8,9-tetrahydro-7H-pyrido[4',3':4,5]pyrrolo[2,3-b]pyridin-7-yl]-2-oxoethyl}bicyclo[2.2.1]heptane-1-carboxylic acid | 50 g |
| Carboxymethylcellulose calcium (disintegrating agent) | 20 g |
| Magnesium stearate (lubricant) | 10 g |
| Microcrystalline cellulose | 920 g |

Preparation Example 2

The following respective ingredients were mixed according to the conventional method, the solution was sterilized by the conventional method, and each 5 mL was filled into an ampoule, and lyophilized by the conventional method to obtain 10000 ampoules, one ampoule containing 20 mg of an active ingredient.

| | |
|---|---|
| 4-{2 [9-(3-ethylbenzyl)-5,6,8,9-tetrahydro-7H-pyrido [4',3':4,5]pyrrolo[2,3-b]pyridin-7-yl]-2-oxoethyl}bicyclo[2.2.1]heptane-1-carboxylic acid | 200 g |
| Mannitol | 20 g |
| Distilled water | 50 L |

INDUSTRIAL APPLICABILITY

The present compound has the ENPP2 inhibitory activity, and is useful as an agent for preventing or treating urinary excretion disorder and/or improving symptoms thereof.

The invention claimed is:

1. A compound represented by the formula (II):

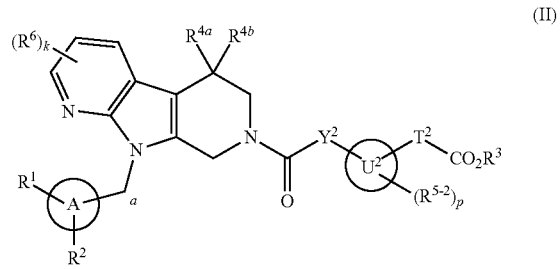

wherein

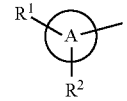

represents:

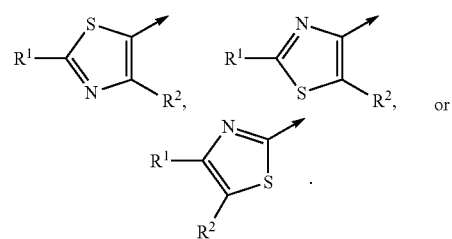

wherein $R^1$ represents a C2-4 alkyl group, a dihalomethyl group, a trihalomethyl group, a dihalomethoxy group, a trihalomethoxy group, or

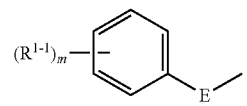

wherein E represents a bond or an oxygen atom; $R^{1-1}$ represents a dihalomethyl group, a trihalomethyl group, a dihalomethoxy group or a trihalomethoxy group, m represents an integer of zero or one, $R^2$ represents a hydrogen atom, a halogen atom or a methyl group, the bond represented by an arrow binds to the methylene group represented by "a" in the general formula(II), $R^3$ represents a hydrogen atom or a C1-4alkyl group;

$R^{4a}$ and $R^{4b}$ each independently represent a hydrogen atom or a methyl group;

the ring $U^2$ represents piperidine, piperazine;

$Y^2$ represents a methylene group, an ethylene group;

$T^2$ represents a methylene group optionally substituted by one or two $R^7(s)$ wherein $R^7$ represents a methyl group;

$R^{5-2}$ represents a methyl group;

p represents an integer of zero to two;

$R^6$ represents a halogen atom or a methyl group;

k represents an integer of zero to three, provided that a plurality of groups represented by $R^{5-2}$ and $R^6$ may be the same or different respectively, a salt thereof or a solvate thereof.

2. The compound according to claim 1, wherein $Y^2$ represents a methylene group.

3. A compound represented by the formula (III):

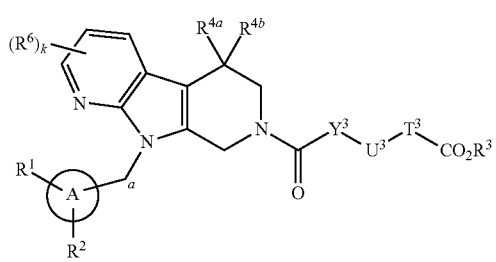

wherein

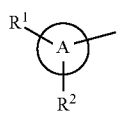

represents:

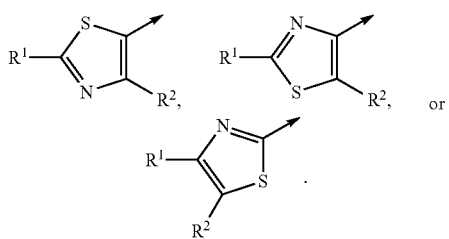

wherein $R^1$ represents a C2-4 alkyl group, a dihalomethyl group, a trihalomethyl group, a dihalomethoxy group, a trihalomethoxy group, or

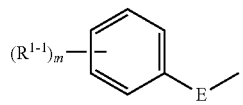

wherein E represents a bond or an oxygen atom; $R^{1-1}$ represents a dihalomethyl group, a trihalomethyl group, a dihalomethoxy group or a trihalomethoxy group, m represents an integer of zero or one, $R^2$ represents a hydrogen atom, a halogen atom or a methyl group, the bond represented by an arrow binds to the methylene group represented by "a" in the general formula (III);

$R^3$ represents a hydrogen atom or a C1-4alkyl group;

$R^{4a}$ and $R^{4b}$ each independently represent a hydrogen atom or a methyl group;

$U^3$ represents a methylene group;

$Y^3$ represents a methylene group or an ethylene group;

$T^3$ represents a methylene or ethylene group optionally substituted by one or two $R^7(s)$ wherein $R^7$ represents a methyl group, two of $R^7$s may form cyclopropyl, together with the same carbon atom to which they are each attached;

$R^6$ represents a halogen atom or a methyl group;

k represents an integer of zero to three, provided that a plurality of groups represented by $R^6$ may be the same or different, provided that $T^3$ does not represent an ethylene group optionally substituted by one or two $R^7(s)$ when $Y^3$ represents an ethylene group, a salt thereof or a solvate thereof.

4. The compound according to claim 1 or 3, wherein k represents zero.

5. The compound according to claim 1 or 3, wherein

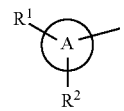

in the formula (II) or (III) each represents

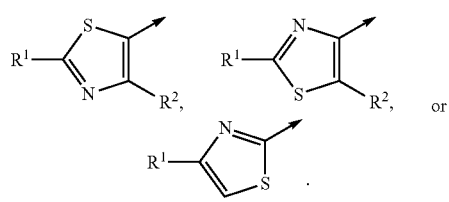

wherein all symbols are as defined in the above-mentioned.

6. The compound according to claim 1 or 3, wherein

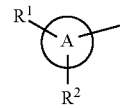

in the formula (II) or (III) each represents

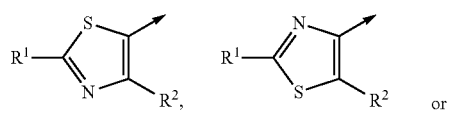

-continued

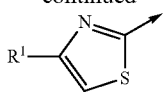

wherein all symbols are as defined in the above-mentioned.

7. A compound represented by the formula (IV):

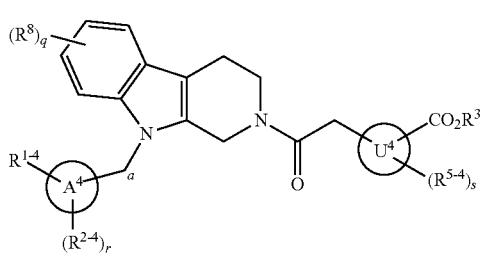

wherein

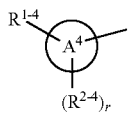

represents

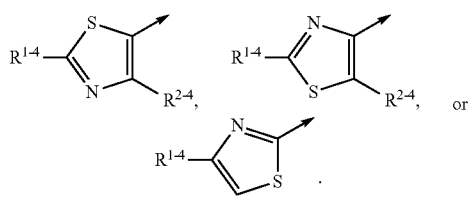

wherein R$^{1-4}$ represents a halogen atom, a dihalomethyl group, a trihalomethyl group, a dihalomethoxy group, a trihalomethoxy group, a phenyl group or a phenoxy group, R$^{2-4}$ represents a halogen atom or a methyl group, the bond represented by an arrow binds to the methylene group represented by "a" in the general formula (IV), r represents an integer of zero to two, provided that a plurality of groups represented by R$^{2-4}$ may be the same or different, respectively;

R$^3$ represents a hydrogen atom or a C1-4alkyl group;

the ring U$^4$ represents piperidine;

R$^{5-4}$ represents a methyl group or a methoxy group;

R$^8$ represents a halogen atom;

q represents an integer of zero to two;

s represents an integer of zero to three, provided that a plurality of groups represented by R$^{5-4}$ may be the same or different, respectively, a salt thereof or a solvate thereof.

8. A compound represented by the formula (V):

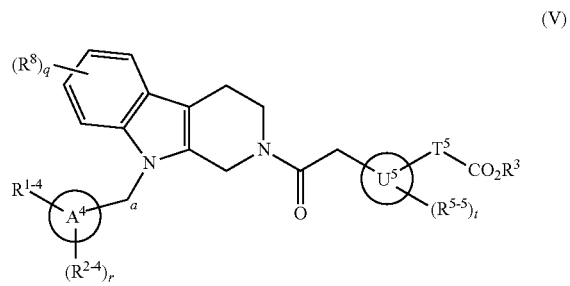

wherein

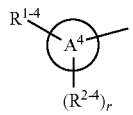

Represents

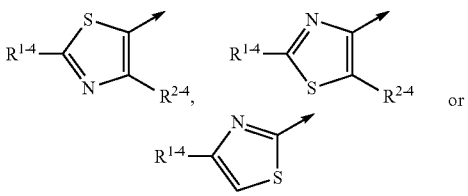

wherein R$^{1-4}$ represents a halogen atom, a dihalomethyl group, a trihalomethyl group, a dihalomethoxy group, a trihalomethoxy group, a phenyl group or a phenoxy group, R$^{2-4}$ represents a halogen atom or a methyl group, the bond represented by an arrow binds to the methylene group represented by "a" in the general formula (IV), r represents an integer of zero to two, provided that a plurality of groups represented by R$^{2-4}$ may be the same or different, respectively;

R$^3$ represents a hydrogen atom or a C1-4alkyl group;

the ring U$^5$ represents piperidine or piperazine;

T$^5$ represents a methylene group optionally substituted by one or two R$^7$(s) wherein R$^7$ represents a methyl group;

R$^{5-5}$ represents a methyl group;

t represents an integer of zero to three, R$^8$ represents a halogen atom;

q represents an integer of zero to two, a salt thereof or a solvate thereof.

9. The compound according to claim 7 or 8, wherein

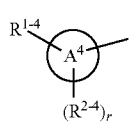

in the formula (IV) or (V) represents

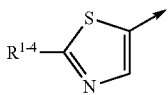

wherein all symbols are as defined in the above-mentioned.

10. A compound represented by the formula (VI):

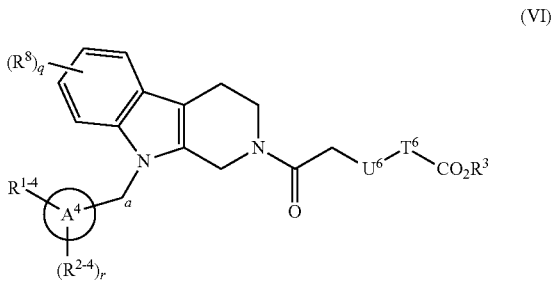

wherein

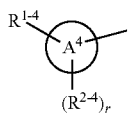

Represents

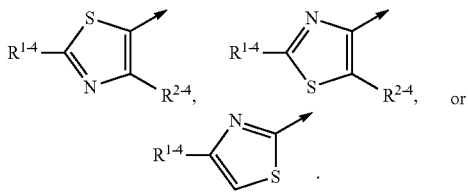

wherein $R^{1-4}$ represents a halogen atom, a dihalomethyl group, a trihalomethyl group, a dihalomethoxy group, a trihalomethoxy group, a phenyl group or a phenoxy group, $R^{2-4}$ represents a halogen atom or a methyl group, the bond represented by an arrow binds to the methylene group represented by "a" in the general formula (IV), r represents an integer of zero to two, provided that a plurality of groups represented by $R^{2-4}$ may be the same or different, respectively;

$R^3$ represents a hydrogen atom or a C1-4alkyl group;

$U^6$ represents a methylene;

$T^6$ represents an ethylene optionally substituted by one or two $R^7$(s) wherein $R^7$ represents a methyl group;

$R^8$ represents a halogen atom;

q represents an integer of zero to two, a salt thereof or a solvate thereof.

11. The compound according to claim 1 or 3, wherein $R^1$ in the formula (II) or (III) represents an ethyl group, a difluoromethyl group, a trifluoromethyl group, a difluoromethoxy group, a trifluoromethoxyl group, a phenyl group or a phenoxy group.

12. The compound according to any one of claims 7, 8 and 10, wherein $R^{1-4}$ in the formula (IV), (V) or (VI) represents a halogen atom, a difluoromethyl group, a trifluoromethyl group, a difluoromethoxy group, a trifluoromethoxyl group, a phenyl group or a phenoxy group.

13. The compound according to any one of claims 3, 7, 8, and 10, wherein $R^3$ represents a hydrogen atom.

14. The compound according to claim 1, wherein the compound represented by the formula (II) is:

(10)    [4-(2-{9-[(4-methyl-2-phenyl-1,3-thiazol-5-yl) methyl]-5,6,8,9-tetrahydro-7H-pyrido[4',3':4,5]pyrrolo[2,3-b]pyridin-7-yl}-2-oxoethyl)-1-piperidinyl]acetic acid,

(27)    [4-(2-{9-[(4-methyl-2-phenyl-1,3-thiazol-5-yl) methyl]-5,6,8,9-tetrahydr-7H-pyrido[4',3':4,5]pyrrolo[2,3-b]pyridin-7-yl}-2-oxoethyl)-1-piperazinyl]acetic acid, or

(29)    [1-(2-{9-[(4-methyl-2-phenyl-1,3-thiazol-5-yl) methyl]-5,6,8,9-tetrahydro-7H-pyrido[4',3':4,5]pyrrolo[2,3-b]pyridin-7-yl}-2-oxoethyl)-4-piperidinyl]acetic acid.

15. The compound according to claim 3, wherein the compound represented by the formula (III) is:

(9) 2,2-dimethyl-6-{9-[(5-methyl-2-phenyl-1,3-thiazol-4-yl)methyl]-5,6,8,9-tetrahydro-7H-pyrido[4',3':4,5]pyrrolo[2,3-b]pyridin-7-yl}-6-oxohexanoic acid,

(45) 2,2-dimethyl-6-oxo-6-(9-{[4-(trifluoromethyl)-1,3-thiazol-2-yl]methyl}-5,6,8,9-tetrahydro-7H-pyrido[4',3':4,5]pyrrolo[2,3-b]pyridin-7-yl)hexanoic acid,

(46) 2,2-dimethyl-6-oxo-6-(9-{[2-(trifluoromethyl)-1,3-thiazol-5-yl]methyl}-5,6,8,9-tetrahydro-7H-pyrido[4',3':4,5]pyrrolo[2,3-b]pyridin-7-yl)hexanoic acid,

(49) 2,2-dimethyl-6-oxo-6-(9-{[2-(trifluoromethyl)-1,3-thiazol-4-yl]methyl}-5,6,8,9-tetrahydro-7H-pyrido[4',3':4,5]pyrrolo[2,3-b]pyridin-7-yl)hexanoic acid,

(51) 2,2-dimethyl-6-{9-[(4-methyl-2-phenyl-1,3-thiazol-5-yl)methyl]-5,6,8,9-tetrahydro-7H-pyrido[4',3':4,5]pyrrolo[2,3-b]pyridin-7-yl}-6-oxohexanoic acid,

(52) 2,2-dimethyl-6-[9-({4-methyl-2-[4-(trifluoromethyl)phenyl]-1,3-thiazol-5-yl}methyl)-5,6,8,9-tetrahydro-7H-pyrido[4',3':4,5]pyrrolo[2,3-b]pyridin-7-yl]-6-oxohexanoic acid,

(53) 2,2-dimethyl-6-(9-{[4-methyl-2-(trifluoromethyl)-1,3-thiazol-5-yl]methyl}-5,6,8,9-tetrahydro-7H-pyrido[4',3':4,5]pyrrolo[2,3-b]pyridin-7-yl)-6-oxohexanoic acid,

(81)    1-[4-oxo-4-(9-{[2-(trifluoromethyl)-1,3-thiazol-5-yl]methyl }-5,6,8,9-tetrahydro-7H-pyrido[4',3':4,5] pyrrolo [2,3-b]pyridin-7-yl)butyl]cyclopropanecarboxylic acid, or

(82)    1-[4-(9-{[4-methyl-2-(trifluoromethyl)-1,3-thiazol-5-yl]methyl }-5,6,8,9-tetrahydro-7H-pyrido [4',3':4,5] pyrrolo [2,3-b]pyridin-7-yl)-4-oxobutyl]cyclopropanecarboxylic acid.

16. The compound according to claim 7, wherein the compound represented by the formula (IV) is:

(1)    cis-4-[2-oxo-2-(9-{[2-(trifluoromethyl)-4-pyridinyl] methyl}-1,3,4,9-tetrahydro-2H-beta-carbolin-2-yl) ethyl]cyclohexanecarboxylic acid, (2)    4-{2-[9-(2,4-difluorobenzyl)-8-fluoro-1,3,4,9-tetrahydro-2H-beta-carbolin-2-yl]-2-oxoethyl}benzoic acid, (3)    4-[2-(8-fluoro-9-{[5-(trifluoromethyl)-2-thienyl] methyl }-1,3,4,9-tetrahydro-2H-beta-carbolin-2-yl)-2-oxoethyl]benzoic acid, (4) 4-{2-[8-fluoro-9-(3-fluorobenzyl)-1,3,4,9-tetrahydro-2H-beta-carbolin-2-yl]-2-oxoethyl}benzoic acid, (5) 4-{2-[9-(2,4-difluorobenzyl)-8-fluoro-1,3,4,9-tetrahydro-2H-beta-carbolin-2-yl]-2-oxoethyl}bicyclo[2.2.2]octane-1-carboxylic acid,
(6) (1R,3R)-1,2,2-trimethyl-3-[2-oxo-2-(9-{[2-(trifluoromethyl)-1,3-thiazol-5-yl]methyl}-1,3,4,9-tetrahydro-2H-beta-carbolin-2-yl)ethyl]cyclopentanec arboxylic aci,
(7) 4-(2-{9-[3-(difluoromethyl)benzyl]-1,3,4,9-tetrahydro-2H-beta-carbolin-2-yl}-2-oxoethyl)bicyclo[2.2.2]octane-1-carboxylic acid,
(8) 4-[2-oxo-2-(9-{[2-(trifluoromethyl)-1,3-thiazol-5-yl]methyl }-1,3,4,9-tetrahydro-2H-beta-carbolin-2-yl)ethyl]bicyclo [2.2.2]octane-1-carboxylic acid,
(9) (1R,3R)-3-(2-{9-[3-(difluoromethyl)benzyl]-1,3,4,9-tetrahydro-2H-beta-carbolin-2-yl}-2-oxoethyl)-1,2,2-trimethylcyclopentanecarboxylic acid,
(10) 4-[2-(8-fluoro-9-{[2-(trifluoromethyl)-1,3-thiazol-5-yl]methyl}-1,3,4,9-tetrahydro-2H-beta-carbolin-2-yl)-2-oxoethyl]bicyclo[2.2.1]heptane-1-carboxylic acid,
(11) 4-{2-[8-fluoro-9-(4-phenoxybenzyl)-1,3,4,9-tetrahydro-2H-beta-carbolin-2-yl]-2-oxoethyl }bicyclo[2.2.1]heptane-1-carboxylic acid,
(12) 4-[2-(6-fluoro-9-{[2-(trifluoromethyl)-1,3-thiazol-5-yl]methyl}-1,3,4,9-tetrahydro-2H-beta-carbolin-2-yl)-2-oxoethyl]bicyclo[2.2.1]heptane-1-carboxylic acid,
(13) 4-[2-(6,8-difluoro-9-{[2-(trifluoromethyl)-1,3-thiazol-5-yl]methyl}-1,3,4,9-tetrahydro-2H-beta-carbolin-2-yl)-2-oxoethyl]bicyclo[2.2.1]heptane-1-carboxylic acid,
(14) 4-(2-{6-fluoro-9-[3-(trifluoromethoxy)benzyl]-1,3,4,9-tetrahydro-2H-beta-carbolin-2-yl}-2-oxoethyl)bicyclo[2.2.1]heptane1carboxylic acid,
(15) 4-{2-[8-fluoro-9-(3-fluorobenzyl)-1,3,4,9-tetrahydro-2H-beta-carbolin-2-yl]-2-oxoethyl}bicyclo[2.2.1]heptane1carboxylic acid,
(16) 1-{2-[9-(3-chloro-2,4-difluorobenzyl)-8-fluoro-1,3,4,9-tetrahydro-2H-beta-carbolin-2-yl]-2-oxoethyl}-4-piperidinecarboxylic acid,
(17) 1-(2-{8-fluoro-9-[4-(trifluoromethoxy)benzyl]-1,3,4,9-tetrahydro-2H-beta-carbolin-2-yl}-2-oxoethyl)-4-piperidinecarboxylic acid,
(18) 1-{2-[9-(3,5-dichlorobenzyl)-8-fluoro-1,3,4,9-tetrahydro-2H-beta-carbolin-2-yl]-2-oxoethyl}-4-piperidinecarboxylic acid,
(19) 1-(2-{8-fluoro-9-[3-fluoro-4-(trifluoromethoxy)benzyl]-1,3,4,9-tetrahydro-2H-beta-carbolin-2-yl}-2-oxoethyl)-4-piperidinecarboxylic acid,
(20) 1-(2-{9-[(5-chloro-2-thienyl)methyl]-8-fluoro-1,3,4,9-tetrahydro-2H-beta-carbolin-2-yl}-2-oxoethyl)-4-piperidinecarboxylic acid,
(21) 1-[2-(8-fluoro-9-{[5-(trifluoromethyl)-2-thienyl]methyl}-1,3,4,9-tetrahydro-2H-beta-carbolin-2-yl)-2-oxoethyl]-4-piperidinecarboxylic acid,
(22) 1-[2-oxo-2-(9-{[5-(trifluoromethyl)-2-thienyl]methyl}-1,3,4,9-tetrahydro-2H-beta-carbolin-2-yl)ethyl]-4-piperidinecarboxylic acid,
(23) 1-(2-{9-[(5-chloro-2-thienyl)methyl]-8-fluoro-1,3,4,9-tetrahydro-2H-beta-carbolin-2-yl}-2-oxoethyl)-4-methyl-4-piperidinecarboxylic acid,
(24) 4-methyl-1-[2-oxo-2-(9-{[5-(trifluoromethyl)-2-thienyl]methyl}-1,3,4,9-tetrahydro-2H-beta-carbolin-2-yl)ethyl]-4-piperidinecarboxylic acid,
(25) 1-[2-(8-fluoro-9-{[5-(trifluoromethyl)-2-thienyl]methyl}-1,3,4,9-tetrahydro-2H-beta-carbolin-2-yl)-2-oxoethyl]-4-methyl-4-piperidinecarboxylic acid,
(26) 1-(2-{8-fluoro-9-[3-(trifluoromethoxy)benzyl]-1,3,4,9-tetrahydro-2H-beta-carbolin-2-yl}-2-oxoethyl)-4-piperidinecarboxylic acid, or
(27) 1-[2-(6,8-difluoro-9-{[2-(trifluoromethyl)-1,3-thiazol-5-yl]methyl}-1,3,4,9-tetrahydro-2H-beta-carbolin-2-yl)-2-oxoethyl]-4-piperidinecarboxylic acid.

17. The compound according to claim 8, wherein the compound represented by the formula (V) is:
(1) {4-[2-(6,8-difluoro-9-{[2-(trifluoromethyl)-1,3-thiazol-5-yl]methyl}-1,3,4,9-tetrahydro-2H-beta-carbolin-2-yl)-2-oxoethyl]-1-piperidinyl}acetic acid,
(2) {4-[2-(8-fluoro-9-{[2-(trifluoromethyl)-1,3-thiazol-5-yl]methyl }-1,3,4,9-tetrahydro-2H-beta-carbolin-2-yl)-2-oxoethyl]-1-piperidinyl}acetic acid,
(27) {4-[2-(6,8-difluoro-9-{[2-(trifluoromethyl)-1,3-thiazol-5-yl]methyl}-1,3,4,9-tetrahydro-2H-beta-carbolin-2-yl)-2-oxoethyl]-1-piperazinyl}acetic acid,
(28) {1-[2-(6,8-difluoro-9-{[2-(trifluoromethyl)-1,3-thiazol-5-yl]methyl}-1,3,4,9-tetrahydro-2H-beta-carbolin-2-yl)-2-oxoethyl]-4-piperidinyl}acetic acid,
(29) {4-[2-(8-fluoro-9-{[2-(trifluoromethyl)-1,3-thiazol-5-yl]methyl }-1,3,4,9-tetrahydro-2H-beta-carbolin-2-yl)-2-oxoethyl]-1-piperazinyl}acetic acid, or
(32) {1-[2-(6-fluoro-9-{[2-(trifluoromethyl)-1,3-thiazol-5-yl]methyl }-1,3,4,9-tetrahydro-2H-beta-carbolin-2-yl)-2-oxoethyl]-4-piperidinyl}acetic acid.

18. The compound according to claim 10, wherein the compound represented by the formula (VI) is:
(11) 2,2-dimethyl-6-oxo-6-(9-{[2-(trifluoromethyl)-1,3-thiazol-5-yl]methyl}-1,3,4,9-tetrahydro-2H-beta-carbolin-2-yl)hexanoic acid.

19. A pharmaceutical composition containing the compound represented by the formula (II) according to claim 1, formula (III) according to claim 3, formula (IV) according to claim 7, formula (V) according to claim 8, or formula (VI) according to claim 10, a salt thereof or a solvate thereof as an active ingredient.

20. A method for treating urinary excretion disorder or tumor comprising administering an effective amount of a composition containing a compound represented by the formula (II) according to claim 1, formula (III) according to claim 3, formula (IV) according to claim 7, formula (V) according to claim 8, or formula (VI) according to claim 10, a salt thereof or a solvate thereof as an active ingredient to a subject in need thereof.

21. A method for inhibiting ENPP2, comprising administering an effective amount of a composition containing a compound represented by the formula (II) according to claim 1, formula (III) according to claim 3, formula (IV) according to claim 7, formula (V) according to claim 8, or formula (VI) according to claim 10, a salt thereof or a solvate thereof as an active ingredient to a subject in need thereof.

* * * * *

UNITED STATES PATENT AND TRADEMARK OFFICE
CERTIFICATE OF CORRECTION

PATENT NO. : 9,862,721 B2
APPLICATION NO. : 14/884211
DATED : January 9, 2018
INVENTOR(S) : Akira Ohata et al.

It is certified that error appears in the above-identified patent and that said Letters Patent is hereby corrected as shown below:

On the Title Page

<u>Item (56), References Cited</u>

Page 2, Column 2, Line 8, delete "Mehtods" and insert --Methods-- therefor;

Page 2, Column 2, Line 11, delete "Nternational" and insert --International-- therefor.

In the Claims

In Claim 1, Column 141, Line 10, delete "group, an" and insert --group or an-- therefor;

In Claim 13, Column 146, Lines 6 and 7, delete "claims 3, 7, 8 and 10" and insert --claims 1, 3, 7, 8 and 10-- therefor;

In Claim 14, Column 146, Line 15, delete "tetrahydr" and insert --tetrahydro-- therefor;

In Claim 15, Column 146, Line 48, delete "methyl }" and insert --methyl}-- therefor;

In Claim 16, Column 146, Line 64, delete "methyl }" and insert --methyl}-- therefor;

In Claim 16, Column 147, Line 6, delete "cyclopentanec arboxylic" and insert --cyclopentanecarboxylic-- therefor;

In Claim 16, Column 147, Line 7, delete "aci" and insert --acid-- therefor;

In Claim 16, Column 147, Line 12, delete "methyl }" and insert --methyl}-- therefor;

In Claim 16, Column 147, Line 22, delete "oxoethyl }" and insert --oxoethyl}-- therefor;

Signed and Sealed this
Sixteenth Day of October, 2018

Andrei Iancu
*Director of the United States Patent and Trademark Office*

CERTIFICATE OF CORRECTION (continued)
U.S. Pat. No. 9,862,721 B2

In Claim 16, Column 147, Line 33, delete "heptane1carboxylic" and insert --heptane-1-carboxylic-- therefor;

In Claim 16, Column 147, Line 36, delete "heptane1carboxylic" and insert --heptane-1-carboxylic-- therefor;

In Claim 17, Column 148, Line 27, delete "methyl }" and insert --methyl}-- therefor;

In Claim 17, Column 148, Line 30, delete "methyl }" and insert --methyl}-- therefor.